(12) United States Patent
Grainger et al.

(10) Patent No.: US 7,700,087 B2
(45) Date of Patent: Apr. 20, 2010

(54) COMPOUNDS AND METHODS TO INHIBIT OR AUGMENT AN INFLAMMATORY RESPONSE

(75) Inventors: David J. Grainger, Cambridge (GB); Lauren Marie Tatalick, Redmond, WA (US); Suzanne T. Kanaly, Seattle, WA (US)

(73) Assignee: Cambridge Enterprise Limited, Cambridge (GB)

(*) Notice: Subject to any disclaimer, the term of this patent is extended or adjusted under 35 U.S.C. 154(b) by 599 days.

(21) Appl. No.: 10/241,375

(22) Filed: Sep. 11, 2002

(65) Prior Publication Data

US 2006/0073114 A1 Apr. 6, 2006

Related U.S. Application Data

(63) Continuation of application No. 09/150,813, filed on Sep. 11, 1998, now Pat. No. 7,067,117, which is a continuation-in-part of application No. 08/927,939, filed on Sep. 11, 1997, now Pat. No. 6,989,435.

(51) Int. Cl.
| | |
|---|---|
| *A61K 45/00* | (2006.01) |
| *A61K 38/00* | (2006.01) |
| *C07K 1/00* | (2006.01) |
| *C07K 11/00* | (2006.01) |
| *C07K 11/02* | (2006.01) |

(52) U.S. Cl. .................. 424/85.1; 530/324; 530/351; 514/2; 514/12

(58) Field of Classification Search .............. None
See application file for complete search history.

(56) References Cited

U.S. PATENT DOCUMENTS

| | | | |
|---|---|---|---|
| 2,726,243 | A | 12/1955 | Huebner |
| 2,740,788 | A | 4/1956 | Grussner et al. |
| 2,743,270 | A | 4/1956 | Blicke |
| 4,108,855 | A | 8/1978 | Karacsony et al. |
| 4,724,232 | A | 2/1988 | Rideout et al. |
| 4,737,580 | A | 4/1988 | Twardzik et al. |
| 4,774,318 | A | 9/1988 | Marquardt et al. |
| 5,079,228 | A | 1/1992 | Cohen et al. |
| 5,155,038 | A | 10/1992 | Eyal et al. |
| 5,190,918 | A | 3/1993 | Deutch et al. |
| 5,190,920 | A | 3/1993 | Eyal et al. |
| 5,192,744 | A | 3/1993 | Bouck et al. |

(Continued)

FOREIGN PATENT DOCUMENTS

EP 0281363 B1 9/1988

(Continued)

OTHER PUBLICATIONS

Bowie et al, 1990, Science 247:1306-1310.*

(Continued)

*Primary Examiner*—Cherie M Woodward
(74) *Attorney, Agent, or Firm*—Schwegman Lundberg & Woessner, P.A.

(57) ABSTRACT

Isolated and purified chemokine peptides, variants, and derivatives thereof, as well as chemokine peptide analogs, are provided. For example, the invention provides peptides of no more than 15 amino acid residues which include chemokine peptide sequences and variants thereof, as well as cyclic reverse derivatives thereof, which inhibit the activity of at least one chemokine.

42 Claims, 23 Drawing Sheets

U.S. PATENT DOCUMENTS

| | | | |
|---|---|---|---|
| 5,202,118 A | 4/1993 | Gillis et al. |
| 5,212,073 A | 5/1993 | Rollins et al. |
| 5,248,666 A | 9/1993 | Twardzik et al. |
| 5,302,384 A | 4/1994 | Gimbrone, Jr. et al. |
| 5,357,041 A | 10/1994 | Roberts et al. |
| 5,401,651 A | 3/1995 | Walz |
| 5,426,100 A | 6/1995 | Deutch et al. |
| 5,458,874 A | 10/1995 | Pereira et al. |
| 5,459,128 A | 10/1995 | Rollins et al. |
| 5,474,983 A | 12/1995 | Kuna et al. |
| 5,491,130 A | 2/1996 | Roberts et al. |
| 5,556,757 A | 9/1996 | Alstyne et al. |
| 5,571,713 A | 11/1996 | Lyle et al. |
| 5,578,714 A | 11/1996 | Pogo et al. |
| 5,589,458 A | 12/1996 | Jameson et al. |
| 5,597,578 A | 1/1997 | Brown et al. |
| 5,605,671 A | 2/1997 | Lyle et al. |
| 5,627,156 A | 5/1997 | Talmadge |
| 5,627,265 A | 5/1997 | Frazier et al. |
| 5,645,837 A | 7/1997 | Jameson et al. |
| 5,646,117 A | 7/1997 | Matsushima et al. |
| 5,650,150 A | 7/1997 | Gillies |
| 5,661,132 A | 8/1997 | Eriksson et al. |
| 5,663,294 A | 9/1997 | Colman et al. |
| 5,684,032 A | 11/1997 | Elliott et al. |
| 5,700,821 A | 12/1997 | Lazo et al. |
| 5,705,360 A | 1/1998 | Rollins et al. |
| 5,707,814 A | 1/1998 | Levy et al. |
| 5,707,815 A | 1/1998 | Charo et al. |
| 5,770,609 A | 6/1998 | Grainger et al. |
| 5,811,449 A | 9/1998 | Medford et al. |
| 5,817,911 A | 10/1998 | Williams et al. |
| 5,824,551 A | 10/1998 | Damme et al. |
| 5,824,647 A | 10/1998 | Postlethwaite et al. |
| 5,827,821 A | 10/1998 | Pierschbacher et al. |
| 5,831,032 A | 11/1998 | Schraufstatter et al. |
| 5,871,740 A | 2/1999 | Smith |
| 5,877,276 A | 3/1999 | Talmadge |
| 5,908,829 A | 6/1999 | Kelly |
| 5,955,485 A | 9/1999 | De Brabander et al. |
| 5,955,492 A | 9/1999 | Thompson et al. |
| 6,162,455 A | 12/2000 | Cleale et al. |
| 6,989,435 B2 | 1/2006 | Grainger et al. |
| 7,238,711 B1 | 7/2007 | Grainger et al. |
| 2002/0182650 A1* | 12/2002 | Sworin et al. ............... 435/7.9 |
| 2008/0045557 A1 | 2/2008 | Grainger et al. |

FOREIGN PATENT DOCUMENTS

| | | |
|---|---|---|
| EP | 0807439 A2 | 11/1997 |
| EP | 0860446 A1 | 8/1998 |
| EP | 0905241 A1 | 3/1999 |
| FR | 2239471 | 2/1975 |
| GB | 1359260 | 7/1974 |
| GB | 1414589 | 11/1975 |
| GB | 2319252 | 5/1998 |
| JP | 36-14610 | 8/1961 |
| JP | 06-025288 | 2/1994 |
| JP | 07-067689 | 3/1995 |
| JP | 09-255570 | 9/1997 |
| WO | WO-86/04334 A1 | 7/1986 |
| WO | WO-90/07863 A1 | 7/1990 |
| WO | WO-91/08483 A1 | 6/1991 |
| WO | WO-91/17179 A1 | 11/1991 |
| WO | WO-92/04372 A1 | 3/1992 |
| WO | WO-92/14455 A1 | 9/1992 |
| WO | WO-92/20372 A1 | 11/1992 |
| WO | WO-93/10796 | 6/1993 |
| WO | WO-93/10796 A1 | 6/1993 |
| WO | WO-93/11159 A1 | 6/1993 |
| WO | WO-9310796 | 6/1993 |
| WO | WO-94/11014 A1 | 5/1994 |
| WO | WO-94/20512 A2 | 9/1994 |
| WO | WO-95/05191 A1 | 2/1995 |
| WO | WO-95/17420 A1 | 6/1995 |
| WO | WO-95/17421 A1 | 6/1995 |
| WO | WO-95/20973 A1 | 8/1995 |
| WO | WO-95/26982 A2 | 10/1995 |
| WO | WO-96/20722 A1 | 7/1996 |
| WO | WO-96/22371 A2 | 7/1996 |
| WO | WO-96/25157 A1 | 8/1996 |
| WO | WO-97/01350 A1 | 1/1997 |
| WO | WO 97/12615 A1 | 4/1997 |
| WO | WO-97/19173 A1 | 5/1997 |
| WO | WO-97/21812 A2 | 6/1997 |
| WO | WO-97/22698 A2 | 6/1997 |
| WO | WO-97/24325 A1 | 7/1997 |
| WO | WO-97/25427 A1 | 7/1997 |
| WO | WO-97/29192 A1 | 8/1997 |
| WO | WO-97/31098 A1 | 8/1997 |
| WO | WO-97/32019 A2 | 9/1997 |
| WO | WO-97/32993 A1 | 9/1997 |
| WO | WO-97/35010 A1 | 9/1997 |
| WO | WO-97/35982 A2 | 10/1997 |
| WO | WO-97/44462 A1 | 11/1997 |
| WO | WO-97/45543 A2 | 12/1997 |
| WO | WO-98/00535 A2 | 1/1998 |
| WO | WO-98/06703 A1 | 2/1998 |
| WO | WO-98/09171 A1 | 3/1998 |
| WO | WO-98/12324 A1 | 3/1998 |
| WO | WO-98/13495 A1 | 4/1998 |
| WO | WO-98/23750 A2 | 6/1998 |
| WO | WO-98/24808 A2 | 6/1998 |
| WO | WO-98/42354 | 10/1998 |
| WO | WO-98/42354 A1 | 10/1998 |
| WO | WO-9842354 | 10/1998 |
| WO | WO-99/37617 A1 | 7/1999 |
| WO | WO-99/37619 A1 | 7/1999 |
| WO | WO-99/37651 A1 | 7/1999 |
| WO | WO-00/00821 A1 | 1/2000 |
| WO | WO-02076399 A2 | 10/2002 |
| WO | WO-02094270 A2 | 11/2002 |
| WO | WO-2007042504 A2 | 4/2007 |

OTHER PUBLICATIONS

Wells, 1990, Biochemistry 29:8509-8517.*
Zhang et al., J Biol Chem Jun. 3, 1994;269(22):15918-19524.*
Steitz et al., FEBS Lett. Jul. 3, 1998;430(3):158-64.*
Gong et al., J Exp Med., Jul. 7, 1997; 186(1):131-137.*
"Blocking CCR5 Stops M-tropic HIV Infection", *Biotechnology News.* 17, (1997), 3 pgs.
Adkins, J. C., et al., "Zafirlukast—A Review of its Pharmacology and Therapeutic Potential in the Management of Asthma", *Drugs*, 55, (1998),121-144.
Albanesi, C., et al., "Cetirizine and Hydrocortisone Differentially Regulate ICAM-I Expression and Chemokine Release in Cultured Human Keratinocytes", *Clinical and Experimental Allergy*, 28(1), (Jan. 1998),101-109.
Alkhatib, G., et al., "HIV-1 Coreceptor Activity of CCR5 and Its Inhibition by Chemokines: Independence from G Protein Signaling and Importance of Coreceptor Downmodulation", *Virology*, 234(2), (Aug. 4, 1997),340-348.
Arenzana-Seisdedos, F., et al., "HIV Blocked by Chemokine Antagonists", *Nature*, 383(6599), (Oct. 3, 1996),400.
Auer, M., et al., "Crystallization and Preliminary X-ray Crystallographic Study of Interleukin-8", *FEBS Letters*, 265(1-2), (Jun. 1990),30-32.
Bacon, K. B., et al.,"Activation of Dual T Cell Signaling Pathways by the Chemokine RANTES", *Science*, 269, (1995),1727-1730.
Bacon, K. B., et al., "Chemokines in Disease Models and Pathogenesis", *Cytokine and Growth Factor Reviews*, 9, (1998),167-173.

Baldwin, E. T., et al., "Crystal Structure of Interleukin 8: Symbiosis of NMR and Crystallography", *Proceedings of the National Academy of Sciences USA*, 88, (Jan. 15, 1991),502-506.

Baldwin, E. T., et al., "Crystallization of Human Interleukin-8", *Journal of Biological Chemistry*, 265(12), (Apr. 25, 1990),6851-6853.

Beck-Schimmer, B., et al., "Hyaluronan Induces Monocyte Chemoattractant Protein-1 Expression in Renal Tubular Epithelial Cells", *Journal of the American Society of Nephrology*9, (1988),2283-2290.

Beers, M., et al., "Myeloproliferative Disorders", *The Merck Manual 7th Edition*, (1999), 1474-1476 & 895-902.

Bernstein, S. H., et al., "A Randomized Phase II Study of BB-10010: a Variant of Human Macrophage Inflammatory Protein-1alpha for Patients Receiving High-Dose Etoposide and Cyclophosphamide for Malignant Lymphoma and Breast Cancer", *British Journal of Haematology*, 99, (1997), 888-895.

Berson, J. F., et al., "Structure-Function Studies of the HIV-1 Coreceptors", *Seminars in Immunology*, 10, (1998),237-248.

Bodaghi, B., et al., "Chemokine sequestration by viral chemoreceptors as a novel viral escape strategy: withdrawal of chemokines from the environment of cytomegalovirus-infected cells", *Journal of Experimental Medicine*, 188(5), (Sep. 7, 1998),855-866.

Boring, L., et al., "Decreased Lesion Formation in CCR2-/-Mice Reveals a Role for Chemokines in the Initiation of Artherosclerosis", *Nature*, 394(6696), (Aug. 27, 1998), 894-897.

Brunden, K. R., et al., "pH-Dependent Binding of Synthetic Beta-Amyloid Peptides to Glycosaminoglycans", *J. Neurochem.*, 61, (1993),2147-2154.

Buckley, C. D., "Treatment of Rheumatoid Arthritis", *BMJ*, 315, (Jul. 26, 1997),236-238.

Businco, L., et al., "From Atopic Dermatitis to Asthma: The Risl Factors and Preventive Measures", *Pediatric Pulmonology, Supplement*, 16, (1997), 19-20.

Cairns, J. S., et al., "Chemokines and HIV-1 Second Receptors: The Therapeutic Connection", *Nature Medicine*, 4, (May 1998), 563-568.

Carron, C. P., et al., "A Peptidomimetic Antagonist of the Integrin alpha(sub v)beta(sub 3) Inhibits Leydig Cell Tumor Growth and the Development of Hypercalcemia of Malignancy", *Cancer Research*, 58, (May 1, 1998 ), 1930-1935.

Chakravarty, L., et al., "Lysine 58 and Histidine 66 at the C-terminal alpha-Helix of Monocyte Chemoattractant Protein-1 are Essential for Glycosaminoglycan Binding", *Journal of Biological Chemistry*, 273, (Nov. 6, 1988),29641-29647.

Chen, S., et al., "In Vivo Inhibition of CC and CX3C Chemokine-induced Leukocyte Infiltration and Attenuation of Glomerulonephritis in Wistar-Kyoto (WKY) Rats by vMIP-II", *J. Exp. Med.*, 188, 1998, 193-198.

Chung, C. W., et al., "The Three-Dimensional Solution Structure of RANTES", *Biochemistry*, 34, (1995),9307-9314.

Clark-Lewis, I., et al., "Platelet Factor 4 Binds to Interleukin 8 Receptors and Activates Neutrophils When its N Terminus is Modified with Glu-Leu-Arg", *Proceedings of the National Academy of Sciences, USA*, 90, (1993),3574-3577.

Clark-Lewis, I., et al., "Structural Requirements for Interleukin-8 Function Identified by Design of Analogs and CXC Chemokine Hybrids", *J. Biol. Chem.*, 269 (Jun. 10, 1994),16075-16801.

Clark-Lewis, I., et al., "Structure-Activity Relationships of Interleukin-8 Determined Using Chemically Synthesized Analogs", *Journal of Biological Chemistry*, 266(34A), (Dec. 5, 1991),23128-23134.

Clore, G. M., et al., "Comparison of the Solution Nuclear Magnetic Resonance and Crystal Structures of Interleukin-8", *J. Mol. Biol.*. 217 (1991),611-620.

Cocchi, F., et al., "Identification of RANTES, MIP-1(alpha), and MIP-1(beta) as the Major HIV-Suppressive Factors Produced by CD8(plus) T Cells", *Science*, 270, (Dec. 15, 1995),1811-1815.

Cocchi, F., et al., "The V3 Domain of the HIV-1 gp120 Envelope Glycoprotein is Critical for Chemokine-Mediated Blockade of Infection", *Nature Medicine*, 11, (Nov. 1996),1244-1247.

Damon, I., et al., "Broad Spectrum Chemokine Antagonistic Activity of a Human Poxvirus Chemokine Homolog", *Proc. Natl. Acad. Sci. USA*, 95, (May 1998),6403-6407.

Debie, J. J., et al., "Modulation of Airway Hyperresponsiveness and Eosinophilia by Selective Histamine and 5-HT Receptor Antagonists in a Mouse Model of Allergic Asthma", *British Journal of Pharmacology*, 124, (1998),857-864.

Donzella, G. A., et al., "AMD3100, A Small Molecule Inhibition of HIV-1 Entry via the CXCR4 Co-receptor", *Nature Medicine*, 4, (Jan. 1998), 72-77.

Doranz, B. J., et al., "A Small-Molecule Inhibitor Directed Against the Chemokine Receptor CXCR4 Prevents its Use as an HIV-1 Coreceptor", *J. Exp. Med.*, 186 (Oct. 20, 1997),1395-1400.

Drazen, J. M., et al., "Treatment of Chronic Stable Asthma with Drugs Active on the 5-Lipoxygenase Pathway", *Int. Arch. Allergy Immunol.*, 107, (1995),319-320.

Elson, C., et al., "Experimental Models of Inflammatory Bowel Disease", *Gastroenterology*, 109, (1995),pp. 1344-1367.

Fairbrother, W. J., et al., "The Solution Structure of Melanoma Growth Stimulating Activity", *Journal of Molecular Biology*, 242, (1994),252-270.

Fiocchi, C., "Inflammatory Bowel Disease: Etiology and Pathogenesis", *Gastroenterology*, 115, (1998),182-205.

Fox, D. J., "Design, Synthesis, and Preliminary Pharmacological Evaluation of N-Acyl-3-aminoglutarimides as Broad-Spectrum Chemokine Inhibitors in Vitro and Anti-inflammatory Agents in Vivo", *J. Med. Chem.*, 45 (2002),pp. 360-370.

Frecker, M., et al., "Immunological Associations in Familial and Non-Familial Alzheimer Patients and Their Families", *The Canadian Journal of NeurologicalSciences*, 21, (1994),pp. 112-119.

Gong, J. H., et al., "An Antagonist of Monocyte Chemoattractant Protein 1 (MCP-1) Inhibits Arthritis in the MRL-*lpr* Mouse Model", *J. Exp. Med.*, 186, (Jul. 7, 1997),131-137.

Gong, J.-H., et al., "Antagonists of Monocyte Chemoattractant Protein 1 Identified by Modification of Functionally Critical $NH_2$-terminal Residues", *J. Exp. Med.*, 181, (1995),631-640.

Gong, J H., et al., "RANTES and MCP-3 antagonists bind multiple chemokine receptors", *Journal of Biological Chemistry*, 271(18), (May 3, 1996),10521-10527.

Gosling, J., et al., "Molecular Uncoupling of C-C Chemokine Receptor 5- Induced Chemotaxis and Signal Transduction from HIV-1 Coreceptor Activity", *Proc. Natl. Acad. Sci. USA*, 94, (May 1997),5061-5066.

Grossman, J., et al., "Results of the First U.S. Double-Blind, Placebo-Controlled, Multicenter Clinical Study in Asthma with Pranlukast, a Novel Leukotriene Receptor Antagonist", *Journal of Asthma*, 34, (1997),321-328.

Hauser, S. L., "Therapeutic Strategies for Multiple Sclerosis", *J. Neurochem.*, 69, *Suppl.*, Abstract A,(1997),S219.

Hendeles, L., et al., "Zafirlukast for Chronic Asthma: Convenient and Generally Safe, But Is It Effective?", *The Annals of Pharmacology*, 31, (Sep. 1997), 1084-1086.

Hesselgesser, J., et al., "Identification and characterization of small molecule functional antagonists of the CCR1 chemokine receptor", *Journal of Biological Chemistry*, 273(25), (Jun. 19, 1998), 15687-15692.

Heveker, N., et al., "Dissociation of the Signalling and Antiviral Properties of SDF-1-Derived Small Peptides", *Current Biology*, 8, (1998), 369-376.

Hilliquin, P., et al., "Treatment of Rheumatoid Arthritis with Platelet Activating Factor Antagonist BN 50730", *J. Rheumatol.*, 22, (1995), 1651-1654.

Hoffman, G. S., et al., "Wegner Granulomatosis: An Analysis of 158 Patients", *Annals of Internal Medicine*, 116, (Mar. 15, 1992), 488-498.

Hogaboam, C. M., et al., "Monocyte Chemoattractant Protein-1 Synthesis by Murine Lung Fibroblasts Modulates $CD4^+$ T Cell Activation", *The Journal of Immunology*, 160, (1998), 606-4614.

Hogan, S. P., et al., "Cytokines as Targets for the Inhibition of Eosinophilic Inflammation", *Pharmacol. Ther.*, 74, (1997), 259-283.

Howard, O. M., et al., "Inhibition of in Vitro and in Vivo HIV Replication by a Distamycin Analogue That Interferes with Chemokine Receptor Function: A Candidate for Chemotherapeutic and Microbicidal Application", *J. Med. Chem.*, 41, (1998), 2184-2193.

Howard, O. M., et al., "Small Molecule Inhibitor of HIV-1 Cell Fusion Blocks Chemokine Receptor-Mediated Function", *Journal of Leukocyte Biology*, 64, (1998), 6-13.

Hunt, III, S. W., et al., "Chemokine Receptors as HIV Co-Receptors: Targets for Therapeutic Intervention in AIDS", *Annual Reports in Medicinal Chemistry*, 33, (1998), 263-272.

Ishikawa, J., et al., "Effect of YM934, a Novel Potassium-Channel Opener, in Various Experimental Asthma Models in Guinea-pigs", *J. Pharm. Pharmacol.*, 48, (1996), 1034-1040.

Israel, E., et al., "Effect of Treatment With Zileuton, a 5-Lipoxygenase Inhibitor, in Patients With Asthma", *JAMA*, 275, (Mar. 27, 1996), 931-936.

Ivacko, J., et al., "Hypoxic-lschemic Injury Induces Monocyte Chemoattractant Protein-1 Expression in Neonatal Rat Brain", *Journal of Cerebral Blood Flow and Metabolism*, 17, (1997), pp. 759-770.

Jameson, B. A., et al., "A Rationally Designed CD4 Analogue Inhibits Experimental Allergic Encephalomyelitis", *Letters to Nature*, 368, (Apr. 21, 1994), 744-746.

Jin, D., et al., "Complement 4 Locus II Gene Deletion and DQA1 0301 Gene: Genetic Risk Factors for IgA Nephropathy and Henoch-Schönlein Nephritis", *Nephron*, 73, (1996), 390-395.

Karpus, W., et al, "An Important Role for the Chemokine Macrophage Inflammatory Protein-1alpha in the Pathogenesis of the T Cell-Mediated Autoimmune Disease., Experimental Autoimmune Encephalomyelitis", *The Journal of Immunology*, (1995), 5003-5010.

Karpus, W. J., et al., "Monocyte Chemotactic Protein 1 Regulates Oral Tolerance Induction by Inhibition of T Helper Cell 1-related Cytokines", *Journal of Experimental Medicine*, 187, (1998), 733-741.

Katz, M. D., et al., "Octreotide, a New Somatostatin Analogue", *Clinical Pharmacy*, 8, (Apr. 1989), 255-273.

Kelloway, J. S., "Zafirlukast: The First Leukotriene-Receptor Antagonist Approved for the Treatment of Asthma", *The Annals of Pharmacology*, 31, (Sep. 1997), 1012-1021.

Kim, J. J., et al., "CD8 Positive T Cells Influence Antigen-Specific Immune Responses through the Expression of Chemokines", *Journal of Clinical Investigation*, 102, (1998), 1112-1124.

Klareskog, L., et al., "Immunopathogenesis and Immunotherapy in Rheumatoid Arthritis: an Area in Transition", *Journal of Internal Medicine*, 238, (1995), 191-206.

Kledel, T. N., et al., "A Broad-Spectrum Chemokine Antagonist Encoded by Kaposi's Sarcoma-Associated Herpesvirus", *Science*, 277, (Sep. 12, 1997), 1656-1659.

Korom, S., et al., "Blockade of Very Late Antigen-4 Integrin Binding to Fibronectin in Allograft Recipients", *Transplantation*, 65, (Mar. 27, 1998), 854-859.

Koyama, S., et al., "Human Lung Fibroblasts Release Chemokinetic Activity for Monocytes Constitutively", *Am. J. Physioll*, 275, (1998), L223-L230.

Kullberg, B. J., et al., "Cytokines as Therapy for Opportunistic Fungal Infections", *Res. Immunol.*, 149, (1998), 478-488.

Kunkel, S., et al., "The role of chemokines in inflammatory joint disease", *Journal of Leukocyte Biology*, 59 (1996), pp. 6-12.

Kuschert, et al., "Identification of a Glycosaminoglycan Binding Surface on Human Interleukin-8", *Biochemistry*, 37, (1998), 11193-11201.

Larkin, et al., "Mycophenolate Mofetil: A New Immunosuppressive for Occular Inflammatory Disease", *Abstract 339: IOVS*, 39, (1998), S215.

Laycock, K. A., et al., "Reproduction of Antiviral Effect in adn In Vivo Model of Human Cytomegalovirus Retinal Infection", *Graefe's Arch. Clin. Exp. Opthalmol.*, 236, (1998), 527-530.

Lecomte-Raclet, L., et al., "New Insights into the Negative Regulation of Hematopoiesis by Chemokine Platelet Factor 4 and Related Peptides", *Blood*, 91, (Apr. 15, 1998), 2772-2780.

Lee, B., et al., "Influence of the CCR2-V641 Polymorphism on Human Immunodeficiency Virus Type 1 Coreceptor Activity and on Chemokine Receptor Function of CCR2b, CCR3, CCR5, and CXCR4", *Journal of Virology*, 72, (1998), 7450-7458.

Leong, S. R., et al., "Complete mutagenesis of the extracellular domain of interleukin-8 (IL-8) type A receptor identifies charged residues mediating IL-8 binding and signal transduction", *Journal of Biological Chemistry*, 269(30), (Jul. 29, 1994), 19343-19348.

Loetscher, P., et al., "N-terminal peptides of stromal cell-derived factor-1 with CXC chemokine receptor 4 agonist and antagonist activities", *Journal of Biological Chemistry*, 273(35), (Aug. 28, 1988), 22279-22283.

Lowe, P. M., et al., "The Endothelium in Psoriasis", *British Journal of Dermatology*, 132, (1995), 497-505.

Lu, B. B., et al., "Abnormalities in Monocyte Recruitment and Cytokine Expression in Monocyte Chemoattractant Protein 1-deficient Mice", *Journal of Experimental Medicine*, 187, (1998), 601-608.

Lucchinetti, C., et al., "Risk factors for developing multiple sclerosis after childhood optic neuritis", *The American Academy of Neurology*, 49, (1997), pp. 1413-1418.

Lukacs, N., et al., "Airway Hyperreactivity is Associated with Specific Leukocyte Subset Infiltration in a Mouse Model of Allergic Airway Inflammation", *Pathobiology*, 64, (1996), 308-313.

Lukacs, N. W., et al., "C-C Chemokines Differentially Alter Interleukin-4 Production from Lymphocytes", *American Journal of Pathology*, 150, (1997), 1861-1868.

Lusti-Narasimhan, M., et al., "A Molecular Switch of Chemokine Receptor Selectivity", *J. Biol. Chem.*, 271, (Feb. 9, 1996), 3148-3153.

Maccarana, et al., "Mode of Interaction Between Platelet Factor 4 and Heparin", *Glycobiology*, 3, (1993), 271-277.

Malkowski, M. G., et al., "The crystal structure of recombinant human neutrophil-activating peptide-2 (M6L) at 1.9-Å resolution", *Journal of Biological Chemistry*, 270(13), (Mar. 31, 1995), 7077-7087.

Marone, G., "Asthma: Recent Advances", *Immunolopy Today*, 19, (1998), 5-9.

Marone, M., et al., "Influence of body composition on the bone mass of post menopausal women", *Sao Paulo Medical Journal*, 115(6), (1997), pp. 1580-1588.

Marra, F., et al., "Increased Expression of Monocyte Chemotactic Protein-1 during Active Hepatic Fibrogenesis", *American Journal of Pathology*, 152, (1998), 423-430.

Maurer, A. M., et al., "Chemokines and the Regulation of Hematopoesis", *C.R. Seances Soc. Biol. Fil.*, 192, Translated abtract,(1998), 917-923.

McFadden, G., et al., "Commentary: New Strategies for Chemokine Induction and Modulation; You Take the High Road and I'll Take the Low Road", *Biochemical Pharmacology*, 54, (1997), 1271-1280.

McGeer, P., et al., "The inflammatory response system of brain: implications for theraapy of Alzheimer and other neurodegenerative diseases", *Brain Research Reviews*, 21, (1995), 195-218.

Mehlhop, P., et al., "Allergen-induced Bronchial Hyperreactivity and Eosinophilic Inflammation Occur in the Absence of IgE in a Mouse Model of Asthma", *Proceedings of the National Academy of Sciences USA*, 94, (1997), 1344-1349.

Mekouar, K., et al., "Styrylquinoline Derivatives: A New Class of Potent HIV-1 lntegrase Inhibitors That Block HIV-1 Replication in CEM Cells", *J. Med. Chem.*, 41, (1998), 2846-2857.

Meltzer, E. O., "Pharmacological Treatment Options for Allergic Rhinitis and Asthma", *Clinical and Experimental Allergy*, 28, (1998), 27-36.

Mikayama, T., et al., "Molecular Cloning and Functional Expression of a cDNA Encoding Glycosylation-inhibiting Factor", *Proc. Natl. Acad. Sci. USA*, 90, (Nov. 1993), 10056-10060.

Miller, E. J., et al., "A Synthetic Peptide which Specifically Inhibits Heat-Treated Interleukin-8 Binding and Chemotaxis for Neutrophils", *Agents Actions*, 40, (1993), 200-208.

Molling, K., "Naked DNA for Vaccine or Therapy", *J. Mol. Med.*, 75, (1997), 242-246.

Monteclaro, F. S., et al., "Role of the Amino Terminus in Ligand Binding and Signal Transduction of the Human Monocyte Chemoattractant Protein-1 Receptor", *Circulation*, 92, (Oct. 15, 1995), 1-160.

Moser, B., et al., "Interleukin-8 Antagonists Generated by N-Terminal Modification", *The Journal of Biological Chemistry*, 268(10), (Apr. 5, 1993), 7125-7128.

Murakami, T., et al., "A Small Molecule CXCR4 Inhibitor that Blocks T Cell Line-tropic HIV-1 Infection", *J. Exp. Med.*, 186, (Oct. 20, 1997),1389-1393.

Myers, L. K., et al., "Collagen-Induced Arthritis, an Animal Model of Autoimmunity", *Life Sciences*, 61, (1997), 1861-1878.

Nagamatsu, A., et al., "Hydrolysis of lysine peptides in plasmin", *Chem. Pharm. Bull.*, 22(11), (1974),2680-2684.

Naldi, L., et al., "Dietary factors and the risk of psoriasis. Results of an Italian case-control study", *British Journal of Dermatology*, 134, (1996),pp. 101-106.

Noguchi, M., et al., "Isolation and identification of acidic oligopeptides occurring in a flavor potentiating fraction from a fish protein hydrolysate", *J. Agric. Food Chem.*, vol. 23, No. 1,(1975),pp. 49-53.

O'Brien, W. A., et al., "Anti-Human Immunodeficiency Virus Type 1 Activity of an Oligocationic Compound Mediated via gp120 V3 Interactions", *Journal of Virology*, 70, (May 1996),2825-2831.

O'Brien, A. D., et al., "Chemotaxis of Alveolar Macrophages in Response to Signals Derived from Alveolar Epithelial Cells", *J. Lab. Clin. Med.*, 131, (1998),417-424.

O'Hehir, R. E., et al., "Regulation of Cytokine and Chemokine Transcription in a Human TH2 Type T-cell Clone During the Induction Phase of Anergy", *Clinical and Experimental Allergy*, 26, (1996),20-27.

Ono, K., et al., "Prevention of Myocardial Reperfusion Injury in Rats by an Antibody against Monocyte Chemotactic and Activating Factor/Monocyte Chemoattractant Protein-1", *Laboratory Investigation*, 79, (1999),pp. 195-203.

Panettieri, R. A., et al., "Effects of LTD4 on Human Airway Smooth Muscle Cell Proliferation, Matrix Expression, and Contraction In Vitro: Differential Sensitivity to Cysteinyl Leukotriene Receptors Antagonists", *American Journal of Respiratory Cell and Molecular Biology*, 19, (1998),453-461.

Paul, W. M., *Fundamental Immunology, Fourth Edition*, Lippincott-Raven Publ., Philadelphia,(1999),184-185.

Paul, W. E., "Fundamental Immunology", *3rd Edition*, (1993),822-826.

Pease, J. E., et al., "Microbial Corruption of the Chemokine System: An Expanding Paradigm", *Seminars in Immunology*, 10, (1998),169-178.

Pease, J. E., et al., "The N-terminal extracellular segments of the chemokine receptors CCR1 and CCR3 are determinants for MIP-1α and eotaxin binding, respectively, but a second domain is essential for efficient receptor activation", *Journal of Biological Chemistry*, 273(32), (Aug. 7, 1998),19972-19976.

Plater-Zyberk C., et al., "A Chemokine Receptor Antagonist Reduces the Incidence of Collagen Induced Arthritis", Abstract No. 399 ; *Arthritis & Rheumatism*, 41, (1998), p. S99.

Plater-Zyberk, C., et al., "Effect of a CC Chemokine Receptor Antagonist on Collagen Induced Arthritis in DBA/1 Mice", *Immunology Letters*, 57, (1997), 117-120.

Porschke, D., et al., "The conformation of signle stranded oliogonucleotides and of oligonucleotide-olgopeptide complexes from their rotation relaxation in the nanosecond time range", *J. Biomol. Struct. Dyn*, vol. 2, No. 6,(1985),pp. 1173-1184.

Postlethwaite, A. E., "Identification of a Chemotactic Epitope in Human Transforming Growth Factor- Beta1 Spanning Amino Acid Residues 368-374", *Journal of Cellular Physiology*, 164, (1995), 587-592.

Premack, B. A., et al., "Chemokine Receptors: Gateways to Inflammation and Infection", *Nature Medicine*, 2, (Nov. 1996), 1174-1178.

Proost, P., et al., "Amino-terminal truncation of chemokines by CD26/dipeptidyl-peptidase IV. Conversion of RANTES into a potent inhibitor of monocyte chemotaxis and HIV-1-infection", *Journal of Biological Chemistry*, 273(13), (Mar. 27, 1998), 7222-7227.

Reiss, T. F., et al., "Effects of Montelukast (MK-0476), a New Potent Cysteinyl Leukotriene ($LTD_4$) Receptor Antagonist, in Patients with Chronic Asthma", *J. Allergy Clin. Immunol.*, 98, (Sep. 1996),528-534.

Rewers, M., et al., "Newborn screening for HLA markers associated with IDDM: Diabetes Autoimmunity Study in the Young (DAISY)", *Diabetologia*, 39, (1996), 807-812.

Roberts, D. J., "Towards the Optimal Antihistamine: Studies with Ebastine", *Inflammation Research*, 47, (1998),S36-S37.

Sadek, M. I., et al., "Chemokines Induced by Infection of Mononuclear Phagocytes with Mycobacteria and Present in Lung Aveoli During Active Pulmonary Tuberculosis", *American Journal of Respiratory Cell and Molecular Biology*, 19, (1998),513-521.

Sanders, V. J., et al., "Chemokines and Receptors in HIV Encephalitis", *AIDS*, 12, (1998),1021-1026.

Sato, A., et al., "A Simple and Rapid Method for Preliminary Evaluation of In Vivo Efficacy of Anti-HIV Compounds in Mice", *Antiviral Research*, 27, (1995),151-163.

Schols, D., et al., "Inhibition of T-tropic HIV Strains by Selective Antagonization of the Chemokine Receptor CXCR4", *J. Exp. Med.*, 186, (Oct. 20, 1997), 1383-1388.

Schultz-Cherry, S., et al., "Regulation of transforming growth factor-β activation by discrete sequences of thrombospondin 1", *The Journal of Biological Chemistry*, 270(13), (Mar. 31, 1995),7304-7310.

Schultz-Cherry, S., et al., "The Type 1 Repeats of Thrombospondin 1 Activate Latent Transforming Growth Factor-β", *The Journal of Biological Chemistry*, 269(43), (Oct. 28, 1994),26783-26788.

Schultz-Cherry, S., et al., "Thrombospondin Causes Activation of Latent Transforming Growth Factor-Beta Secreted by Endothelial Cells by a Novel Mechanism", *The Journal of Cell Biology*, 122, (Aug. 1993),923-932.

Sekiguchi, K., et al., "Binding of Fibronectin and Its Proteolytic Fragments to Glycosaminoglycans", *J. Biol. Chem.*, 258, (1983),14359-14365.

Simmons, G., et al., "Potent Inhibition of HIV-1 Infectivity in Macrophages and Lymphocytes by a Novel CCR5 Antagonist", *Science*, 276, (Apr. 11, 1997),276-279.

Skelton, N. J., et al., "Proton NMR Assignments and Solution Conformation of RANTES, a Chemokine of the C-C Type", *Biochemistry*, 34, (1995),5329-5342.

Smith, L. J., et al., "Inhibition of Leukotriene $D_4$-Induced Bronchoconstriction in Subjects With Asthma: A Concentration-Effect Study of ICI 204,219", *Clin. Pharmacol, Ther.*, 54, (1993),430-436.

Sneller, M. C., et al., "An Analysis of Forty-Two Wegener's Granulomatosis Patients Treated with Methotrexate and Prednisone", *Arthritis and Rheumatism*, 38, (May 1995),608-613.

Sozzani, S., et al., "Stimulating Properties of 5-Oxo-Eicosansoids for Human Monocytes", *The Journal of Immunology*, 151, (1996),4664-4671.

Spector, S. L., et al., "Effects of 6 Weeks of Therapy with Oral Doses of ICI 204,219, a Leukotriene $D_4$ Receptor Antagonist, in Subjects with Bronchial Asthma", *Am. J. Respir. Crit. Care Med.*, 150, (1994),618-623.

Spector, S. L., "Leukotriene Activity Modulation in Asthma", *Drugs*, 54, (Sep. 1997),369-384.

Spence, J., "Advances in Atherosclerosis", *Bailliere's Clinical Neurology*, 4(2), (1995), 191-205.

Steitz, S. A., et al., "Mapping of MCP-1 Functional Domains by Peptide Analysis and Site-Directed Mutagenesis", *FEBS Letters*, 430, (1998),158-164.

Struyf, S., et al., "Cutting Edge: Enhanced Anti-HIV-1 Activity and Altered Chemotactic Potency of NH2-Terminally Processed Macrophage-Derived Chemokine (MDC) Imply an Additional MDC Receptor", *The Journal of Immunology*, 161, (1998), 2672-2675.

Suda, T., et al., "Modulation of Osteoclast Differentiation by Local Factors", *Bone*, 17(2), (1995), 87S-91S.

Suissa, S., et al., "Effectiveness of the Leukotriene Receptor Antagonist Zafirlukast for Mild-to-Moderate Asthma", *Ann. Intern. Med.*, 126, (1997),177-183.

Szabo, M. C., et al., "Chemokine class differences in binding to the Duffy antigen-erythrocyte chemokine receptor", *The Journal of Biological Chemistry*, 270(43), (Oct. 27, 1995),25348-25351.

Tamura, G., et al., "Effect of a Potent Platelet-Activating Factor Antagonist, WEB-2086, on Asthma", *In: Platelet-Activating Factor and Related Lipid Mediators*, 2, Nigam, et al., (eds.), Plenum Press, New York,(1996),371-380.

Taylor, I. K., et al., "The Mechanism of Action of Corticosteroids in Asthma", *Respiratory Medicine*, 87, (1993),261-277.

Terkeltaub, R., et al., "The Murine Homolog of the Interleukin-8 Receptor CXCR-2 is Essential for the Occurrence of Neutrophilic Inflammation in the Air Pouch Model of Acute Urate Crystal-induced Gouty Synovitis", *Arthritis and Rheumatism*, 41, (1998),900-909.

Thompson,. K., et al., "Design and evaluation of small peptides mapping the exposed surface of IL-8", *Int. J. Peptide Protein Res*, vol. 47,,(1996), 214-218.

Tian, S. S., et al., "A Small, Nonpeptidyl Mimic of Granulocyte—Colony-Stimulating Factor", *Science*, 281, (Jul. 10, 1998),257-259.

Tomita, H., et al., "Inhibition of NO Synthesis Induces Inflammatory Changes and Monocyte Chemoattractant Protein-1 Expression in Rat Hearts and Vessels", *Arterioscler. Thromb. Vasc. Biol.*, 18, (1998),1456-1464.

Valente, A. J., et al., "Characterization of Monocyte Chemotactic Protein-1 Binding to Human Monocytes", *Biochemical and Biophysical Research Communications*, 176, (Apr. 15, 1991),309-314.

Van Coillie, E., et al., "Functional Comparison of Two Human Monocyte Chemotactic Protein-2 Isoforms, Role of the Amino-Terminal Pyroglutamic Acid and Processing by CD26/Dipeptidyl Peptidase IV", *Biochemistry*, 37, (1998),12672-12680.

Verma, M., et al., "Chemokines in acute anterior uveitis", *Current Eye Research*, (1997), 1202-1208.

Voet, et al., *In: Biochemistry*, John Wiley & Sons, Inc.,(1990), pp. 126-128, 228-234.

Waltenberger, J., "Modulation of Growth Factor Action—Implications for the Treatment of Cardiovascular Diseases", *Circulation*, 96, (1997), 4083-4094.

Wang, J. M., et al., "Chemokines, Receptors and Their Role in Cardiovascular Pathology", *Int. J. Clin. Lab. Res.*, 28, (1998),83-90.

Wang, N., et al., "Induction of Interleukin-8 in Foam Cells Induced by Acetylated LDL", *Circulation*, 92, (Oct. 15, 1995),1-160.

Watanabe, T., et al., "Atherosclerosis and inflammation Mononuclear cell recruitment and adhesion molecules with reference to the implication of ICAM-1/LFA pathway in atherogenesis", *International Journal of Cardiology*, 66, (1998), S45-S53.

Weber, M., et al., "Deletion of the NH2-Terminal Residue Converts Monocyte Chemotactic Protein 1 from an Activator of Basophil Mediator Release to an Eosinophil Chemoattractant", *J. Exp. Med.*, 183, (Feb. 1996),681-685.

Wells, T. N., et al., "The Molecular Basis of Selectivity Between CC and CXC Chemokines: The Possibility of Chemokine Antagonists as Anti-Inflammatory Agents", *Annals of New York Academy of Sciences*, 796, (Oct. 31, 1996), 245-257.

Wells, E A., "The Molecular Basis of the Chemokine/Chemokine Receptor Interaction—Scope for Design of Chemokine Antagonists", *Methods: A Companion to Methods in Enzymology*, 10, (1996), 126-134.

White, J. R., et al., "Identification of a Potent, Selective Non-peptide CXCR2 Antagonist That Inhibits Interleukin-8-induced Neutrophil Migration", *Journal of Biological Chemistry*, 273(17), (Apr. 24, 1998), 10095-10098.

Wooley, P. H., et al., "Influence of a Recombinant Human Soluble Tumor Necrosis Factor Receptor FC Fusion Protein on Type II Collagen-Induced Arthritis in Mice", *The Journal of Immunology*, 151, (Dec. 1, 1993), 6602-6607.

Yahi, N., et al., "SPC3, a Synthetic Peptide Derived from the V3 Domain of Human Immunodeficiency Virus Type 1 (HIV-1) Gp120, Inhibits HIV-1 Entry into CD4(plus) and CD4(minus) Cells by Two Distinct Mechanisms", *Natl. Acad. Sci. USA*, 92, (May 1995), 4867-4871.

Yang, Y., et al., "Antigen-Induced Eosinophilic Lung Inflammation Develops in Mice Deficient in Chemokine Eotaxin", *Blood*, 92, (1998), 3912-3923.

Yang, A. G., et al., "Phenotypic Knockout of HIV Type 1 Chemokine Coreceptor CCR-5 by Intrakines as Potential Therapeutic Approach for HIV-1 Infection", *Proc. Natl. Acad. Sci. USA*, 94, (Oct. 1997), 11567-11572.

Zagorski, J., et al., "Inhibition of Acute Peritoneal Inflammation in Rats by a Cytokine-induced Neutrophil Chemoattractant Receptor Antagonist", *The Journal of Immunology*, 159, (1997), 1059-1062.

Zeyneloglu, H. B., et al., "The Effect of Monocyte Chemotactic Protein 1 in Intraperitoneal Adhesion Formation in a Mouse Model", *Am. J. Obstet. Gynecol.*, 179, (1998), 438-443.

Zhang, Y., et al., "A Dominant Negative Inhibitor Indicates that Monocyte Chemoattractant Protein 1 Functions as a Dimer", *Mol. and Cell Biol.*, 15, (Sep. 1995), 4851-4855.

Zhang, Y., et al., "Structure/Activity Analysis of Human Monocyte Chemoattractant Protein-1 (MCP-1) by Mutagenesis", *J. Biol. Chem.*, 269, (1994),15918-15924.

Zou, Y-R., et al., "Function of the Chemokine Receptor CXCR4 in Haematopoiesis and in Cerebellar Development", *Nature*, 393, (1998),595-598.

Zou, L. P., et al., "Treatment with P2 Protein Peptide 57-81 by Nasal Route is Effective in Lewis Rat Experimental Autoimmune Neuritis", *Journal of Neuroimmunology*, 85, (1998),137-145.

"U.S. Appl. No. 08/927,939 Final Office Action mailed Oct. 12, 1999", 18 pgs.

"U.S. Appl. No. 08/927,939 Final Office Action mailed Sep. 29, 2003", 10 pgs.

"U.S. Appl. No. 08/927,939 Non-Final Office Action mailed Mar. 5, 2001", 12 pgs.

"U.S. Appl. No. 08/927,939 Non-Final Office Action mailed Apr. 7, 1999", 21 pgs.

"U.S. Appl. No. 08/927,939 Notice of Allowance mailed Aug. 30, 2005", 7 pgs.

"U.S. Appl. No. 08/927,939 Notice of Allowance mailed Sep. 3, 2004", 6 pgs.

"U.S. Appl. No. 08/927,939 Response to Final Office Action filed Jan. 29, 2004", 8 pgs.

"U.S. Appl. No. 08/927,939 Response to Final Office Action filed May 12, 2000", 12 pgs.

"U.S. Appl. No. 08/927,939 Response to Non-Final Office Action filed Oct. 7, 1999", 13 pgs.

"U.S. Appl. No. 08/927,939 Response to Non-Final Office Action filed Sep. 5, 2001", 5 pgs.

"U.S. Appl. No. 08/927,939 Supplemental Amendment filed Apr. 29, 2004", 3 pgs.

"U.S. Appl. No. 09/150,813 Advisory Action mailed Jan. 28, 2002", 4 pgs.

"U.S. Appl. No. 09/150,813 Advisory Action mailed Mar. 28, 2002", 3 pgs.

"U.S. Appl. No. 09/150,813 Final Office Action mailed Jun. 1, 2004", 8 pgs.

"U.S. Appl. No. 09/150,813 Final Office Action mailed Aug. 10, 2001", 13 pgs.

"U.S. Appl. No. 09/150,813 Non Final Office Action mailed Feb. 23, 2000", 24 pgs.

"U.S. Appl. No. 09/150,813 Non Final Office Action mailed Sep. 10, 2002", 11 pgs.

"U.S. Appl. No. 09/150,813 Non Final Office Action mailed Sep. 12, 2002", 13 pgs.

"U.S. Appl. No. 09/150,813 Non Final Office Action mailed Nov. 15, 2004", 5 pgs.

"U.S. Appl. No. 09/150,813 Non Final Office Action mailed Nov. 29, 2000", 13 pgs.

"U.S. Appl. No. 09/150,813 Non Final Office Action mailed Dec. 7, 2003", 10 pgs.

"U.S. Appl. No. 09/150,813 Notice of Allowance mailed Oct. 31, 2005", 7 pgs.

"U.S. Appl. No. 09/150,813 Response filed Feb. 11, 2002 to Advisory Action mailed Jan. 28, 2002", 7 pgs.

"U.S. Appl. No. 09/150,813 Response filed Feb. 15, 2005 to Non Final Office Action mailed Nov. 15, 2004", 7 pgs.

"U.S. Appl. No. 09/150,813 Response filed Mar. 18, 2004 to Non Final Office Action mailed Dec. 7, 2003", 11 pgs.

"U.S. Appl. No. 09/150,813 Response filed Apr. 11, 2002 to Advisory Action mailed Mar. 28, 2002", 5 pgs.

"U.S. Appl. No. 09/150,813 Response filed May 29, 2001 to Non Final Office Action mailed Nov. 29, 2000", 13 pgs.

"U.S. Appl. No. 09/150,813 Response filed Aug. 2, 2004 to Final Office Action mailed Jun. 1, 2004", 12 pgs.

"U.S. Appl. No. 09/150,813 Response filed Aug. 23, 2000 to Non Final Office Action mailed Feb. 23, 2000", 17 pgs.

"U.S. Appl. No. 09/150,813 Response filed Nov. 9, 2001 to Final Office Action mailed Aug. 10, 2001", 6 pgs.

"U.S. Appl. No. 09/150,813, Response filed Dec. 17, 1999 to Restriction Requirement Dec. 17, 1999", 2 pgs.

"U.S. Appl. No. 09/150,813, Response filed Aug. 31, 1999 to Restriction Requirement mailed Mar. 3, 1999", 7 pgs.

"U.S. Appl. No. 09/150,813, Restriction Requirement mailed Oct. 18, 1999", 4 pgs.

"U.S. Appl. No. 09/150,813, Restriction Requirement mailed Mar. 3, 1999", 8 pgs.

"U.S. Appl. No. 09/452,406 Final Office Action mailed Oct. 6, 2004", 41 pgs.

"U.S. Appl. No. 09/452,406 Final Office Action mailed Dec. 15, 2005", 12 pgs.

"U.S. Appl. No. 09/452,406 Non-Final Office Action mailed Jan. 15, 2003", 11 pgs.

"U.S. Appl. No. 09/452,406 Non-Final Office Action mailed Jun. 6, 2005", 17 pgs.

"U.S. Appl. No. 09/452,406 Notice of Allowance mailed Mar. 20, 2006", 6 pgs.

"U.S. Appl. No. 09/452,406 Response to Final Office Action filed Dec. 29, 2005", 8 pgs.

"U.S. Appl. No. 09/452,406 Response to Final Office Action filed Mar. 7, 2005", 22 pgs.

"U.S. Appl. No. 09/452,406 Response to Non-Final Office Action filed May 14, 2003", 20 pgs.

"U.S. Appl. No. 09/452,406 Response to Non-Final Office Action filed Sep. 6, 2005", 18 pgs.

Atuegbu, Andy, et al., "Combinatorial Modification of Natural Products: Preparation of Unencoded and Encoded Libraries of Rauwolfia Alkaloids", *Bioorganic & Medicinal Chemistry 4*(7), (1996), 1097-1106.

Bavadekar, Supriya A., et al., "Tethered Yohimbine Analogs as Selective Human a2c-Adrenergic Receptor Ligands", *Journal of Pharmacology and Experimental Therapeutics 319*(2), (2006), 739-748.

Baxter, Ellen W., et al., "Formal Total Synthesis of Deserpidine Demonstrating a Versatile Amino-Claisen Rearrangement/Wenkert Cyclization Strategy for the Preparation of Functionalized Yohimbine Ring Systems", *J. Am. Chem. Soc. 112*, (1990), 7682-7692.

Bhat, U. G., et al., "A Structure-Function Relationship Among Reserpine and Yohimbine Analogues in Their Ability to Increase Expression of mdr1 and P-Glycoprotein in a Human Colon Carcinoma Cell Line", *American Society for Pharmacology and Experimental Therapeutics 48*, (1995), 682-689.

Chanh, Pham Huu, et al., "Cardiovascular Effects of Some Acylated Derivatives of Yohimbo-hydrazide", *Drugs Exptl. Clin. Res. 4*(2), (1978), 25-30.

Chanh, Pham Huu, et al., "Effect of the Hydrazide Function on the Cardiovascular Activities of Yohimbine", *Agressologie 14*(1), (1973), 31-37.

Chanh, Pham Huu, et al., "Study of the Action of the N-Methyl-N'-yohimbohydrazide on General Metabolism and Respiration and on Systemic Hemodynamics", *Drug Res. 23*(8), (1973), 1014-1016.

Dossin, Olivier, et al., "Characterization of a new radioiodinated probe for the a2c adrenoreceptor in the mouse brain", *Neurochemistry International 36*, (2000), 7-18.

Edwards, O. E., et al., "Atisine: The Functional Groups", *Canadian Journal of Chemistry 33*, (1955), 448-451.

Huebner, Charles F., et al., "Rauwolfia Alkaloids. XIV. Derivatives of Yohimbe Alkaloids", *Journal of the American Chemical Society 77*, (1955), 469-72.

Kaga, "Anti polypeptide monoclonal antibody diagnose treat auto immune diease ulcer colitis", This is really JP 7-67689.

Lalchandani, Shilpa G., et al., "Yohimbine Dimers Exhibiting Selectivity for the Human a2c-Adrenoreceptor Subtype", *The Journal of Pharmacology and Experimental Therapeutics 303*(3), (2002), 979-984.

Lanier, Stephen M., et al., "Photoaffinity labeling of the porcine brain a2-adrenergic receptor using a radioiodinated arylazide derivative of rauwolscine: Identification of the hormone-binding subunit", *Proc. Natl. Acad. Sci. USA 83*, (Dec. 1986), 9358-9362.

Lanier, Stephen M., et al., "Synthesis and Characterization of a High Affinity Radioiodinated Probe for the a2-Adrenergic Receptor", *Molecular Pharmacology 29*, (1985), 219-227.

Mustafa, Suni M., et al., "Synthesis and biological studies of yohimbine derivatives on human a2c-adrenergic receptors (abstract)", *Bioorganic & Medicinal Chemistry Letters 15*(11), (Jun. 2, 2005), 2758-2760.

Repaske, Mary G., et al., "Purification of the a2-Adrenergic Receptor from Porcine Brain Using a Yohimbine-Agarose Affinity Matrix", *Journal of Biological Chemistry 262*(25), (Sep. 5, 1987), 12381-12386.

Saint-Ruf, Germain, et al., "Sur quelques derives du yohimbohydrazide d'interet biologique (with English-language abstract)", *Chime therapeutique 6*, (Nov.-Dec. 1973), 672-675, Abstract only.

Szantay, Csaba, et al., "Ueber eine einfache Synthese der Yohimbinalkaloide (with English-language abstract)", *Chem. Ber. 109*, (1976), 1737-1748, Abstract only.

Toke, Laszlo, et al., "Die Totalsynthese des (+)-Yohimbins und (−)-B-Yohimbins1) (with English-language abstract)", *Chem. Ber. 102*, (1969), 3248-3259, Abstract only.

Toke, Laszlo, et al., "Synthesis of Yohimbines. I. Total Synthesis of Alloyohimbine, a-Yohimbine, and Their Epimers. Revised Structure of Natural Alloyohimbine", *J. Org. Chem. 38*(14), (1973), 2496-2500.

Toke, Laszlo, et al., "Synthesis of Yohimbines. II. An Alternative Route to Alloyohimbine Alkaloids", *J. Org. Chem. 38*(14), (1973), 2501-2509.

Zheng, Weiping, et al., "Yohimbine Dimers Exhibiting Binding Selectivities for Human a2a- versus a2b Adrenergic Receptors", *Bioorganic & Medicinal Chemistry Letters 10*, (2000), 627-630.

* cited by examiner

TOP COMPARTMENT

LOWER COMPARTMENT

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 12

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 13

PEPTIDE-3

LFL peptide 3(1-12)[MCP-1]: Residues 50-61 of mature hMCP-1
E-I-C-A-D-P-K-Q-K-W-V-Q (SEQ. ID. NO.: 1)
L amino acids LFL peptide 3(3-12)[MCPI] Residues 52-61 of mature hMCP-1
C-A-D-P-K-Q-K-W-V-Q (SEQ. ID. NO.: 7)
L amino acids LFL peptide 3(1-6)[MCP1]: Residues 50-55 of mature hMCP-1
E-I-C-A-D-P (SEQ. ID. NO.: 8)
L amino acids LFL peptide 3(7-12)[MCP1]: Residues 56-61 of mature hMCP-1
K-Q-K-W-V-Q (SEQ. ID. NO.: 9)
L amino acids LFL Leu$_4$peptide3(1-12)[MCP-1]
E-I-C-L-D-P-K-Q-K-W-V-Q (SEQ. ID. NO.: 10)
L amino acids LFL Ser$_7$peptide3(1-12)[MCP-1]
E-I-C-A-D-P-S-Q-K-W-V-Q (SEQ. ID. NO.: 11)
L amino acids LFL Ile$_{11}$peptide3(1-12)[MCP-1]
E-I-C-A-D-P-K-Q-K-W-I-Q (SEQ. ID. NO.: 13)
L amino acids LFL Leu$_4$Ile$_{11}$peptide3(1-12)[MCP-1]
E-I-C-L-D-P-K-Q-K-W-I-Q (SEQ. ID. NO.: 14)
L amino acids CFL Cys$_0$Leu$_4$Ile$_{11}$Cys$_{13}$peptide3(1-12)[MCP-1]
C-E-I-C-L-D-P-K-Q-K-W-I-Q-C (SEQ. ID. NO.: 106)
L amino acids LRD Leu$_4$Ile$_{11}$ peptide 3(1-12)[MCP-1]
q-i-w-k-q-k-p-d-l-c-i-e
D amino acids

FIG. 14A

CRD Cys₀Leu₄Ile₁₁Cys₁₃peptide 3(1-12)[MCP-1]
c-q-i-w-k-q-k-p-d-l-c-i-e-c
D amino acids LFL Ser₇Glu₈Glu₉peptide3(1-12)[MCP1]:Residues 50-61 of mature hMIP1α
E-I-C-A-D-P-S-E-E-W-V-Q (SEQ. ID. NO.: 12)
L amino acids LFL peptide3(10-12)[MCP-1]
W-V-Q
L amino acids CFL Cys₀Cys₄ peptide3(10-12)[MCP-1]
C-W-V-Q-C (SEQ. ID. NO.: 107)
L amino acids LRD peptide3(10-12)[MCP-1]
q-v-w
D amino acids LFL peptide3(7-9)[MCP-1]
K-Q-K
L amino acids LRD peptide3(7-9)[MCP-1]
k-q-k
D amino acids LFL peptide 3(7-9)[MIP1α](MIP1α specific inhibitor)
S-E-E
L amino acids LRD peptide3(7-9)[MIP1α] (MIP1α specific inhibitor)
e-e-s
D amino acids LFL peptide3(7-9)[IL-8](IL-8 specific inhibitor)
K-E-N
L amino acids LRD peptide3(7-9)[IL-8](IL-8 specific inhibitor)
n-e-k
D amino acids

FIG. 14B

LFL peptide3(7-9)[SDF-1α](SDF-1α specific inhibitor)
K-L-K
L amino acids

LRD peptide3(7-9)[SDF1α] (SDF-1α specific inhibitor)
k-l-k
D amino acids

LFL Leu$_4$Ile$_{11}$Cys$_{13}$ peptide3(3-12)[MCP-1]
L-D-P-K-Q-K-W-I-Q-C (SEQ. ID. NO.: 84)
L amino acids CRD Leu$_4$Ile$_{11}$Cys$_{13}$ peptide3(3-12)[MCP-1]
c-q-i-w-k-q-k-p-d-l-c
D amino acids $^3$H-Ala CRD-Leu$_4$Ile$_{11}$ Cys$_{13}$ peptide 3(3-12)[MCP-1](D-Ala attached to Asp residue of CRD-Leu$_4$Ile$_{11}$Cys$_{13}$ peptide 3(3-12)[MCP-1])

$^3$H-L-Leu LRD Cys$_{13}$ peptide3(3-12)[MCP-1]
c-q-i-w-k-q-k-p-d-L-c
D and L amino acids LFL SES
S-E-S
L amino acids LFL KKK
K-K-K
L amino acids LFL Cys$_4$ peptide3(10-12)[MCP-1]
W-V-Q-C (SEQ. ID. NO.: 85)
L amino acids LRD Cys$_4$ peptide3(10-12)[MCP-1]
c-q-v-w
D amino acids LFL Ile$_{11}$Cys$_{13}$peptide3(10-12)[MCP-1]
W-I-Q-C (SEQ. ID. NO.: 86)
L amino acids

FIG. 14C

LRD Cys₁₃Ile₁₁peptide3(10-12)[MCP-1]
cqiw
D amino acids

LRD peptide3(7-12)[MCP-1]
q-v-w-k-q-k
D amino acids

CFL Cys₀Cys₁₃peptide3(7-12)[MCP-1]
C-K-Q-K-W-V-Q-C (SEQ. ID. NO.: 108)
L amino acids CRD Cys₀Cys₁₃peptide3(7-12)[MCP-1]
c-q-v-w-k-q-k-c
D amino acids LFL peptide3(10-12)[RANTES]
WVR
L amino acids LRD peptide3(10-12)[RANTES]
rvw
D amino acids LFL peptide3(10-12)[SDF-1]
W-I-Q
L amino acids

Peptide 2

LFL peptide 2(1-15)[MCP-1]: Residues 28-42 of hMCP-1
S-Y-R-R-I-T-S-S-K-C-P-K-E-A-V (SEQ. ID. NO.: 3)
L amino acids CFL Cys₀Cys₁₆peptide 2(1-15)[MCP-1]: Residues 28-42 of hMCP-1
C-S-Y-R-R-I-T-S-S-K-C-P-K-E-A-V-C (SEQ. ID. NO.: 109)
L amino acids LRD peptide 2(1-15)[MCP-1]: Residues 28-42 of hMCP-1
v-a-e-k-p-c-k-s-s-t-i-r-r-y-s
D amino acids

FIG. 14D

CRD Cys₀Cys₁₆peptide 2(1-15)[MCP-1]: Residues 28-42 of hMCP-1
c-v-a-e-k-p-c-k-s-s-t-i-r-r-y-s-c
D amino acids LFL peptide 2(1-15)[SDF1]: Residues 26-40 of mature hSDF-1β
H-L-K-I-L-N-T-P-N-C-A-L-Q-I-V (SEQ. ID. NO.: 103)
L amino acids CFL Cys₀Cys₁₆peptide 2(1-15)[SDF1]: Residues 26-40 of mature hSDF-1β
C-H-L-K-I-L-N-T-P-N-C-A-L-Q-I-V-C (SEQ. ID. NO.: 110)
L amino acids LRD peptide 2(1-15)[SDF1]: Residues 26-40 of mature hSDF-1β
v-i-q-l-a-c-n-p-t-n-l-i-k-l-h
D amino acids CRD Cys₀Cys₁₆peptide 2(1-15)[SDF1]: Residues 26-40 of mature hSDF-1β
c-v-i-q-l-a-c-n-p-t-n-l-i-k-l-h-c
D amino acids LFL peptide 2(1-14)[MIP-1α]: Residues 28-41 of hMIP-1α
D-Y-F-E-T-S-S-Q-C-S-K-P-G-V (SEQ. ID. NO.: 5)
L amino acids LRD peptide 2(1-14)[MIP1α]: Residues 28-41 of mature hMIP1α
v-g-p-k-s-c-q-s-s-t-e-f-y-d
D amino acids LFL peptide 2(1-16)[IL8]: Residues 27-42 of mature hIL8
E-L-R-V-I-E-S-G-P-H-C-A-N-T-E-I (SEQ. ID. NO.: 6)
L amino acids LFL Peptide 2(1-10)[MCP-1]: Residues 28-37 of hMCP-1
S-Y-R-R-I-T-S-S-K-C (SEQ. ID. NO.: 87)
L amino acids LFL peptide 2(10-15)[MCP-1]: Residues 37-42 of hMCP-1
C-P-K-E-A-V (SEQ. ID. NO.: 88)
L amino acids LFL peptide 2(1-5)[MCP-1]: Residues 28-32 of hMCP-1
S-Y-R-R-I (SEQ. ID. NO.: 89)
L amino acids

FIG. 14E

LFL peptide 2(6-10)[MCP-1]: Residues 33-37 of hMCP-1
T-S-S-K-C (SEQ. ID. NO.: 90)
L amino acids LFL peptide 2(1-9)[MIP-1α]: Residues 28-36 of hMIP-1α
D-Y-F-E-T-S-S-Q-C (SEQ. ID. NO.: 91)
L amino acids LFL peptide 2(9-14)[MIP-1α]: Residues 36-41 of hMIP-1α
C-S-K-P-G-V (SEQ. ID. NO.: 92)
L amino acid LFL $Cys_0Ser_{10}Cys_{16}$peptide 2(1-15)[MCP-1]: Residues 28-42 of hMCP-1
C-S-Y-R-R-I-T-S-S-K-S-P-K-E-A-V-C (SEQ. ID. NO.: 93)
L amino acids CFL $Cys_0Ser_{10}Cys_{16}$peptide 2(1-15)[MCP-1]: Residues 28-42 of hMCP-1
C-S-Y-R-R-I-T-S-S-K-S-P-K-E-A-V-C (SEQ. ID. NO.: 111)
L amino acids LRD $Cys_0Ser_{10}Cys_{16}$peptide 2(1-15)[ [MCP-1]: Residues 28-42 of hMCP-1
c-v-a-e-k-p-s-k-s-s-t-i-r-r-y-s-c
D amino acids CRD $Cys_0Ser_{10}Cys_{16}$peptide 2(1-15)[MCP-1]: Residues 28-42 of hMCP-1
c-v-a-e-k-p-s-k-s-s-t-i-r-r-y-s-c
D amino acids

FIG. 14F

| SEQUENCE | | DARC BINDING | THP-1 MIGRATION | | |
|---|---|---|---|---|---|
| | | | MCP-1 | MIP-1α | SDF-1α |
| (SEQ ID NO:3) | SYRRITSSKCPKEAV | 350nM | ns | ns | ns |
| | VAEKPCKSSTIRRYS | 18μM | ns | ns | ns |
| (SEQ ID NO:94) | SYRRITSK | 22μM | ns | ns | ns |
| (SEQ ID NO:89) | SYRRI | >100μM | ns | ns | ns |
| (SEQ ID NO:90) | TSSKC | >100μM | ns | ns | ns |
| (SEQ ID NO:88) | CPKEAV | >100μM | ns | ns | ns |
| (SEQ ID NO:103) | HLKILNTPNCALQIV | 19μM | 10μM | 40μM | 7μM |
| (SEQ ID NO:5) | DYFETSSQCSKPGV | >100μM | ns | ns | ns |
| | VGPKSCQSSTEFYD | >100μM | ns | ns | ns |
| (SEQ ID NO:91) | DYFETSSQC | >100μM | ns | ns | ns |
| (SEQ ID NO:92) | CSKPGV | >100μM | ns | ns | ns |

FIG 15

| SEQUENCE | MOL WT. | DUFFY BINDING BD-50 | MCP-1 ED-50 | MIP-1α ED-50 | RANTES ED-50 | SDF-1α ED-50 | IL-8 ED-50 | OTHER DATA |
|---|---|---|---|---|---|---|---|---|
| AQPDAINAPVTCC | 1302 | 90μM | ns | ns | – | ns | ns | |
| SYRRITSSKCPKEAV | 1725 | 100μM | ns | ns | – | ns | – | |
| VAEKPCKSSTIRRYS | 1725 | 18μM | ns | ns | – | ns | – | |
| HLKILNTPNCALQIV | 1677.3 | 19μM | 10μM | 40μM | – | 7μM | – | |
| DYFETSSQCSKPGV | 1549 | >100μM | ns | ns | – | ns | – | |
| VQPKSCQSSTEFYD | 1549 | >100μM | ns | ns | – | ns | – | |
| SYRRITSSKC | 1097.4 | 22μM | ns | ns | – | ns | – | |
| CPKEAV | 645.8 | >100μM | ns | ns | – | ns | – | |
| SYRRI | 693.9 | >100μM | ns | ns | – | ns | – | |
| TSSKC | 525.7 | >100μM | ns | ns | – | ns | – | |
| DYFETSSQC | 1079.2 | >100μM | ns | ns | – | ns | – | |
| CSKPGV | 589.8 | >100μM | ns | ns | – | ns | – | |

SEQ ID NO: 2
SEQ ID NO: 3
SEQ ID NO: 4
SEQ ID NO: 5
SEQ ID NO: 87
SEQ ID NO: 88
SEQ ID NO: 89
SEQ ID NO: 90
SEQ ID NO: 91
SEQ ID NO: 92

FIG. 16A

| | | | | | | | |
|---|---|---|---|---|---|---|---|
| SICADPKQKNVQ | 1445 | 6μM | 8μM | 7.5μM | – | 13.5μM | 10μM |
| CADPKQKNVQ | 1202 | – | 8μM | 6.5μM | – | 9μM | 8.5μM |
| CQWKQKPDAC | 1305 | 3μM | 100nM | – | – | – | – |
| CQWKQKPDAC | 1305 | 40μM | 30nM | – | – | – | – |
| BICADP (SEQ ID NO: 8) | 647 | – | 25μM | 20μM | – | 18.5μM | 16μM |
| KQKWVQ (SEQ ID NO: 9) | 816 | 15μM | 7μM | 5μM | – | 5.5μM | 5μM |
| BICLDPKQKWVQ (SEQ ID NO: 10) | 1487 | – | 8μM | 7μM | – | 2.5μM | 3μM |
| EICADPSQKWVQ (SEQ ID NO: 11) | 1404 | 25μM | 7μM | 5.5μM | – | 4μM | 3μM |
| EICADPKQKWIQ (SEQ ID NO: 13) | 1459 | – | 5.5μM | 3.5μM | – | 7μM | 2μM |
| EICLDPKQKWIQ (SEQ ID NO: 14) | 1501 | 90μM | 2μM | 2μM | – | 4μM | 3.5μM |
| WVQ | 431.5 | 1μM | 8μM | 7.5μM | 1.5μM | 2.25μM | 1μM |
| KQK | 464.5 | 50μM | 7μM | >100μM | >100μM | >100μM | >100μM |
| SEE | 399.4 | >100μM | >100μM | – | >100μM | >100μM | >100μM |
| KEN | 425.4 | >100μM | >100μM | >100μM | >100μM | >100μM | – |

FIG. 16B

| | | | | | | | |
|---|---|---|---|---|---|---|---|
| KLK | 516.6 | >100μM | >100μM | >100μM | – | >100μM | |
| CQIWKQKPDLC | 1359 | >100μM | 1μM | – | 350nM | 10nM | NOTE 1 |
| CQIWKQKPDLAC | 1448 | – | 100nM | – | – | – | NOTE 2 |
| CQIWKQKPDLC | 1472.2 | – | 10nM | – | – | – | |
| SES | 357.3 | >100μM | >100μM | – | – | – | |
| KKK | 609.8 | – | – | – | – | – | |

NOTE1: IN VIVO EFFECT ABOLISHES MACROPHAGES IN AN IN VIVO RATE INTRADEMAL STUDY INDUCED BY 500 ng MCP-1, 300 g IV, AND 10mg SQ 30 MINUTES PRIOR TO MCP-1, D-ALA ("a") IS ATTACHED TO D-ASP ("d").
NORE 2: IN SAME STUDY AS NOTE 1 ABOVE, NO EFFECT ON MACROPHAGES SEEN

FIG.16C

STUDY DESIGN TABLE

| GROUP | ANIMAL# | N | RX | RX DOSE/ROUTE T=30 MIN | DERMAL AGONIST | DERMAL AGONIST DOSE (ng IN 50 ul) T=0 | HOUR OF SACRIFICE |
|---|---|---|---|---|---|---|---|
| 1 | 1,2,3 | 3 | PBS | 200 ul:I.V. 200 ul:SQ BACK | PBS LPS MCP-1 MCP-1 | 0 50 100 500 | 20-24 |
| 2 | 4,5,6 | 3 | NR58-3.14.3 | 3 ug:I.V. 100 ug:SQ BACK | PBS LPS MCP-1 MCP-1 | 0 50 100 500 | 20-24 |
| 3 | 7,8,9 | 3 | NR58-3.14.3 | 30 ug:I.V. 1 mg:SQ BACK | PBS LPS MCP-1 MCP-1 | 0 50 100 500 | 20-24 |
| 4 | 10,11,12 | 3 | NR58-3.14.3 | 300 ug:I.V. 10 mg:SQ BACK | PBS LPS MCP-1 MCP-1 | 0 50 100 500 | 20-24 |

FIG. 17

SEQUENCE LISTING

```
<160> NUMBER OF SEQ ID NOS: 116

<210> SEQ ID NO 1
<211> LENGTH: 12
<212> TYPE: PRT
<213> ORGANISM: Homo sapiens

<400> SEQUENCE: 1

Glu Ile Cys Ala Asp Pro Lys Gln Lys Trp Val Gln
 1               5                  10

<210> SEQ ID NO 2
<211> LENGTH: 13
<212> TYPE: PRT
<213> ORGANISM: Homo sapiens

<400> SEQUENCE: 2

Ala Gln Pro Asp Ala Ile Asn Ala Pro Val Thr Cys Cys
 1               5                  10

<210> SEQ ID NO 3
<211> LENGTH: 15
<212> TYPE: PRT
<213> ORGANISM: Homo sapiens

<400> SEQUENCE: 3

Ser Tyr Arg Arg Ile Thr Ser Ser Lys Cys Pro Lys Glu Ala Val
 1               5                  10                  15

<210> SEQ ID NO 4
<211> LENGTH: 15
<212> TYPE: PRT
<213> ORGANISM: Homo sapiens

<400> SEQUENCE: 4

His Leu Lys Ile Leu Asn Thr Pro Asn Cys Ala Leu Gln Ile Val
 1               5                  10                  15
```

-continued

```
<210> SEQ ID NO 5
<211> LENGTH: 14
<212> TYPE: PRT
<213> ORGANISM: Homo sapiens

<400> SEQUENCE: 5

Asp Tyr Phe Glu Thr Ser Ser Gln Cys Ser Lys Pro Gly Val
1               5                   10

<210> SEQ ID NO 6
<211> LENGTH: 16
<212> TYPE: PRT
<213> ORGANISM: Homo sapiens

<400> SEQUENCE: 6

Glu Leu Arg Val Ile Glu Ser Gly Pro His Cys Ala Asn Thr Glu Ile
1               5                   10                  15

<210> SEQ ID NO 7
<211> LENGTH: 10
<212> TYPE: PRT
<213> ORGANISM: Homo sapiens

<400> SEQUENCE: 7

Cys Ala Asp Pro Lys Gln Lys Trp Val Gln
1               5                   10

<210> SEQ ID NO 8
<211> LENGTH: 6
<212> TYPE: PRT
<213> ORGANISM: Homo sapiens

<400> SEQUENCE: 8

Glu Ile Cys Ala Asp Pro
1               5

<210> SEQ ID NO 9
<211> LENGTH: 6
<212> TYPE: PRT
<213> ORGANISM: Homo sapiens

<400> SEQUENCE: 9

Lys Gln Lys Trp Val Gln
1               5

<210> SEQ ID NO 10
<211> LENGTH: 12
<212> TYPE: PRT
<213> ORGANISM: Artificial Sequence
<220> FEATURE:
<223> OTHER INFORMATION: A synthetic chemokine peptide variant

<400> SEQUENCE: 10

Glu Ile Cys Leu Asp Pro Lys Gln Lys Trp Val Gln
1               5                   10

<210> SEQ ID NO 11
<211> LENGTH: 12
<212> TYPE: PRT
<213> ORGANISM: Artificial Sequence
<220> FEATURE:
<223> OTHER INFORMATION: A synthetic chemokine peptide variant

<400> SEQUENCE: 11

Glu Ile Cys Ala Asp Pro Ser Gln Lys Trp Val Gln
1               5                   10
```

<210> SEQ ID NO 12
<211> LENGTH: 12
<212> TYPE: PRT
<213> ORGANISM: Artificial Sequence
<220> FEATURE:
<223> OTHER INFORMATION: A synthetic chemokine peptide variant

<400> SEQUENCE: 12

Glu Ile Cys Ala Asp Pro Ser Glu Glu Trp Val Gln
1               5                   10

<210> SEQ ID NO 13
<211> LENGTH: 12
<212> TYPE: PRT
<213> ORGANISM: Artificial Sequence
<220> FEATURE:
<223> OTHER INFORMATION: A synthetic chemokine peptide variant

<400> SEQUENCE: 13

Glu Ile Cys Ala Asp Pro Lys Gln Lys Trp Ile Gln
1               5                   10

<210> SEQ ID NO 14
<211> LENGTH: 12
<212> TYPE: PRT
<213> ORGANISM: Artificial Sequence
<220> FEATURE:
<223> OTHER INFORMATION: A synthetic chemokine peptide variant

<400> SEQUENCE: 14

Glu Ile Cys Leu Asp Pro Lys Gln Lys Trp Ile Gln
1               5                   10

<210> SEQ ID NO 15
<211> LENGTH: 12
<212> TYPE: PRT
<213> ORGANISM: Homo sapiens

<400> SEQUENCE: 15

Cys Pro Ser Leu Glu Asp Ser Phe Ile Gln Val Ala
1               5                   10

<210> SEQ ID NO 16
<211> LENGTH: 77
<212> TYPE: PRT
<213> ORGANISM: Homo sapiens

<400> SEQUENCE: 16

Ala Gln Pro Asp Ala Ile Asn Ala Pro Val Thr Cys Cys Tyr Asn Phe
1               5                   10                  15

Thr Asn Arg Lys Ile Ser Val Gln Arg Leu Ala Ser Tyr Arg Arg Ile
            20                  25                  30

Thr Ser Ser Lys Cys Pro Lys Glu Ala Val Ile Phe Lys Thr Ile Val
        35                  40                  45

Ala Lys Glu Ile Cys Ala Asp Pro Lys Gln Lys Trp Val Gln Asp Ser
    50                  55                  60

Met Asp His Leu Asp Lys Gln Thr Gln Thr Pro Lys Thr
65                  70                  75

<210> SEQ ID NO 17
<211> LENGTH: 77
<212> TYPE: PRT
<213> ORGANISM: Homo sapiens

<400> SEQUENCE: 17

Ala Gln Pro Asp Ser Val Ser Ile Pro Ile Thr Cys Cys Pro Asn Val
1               5                   10                  15

Ile Asn Arg Lys Ile Pro Ile Gln Arg Leu Glu Ser Tyr Arg Arg Ile
            20                  25                  30

Thr Asn Ile Gln Cys Pro Lys Glu Ala Val Ile Phe Lys Thr Lys Arg
        35                  40                  45

Gly Lys Glu Val Cys Ala Asp Pro Lys Glu Arg Trp Val Arg Asp Ser
    50                  55                  60

Asn Lys His Leu Asp Gln Ile Phe Gln Asn Leu Lys Pro
65                  70                  75

<210> SEQ ID NO 18
<211> LENGTH: 77
<212> TYPE: PRT
<213> ORGANISM: Homo sapiens

<400> SEQUENCE: 18

Ala Gln Pro Val Gly Ile Asn Thr Ser Thr Thr Cys Cys Tyr Arg Phe
1               5                   10                  15

Ile Asn Lys Lys Ile Pro Lys Gln Arg Leu Glu Ser Tyr Arg Arg Thr
            20                  25                  30

Thr Ser Ser His Cys Pro Arg Glu Ala Val Ile Phe Lys Thr Lys Leu
        35                  40                  45

Asp Lys Glu Ile Cys Ala Asp Pro Thr Gln Lys Trp Val Gln Asp Phe
    50                  55                  60

Met Lys His Leu Asp Lys Lys Thr Gln Thr Pro Lys Leu
65                  70                  75

<210> SEQ ID NO 19
<211> LENGTH: 71
<212> TYPE: PRT
<213> ORGANISM: Homo sapiens

<400> SEQUENCE: 19

Ser Ala Ser Leu Ala Ala Asp Thr Pro Thr Ala Cys Cys Phe Ser Tyr
1               5                   10                  15

Thr Ser Arg Gln Ile Pro Gln Asn Phe Ile Ala Asp Tyr Phe Glu Thr
            20                  25                  30

Ser Ser Gln Cys Ser Lys Pro Gly Val Ile Phe Leu Thr Lys Arg Ser
        35                  40                  45

Arg Gln Val Cys Ala Asp Pro Ser Glu Glu Trp Val Gln Lys Tyr Val
    50                  55                  60

Ser Asp Leu Glu Leu Ser Ala
65                  70

<210> SEQ ID NO 20
<211> LENGTH: 70
<212> TYPE: PRT
<213> ORGANISM: Homo sapiens

<400> SEQUENCE: 20

Ser Ala Pro Met Gly Ser Asp Pro Pro Thr Ala Cys Cys Phe Ser Tyr
1               5                   10                  15

Thr Ala Arg Lys Leu Pro Arg Asn Phe Val Val Asp Tyr Tyr Glu Thr
            20                  25                  30

Ser Ser Leu Cys Ser Gln Pro Ala Val Val Phe Gln Thr Lys Arg Ser

-continued

```
                35                  40                  45
Lys Gln Val Cys Ala Asp Pro Ser Glu Ser Trp Val Gln Glu Tyr Val
 50                  55                  60

Tyr Asp Leu Glu Leu Asn
 65                  70

<210> SEQ ID NO 21
<211> LENGTH: 70
<212> TYPE: PRT
<213> ORGANISM: Homo sapiens

<400> SEQUENCE: 21

Ser Ala Pro Met Gly Ser Asp Pro Pro Thr Ala Cys Cys Phe Ser Tyr
  1               5                  10                  15

Thr Ala Arg Lys Leu Pro Arg Asn Phe Val Val Asp Tyr Tyr Glu Thr
                 20                  25                  30

Ser Ser Leu Cys Ser Gln Pro Ala Val Val Phe Gln Thr Lys Arg Ser
                35                  40                  45

Lys Gln Val Cys Ala Asp Pro Ser Glu Ser Trp Val Gln Glu Tyr Val
 50                  55                  60

Tyr Asp Leu Glu Leu Asn
 65                  70

<210> SEQ ID NO 22

<400> SEQUENCE: 22

000

<210> SEQ ID NO 23
<211> LENGTH: 74
<212> TYPE: PRT
<213> ORGANISM: Homo sapiens

<400> SEQUENCE: 23

Leu Pro Arg Ser Ala Lys Glu Leu Arg Cys Gln Cys Ile Lys Thr Tyr
  1               5                  10                  15

Ser Lys Pro Phe His Pro Lys Phe Ile Lys Glu Leu Arg Val Ile Glu
                 20                  25                  30

Ser Gly Pro His Cys Ala Asn Thr Glu Ile Ile Val Arg Leu Ser Asp
                35                  40                  45

Gly Arg Glu Leu Cys Leu Asp Pro Lys Glu Asn Trp Val Gln Arg Val
 50                  55                  60

Glu Lys Phe Leu Lys Arg Ala Glu Asn Ser
 65                  70

<210> SEQ ID NO 24

<400> SEQUENCE: 24

000

<210> SEQ ID NO 25
<211> LENGTH: 73
<212> TYPE: PRT
<213> ORGANISM: Homo sapiens
<220> FEATURE:
<221> NAME/KEY: SITE
<222> LOCATION: 54, 55, 70
<223> OTHER INFORMATION: Xaa = any amino acid

<400> SEQUENCE: 25
```

```
His Pro Gly Ile Pro Ser Ala Cys Cys Tyr Asn Phe Thr Asn Lys Lys
 1               5                  10                  15

Ile Ser Phe Gln Arg Leu Lys Ser Tyr Lys Ile Ile Thr Ser Ser Lys
                20                  25                  30

Cys Pro Gln Thr Ala Ile Val Phe Glu Ile Lys Pro Asp Lys Met Ile
                35                  40                  45

Cys Ala Asp Pro Lys Xaa Xaa Trp Val Gln Asp Ala Lys Lys Tyr Leu
50                  55                  60

Asp Gln Ile Ser Gln Xaa Thr Lys Pro
65                  70

<210> SEQ ID NO 26
<211> LENGTH: 74
<212> TYPE: PRT
<213> ORGANISM: Mus musculus

<400> SEQUENCE: 26

Ala Gln Pro Asp Ala Val Asn Ala Pro Leu Thr Cys Cys Tyr Ser Pro
 1               5                  10                  15

Thr Ser Lys Met Ile Pro Met Ser Arg Leu Glu Ser Tyr Lys Arg Ile
                20                  25                  30

Thr Ser Ser Arg Cys Pro Lys Glu Ala Val Val Phe Val Thr Lys Leu
                35                  40                  45

Lys Arg Glu Val Cys Ala Asp Pro Lys Lys Glu Trp Val Gln Thr Tyr
50                  55                  60

Ile Lys Asn Leu Asp Arg Asn Gln Met Arg
65                  70

<210> SEQ ID NO 27
<211> LENGTH: 10
<212> TYPE: PRT
<213> ORGANISM: Artificial Sequence
<220> FEATURE:
<223> OTHER INFORMATION: A synthetic chemokine peptide variant

<400> SEQUENCE: 27

Cys Leu Asp Pro Lys Lys Glu Trp Ile Gln
 1               5                  10

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000
```

```
<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38
<211> LENGTH: 12
<212> TYPE: PRT
<213> ORGANISM: Homo sapiens

<400> SEQUENCE: 38

Gln Val Cys Ile Asp Pro Lys Leu Lys Trp Ile Gln
 1               5                  10

<210> SEQ ID NO 39

<400> SEQUENCE: 39

000

<210> SEQ ID NO 40
<211> LENGTH: 12
<212> TYPE: PRT
<213> ORGANISM: Homo sapiens

<400> SEQUENCE: 40

Glu Leu Cys Leu Asp Pro Lys Glu Asn Trp Val Gln
 1               5                  10

<210> SEQ ID NO 41

<400> SEQUENCE: 41

000
```

```
<210> SEQ ID NO 42
<211> LENGTH: 12
<212> TYPE: PRT
<213> ORGANISM: Homo sapiens

<400> SEQUENCE: 42

Gln Val Cys Ala Asp Pro Ser Glu Glu Trp Val Gln
 1               5                  10

<210> SEQ ID NO 43
<211> LENGTH: 12
<212> TYPE: PRT
<213> ORGANISM: Homo sapiens

<400> SEQUENCE: 43

Gln Val Cys Ala Asp Pro Ser Glu Ser Trp Val Gln
 1               5                  10

<210> SEQ ID NO 44
<211> LENGTH: 12
<212> TYPE: PRT
<213> ORGANISM: Homo sapiens

<400> SEQUENCE: 44

Gln Val Cys Ala Asp Pro Ser Glu Ser Trp Val Gln
 1               5                  10

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51
```

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56
<211> LENGTH: 68
<212> TYPE: PRT
<213> ORGANISM: Homo sapiens

<400> SEQUENCE: 56

Gly Lys Pro Val Ser Leu Ser Tyr Arg Cys Pro Cys Arg Phe Phe Glu
1               5                   10                  15

Ser His Ile Ala Arg Ala Asn Val Lys His Leu Lys Ile Leu Asn Thr
            20                  25                  30

Pro Asn Cys Ala Leu Gln Ile Val Ala Arg Leu Lys Asn Asn Asn Arg
        35                  40                  45

Gln Val Cys Ile Asp Pro Lys Leu Lys Trp Ile Gln Glu Tyr Glu Lys
    50                  55                  60

Ala Leu Asn Lys
65

<210> SEQ ID NO 57

<400> SEQUENCE: 57

000

<210> SEQ ID NO 58

<400> SEQUENCE: 58

000

<210> SEQ ID NO 59
<211> LENGTH: 15
<212> TYPE: PRT
<213> ORGANISM: Homo sapiens

<400> SEQUENCE: 59

Asn Leu Gln Val Phe Ala Ile Gly Pro Gln Cys Ser Lys Val Glu
1               5                   10                  15

```
<210> SEQ ID NO 60
<211> LENGTH: 14
<212> TYPE: PRT
<213> ORGANISM: Homo sapiens

<400> SEQUENCE: 60

Val Asp Tyr Tyr Glu Thr Ser Ser Leu Cys Ser Gln Pro Ala
1               5                   10

<210> SEQ ID NO 61
<211> LENGTH: 15
<212> TYPE: PRT
<213> ORGANISM: Homo sapiens

<400> SEQUENCE: 61

Val Asp Tyr Tyr Glu Thr Ser Ser Leu Cys Ser Gln Pro Ala Val
1               5                   10                  15

<210> SEQ ID NO 62
<211> LENGTH: 15
<212> TYPE: PRT
<213> ORGANISM: Homo sapiens

<400> SEQUENCE: 62

Glu Ser Tyr Arg Arg Ile Thr Asn Ile Gln Cys Pro Lys Glu Ala
1               5                   10                  15

<210> SEQ ID NO 63
<211> LENGTH: 15
<212> TYPE: PRT
<213> ORGANISM: Homo sapiens

<400> SEQUENCE: 63

Glu Ser Tyr Arg Arg Thr Thr Ser Ser His Cys Pro Arg Glu Ala
1               5                   10                  15

<210> SEQ ID NO 64
<211> LENGTH: 15
<212> TYPE: PRT
<213> ORGANISM: Homo sapiens

<400> SEQUENCE: 64

Lys Ser Tyr Val Ile Thr Thr Ser Arg Cys Pro Gln Lys Ala Val
1               5                   10                  15

<210> SEQ ID NO 65

<400> SEQUENCE: 65

000

<210> SEQ ID NO 66
<211> LENGTH: 12
<212> TYPE: PRT
<213> ORGANISM: Homo sapiens

<400> SEQUENCE: 66

Glu Ile Cys Ala Asp Pro Thr Gln Lys Trp Val Gln
1               5                   10

<210> SEQ ID NO 67
<211> LENGTH: 12
<212> TYPE: PRT
<213> ORGANISM: Homo sapiens
```

-continued

<400> SEQUENCE: 67

Glu Ile Cys Ala Asp Pro Lys Glu Arg Trp Val Arg
1               5                   10

<210> SEQ ID NO 68
<211> LENGTH: 12
<212> TYPE: PRT
<213> ORGANISM: Homo sapiens
<220> FEATURE:
<221> NAME/KEY: SITE
<222> LOCATION: 8, 9
<223> OTHER INFORMATION: Xaa = any amino acid

<400> SEQUENCE: 68

Met Ile Cys Ala Asp Pro Lys Xaa Xaa Trp Val Gln
1               5                   10

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75
<211> LENGTH: 12
<212> TYPE: PRT
<213> ORGANISM: Homo sapiens

<400> SEQUENCE: 75

Lys Ser Tyr Lys Ile Ile Thr Ser Ser Lys Cys Pro
1               5                   10

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84
<211> LENGTH: 10
<212> TYPE: PRT
<213> ORGANISM: Artificial Sequence
<220> FEATURE:
<223> OTHER INFORMATION: A synthetic chemokine peptide variant

<400> SEQUENCE: 84

```
Leu Asp Pro Lys Gln Lys Trp Ile Gln Cys
 1               5                  10
```

<210> SEQ ID NO 85
<211> LENGTH: 4
<212> TYPE: PRT
<213> ORGANISM: Homo sapiens

<400> SEQUENCE: 85

```
Trp Val Gln Cys
 1
```

<210> SEQ ID NO 86
<211> LENGTH: 4
<212> TYPE: PRT
<213> ORGANISM: Artificial Sequence

```
<220> FEATURE:
<223> OTHER INFORMATION: A synthetic chemokine peptide variant

<400> SEQUENCE: 86

Trp Ile Gln Cys
1

<210> SEQ ID NO 87
<211> LENGTH: 10
<212> TYPE: PRT
<213> ORGANISM: Homo sapiens

<400> SEQUENCE: 87

Ser Tyr Arg Arg Ile Thr Ser Ser Lys Cys
1               5                   10

<210> SEQ ID NO 88
<211> LENGTH: 6
<212> TYPE: PRT
<213> ORGANISM: Homo sapiens

<400> SEQUENCE: 88

Cys Pro Lys Glu Ala Val
1               5

<210> SEQ ID NO 89
<211> LENGTH: 5
<212> TYPE: PRT
<213> ORGANISM: Homo sapiens

<400> SEQUENCE: 89

Ser Tyr Arg Arg Ile
1               5

<210> SEQ ID NO 90
<211> LENGTH: 5
<212> TYPE: PRT
<213> ORGANISM: Homo sapiens

<400> SEQUENCE: 90

Thr Ser Ser Lys Cys
1               5

<210> SEQ ID NO 91
<211> LENGTH: 9
<212> TYPE: PRT
<213> ORGANISM: Homo sapiens

<400> SEQUENCE: 91

Asp Tyr Phe Glu Thr Ser Ser Gln Cys
1               5

<210> SEQ ID NO 92
<211> LENGTH: 6
<212> TYPE: PRT
<213> ORGANISM: Homo sapiens

<400> SEQUENCE: 92

Cys Ser Lys Pro Gly Val
1               5

<210> SEQ ID NO 93
<211> LENGTH: 17
<212> TYPE: PRT
<213> ORGANISM: Artificial Sequence
```

```
<220> FEATURE:
<223> OTHER INFORMATION: A synthetic chemokine peptide variant

<400> SEQUENCE: 93

Cys Ser Tyr Arg Arg Ile Thr Ser Ser Lys Ser Pro Lys Glu Ala Val
1               5                   10                  15
Cys

<210> SEQ ID NO 94
<211> LENGTH: 9
<212> TYPE: PRT
<213> ORGANISM: Homo sapiens

<400> SEQUENCE: 94

Ser Tyr Arg Arg Ile Thr Ser Ser Lys
1               5

<210> SEQ ID NO 95
<211> LENGTH: 11
<212> TYPE: PRT
<213> ORGANISM: Homo sapiens

<400> SEQUENCE: 95

Cys Gln Val Trp Lys Gln Lys Pro Asp Ala Cys
1               5                   10

<210> SEQ ID NO 96
<211> LENGTH: 4
<212> TYPE: PRT
<213> ORGANISM: Homo sapiens

<400> SEQUENCE: 96

Lys Lys Phe Lys
1

<210> SEQ ID NO 97
<211> LENGTH: 4
<212> TYPE: PRT
<213> ORGANISM: Homo sapiens

<400> SEQUENCE: 97

Arg Lys Pro Lys
1

<210> SEQ ID NO 98
<211> LENGTH: 4
<212> TYPE: PRT
<213> ORGANISM: Homo sapiens

<400> SEQUENCE: 98

Lys Arg Phe Lys
1

<210> SEQ ID NO 99
<211> LENGTH: 13
<212> TYPE: PRT
<213> ORGANISM: Homo sapiens

<400> SEQUENCE: 99

Leu Tyr Ile Asp Phe Arg Gln Asp Leu Gly Trp Lys Trp
1               5                   10

<210> SEQ ID NO 100
<211> LENGTH: 11
```

```
<212> TYPE: PRT
<213> ORGANISM: Homo sapiens

<400> SEQUENCE: 100

His Glu Pro Lys Gly Tyr His Ala Asn Phe Cys
1               5                   10

<210> SEQ ID NO 101
<211> LENGTH: 7
<212> TYPE: PRT
<213> ORGANISM: Homo sapiens

<400> SEQUENCE: 101

Val Tyr Tyr Val Gly Arg Lys
1               5

<210> SEQ ID NO 102
<211> LENGTH: 13
<212> TYPE: PRT
<213> ORGANISM: Homo sapiens

<400> SEQUENCE: 102

Lys Val Glu Gln Leu Ser Asn Met Val Val Lys Ser Cys
1               5                   10

<210> SEQ ID NO 103
<211> LENGTH: 15
<212> TYPE: PRT
<213> ORGANISM: Homo sapiens

<400> SEQUENCE: 103

His Leu Lys Ile Leu Asn Thr Pro Asn Cys Ala Leu Gln Ile Val
1               5                   10                  15

<210> SEQ ID NO 104
<211> LENGTH: 23
<212> TYPE: PRT
<213> ORGANISM: Homo sapiens

<400> SEQUENCE: 104

Tyr Asn Phe Thr Asn Arg Lys Ile Ser Val Gln Arg Leu Ala Ser Tyr
1               5                   10                  15

Arg Arg Ile Thr Ser Ser Lys
            20

<210> SEQ ID NO 105
<211> LENGTH: 15
<212> TYPE: PRT
<213> ORGANISM: Artificial Sequence
<220> FEATURE:
<223> OTHER INFORMATION: A synthetic chemokine peptide variant

<400> SEQUENCE: 105

Ser Tyr Arg Arg Ile Thr Ser Ser Lys Ser Pro Lys Glu Ala Val
1               5                   10                  15

<210> SEQ ID NO 106
<211> LENGTH: 14
<212> TYPE: PRT
<213> ORGANISM: Artificial Sequence
<220> FEATURE:
<223> OTHER INFORMATION: A synthetic peptide

<400> SEQUENCE: 106

Cys Glu Ile Cys Leu Asp Pro Lys Gln Lys Trp Ile Gln Cys
```

-continued

```
          1               5                  10
```

<210> SEQ ID NO 107
<211> LENGTH: 5
<212> TYPE: PRT
<213> ORGANISM: Artificial Sequence
<220> FEATURE:
<223> OTHER INFORMATION: A synthetic peptide

<400> SEQUENCE: 107

```
Cys Trp Val Gln Cys
  1               5
```

<210> SEQ ID NO 108
<211> LENGTH: 8
<212> TYPE: PRT
<213> ORGANISM: Artificial Sequence
<220> FEATURE:
<223> OTHER INFORMATION: A synthetic peptide

<400> SEQUENCE: 108

```
Cys Lys Gln Lys Trp Val Gln Cys
  1               5
```

<210> SEQ ID NO 109
<211> LENGTH: 17
<212> TYPE: PRT
<213> ORGANISM: Artificial Sequence
<220> FEATURE:
<223> OTHER INFORMATION: A synthetic peptide

<400> SEQUENCE: 109

```
Cys Ser Tyr Arg Arg Ile Thr Ser Ser Lys Cys Pro Lys Glu Ala Val
  1               5                  10                  15

Cys
```

<210> SEQ ID NO 110
<211> LENGTH: 17
<212> TYPE: PRT
<213> ORGANISM: Artificial Sequence
<220> FEATURE:
<223> OTHER INFORMATION: A synthetic peptide

<400> SEQUENCE: 110

```
Cys His Leu Lys Ile Leu Asn Thr Pro Asn Cys Ala Leu Gln Ile Val
  1               5                  10                  15

Cys
```

<210> SEQ ID NO 111
<211> LENGTH: 17
<212> TYPE: PRT
<213> ORGANISM: Artificial Sequence
<220> FEATURE:
<223> OTHER INFORMATION: A synthetic peptide

<400> SEQUENCE: 111

```
Cys Ser Tyr Arg Arg Ile Thr Ser Ser Lys Ser Pro Lys Glu Ala Val
  1               5                  10                  15

Cys
```

<210> SEQ ID NO 112
<211> LENGTH: 9
<212> TYPE: PRT
<213> ORGANISM: Artificial Sequence
<220> FEATURE:

```
<223> OTHER INFORMATION: A synthetic peptide
<220> FEATURE:
<221> NAME/KEY: VARIANT
<222> LOCATION: 1
<223> OTHER INFORMATION: Xaa = Ala, Ile, or Leu
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 8
<223> OTHER INFORMATION: Xaa = Val or Ile

<400> SEQUENCE: 112

Xaa Asp Pro Lys Xaa Lys Trp Xaa Gln
 1               5

<210> SEQ ID NO 113
<211> LENGTH: 9
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 1
<223> OTHER INFORMATION: Xaa = Ala, Ile or Leu
<220> FEATURE:
<221> NAME/KEY: VARIANT
<222> LOCATION: 4
<223> OTHER INFORMATION: Xaa = Lys, Ser or Thr
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = Lys, Glu, Ser or Arg

<400> SEQUENCE: 113

Xaa Asp Pro Xaa Xaa Xaa Trp Val Gln
 1               5

<210> SEQ ID NO 114
<211> LENGTH: 10
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 2
<223> OTHER INFORMATION: Xaa = Ala or Leu
<220> FEATURE:
<221> NAME/KEY: VARIANT
<222> LOCATION: 5
<223> OTHER INFORMATION: Xaa = a basic or acidic residue
<220> FEATURE:
<221> NAME/KEY: VARIANT
<222> LOCATION: 6
<223> OTHER INFORMATION: Xaa = Gln, Glu or Leu
<220> FEATURE:
<221> NAME/KEY: VARIANT
<222> LOCATION: 7
<223> OTHER INFORMATION: Xaa = a basic residue if the residue at
      position 5 is a basic residue, or an acidic residue if the residue
      at position 5 is an acidic residue
<220> FEATURE:
<221> NAME/KEY: VARIANT
<222> LOCATION: 9
<223> OTHER INFORMATION: Xaa = Val, Ile or Leu

<400> SEQUENCE: 114
```

```
Cys Xaa Asp Pro Xaa Xaa Xaa Trp Xaa Gln
 1               5                   10
```

<210> SEQ ID NO 115
<211> LENGTH: 9
<212> TYPE: PRT
<213> ORGANISM: Artificial Sequence
<220> FEATURE:
<223> OTHER INFORMATION: A synthetic peptide
<220> FEATURE:
<221> NAME/KEY: VARIANT
<222> LOCATION: 1
<223> OTHER INFORMATION: Xaa = Ala or Leu
<220> FEATURE:
<221> NAME/KEY: VARIANT
<222> LOCATION: 4
<223> OTHER INFORMATION: Xaa = Lys, Ser or Thr
<220> FEATURE:
<221> NAME/KEY: VARIANT
<222> LOCATION: 5
<223> OTHER INFORMATION: Xaa = any amino acid
<220> FEATURE:
<221> NAME/KEY: VARIANT
<222> LOCATION: 6
<223> OTHER INFORMATION: Xaa = Lys, Glu, Ser or Arg
<220> FEATURE:
<221> NAME/KEY: VARIANT
<222> LOCATION: 8
<223> OTHER INFORMATION: Xaa = Val or Ile

<400> SEQUENCE: 115

```
Xaa Asp Pro Xaa Xaa Xaa Trp Xaa Gln
 1               5
```

<210> SEQ ID NO 116
<211> LENGTH: 10
<212> TYPE: PRT
<213> ORGANISM: Artificial Sequence
<220> FEATURE:
<223> OTHER INFORMATION: A synthetic peptide

<400> SEQUENCE: 116

```
Cys Leu Asp Pro Lys Gln Lys Trp Ile Gln
 1               5                   10
```

COMPOUNDS AND METHODS TO INHIBIT OR AUGMENT AN INFLAMMATORY RESPONSE

CROSS-REFERENCE TO RELATED APPLICATIONS

This application is a continuation of U.S. patent application Ser. No. 09/150,813, filed Sep. 11, 1998 now U.S. Pat. No. 7,067,117, which is a continuation-in-part application of U.S. application Ser. No. 08/927,939, filed Sep. 11, 1997 now U.S. Pat. No. 6,989,435, the disclosures of which are incorporated by reference herein.

BACKGROUND OF THE INVENTION

Macrophage/monocyte recruitment plays a role in the morbidity and mortality of a broad spectrum of diseases, including autoimmune diseases, granulomatous diseases, allergic diseases, infectious diseases, osteoporosis and coronary artery disease. For example, in atherosclerosis early during lipid lesion formation, circulating monocytes adhere to the activated endothelium overlying the incipient plaque. Under appropriate conditions, the monocytes then migrate into the developing intima. In the intima, macrophage accumulate lipoprotein and excrete an excess of proteases relative to protease inhibitors. If the lipoproteins are oxidized, they are toxic to macrophage, which results in macrophage death and an increase in an unstable, necrotic, extracellular lipid pool. An excess of proteases results in loss of extracellular matrix and destabilization of the fibrous plaque. Plaque instability is the acute cause of myocardial infarction.

Many molecules have been identified that are necessary for the recruitment of monocytes and other inflammatory cell types. These molecules represent targets for the inhibition of monocyte recruitment. One class of such molecules is adhesion molecules, e.g., receptors, for monocytes. Another class of molecules includes inflammatory mediators, such as TNF-α and related molecules, the interleukins, e.g., IL-1β, and chemokines, e.g., monocyte chemoattractant protein-1 (MCP-1). As a result, agents which modulate the activity of chemokines are likely to be useful to prevent and treat a wide range of diseases. For example, Rollins et al. (U.S. Pat. No. 5,459,128) generally disclose analogs of MCP-1 that inhibit the monocyte chemoattractant activity of endogenous MCP-1. Analogs that are effective to inhibit endogenous MCP-1 are disclosed as analogs which are modified at 28-tyrosine, 24-arginine, 3-aspartate and/or in amino acids between residues 2-8 of MCP-1. In particular, Rollins et al. state that "[s]uccessful inhibition of the activity is found where MCP-1 is modified in one or more of the following ways: a) the 28-tyrosine is substituted by aspartate, b) the 24-arginine is substituted by phenylalanine, c) the 3-aspartate is substituted by alanine, and/or d) the 2-8 amino acid sequence is deleted" (col. 1, lines 49-54). The deletion of amino acids 2-8 of MCP-1 ("MCP-1(Δ2-8)") results in a polypeptide that is inactive, i.e., MCP-1(Δ2-8) is not a chemoattractant (col. 5, lines 22-23). The only effective MCP-1 inhibitor disclosed in Rollins et al. is MCP-1(Δ2-8).

Recent studies suggest that MCP-1(Δ2-8) exhibits a dominant negative effect, i.e., it forms heterodimers with wild-type MCP-1 that cannot elicit a biological effect (Zhang et al., *J. Biol. Chem.*, 269, 15918 (1994); Zhang et al., *Mol. Cell. Biol.*, 15, 4851 (1995)). Thus, MCP-1(Δ2-8) does not exhibit properties of a classic receptor antagonist. Moreover, MCP-1(Δ2-8) is unlikely to be widely useful for inhibition of MCP-1 activity in vivo, as MCP-1(Δ2-8) is a large polypeptide with undesirable pharmacodynamic properties. Furthermore, it is unknown whether MCP-1(Δ2-8) is active as a dominant-negative inhibitor of other chemokines associated with inflammation.

Thus, there is a need to identify agents that inhibit or enhance chemokine-induced macrophage and/or monocyte recruitment and which have desirable pharmacodynamic properties. Moreover, there is a need to identify agents that inhibit or enhance chemokine-induced activities of other cell types, such as lymphocytes. Further, there is a need to identify agents that are pan-selective chemokine inhibitors.

SUMMARY OF THE INVENTION

The invention provides a therapeutic agent comprising an isolated and purified chemokine peptide, chemokine peptide variant, chemokine analog, or a derivative thereof. Preferably, the therapeutic agent of the invention inhibits the activity of more than one chemokine, although the agent may not inhibit the activity of all chemokines to the same extent. Alternatively, a preferred therapeutic agent of the invention specifically inhibits the activity of one chemokine to a greater extent than other chemokines. Yet another preferred therapeutic agent of the invention mimics the activity of a chemokine, e.g., it acts as an agonist. Thus, therapeutic agents that are chemokine antagonists and agonists are within the scope of the invention. A further preferred therapeutic agent of the invention is an agent that does not inhibit or mimic the activity of a chemokine but binds to or near the receptor for that chemokine, i.e., it is a neutral agent.

A preferred embodiment of the invention is an isolated and purified CC chemokine peptide 3, e.g., a peptide derived from MCP-1 which corresponds to about residue 46 to about residue 67 of mature MCP-1 ("peptide 3[MC-1]"), a variant, an analog, or a derivative thereof. It is contemplated that chemokine peptide 3, a variant, an analog or a derivative thereof is a chemokine receptor antagonist, although these therapeutic agents may exert their effect by a different mechanism, e.g., by inhibiting the arachidonic acid pathway (e.g., inhibition of leukotriene, thromboxane, or prostaglandin synthesis or stability) or by elevating TGF-beta levels, or by more than one mechanism.

A preferred peptide 3 of the invention is a compound of formula (I):

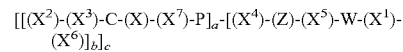

wherein $X^2$ is E, Q, D, N, L, P, I or M, wherein $X^3$ is I, V, M, A, P, norleucine or L, wherein X is A, L, V, M, P, norleucine or I, wherein $X^4$ is K, S, R, R, Q, N or T, wherein Z is Q, K, E, N, R, I, V, M, A, P, norleucine or L, wherein $X^7$ is D or P, wherein $X^5$ is K, E, R, S, Q, D, T, H or N, wherein $X^1$ is V, L, M, P, A, norleucine, or I, wherein $X^6$ is Q, N, K or R, wherein a is 0-6, wherein b is 0-6, and wherein c is 1-6, with the proviso that a and b cannot both be 0. The letters in formulas (I)-(III) that are not X, Y or Z represent peptidyl residues as shown in FIG. 13. A more preferred peptide 3 of the invention is a compound of formula (I):

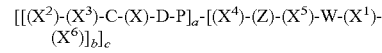

wherein $X^2$ is E, Q or M, wherein $X^3$ is I, V or L, wherein X is A, L or I, wherein $X^4$ is K, S or T, wherein Z is Q, K, E or L, wherein $X^5$ is K, E, R, S or T, wherein $X^1$ is V or I, wherein $X^6$ is Q or R, wherein a is 0-6, wherein b is 0-6, and wherein c is 1-6, with the proviso that a and b cannot both be 0.

Yet another preferred peptide 3 of the invention is a compound of formula (II):

$$[[(X^4)-(Z)-(X^5)]_a-[W-(X^1)-(X^6)]_b]_c$$

wherein $X^4$ is K, S or T, wherein Z is Q, K, E or L, wherein $X^5$ is K, E, R, S or T, wherein $X^1$ is V or I, wherein $X^6$ is Q or R, wherein a is 0-6, wherein b is 0-6, and wherein c is 1-6, with the proviso that a and b cannot both be 0.

Another preferred peptide 3 of the invention is a compound of formula (II):

$$[[(X^4)-(Z)-(X^5)]_a-[W-(X^1)-(X^6)]_b]_c$$

wherein $X^4$ is K, S, R, R, Q, N or T, wherein Z is Q, K, E, N, R, I, V, M, A, P, norleucine or L, wherein $X^5$ is K, E, R, S, Q, D, T, H or N, wherein $X^1$ is V, L, M, P, A, norleucine, or I, wherein $X^6$ is Q, N, K or R, wherein a is 0-6, wherein b is 0-6, and wherein c is 1-6, with the proviso that a and b cannot both be 0.

A more preferred peptide 3 of the invention is a compound of formula (X):

$$(X^8)-(X)-D-(X^2)-(X^4)-(Z)-(X^5)-W-(X^1)-Q-(X^7)$$

wherein X is A, L, V or I, wherein $X^2$ is P, G or L, wherein $X^4$ is K, T, R or N, wherein Z is Q, K, A or L, wherein $X^5$ is K, E, R, Q or P, wherein $X^1$ is V, L, A, M, F or I, and wherein $X^8$ and $X^7$ Are Independently C or Absent.

A preferred embodiment of the invention is an isolated and purified CC chemokine peptide 3, e.g., a peptide derived from MCP-1 which corresponds to SEQ ID NO:1 ("peptide 3(1-12)[MCP-1]") or SEQ ID NO:7 ("peptide 3(3-12)[MCP-1]"), a fragment, a variant, an analog, or a derivative thereof. As described hereinbelow, peptide 3(1-12)[MCP-1] (SEQ ID NO:1) and peptide 3(3-12)[MCP-1] (SEQ ID NO:7) are pan-chemokine inhibitors, bioavailable, and have desirable pharmacokinetics. Another preferred CC chemokine peptide 3 of the invention is peptide 3[MIP1α], and more preferably peptide 3(1-12)[MIP1α] which has an amino acid sequence corresponding to SEQ ID NO:42, a variant, an analog, a fragment or a derivative thereof.

Further preferred embodiments of the invention are a CC chemokine peptide 3 such as peptide 3(1-12)[MCP-4], peptide 3(1-12)[MCP-3] (e.g., SEQ ID NO:66), peptide 3(1-12)[MCP-2] (e.g., SEQ ID NO:67), peptide 3(1-12)[eotaxin] (e.g., SEQ ID NO:68), peptide 3(1-12)[MIP1α], (e.g., SEQ ID NO:42), peptide 3(1-12)[MIP1β] (e.g., SEQ ID NO:43), peptide 3(1-12)[RANTES] (e.g., SEQ ID NO:44), or a fragment thereof.

Another preferred embodiment of the invention includes a CXC chemokine peptide 3, a variant, an analog or a derivative thereof. A preferred CXC peptide 3 of the invention is a compound of formula (III):

$$[[(X^2)-(X^3)-C-L-(X)-(X^7)]_a-[(X^4)-(Z)-(X^5)-(X^8)-(X^1)-(X^6)]_b]_c$$

wherein $X^2$ is E or K, wherein $X^3$ is I, A, R or L, wherein X is D or N, wherein $X^7$ is Q, P or L, wherein $X^4$ is E, K, D, A or Q, wherein Z is A, R, S or E, wherein $X^5$ is P, N or K, wherein $X^8$ is F, W, R, I, M, L or A, wherein $X^1$ is L, V, Y or I, wherein $X^6$ is K or Q, wherein a is 0-6, wherein b is 0-6, and wherein c is 1-6, with the proviso that a and b cannot both be 0.

Further preferred embodiments of the invention are a CXC chemokine peptide 3 such as peptide 3(1-12)[IL8] (e.g., SEQ ID NO:40), peptide 3(1-12)[SDF-1] (e.g., SEQ ID NO:38), peptide 3(1-12)[ENA-78], peptide 3(1-12)[GROα], peptide 3(1-12)[GROβ], peptide 3(1-12)[GROγ], or fragments thereof.

Yet other preferred embodiments of the invention are a $CX_2C$, $CX_3C$ or C chemokine peptide 3, a variant, an analog or a derivative thereof.

Preferably, a chemokine peptide 3, its variants, analogs or derivatives inhibits the arachidonic acid pathway, e.g., inhibits the synthesis or stability, or binding, of thromboxane, prostaglandin, leukotriene, or any combination thereof.

Other compounds of the invention include compounds of formula (VIII):

wherein

R is $(C_1-C_6)$alkyl, $(C_1-C_6)$alkanoyl, aryl, heteroaryl, $(C_1-C_6)$alkoxycarbonyl, or benzyloxycarbonyl, wherein aryl, heteroaryl, and the phenyl ring of the benzyloxycarbonyl can optionally be substituted with one or more (e.g. 1, 2, 3, or 4), halo, hydroxy, cyano nitro, trifluoromethyl, trifluoromethoxy, $(C_1-C_6)$alkyl, $(C_1-C_6)$alkoxy, $(C_1-C_6)$alkanoyl, $(C_2-C_6)$alkanoyloxy or $(C_1-C_6)$alkoxycarbonyl;

R' is $(C_1-C_6)$alkoxy, aryloxy, or $NR_aR_b$, wherein $R_a$ and $R_b$ are each independently hydrogen, $(C_1-C_6)$alkyl, aryl, benzyl, or phenethyl; or $R_a$ and $R_b$ together with the nitrogen to which they are attached are a 5-6 membered heterocyclic ring (e.g. pyrrolidino, piperidino, or morpholino); and each R" is independently hydrogen, $(C_1-C_6)$alkyl, phenyl, benzyl, or phenethyl;

or a pharmaceutically acceptable salt thereof. Preferably, R is benzyloxycarbonyl and R' is dimethylamino or diethylamino, or R is benzyloxycarbonyl; and R' is benzyloxy.

Other compounds of the invention include compounds of formula (IX):

wherein

R is $(C_1-C_6)$alkyl, $(C_1-C_6)$alkanoyl, aryl, heteroaryl, $(C_1-C_6)$alkoxycarbonyl, or benzyloxycarbonyl, wherein aryl, heteroaryl, and the phenyl ring of the benzyloxycarbonyl can optionally be substituted with one or more (e.g. 1, 2, 3, or 4), halo, hydroxy, cyano nitro, trifluoromethyl, trifluoromethoxy, $(C_1-C_6)$alkyl, $(C_1-C_6)$alkoxy, $(C_1-C_6)$alkanoyl, $(C_2-C_6)$alkanoyloxy or $(C_1-C_6)$alkoxycarbonyl;

R' is $(C_1-C_6)$alkoxy, aryloxy, or $NR_aR_b$, wherein $R_a$ and $R_b$ are each independently hydrogen, $(C_1-C_6)$alkyl, aryl, benzyl, or phenethyl; or $R_a$ and $R_b$ together with the nitrogen to which they are attached are a 5-6 membered heterocyclic ring (e.g. pyrrolidino, piperidino, or morpholino); and each R" is independently hydrogen, $(C_1-C_6)$alkyl, phenyl, benzyl, or phenethyl;

or a pharmaceutically acceptable salt thereof. Preferably, R is benzyloxycarbonyl and R' is dimethylamino or diethylamino, or R is benzyloxycarbonyl; and R' is benzyloxy.

Another preferred embodiment of the invention includes a chemokine peptide 3 that is at least a tripeptide, a variant thereof or a derivative thereof. A preferred embodiment of the invention is the MCP-1 tripeptide KQK (i.e., peptide 3(9-12) [MCP-1], which specifically inhibits MCP-1, but not MIP1α, IL8 and SDF1α, chemokine-induced activity. Other preferred embodiments of the invention include isolated and purified chemokine tripeptides that specifically inhibit IL8, MIP1α, SDF1, murine MCP-1, MCP-2, MCP-3, and MIP1β, e.g., KEN, SEE, KLK, KKE, KER, TQK, and SES, respectively. A further preferred embodiment of the invention is a chemokine peptide 3 tripeptide that inhibits the activity of more than one chemokine, e.g., WVQ or WIQ. Preferably, a tripeptide of the invention is not RFK.

Yet another embodiment of the invention is a peptide which includes the amino acid sequence KXK, wherein X is an amino acid, preferably one of the twenty naturally occurring amino acids, and which peptide is a chemokine antagonist, activates TGF-beta (TGF-beta1, TGF-beta2, TGF-beta3, or a combination thereof), or a combination thereof. Preferably, the peptide increases the activation of TGF-beta1. It is preferred that a peptide which includes the amino acid sequence KXK is less than about 15, preferably about 10, and more preferably about 8 amino acid residues in length. Preferably, the peptide is not KKFK or RKPK. A further embodiment of the invention is a peptide which includes a basic amino acid residue followed by phenylalanine followed by another basic residue, wherein the peptide is not RFK, is not KRFK, or does not contain RFK or KRFK.

Another preferred peptide of the invention is a compound of formula (VII):

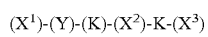

wherein $X^2$ is V, A, D, E, P, R, C, H, M, F, K, L, N, Q, Y, or I; wherein Y is absent or is an amino acid that is not R or K; and wherein $X^1$ and $X^3$ are independently 0-20 amino acid residues or absent. Preferably, $X^2$ is F, K, L, N, Q, Y, or I. More preferably, $X^2$ is F, K, L, N, Q, Y, or I, and Y, $X^1$ and $X^3$ are absent.

To identify a peptide of the invention useful in the methods of the invention, a sequence comparison of chemokines from different species is performed. Then the cross-reactivity of a non-human chemokine for the human receptor is assessed. A preferred chemokine is one from a species which has the least sequence homology to the corresponding human chemokine, but which still cross-reacts by binding to the human receptor. Regions which have a high degree of sequence similarity or identity are employed to prepare a peptide of the invention. For example, to identify peptides of TGF-beta having antagonist, agonist or neutral properties, the amino acid sequence of human TGF-beta was compared to that of *Xenopus*. Peptides identified by this method include LYIDFRQDLGWKW ("T1"; SEQ ID NO:99); HEPKGYHANFC ("T2"; SEQ ID NO:100); VYYVGRK ("T3"; SEQ ID NO:101) and KVEQLSNMVVKSC ("T4"; SEQ ID NO:102). Biotinylated T1 bound to the TGF-beta receptor of THP-1 cells with an $ED_{50}$ of 18 μM and is a receptor neutral agent (i.e., neither agonist nor antagonist). Biotinylated T2 bound to the TGF-beta receptor of THP-1 cells with an ED50 of 30 μM and is a weak receptor antagonist.

Another preferred embodiment of the invention is an isolated and purified CC chemokine peptide 2, such as a peptide corresponding to SEQ ID NO:3 ("peptide 2(1-15)[MCP-1]"), SEQ ID NO:5 ("peptide 2(1-14)[MIP1α]"), a fragment, a variant, an analog, or a derivative thereof. It is contemplated that chemokine peptide 2, a variant, an analog or a derivative thereof is a chemokine receptor agonist, although these therapeutic agents may exert their effect by a different mechanism, or by more than one mechanism. It is also envisioned that chemokine peptide 2, a variant, an analog or a derivative thereof is a chemokine receptor antagonist. Preferably, a variant, an analog or a derivative of peptide 2 has reduced Duffy antigen binding, and also preferably, enhanced receptor binding properties, relative to the corresponding peptide 2 having a native or wild-type amino acid sequence.

Other preferred CC chemokine peptides 2 include peptide 2(1-14)[MIP1β] (e.g., SEQ ID NO:60), peptide 2(1-15) [RANTES] (e.g., SEQ ID NO:61), peptide 2(1-15)[MCP-2] (e.g., SEQ ID NO:62), peptide 2(1-15)[MCP-3] (e.g., SEQ ID NO:63), peptide 2(1-15)[MCP-4] (e.g., SEQ ID NO:64), peptide 2(1-15)[eotaxin] (e.g., SEQ ID NO:75), or a fragment thereof.

Another preferred embodiment of the invention includes a CXC chemokine peptide 2, a variant, an analog or a derivative thereof. Preferred CC chemokine peptide 2 includes peptide 2(1-15)[IL8] (e.g., SEQ ID NO:6), peptide 2(1-15)[SDF1 (e.g., SEQ ID NO:4), peptide 2(1-15)[ENA78] (e.g., SEQ ID NO:59), peptide 2(1-15)[GROα], peptide 2(1-15)[GROβ], peptide 2(1-15)[GROγ], or a fragment thereof.

Yet another preferred embodiment of the invention is a $CX_2C$, $CX_3C$ or C chemokine peptide 2, a variant, an analog or a derivative thereof.

Other preferred peptide 2s include TSSKC (peptide 2(1-5) [MIP-1]; SEQ ID NO:90); DYFETSSQC (peptide 2(1-9) [MIP1α]; SEQ ID NO:91); CSKPGV (peptide 2(9-14) [MIP1α]; SEQ ID NO:92); HLKILNTPNCALQIV (peptide 2(1-5)[MIP-1α]; SEQ ID NO:103); SYRRITSSK (peptide 2(1-5)[MCP-1]; SEQ ID NO:94); CPKEAV (peptide 2(10-15)[MCP-1]; SEQ ID NO:88); SYRRI (peptide 2(1-5)[MCP-1]; SEQ ID NO:89); and CSYRRITSSKSPKEAVC (SEQ ID NO:93); as well as a peptide having D isomers of the sequence VGPKSCQSSTEFYD (corresponding to residues 1-14 of peptide 2(1-14)[MIP1α], lowercase letters are used herein to indicate D isomers as well as the letter "D" in CRD and LRD); a peptide corresponding to vaekpcksstirry; and a variant peptide 2 of vgpkscqsstefyd (LRD peptide 2(1-14) [MIP1α] which includes a D isomer of serine at position 10, and the D isomer of cysteine at the amino and carboxy termini of the peptide (designated LRD-$Cys_0Ser_{10}Cys_{16}$ peptide 2(1-15)[MCP-1], where L=linear, F=forward, D=D isomer).

A more preferred peptide 2 of the invention is a compound of formula (XII):

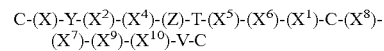

wherein X is S or D, wherein $X^2$ is R, K, F or Y, wherein $X^4$ is R, E or F, wherein Z is T or a peptide bond, wherein $X^5$ is S or N, wherein $X^6$ is S or I, wherein $X^1$ is K, R, Q or L, wherein $X^8$ is P or S, wherein $X^7$ is K, R or Q, wherein $X^9$ is E or P, and wherein $X^{10}$ is A or G.

Also provided is an isolated and purified chemokine peptide variant, or a derivative thereof. A chemokine peptide variant has at least about 50%, preferably at least about 80%, and more preferably at least about 90% but less than 100%, contiguous amino acid sequence homology or identity to the amino acid sequence of the corresponding native chemokine, e.g., $Ser_7$ peptide 3(1-12)[MCP1] (SEQ ID NO:11) has less than 100% contiguous homology to the corresponding amino acid sequence of MCP-1, i.e., a peptide having SEQ ID NO:1. A preferred peptide 3 variant is $Leu_4Ile_{11}$peptide 3(3-12) [MCP-1].

The invention also provides derivatives of chemokine peptides and peptide variants. A preferred derivative is a cyclic reverse sequence D isomer (CRD) derivative of a chemokine peptide, a variant or an analog thereof of the invention. For example, LRD derivatives of peptide 2, CRD-$Cys_0Ser_{10}Cys_{16}$ peptide 2[MCP-1] and CRD-$Cys_{13}Leu_4Ile_{11}$peptide 3(3-12)[MCP-1] are compounds of the invention that are particularly useful in the practice of the methods of the invention, as described hereinbelow.

Also provided are certain analogs of chemokines. In particular, analogs of chemokine peptide 2, chemokine peptide 3, or variants thereof are contemplated. A preferred analog of chemokine peptide 3 is an analog of WIQ. Thus, a preferred chemokine analog of the invention includes a compound of formula (IV):

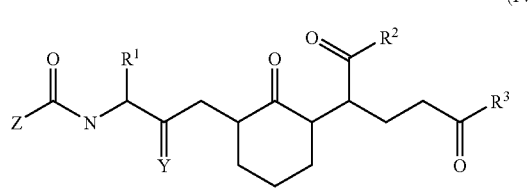

(IV)

wherein $R^1$ is aryl, heteroaryl, aryl($C_1$-$C_3$)alkyl, heteroaryl ($C_1$-$C_3$)alkyl, coumaryl, coumaryl($C_1$-$C_3$)alkyl, chromanyl or chromanyl($C_1$-$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$-$C_6$)alkyl, ($C_1$-$C_6$)alkoxy, ($C_1$-$C_6$)alkanoyl, ($C_2$-$C_6$)alkanoyloxy, —C(=O)($C_1$-$C_6$)alkoxy, C(=O)$NR^gR^h$, $NR^iR^j$;

wherein $R^2$ is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy or $N(R^a)(R^b)$;

wherein $R^3$ is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy or $N(R^c)(R^d)$;

wherein Y is oxo or thioxo;

wherein Z is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy or $N(R^e)(R^f)$; and wherein $R^a$-$R^j$ are each independently hydrogen, ($C_1$-$C_{10}$)alkyl, ($C_1$-$C_{10}$)alkanoyl, phenyl, benzyl, or phenethyl; or $R^a$ and $R^b$, $R^c$ and $R^d$, $R^e$ and $R^f$, $R^g$ and $R^h$, or $R^i$ and $R^j$ together with the nitrogen to which they are attached form a ring selected from pyrrolidino, piperidino, or morpholino; or a pharmaceutically acceptable salt thereof.

A preferred embodiment of a compound of formula (IV) includes a compound of a formula (IV) wherein $R^1$ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein $R^2$ is $N(R^a)(R^b)$; and $R^3$ is $N(R^c)(R^d)$. Yet another preferred embodiment of a compound of formula (IV) includes a compound of a formula (IV) wherein Z is ($C_1$-$C_{10}$)alkyl.

A further preferred compound is a compound of formula (IV) wherein $R^1$ is indolyl; $R^2$ is $N(R^a)(R^b)$; $R^3$ is $N(R^c)(R^d)$; Y is S; Z is hydrogen; and $R^a$, $R^b$, $R^c$, and $R^d$ are each methyl.

Another preferred analog of chemokine peptide 3 is an analog of KXK. Thus, the invention includes a compound of formula (V):

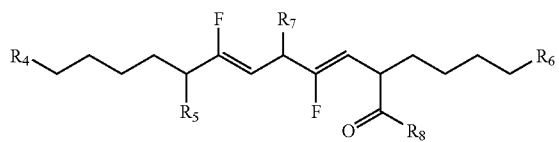

wherein
$R^4$ is $NR_kR_l$;
$R^5$ is $NR_mR_n$;
$R^6$ is $NR_oR_p$;
$R^7$ is the side chain of a natural or unnatural amino acid or is —$(CH_2)_2C(=O)NR_qR_r$;
$R^8$ is hydrogen, hydroxy, ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl($C_1$-$C_6$)alkoxy, $NR_sR_t$, the amino terminus of an amino acid or the N-terminal residue of a peptide of 2 to about 25 amino acid residues;

$R_k$, $R_l$, $R_o$, and $R_p$ are each independently hydrogen, ($C_1$-$C_{10}$)alkyl, ($C_3$-$C_6$)cycloalkyl, ($C_3$-$C_6$)cycloalkyl($C_1$-$C_6$) alkyl, ($C_1$-$C_{10}$)alkanoyl, phenyl, benzyl or phenethyl;

$R_m$ are $R_n$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$) alkoxy, ($C_1$-$C_{10}$)alkanoyl, ($C_1$-$C_{10}$)alkoxycarbonyl, 9-fluorenylmethoxycarbonyl, phenyl, benzyl, phenethyl, the C-terminal residue of an amino acid or a peptide of 2 to about 25 amino acid residues;

$R_q$ are $R_r$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, phenyl, benzyl or phenethyl;

wherein $R_s$ are $R_t$ are each independently hydrogen, ($C_1$-$C_{10}$)alkyl, ($C_3$-$C_6$)Cycloalkyl, ($C_3$-$C_6$)cycloalkyl($C_1$-$C_6$) alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, ($C_1$-$C_{10}$)alkyl, ($C_3$-$C_6$)cycloalkyl, propoxy, butoxy, tert-butoxycarbonyl, 9-fluorenylmethoxycarbonyl or the C-terminal residue of an amino acid or a peptide of 2 to about 25 amino acid residues; and $R_q$ are $R_r$ are each independently hydrogen, ($C_1$-$C_{10}$)alkyl, or ($C_3$-$C_6$)cycloalkyl.

Preferably, $R^7$ is —$(CH_2)_2C(=O)NR_qR_r$.

Preferably, $R^7$ is methyl, 3-guanidinopropyl, aminocarbonylmethyl, carboxymethyl, mercaptomethyl, (2-carboxy-2-aminoethyl)dithiomethyl, 2-carboxyethyl, 2-(aminocarbonyl)ethyl, hydrogen, 5-imadazoylmethyl, 4-amino-3-hydroxypropyl, 2-butyl, 2-methylprop-1-yl, 4-aminobutyl, 2-(methylthio)ethyl, benzyl, hydroxymethyl, 1-hydroxyethyl, 3-indolylmethyl, 4-hydroxybenzyl, or isopropyl.

More preferably, $R^7$ is hydrogen, benzyl, 4-hydroxybenzyl, methyl, 2-hydroxymethyl, or mercaptomethyl.

A preferred compound of formula (V) includes an analog of KGK, KFK, KYK, KAK, KSK, KCK or KQK. For example, an analog of KQK includes a compound of formula (V):

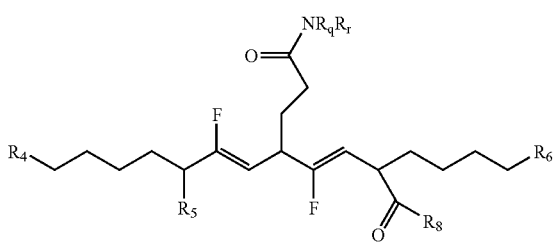

wherein R⁴ is $NR_kR_l$;
  wherein R⁵ is $NR_mR_n$;
  wherein R⁶ is $NR_oR_p$;
  wherein R⁷ is $NR_qR_r$;
  wherein R⁸ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues;
  wherein $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl;
  wherein $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues;
  wherein $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl;
  wherein $R_s$ are $R_t$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; or a pharmaceutically acceptable salt thereof.

Preferably $R_k$, $R_l$, $R_o$, and $R_p$ are each hydrogen; $R_m$ are $R_n$ are each independently hydrogen, acetyl, $(C_1-C_{10})$alkyl, $(C_3-C_6)$cycloalkyl, propoxy, butoxy, tert-butoxycarbonyl, 9-fluorenylmethoxycarbonyl or the C-terminal residue of an amino acid or a peptide of 2 to about 25 amino acid residues; and $R_q$ are $R_r$ are each independently hydrogen, $(C_1-C_{10})$alkyl, or $(C_3-C_6)$cycloalkyl.

Another preferred analog of chemokine peptide 3 is an analog of WVQ (see FIG. 8). Thus, the invention provides a compound of formula (VI):

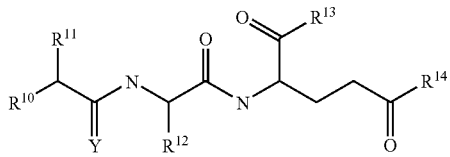

(VI)

wherein
  R¹⁰ is $NR^iR^j$;
  R¹¹ is aryl, heteroaryl, aryl$(C_1-C_3)$alkyl, heteroaryl$(C_1-C_3)$alkyl, coumaryl, coumaryl$(C_1-C_3)$alkyl, chromanyl or chromanyl$(C_1-C_3)$alkyl; wherein any aryl or heteroaryl group, or the benz-ring of any coumaryl or chromanyl group may optionally be substituted with one, two or three substituents selected from the group consisting of halo, nitro, cyano, hydroxy, $(C_1-C_6)$alkyl, $(C_1-C_6)$alkoxy, $(C_1-C_6)$alkanoyl, $(C_2-C_6)$alkanoyloxy, $-C(=O)(C_1-C_6)$alkoxy, $C(=O)NR^gR^h$, $NR^eR^f$;
  R¹² is $(C_1-C_6)$alkyl;
  R¹³ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, hydroxy, or $N(R^a)(R^b)$;
  R¹⁴ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^c)(R^d)$;
  Y is oxo or thioxo;
  wherein $R^a$-$R^j$ are each independently hydrogen, $(C_1-C_{10})$alkyl, $(C_1-C_{10})$alkanoyl, phenyl, benzyl, or phenethyl; or $R^a$ and $R^b$, $R^c$ and $R^d$, $R^e$ and $R^f$, $R^g$ and $R^h$ or $R^i$ and $R^j$ together with the nitrogen to which they are attached form a ring selected from pyrrolidino, piperidino, or morpholino; or a pharmaceutically acceptable salt thereof.

Preferably, R¹⁰ is amino; R¹¹ is 2-benzimidazolyl; R¹² is $(C_1-C_6)$alkyl; R¹³ is hydroxy; and R¹⁴ is amino.

It is envisioned that the therapeutic agents of the invention include compounds having a chiral center that can be isolated in optically active and racemic forms.

Further provided are isolated and purified nucleic acid molecules, e.g., DNA molecules, comprising a preselected nucleic acid segment which encodes at least a portion of a chemokine, i.e., they encode a chemokine peptide or a variant thereof as described herein, e.g., a chemokine 3 peptide, a variant or derivative thereof or a chemokine peptide 2, a variant or derivative thereof. For example, the invention provides an expression cassette comprising a preselected DNA segment which codes for an RNA molecule which is substantially identical (sense) to all or a portion of a messenger RNA ("target" mRNA), i.e., an endogenous or "native" chemokine mRNA. The preselected DNA segment in the expression cassette is operably linked to a promoter. As used herein, "substantially identical" in sequence means that two nucleic acid sequences have at least about 65%, preferably about 70%, more preferably about 90%, and even more preferably about 98%, contiguous nucleotide sequence identity to each other. Preferably, the preselected DNA segment hybridizes under hybridization conditions, preferably under stringent hybridization conditions, to a nucleic acid molecule encoding the corresponding native chemokine.

The present invention also provides isolated and purified DNA molecules which provide "anti-sense" mRNA transcripts of the DNA segments that encode a chemokine which, when expressed from an expression cassette in a host cell, can alter chemokine expression. As used herein, the term "antisense" means a sequence of nucleic acid which is the reverse complement of at least a portion of a RNA molecule that codes for a chemokine. Preferably, the antisense sequences of the invention are substantially complementary to a DNA segment encoding a peptide or peptide variant of the invention. As used herein, "substantially complementary" means that two nucleic acid sequences have at least about 65%, preferably about 70%, more preferably about 90%, and even more preferably about 98%, contiguous nucleotide sequence complementarity to each other. A substantially complementary RNA molecule is one that has sufficient sequence complementarity to the mRNA encoding a chemokine so as to result in a reduction or inhibition of the translation of the mRNA. It is envisioned that the duplex formed by the antisense sequence and the mRNA inhibits translation of the mRNA, as well as promotes RNA degradation, although antisense sequences may exert their effect by other mechanisms, or by a combination of mechanisms. Preferably, the preselected antisense DNA segment hybridizes under hybridization conditions, preferably under stringent hybridization conditions, to a nucleic acid molecule comprising the corresponding chemokine gene.

The introduction of chemokine sense or antisense nucleic acid into a cell ex vivo or in vivo can result in a molecular genetic-based therapy directed to controlling the expression of the chemokine. Thus, the introduced nucleic acid may be useful to correct or supplement the expression of the gene in patients with a chemokine-associated indication. For example, the administration of an expression vector encoding a peptide of the invention which is a chemokine receptor agonist may increase the chemokine signaling and thus be efficacious for diseases which are characterized by decreased levels of the chemokine. Likewise, the administration of an expression vector comprising antisense chemokine sequences may be useful to prevent or treat a disorder associated with increased chemokine expression. For example, an expression vector containing antisense peptide 3(1-12) [MCP-1] which is introduced into the lungs may be efficacious to prevent or treat asthma.

Also provided are pharmaceutical compositions, delivery systems, and kits comprising the therapeutic agents of the invention.

The invention further provides methods to treat chemokine-associated indications. For example, the invention provides a method of preventing or inhibiting an indication associated with chemokine-induced activity. The method comprises administering to a mammal afflicted with, or at risk of, the indication an amount of a chemokine peptide 3, a chemokine peptide 2, a fragment thereof, a variant thereof, a derivative thereof, a compound of formula (VII), a compound of formula (VIII), a compound of formula (IX), a compound of formula (X), a compound of formula (XI), a compound of formula (XII), or a combination thereof, effective to prevent or inhibit said activity. Preferably, the peptide is not an IL-8 peptide, a NAP-2 peptide, or a PF4 peptide. Preferably, the administration is effective to inhibit the activity of more than one chemokine (i.e., the peptide is a pan-selective inhibitor). Preferred pan-chemokine inhibitors are WVQ, WIQ, Leu$_4$Ile$_{11}$peptide 3(3-12)[MCP-1], Leu$_4$Ile$_{11}$peptide 3(1-12) [MCP-1] and CRD-Cys$_{13}$Leu$_4$Ile$_{11}$peptide 3(3-12). These agents are useful to treat indications such as multiple sclerosis, asthma, psoriasis, allergy, rheumatoid arthritis, organ transplant rejection, and autoimmune disorders. Preferred chemokine peptides useful to treat or inhibit these indications include peptide 2 and/or peptide 3 from MCP-1, MCP-2, MCP-3, MCP-4, RANTES, MIP1α, ENA78, MIG, GROβ, eotaxin, IP10, MIPβ and SDF-1.

The invention also provides a method of treating a mammal afflicted with, or at risk of, an indication associated with chemokine-induced activity, comprising: administering to the mammal an effective amount of a compound of formula (IV):

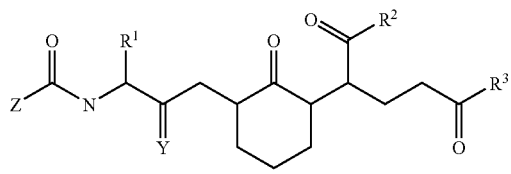

(IV)

wherein $R^1$ is aryl, heteroaryl, coumaryl or chromanyl; wherein $R^2$ is $N(R^a)(R^b)$; wherein $R^3$ is $N(R^c)(R^d)$; wherein Y is oxo or thioxo; wherein Z is $(C_1-C_{10})$alkyl; wherein $R^a$-$R^d$ are each independently hydrogen, $(C_1-C_{10})$alkyl, $(C_1-C_{10})$alkanoyl, phenyl, benzyl or phenethyl; or wherein $R^a$ and $R^b$, or $R^c$ and $R^d$, together with the nitrogen to which they are attached form a pyrrolidino, piperidino or morpholino ring; or a pharmaceutically acceptable salt thereof.

Further provided is a method of treating a mammal afflicted with, or at risk of, an indication associated with chemokine-induced activity, comprising: administering to the mammal an effective amount of a compound of formula (V):

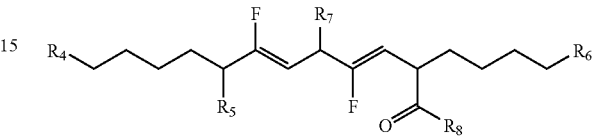

wherein $R^4$ is $NR_kR_l$; $R^5$ is $NR_mR_n$; $R^6$ is $NR_oR_p$; $R^7$ is the side chain of a natural or unnatural amino acid or is —$(CH_2)_2C(=O)NR_qR_r$; $R^8$ is hydrogen, hydroxy, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, $NR_sR_t$, the amino terminus of an amino acid or the N-terminal residue of a peptide of 2 to about 25 amino acid residues; $R_k$, $R_l$, $R_o$, and $R_p$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkanoyl, phenyl, benzyl or phenethyl; $R_m$ are $R_n$ are each independently hydrogen, $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_1-C_{10})$alkanoyl, $(C_1-C_{10})$alkoxycarbonyl, 9-fluorenylmethoxycarbonyl, phenyl, benzyl, phenethyl, the C-terminal residue of an amino acid or a peptide of 2 to about 25 amino acid residues; $R_q$ are $R_r$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; wherein $R_s$ are $R_t$ are each independently hydrogen, $(C_1-C_{10})$alkyl, $(C_3-C_6)$cycloalkyl, $(C_3-C_6)$cycloalkyl$(C_1-C_6)$alkyl, phenyl, benzyl or phenethyl; or a pharmaceutically acceptable salt thereof.

Also provided is a method of treating a mammal afflicted with, or at risk of, an indication associated with chemokine-induced activity, comprising: administering to the mammal an effective amount of a compound of formula (VI):

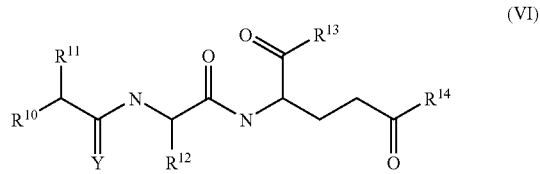

(VI)

wherein
$R^{10}$ is $NR^iR^j$;
$R^{11}$ is aryl, heteroaryl, aryl$(C_1-C_3)$alkyl, heteroaryl$(C_1-C_3)$alkyl, coumaryl, coumaryl$(C_1-C_3)$alkyl, chromanyl or chromanyl$(C_1-C_3)$alkyl; wherein any aryl or heteroaryl group, or the benz-ring of any coumaryl or chromanyl group may optionally be substituted with one, two or three substituents selected from the group consisting of halo, nitro, cyano, hydroxy, $(C_1-C_6)$alkyl, $(C_1-C_6)$alkoxy, $(C_1-C_6)$alkanoyl, $(C_2-C_6)$alkanoyloxy, —$C(=O)(C_1-C_6)$alkoxy, $C(=O)NR^gR^h$, $NR^eR^f$;

R¹² is $(C_1-C_6)$alkyl;

R¹³ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy, hydroxy, or $N(R^a)(R^b)$;

R¹⁴ is $(C_1-C_{10})$alkyl, $(C_3-C_6)$cycloalkyl, $(C_3-C_6)$cycloalkyl$(C_1-C_6)$alkyl, $(C_1-C_{10})$alkoxy, $(C_3-C_6)$cycloalkyl$(C_1-C_6)$alkoxy or $N(R^c)(R^d)$;

Y is oxo or thioxo;

wherein $R^a$-$R^j$ are each independently hydrogen, $(C_1-C_{10})$alkyl, $(C_1-C_{10})$alkanoyl, phenyl, benzyl, or phenethyl; or $R^a$ and $R^b$, $R^c$ and $R^d$, $R^e$ and $R^f$, $R^g$ and $R^h$, or $R^i$ and $R^j$ together with the nitrogen to which they are attached form a ring selected from pyrrolidino, piperidino, or morpholino; or a pharmaceutically acceptable salt thereof.

The invention further provides a method to increase, augment or enhance a chemokine-associated inflammatory response in a mammal, comprising: administering to the mammal an amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof, effective to increase, augment or enhance said response. Moreover, as peptide 3, its variants and derivatives may decrease Th2 responses and increase Th1 responses, these compounds may be particularly useful to treat or prevent specific diseases in which a decrease in Th2 response and an increase in Th1 response is indicated. It is preferred that the agent employed to increase, augment or enhance the chemokine-associated inflammatory response is not YNFTNRKISVQRLASYRRITSSK. These therapeutic agents are useful to increase an inflammatory response to, for example, intracellular pathogens or parasites, which often are associated with a poor immune response. Thus, these agents may be useful to treat or prevent tuberculosis and malaria. Therefore, the invention also provides a therapeutic method to prevent or treat parasitic infection.

The invention also provides a method of preventing or inhibiting an indication associated with histamine release from basophils or mast cells. The method comprises administering to a mammal at risk of, or afflicted with, the indication an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof.

Also provided is a method of preventing or inhibiting an indication associated with monocyte, macrophage, neutrophil, B cell, T cell or eosinophil recruitment, or B cell or T cell activation or proliferation. The method comprises administering an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. For example, a chemokine peptide 3, a chemokine peptide 2, a variant thereof, or a derivative thereof may be useful to prevent or treat autoimmune or granulomatous indications.

Further provided is a therapeutic method to prevent or treat vascular indications, comprising: administering to a mammal in need of such therapy an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof, wherein the indication is coronary artery disease, myocardial infarction, unstable angina pectoris, atherosclerosis or vasculitis. Preferred chemokine peptides for this embodiment of the invention include chemokine peptides of MCP-1, RANTES, GROα, MIP1α, IP10, MCP-4, and MIP1β.

The invention also provides a method to prevent or treat an autoimmune disorder. The method comprises administering to a mammal in need of said therapy an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. A preferred variant of peptide 3 useful to prevent or treat autoimmune disorders is Leu₄Ile₁₁peptide 3(1-12)[MCP-1] (SEQ ID NO:14) or peptide 3 having WVQ. A preferred chemokine peptide 3 for use in preventing or treating multiple sclerosis includes SEE and peptide 3(1-14) [MIP1α] (SEQ ID NO:42). Other preferred peptides are chemokine peptides of RANTES.

Further provided is a method to modulate the chemokine-induced activity of macrophage, B cells, T cells or other hematopoietic cells, e.g., neutrophils, eosinophils or mast cells, at a preselected physiological site. The method comprises administering a dosage form comprising an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof, wherein the dosage form is linked, either covalently or noncovalently, to a targeting moiety. The targeting moiety binds to a cellular component at the preselected physiological site.

Moreover, it is also envisioned that an agent of the invention may be a targeting moiety, as some of the agents are selective chemokine inhibitors, rather than pan-chemokine inhibitors. For example, an agent of the invention, e.g., peptide 2, may be useful in the targeted delivery of an isotope or other cytotoxic molecule to red cells for the treatment of disorders such as erythroid leukemia, erythroid myelosis, polycythemia vera or other erythroid dysplasias. Similarly, an agent of the invention that specifically targets a particular cell type may be useful in diagnostics. Thus, these agents can be radiolabeled (Chianelli et al., *Nucl. Med. Comm.*, 18, 437 (1997)), or labeled with any other detectable signal, such as those useful in diagnostic imaging (e.g., MRI and CAT) to image sites of inflammation in disorders like rheumatoid arthritis and diabetes mellitus (type I).

Also provided is a therapeutic method to augment an immune response. The method comprises administering to a mammal an immunogenic moiety and an amount of a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof, wherein the amount is effective to augment the immune response of the mammal to the immunogenic moiety. Thus, the invention also provides a vaccine comprising an immunogenic moiety and an amount of a chemokine peptide 2, a variant thereof or a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. As used herein, an "immunogenic moiety" means an isolated or purified composition or compound (e.g., a purified virus preparation or a native or recombinant viral or bacterial antigen) that, when introduced into an animal, preferably a mammal, results in a humoral and/or cellular immune response by the animal to the composition or compound. Also provided are modified vaccines, wherein the immunogenic moiety is coupled to peptide 2, a variant or derivative thereof. Peptide 2 increases the binding of the modified vaccine to the red blood cell pool and blocks Duffy binding of chemokines and so prolongs the residency time of the vaccine in the circulation and decreases chemokine-induced activity, either of which result in an augmented antibody response. It is envisaged that the modified vaccine is delivered by the same routes as those used for unmodified immunogen (e.g., intravenous, intramuscular or orally).

The invention also provides a therapeutic method to prevent or inhibit asthma. The method comprises administering to a mammal in need of such therapy an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. As described hereinbelow in Example 12, a peptide of the invention inhibited cellular inflammation and IgE responses in the lung of mice exposed to ovalbumin. Preferably, in this embodiment of the invention, a therapeutic agent is administered to the upper and/or lower respiratory tract. Preferred peptides useful in this embodiment of the invention are chemokine peptides of RANTES, MCP-1 and MIP1α.

Further provided is a therapeutic method to prevent or inhibit viral, e.g., poxvirus, herpesvirus (e.g., *Herpesvirus samiri*), cytomegalovirus (CMV) or lentivirus, infection or replication. The method comprises administering to a mammal in need of such therapy an effective amount of a chemokine peptide 3, a chemokine peptide 2, a variant thereof, a derivative thereof, a compound of formula (IV), or a compound of formula (V), a compound of formula (VI), a compound of formula (VII), a compound of formula (VIII), a compound of formula (LX), a compound of formula (X), a compound of formula (XI), a compound of formula (XII), or a combination thereof. Preferably, the therapeutic agents are employed to prevent or treat HIV. More preferably, the agent is administered before, during or after the administration of an anti-viral agent, e.g., for HIV AZT, a non-nucleoside reverse transcriptase inhibitor, a protease inhibitor or a combination thereof. It is also envisioned that a combination of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), or a compound of formula (XII) may be useful in the anti-viral methods and compositions of the invention. Preferred chemokine peptides useful to prevent or inhibit viral infection are those from IP10, MIP1α, MIP1β, SDF-1, IL-8, GROα, RANTES and MCP-1.

A therapeutic method to prevent or treat low bone mineral density is also provided. The method comprises administering to a mammal in need of such therapy an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. A preferred derivative of a variant of peptide 3 to prevent or treat low mineral bone density is CRD-$Cys_{13}Leu_4Ile_{11}$peptide 3(3-12)[MCP-1]. A preferred fragment of SEQ ID NO:1 useful in preventing or treating low mineral bone density is KQK.

Also provided is a method of suppressing tumor growth in a vertebrate animal comprising administering to said vertebrate a therapeutically effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. Preferably, the method increases or enhances macrophage, B cell-, T cell- or other immune cell-associated activity at a tumor site. A preferred peptide for use in this embodiment of the invention is a MCP-1 peptide.

Further provided is a method for preventing or treating rheumatoid arthritis in a mammal, comprising: administering to the mammal an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. For this embodiment of the invention, a preferred peptide is a MCP-1, MIP1α, MIP1β, GROα, and ENA78 peptide.

Also provided is a method to prevent or treat organ transplant rejection. The method comprises administering an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof.

Further provided is a method for preventing or treating psoriasis in a mammal, comprising: administering to the mammal an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. Preferred peptides to prevent or treat psoriasis are peptides of MCP-1, RANTES, MIP1α, MIG, IP10, GROβ, GROα or MCP-3. A preferred derivative to prevent or treat psoriasis is a CRD-derivative of peptide 3.

Also provided is a method to enhance wound healing. The method comprises administering an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof.

Further provided is a method for preventing or treating an allergy in a mammal, comprising: administering to the mammal an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof. Preferred peptides to prevent or treat allergies include peptides of RANTES, MIP1α, MCP-1, MCP-2, MCP-3, MCP-4, eotaxin or MIP1β.

Yet another embodiment of the invention is a method to prevent or inhibit an indication associated with elevated TNF-α. The method comprises administering an effective amount of a chemokine peptide 3, a chemokine peptide 2, a variant thereof, a derivative thereof, a compound of formula (IV), a compound of formula (V), a compound of formula (VI), a compound of formula (VII), a compound of formula (VIII), a compound of formula (IX), a compound of formula (X), a compound of formula (XI), a compound of formula (XII), or a combination thereof.

The invention also provides methods in which the nucleic acid molecules of the invention are administered to a mammal afflicted with, or at risk of, an indication associated with a chemokine-induced activity.

The invention also provides methods whereby the pharmacokinetics of desirable pharmaceutical agents may be modulated. In particular, agents which are normally rapidly cleared from the circulation may be retained longer by the addition of a peptide of the invention that has affinity for the Duffy antigen on red blood cells. This methodology may be particularly suited to modifying the pharmacokinetics of other biologically active, pharmaceutically useful peptides, as well as larger polypeptide or proteins. For example, a Duffy binding peptide (such as peptide 2[MCP-1] may be coupled or linked, either covalently or non-covalently, to a molecule such as recombinant human growth hormone (HGH) or insulin, and administered via a depo injection. By partitioning the modified HGH to the red blood cells, HGH may have much more suitable pharmacokinetics, with longer half times and less rapid changes in plasma concentrations. In another example, insulin coupled to a peptide of the invention may be particularly useful as a treatment for the highly insulin-resistant type II diabetic whose disease has progressed significantly. It is also envisioned that other small molecules may be coupled to Duffy binding molecules in a manner which preserves the intended function of the active molecule and of the Duffy binding molecule. For coupling to recombinant proteins and peptides, Duffy binding peptides are preferred. For coupling to small molecule drugs, analogs (e.g., isosteres) of Duffy binding peptides are preferred.

BRIEF DESCRIPTION OF THE FIGURES

FIG. 12 depicts codons for various amino acids.

FIG. 13 depicts exemplary amino acid substitutions.

FIG. 14 shows exemplary therapeutic agents of the invention.

FIG. 15 shows the Duffy binding affinity and inhibition of THP-1 migration for selected peptide 2 compounds. LFL=linear forward L isomer; LRD=linear reverse D isomer; CRD=cyclic reverse D isomer; CFL=cyclic forward L isomer.

FIG. 16 summarizes binding and ED$_{50}$ data for selected peptides of the invention.

FIG. 17 shows an exemplary protocol to test agents in a rat dermal inflammation model (CRD-Cys$_{13}$Leu$_4$Ile$_{11}$ peptide 3(3-12)[MCP-1]=NR58-3.14.3).

DETAILED DESCRIPTION OF THE INVENTION

Definitions

Figure 1:
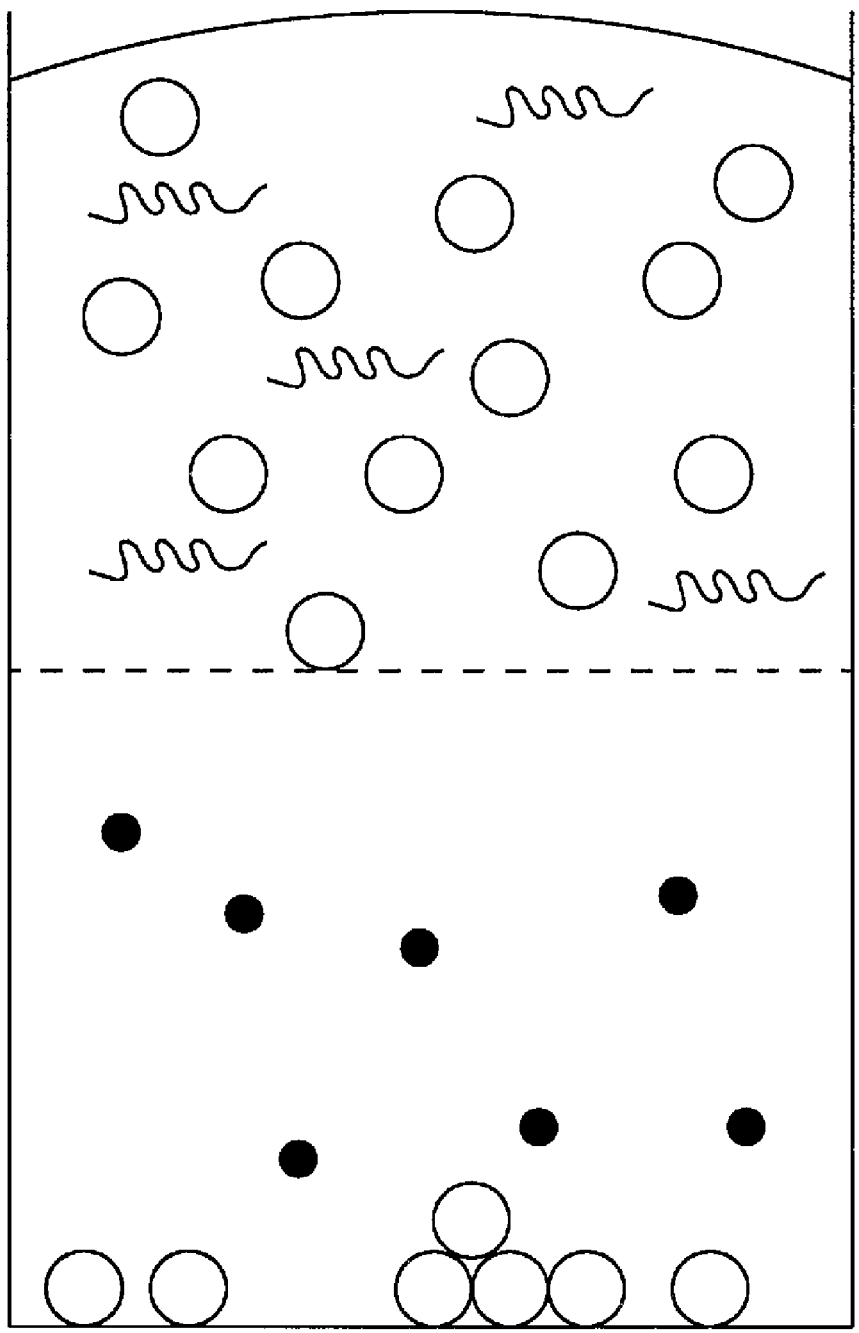
FIG. 1 is a schematic of the trans-well migration assay. In most experiments, the peptide (wavy line) is added to the upper well with about 50,000 cells (○). The upper and lower wells are separated by a 5 μm or 8 μm pore size PVP-free membrane (----). Chemokine (●) is added to the lower well. After 4 hours, the number of cells that have migrated through the membrane are measured (○ in lower well).

"Chemokines" refers to a family of proinflammatory signaling molecules which act on macrophage, B cells, T cells, neutrophils, eosinophils, basophils, mast cells, smooth muscle cells, e.g., vascular smooth muscle cells, and the like (e.g., by affecting their migration, proliferation, or degranulation, or the immunomodulation of T cell development to Th1 and Th2 subtypes). Preferred chemokines are primate in origin, e.g., human, although the invention includes other mammalian chemokines, such as those of bovine, ovine, equine, canine, feline or rodent origin, as well as virally encoded chemokines. Chemokines include, but are not limited to, MCP-1 (SEQ ID NO:16), MCP-2 (SEQ ID NO:17), MCP-3 (SEQ ID NO:18), MIG, MIP1α (SEQ ID NO:19), MIP1β (SEQ ID NO:20), RANTES (SEQ ID NO:21), PF4, I-309, HCC-1 (SEQ ID NO:48), eotaxin (SEQ ID NO:25), C10, CCR-2, ENA-78, GROα (SEQ ID NO:24), GROβ, IL-8 (SEQ ID NO:23), IP-10, SDF1α, SDF1β (SEQ ID NO:56), GROα, MIP3α, TCA-3, CTAPIII, MARC/FYK, β-thromboglobulin, GCP-2, PBP, HC14, MDC, TECK, PARC, 6Ckine, fractaline, DC-CK1, LIX, TARC, LARC, MIG, Ckβ8, CCF18/MRP-2, CCIII, CKα2, H1305, Dvic-1, MGSA, Ckβ34, DGWCC, TCA4, dendrokine (see WO 97/29192), CC2/HCC1, CC3, and MIP1τ, as well as virally encoded chemokines such as vMIP-I, vMIP-II and vMIP-III (see Kledal et al., *Science,* 277, 1656 (1997)). "CXC" or "α" chemokines include, but are not limited to, IL-8, PF4, IP10, NAP-2, GROα, GROβ, GROγ, SDF1, MIP2, MGSA, γIP, CTAPIII, β-thromboglobulin, MIG, PBP, NAP-2 and ENA78. "CC" or "β" chemokines include, but are not limited to, MCP-1, MCP-2, MCP-3, MCP-4, MCP-5, RANTES, eotaxin, LARC, TARC, C10, MIP1α, MIP1β, I309, HCC-1, CKβ8, CCF18/MRP-2, MIP1τ. A third type of chemokines are "C" chemokines, e.g., lymphotactin. A fourth type of chemokines are "CX$_3$C" chemokines such as fractaline or neurotactin (Rollins et al., *Blood,* 90, 404 (1997)). A fifth type of chemokines, CX$_2$C chemokines, include CCIII.

"Peptide 3" refers to a peptide derived from a chemokine, which is generally located in the carboxy-terminal half of the chemokine, and which inhibits the activity of at least the corresponding native chemokine, as determined by methods well known to the art. Peptide 3 comprises no more than 30, preferably about 3 to about 25, more preferably about 3 to about 15, and even more preferably about 3 to about 11, peptidyl residues which have 100% contiguous amino acid sequence homology or identity to the amino acid sequence of the corresponding native chemokine, preferably a mammal chemokine, e.g., a primate chemokine such as a human chemokine, or a virally-encoded chemokine. For example, a preferred peptide 3 of MCP-1 that inhibits at least the activity of MCP-1 is peptide 3(1-12)[MCP-1], e.g., a peptide which has an amino acid sequence corresponding to SEQ ID NO:1, or a fragment or derivative thereof. Another preferred embodiment of the invention is peptide 3(3-12)[MCP-1], e.g., a peptide having an amino acid sequence corresponding to SEQ ID NO:7, or a fragment or derivative thereof. Preferably, a chemokine peptide 3 of the invention does not include a peptide of IL-8, PF-4 or NAP-2.

An alignment of chemokine amino acid sequences, such as the alignment depicted in Table 1, provides a general method to identify the location of peptide 3 sequences in chemokines. Generally, peptide 3 in non-MCP-1 chemokines corresponds to about residue 46 to about residue 67 of mature human MCP-1. Moreover, it is envisioned that peptide 3 may comprise moieties other than the amino acid sequence which inhibits chemokine activity, e.g., amino acid residues not present in the native chemokine (i.e., a fusion protein), nucleic acid molecules or targeting moieties such as antibodies or fragments thereof or biotin, so long as these moieties do not substantially reduce the biological activity of peptide 3. A substantial reduction in activity means a reduction in activity of greater than about 99%.

"Peptide 2" refers to a peptide derived from a chemokine, which is generally located in the amino-terminal two-thirds of the chemokine, and which does not include the amino-terminal about 20 to about 24 amino acid residues of the native mature chemokine. Generally, peptide 2 is a chemokine agonist, but peptide 2 may also have neither agonist or antagonist activities (i.e., it is "neutral"), or may be a chemokine antagonist, so long as the peptide specifically binds to at least one chemokine receptor. Peptide 2 comprises no more than 30, preferably about 3 to about 25, more preferably about 10 to about 25, and even more preferably about 10 to about 18, peptidyl residues which have 100% contiguous amino acid sequence homology or identity to the amino acid sequence of the corresponding native chemokine. For example, a preferred peptide 2 of MCP-1 is peptide 2(1-15)[MCP-1], for example a peptide which has an amino acid sequence corresponding to SEQ ID NO:3, or a fragment or derivative thereof. A more preferred peptide 2 is a peptide 2 comprising at least one D isomer. Preferably, a chemokine peptide 2 of the invention is not peptide 2[PF4], peptide 2[IL-8], peptide 2 [NAP-2] or YNFTNRKISVQRLASYRRITSSK.

An alignment of chemokine amino acid sequences, such as the alignment depicted in Table 1, provides a general method to identify the location of peptide 2 sequences in other chemokines. Generally, peptide 2 in non-MCP-1 chemokines corresponds to about residue 27 to about residue 45 on mature human MCP-1. It is also envisioned that peptide 2 may comprise moieties other than the amino acid sequence which mimics, enhances or does not affect (i.e., neutral) chemokine activity, e.g., amino acid residues not present in the native chemokine, nucleic acid molecules or targeting moieties such as those described above for peptide 3, so long as these moieties do not substantially alter the biological activity of peptide 2. A substantial alteration in activity means an alteration of greater than about 99%.

Also preferably, a peptide, variant, analog or derivative of the invention, has increased affinity for at least one chemokine receptor, e.g., about 1 μM to about 1 nM, more preferably about 1 nM to about 1 pM, and also preferably has decreased Duffy binding, relative to a corresponding peptide having the native ("wild-type") sequence or relative to the corresponding native chemokine. However, certain populations have individuals who are Duffy$^-$, e.g., a certain percentage of African Americans are Duffy$^-$. Thus, agents useful to treat these populations may have Duffy binding affinity that is equal to or greater than that of the corresponding native chemokine.

As used herein, the terms "isolated and/or purified" refer to in vitro preparation, isolation and/or purification of a therapeutic agent of the invention, so that it is not associated with in vivo substances. Thus, with respect to an "isolated nucleic acid molecule", which includes a polynucleotide of genomic, cDNA, or synthetic origin or some combination thereof, the "isolated nucleic acid molecule" (1) is not associated with all or a portion of a polynucleotide in which the "isolated nucleic acid molecule" is found in nature, (2) is operably linked to a polynucleotide which it is not linked to in nature, or (3) does not occur in nature as part of a larger sequence. An isolated nucleic acid molecule means a polymeric form of nucleotides of at least 10 bases in length, either ribonucleotides or deoxynucleotides or a modified form of either type of nucleotide. The term includes single and double stranded forms of DNA. The term "oligonucleotide" referred to herein includes naturally occurring, and modified nucleotides linked together by naturally occurring, and non-naturally occurring oligonucleotide linkages. Oligonucleotides are a polynucleotide subset with 200 bases or fewer in length. Preferably, oligonucleotides are 10 to 60 bases in length and most preferably 12, 13, 14, 15, 16, 17, 18, 19, or 20 to 40 bases in length. Oligonucleotides are usually single stranded, e.g., for probes; although oligonucleotides may be double stranded, e.g., for use in the construction of a variant. Oligonucleotides of the invention can be either sense or antisense oligonucleotides. The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phosphoraniladate, phosphoroamidate, and the like. An oligonucleotide can include a label for detection, if desired.

The term "isolated polypeptide" means a polypeptide encoded by cDNA or recombinant RNA, or is synthetic origin, or some combination thereof, which isolated polypeptide (1) is not associated with proteins found in nature, (2) is free of other proteins from the same source, e.g., free of human proteins, (3) is expressed by a cell from a different species, or (4) does not occur in nature.

The term "sequence homology" means the proportion of base matches between two nucleic acid sequences or the proportion amino acid matches between two amino acid sequences. When sequence homology is expressed as a percentage, e.g., 50%, the percentage denotes the proportion of matches over the length of sequence from a chemokine that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

The term "selectively hybridize" means to detectably and specifically bind. Polynucleotides, oligonucleotides and fragments of the invention selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the invention and a nucleic acid sequence of interest is at least 65%, and more typically with preferably increasing homologies of at least about 70%, about 90%, about 95%, about 98%, and 100%.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) *Adv. Appl. Math.* 2: 482, by the homology alignment algorithm of Needleman and Wunsch (1970) *J. Mol. Biol.* 48: 443, by the search for similarity method of Pearson and Lipman (1988) *Proc. Natl. Acad. Sci. (U.S.A.)* 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denote a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 20-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence, for example, as a segment of human MCP-1.

As applied to polypeptides, the term "substantial identity" means that two peptide sequences, when optimally aligned, such as by the programs GAP or BESTFIT using default gap weights, share at least about 80 percent sequence identity, preferably at least about 90 percent sequence identity, more preferably at least about 95 percent sequence identity, and most preferably at least about 99 percent sequence identity.

As used herein, the terms "label" or "labeled" refer to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). Various methods of labeling polypeptides are known in the art and may be used. Examples of labels for polypeptides include, but are not limited to, the following: radioisotopes (e.g., $^3$H, $^{14}$C, $^{35}$S, $^{125}$O, $^{131}$I), fluorescent labels (e.g., FITC, rhodamine, lanthanide, phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 80 percent of all macromolecular species present in the composition, more preferably more than about 85%, about 90%, about 95%, and about 99%. Most preferably, the object species is purified to essential homogeneity (contaminant species cannot be detected in the composition by conventional detection methods) wherein the composition consists essentially of a single macromolecular species.

An isolated "chemokine peptide variant" of peptide 3 or peptide 2 is a peptide comprising no more than 30, preferably about 3 to about 25, and more preferably about 3 to about 18, and even more preferably about 3 to about 11, peptidyl residues which have at least 50%, preferably at least about 80%, and more preferably at least about 90% but less than 100%, contiguous amino acid sequence homology or identity to the amino acid sequence of the corresponding native chemokine, e.g., $Ser_7$ peptide 3(1-12)[MCP1] (SEQ ID NO:11) has less than 100% homology to the corresponding amino acid sequence of MCP-1, i.e., peptide 3(1-12)[MCP-1] (SEQ ID NO:1). A variant of the invention may include amino acid residues not present in the corresponding native chemokine, and internal deletions relative to the corresponding native chemokine. Chemokine peptide variants include peptides having at least one D-amino acid.

Chemokine peptides or peptide variants which are subjected to chemical modifications, such as esterification, amidation, reduction, protection and the like, are referred to as chemokine "derivatives." For example, a modification known to improve the stability and bioavailability of peptides in vivo is the cyclization of the peptide, for example through one or more disulfide bonds. A preferred modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like. A preferred derivative of the invention is CRD-$Cys_0Cys_{13}Leu_4Ile_{11}$peptide 3[MCP-1] or CRD-$Cys_{13}Leu_4Ile_{11}$ peptide 3(3-12)[MCP-1].

Also included within the scope of the term "derivative" is linear reverse D (LRD) and cyclized forward L (CFL) derivatives. LRD derivatives have the reverse (i.e., C-terminal to N-terminal) sequence of the peptide with all D-form amino acids, but are not cyclized. CFL derivatives have the forward (i.e., N-terminal to C-terminal) sequence of the peptide with all L-form amino acids, but with additional N and C terminal cys residues (if the peptide sequence does not already have cys residues at either the N or the C terminal position), followed by oxidative cyclization, or cyclization by an alternative method. Other "derivatives" of the invention include branched peptides, circular, branched and branched circular peptides.

A "chemokine analog" means a moiety that mimics or inhibits a chemokine-induced activity, or binds to or near a chemokine receptor but does not mimic or inhibit chemokine activity (neutral), wherein the portion of the moiety that mimics or inhibits the chemokine-induced activity, or binds to or near the receptor but is neutral, is not a peptide, and wherein the active portion of the analog is not a nucleic acid molecule. As used herein, the term "mimics" means that the moiety induces an activity that is induced by a native chemokine, but that the induction by the analog is not necessarily of the same magnitude as the induction of activity by the native chemokine.

It is also envisioned that the chemokine peptides, variants, analogs and derivatives thereof, of the invention may comprise moieties other than the portion which inhibits or mimics chemokine activity, or binds to or near a chemokine receptor without eliciting or inhibiting signaling, e.g., peptide or polypeptide molecules, such as antibodies or fragments thereof or fusion proteins, nucleic acid molecules, sugars, lipids, fats, a detectable signal molecule such as a radioisotope, e.g., gamma emitters, paramagnetic molecules or sound wave emitters, small chemicals, metals, salts, synthetic polymers, e.g., polylactide and polyglycolide, surfactants and glycosaminoglycans, which preferably are covalently attached or linked to the portion of the peptide, variant, analog or derivative that mimics or inhibits the chemokine-induced activity, so long as the other moieties do not alter the biological activity of the peptide, variant, analog or derivative. Also envisioned is a chemokine peptide, variant, analog or derivative that is non-covalently associated with the moieties described above.

A preferred chemokine analog of the invention is a compound of formula (IV):

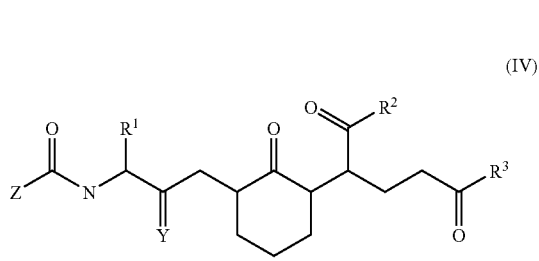

(IV)

wherein R¹ is aryl, heteroaryl, aryl($C_1$-$C_3$)alkyl, heteroaryl ($C_1$-$C_3$)alkyl, coumaryl, coumaryl($C_1$-$C_3$)alkyl, chromanyl or chromanyl($C_1$-$C_3$)alkyl; wherein any aryl or heteroaryl group, or the benz-ring of any coumaryl or chromanyl group may optionally be substituted with one, two or three substituents selected from the group consisting of halo, nitro, cyano, hydroxy, ($C_1$-$C_6$)alkyl, ($C_1$-$C_6$)alkoxy, ($C_1$-$C_6$)alkanoyl, ($C_2$-$C_6$)alkanoyloxy, —C(=O)($C_1$-$C_6$)alkoxy, C(=O)NR$^g$R$^h$, NR$^i$R$^j$;

wherein R² is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl($C_1$-$C_6$)alkoxy or N(R$^a$)(R$^b$);

wherein R³ is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl($C_1$-$C_6$)alkoxy or N(R$^c$)(R$^d$);

wherein Y is oxo or thioxo;

wherein Z is ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl($C_1$-$C_6$)alkoxy or N(R$^e$)(R$^f$); and wherein R$^a$-R$^j$ are each independently hydrogen, ($C_1$-$C_{10}$)alkyl, ($C_1$-$C_{10}$)alkanoyl, phenyl, benzyl, or phenethyl; or R$^a$ and R$^b$, R$^c$ and R$^d$, R$^e$ and R$^f$, R$^g$ and R$^h$, or R$^i$ and R$^j$ together with the nitrogen to which they are attached form a ring selected from pyrrolidino, piperidino, or morpholino; or a pharmaceutically acceptable salt thereof.

A preferred embodiment of a compound of formula (IV) includes a compound of formula (IV) wherein R¹ is aryl, heteroaryl, coumaryl, or chromanyl. Preferably aryl is phenyl; and heteroaryl is indolyl or pyridinyl. Another preferred embodiment of a compound of formula (IV) includes a compound of a formula (IV) wherein R² is N(R$^a$)(R$^b$); and R³ is N(R$^c$)(R$^d$). Yet another preferred embodiment of a compound of formula (IV) includes a compound of a formula (IV) wherein Z is ($C_1$-$C_{10}$)alkyl.

A further preferred compound is a compound of formula (IV) wherein R¹ is indolyl; R² is N(R$^a$)(R$^b$); R³ is N(R$^c$)(R$^d$); Y is S; Z is hydrogen; and R$^a$, R$^b$, R$^c$, and R$^d$ are each methyl.

Yet another preferred compound of formula (IV) includes a compound wherein R¹ is 2-benzimidazolyl; for R² is N(R$^a$)(R$^b$); R³ is N(R$^c$)(R$^d$); Y is oxo; and Z is N(R$^e$)(R$^f$) or a pharmaceutically acceptable salt thereof. Another preferred compound of formula (IV) is a compound wherein R¹ is 2-benzimidazolyl; R² is N(Me)$_2$; R³ is N(Me)$_2$; Y is oxo; and Z is N(Me)$_2$; or a pharmaceutically acceptable salt thereof.

Another preferred chemokine analog of the invention is a compound of formula (V):

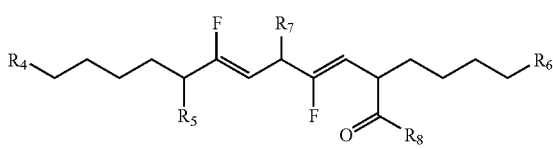

wherein R⁴ is NR$_k$R$_l$; wherein R⁵ is NR$_m$R$_n$; wherein R⁶ is NR$_o$R$_p$; wherein R⁷ is Nr$_q$R$_r$; wherein R⁸ is hydrogen, hydroxy, ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkoxy, ($C_3$-$C_6$)cycloalkyl ($C_1$-$C_6$)alkoxy, NR$_s$R$_t$, the amino terminus of an amino acid or the N-terminal residue of a peptide of 2 to about 25 amino acid residues; wherein R$_k$, R$_l$, R$_o$, and R$_p$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, ($C_1$-$C_{10}$)alkanoyl, phenyl, benzyl or phenethyl; wherein R$_m$ are R$_n$ are each independently hydrogen, ($C_1$-$C_{10}$)alkyl, ($C_3$-$C_6$)cycloalkyl, ($C_3$-$C_6$)cycloalkyl ($C_1$-$C_6$)alkyl, ($C_1$-$C_{10}$)alkoxy, ($C_1$-$C_{10}$)alkanoyl, ($C_1$-$C_{10}$)alkoxycarbonyl, 9-fluorenylmethoxycarbonyl, phenyl, benzyl, phenethyl, the C-terminal residue of an amino acid or a peptide of 2 to about 25 amino acid residues; wherein R$_q$ are R$_r$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, phenyl, benzyl or phenethyl; wherein R$_s$ are R$_t$ are each independently hydrogen, ($C_1$-$C_{10}$)alkyl, ($C_3$-$C_6$)cycloalkyl, ($C_3$-$C_6$)cycloalkyl($C_1$-$C_6$)alkyl, phenyl, benzyl or phenethyl; or a pharmaceutically acceptable salt thereof.

Preferably R$_k$, R$_l$, R$_o$, and R$_p$ are each hydrogen; R$_m$ are R$_n$ are each independently hydrogen, acetyl, ($C_1$-$C_{10}$)alkyl, ($C_3$-$C_6$)cycloalkyl, propoxy, butoxy, tert-butoxycarbonyl, 9-fluorenylmethoxycarbonyl, the C-terminal residue of an amino acid or a peptide of 2 to about 25 amino acid residues; and R$_q$ are R$_r$ are each independently hydrogen, ($C_1$-$C_{10}$)alkyl, or ($C_3$-$C_6$)cycloalkyl.

A further preferred chemokine analog of the invention is a compound of formula (VI):

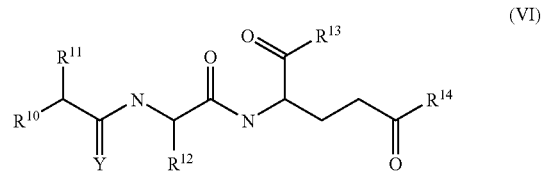

As used herein, halo is fluoro, chloro, bromo, or iodo. The terms alkyl and alkoxy denote both straight and branched groups, but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(R⁴) wherein R⁴ is absent or is hydrogen, ($C_1$-$C_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

It will be appreciated by those skilled in the art that compounds of formula (IV), (V), or (VI) including compounds of the invention which are peptides having chiral centers, may exist in and be isolated in optically active and racemic forms. For example, compounds of the invention comprise α-amino acid residues in D or L form, or mixtures thereof. Some compounds may exhibit polymorphism. It is to be understood that the present invention encompasses any racemic, optically-active, polymorphic, or stereoisomeric form, or mixtures thereof, of a compound of the invention, which possess the useful properties described herein. It is well known in the art how to prepare optically active forms (for example, by resolution of the racemic form by recrystallization techniques, by synthesis, from optically-active starting materials, by chiral synthesis, or by chromatographic separation using a chiral stationary phase). It is also well known to the art how to determine a compounds ability to inhibit or enhance chemokine-induced activity using the standard tests described herein, or using other tests which are well known in the art.

Specific and preferred values listed herein for radicals, substituents, and ranges, are for illustration only and they do not exclude other defined values or other values within defined ranges for the radicals and substituents. Specifically, ($C_1$-$C_{10}$)alkyl can be methyl, ethyl, propyl, isopropyl, butyl, iso-butyl, sec-butyl, pentyl, 3-pentyl, hexyl, heptyl, octyl, nonyl, or decyl; ($C_1$-$C_6$)alkyl can be methyl, ethyl, propyl, isopropyl, butyl, iso-butyl, sec-butyl, pentyl, 3-pentyl, or hexyl; ($C_1$-$C_3$)alkyl can be methyl, ethyl, or propyl; ($C_3$-$C_6$) cycloalkyl can be cyclopropyl, cyclobutyl, cyclopentyl, or cyclohexyl; ($C_1$-$C_{10}$)alkoxy can be methoxy, ethoxy, propoxy, isopropoxy, butoxy, iso-butoxy, sec-butoxy, pentoxy, 3-pentoxy, hexyloxy, heptyloxy, octyloxy, nonyloxy, or decyloxy; ($C_1$-$C_6$)alkoxy can be methoxy, ethoxy, propoxy, isopropoxy, butoxy, iso-butoxy, sec-butoxy, pentoxy, 3-pentoxy, or hexoxy; ($C_1$-$C_{10}$)alkanoyl can be formyl, acetyl, propanoyl, butanoyl, pentanoyl, hexanoyl, heptanoyl, octanoyl, nonanoyl, or decanoyl; ($C_1$-$C_6$)alkanoyl can be formyl, acetyl, propanoyl, butanoyl, pentanoyl, or hexanoyl; ($C_2$-$C_6$) alkanoyloxy can be acetoxy, propanoyloxy, butanoyloxy, pentanoyloxy, or hexanoyloxy; aryl can be phenyl, indenyl, or naphthyl; and heteroaryl can be furyl, imidazolyl, tetrazolyl, pyridyl, (or its N-oxide), thienyl, benzimidazolyl (or its N-oxide), pyrimidinyl (or its N-oxide), indolyl, or quinolyl (or its N-oxide).

Preferably, the therapeutic agents of the invention are biologically active. The biological activity of a chemokine peptide, peptide variant, analog or derivative thereof, can be measured by methods known to the art, some of which are described hereinbelow. For example, biologically active peptide 3[MCP-1] variants falling within the scope of the invention have at least about 1%, preferably at least about 10%, more preferably at least about 50%, and even more preferably at least about 90%, the activity of the corresponding native peptide sequence, e.g., peptide 3(1-12)[MCP-1] (SEQ ID NO:1), or the native chemokine, e.g., MCP-1 (SEQ ID NO:16). Thus, a peptide 3 variant, e.g., Leu$_4$Ile$_{11}$peptide 3(1-12)[MCP-1], falling within the scope of the invention has an $ED_{50}$ for inhibition that is at least about 1%, preferably at least about 10%, more preferably at least about 50%, and even more preferably at least about 90%, the maximal activity of peptide 3(1-12)[MCP-1] (SEQ ID NO:1) at 100 µM.

Similarly, for example, peptide 2[MCP-1], variants, analogs or derivatives falling within the scope of the invention have an $ED_{50}$ for a chemokine-like activity which is at least about 1%, preferably at least about 10%, more preferably at least about 50%, and even more preferably at least about 90%, the maximal activity of SEQ ID NO:3 at 100 µM. Alternatively, peptide 2, variants, analogs or derivatives falling within the scope of the invention bind to cells having at least one chemokine receptor with an association constant that is at least about 1%, preferably at least about 10%, more preferably at least about 50%, and even more preferably at least about 90%, the affinity of peptide 2(1-15)[MCP-1] (SEQ ID NO:3) for the same receptor.

As used herein, "a chemokine-induced activity" includes, but is not limited to, an activity that is elicited through the binding of a chemokine, a therapeutic agent of the invention or other moiety, e.g., viral protein, to a chemokine receptor, or the binding of a therapeutic agent or other moiety in close physical proximity to the receptor so that the activity is altered. Chemokine receptors include, but are not limited to, CCR1, CCR2a, CCR2b, CCR3, CCR4, CCR5, CCR6, CCR7, CCR8, IL8R1, IL8R2, CC-CKRI, CC-CKR2, CC-CKR3, CXCR1, CXCR2, CXCR3, CX$_3$CR1 and CXCR4. Chemotide receptors play a role in cell migration, cell activation, viral or parasite entry, release of proinflammatory compounds, and the like.

As used herein, "indications associated with chemokine-induced activity" includes, but is not limited to, atherosclerosis and other forms of local or systemic vasculitis, diseases such as myocardial infarction, stroke and acute ischemia which are secondary to atherosclerosis; hypertension; reperfusion injury (Kumar et al., *Circulation*, 95, 693 (1997)); aortic aneurysms; vein graft hyperplasia; angiogenesis; hypercholesterolemia; congestive heart failure; Kawasaki's disease; stenosis or restenosis, particularly in patients undergoing angioplasty; pathologically low bone mineral density, such as osteoporosis (Posner et al., *Bone,* 21, 321 (1997)); ulcerative colitis; chronic obstructive pulmonary disease; infection with human immunodeficiency virus (HIV), other lentiviruses or retroviruses with similar mechanisms of cell entry via chemokine receptor(s), or infection with other viruses, e.g., cytomegalovirus (Sozzani et al., *J. Leukoc. Biol.*, 62, 30 (1997)), or viral infection resulting in viral meningitis; organ transplantation, such as acute transplant rejection, allograft rejection and graft versus host disease; transplant vasculopathy; malaria and other consequences of infection by parasites related to plasmodium; asthma; allergic diseases, such as atopy (IgE-mediated components), allergic rhinitis, atopic dermatitis, anaphylaxis, allergic bronchopulmonary aspergillosis (IgE-mediated), and hypersensitivity pneumonitis (high IgG and reactive T cells) (pigeon breeders disease, farmer's lung disease, humidifier lung disease, malt workers' lung disease); allergies, including flea allergy dermatitis in mammals such as domestic animals, e.g., dogs and cats, contact allergens including mosquito bites or other insect sting allergies, poison ivy, poison oak, poison sumac, or other skin allergens; urticaria; eczema; pulmonary fibrosis such as idiopathic pulmonary fibrosis; cystic fibrosis; hemolytic uremic syndrome (Van Setten et al., *Pediatr. Res.*, 43, 759 (1998)); autoimmune disorders, including, but not limited to, type I diabetes, Crohn's disease, multiple sclerosis, arthritis, rheumatoid arthritis (Ogata et al., *J. Pathol.,* 182, 106 (1997); Gong et al., *J. Exp. Med.,* 186, 131 (1997)), systemic lupus erythematosus, autoimmune (Hasimoto's) thyroiditis, autoimmune liver diseases such as hepatitis and primary biliary cirrhosis, hyperthyroidism (Graves' disease; thyrotoxicosis), insulin-resistant diabetes, autoimmune adrenal insufficiency (Addison's disease), autoimmune oophoritis, autoimmune orchitis, autoimmune hemolytic anemia, paroxysmal cold hemoglobinuria, Behcet's disease, autoimmune thrombocytopenia, autoimmune neutropenia, pernicious anemia, pure red cell anemia, autoimmune coagulopathies, myasthenia gravis, autoimmune polyneuritis, experimental allergic encephalomyelitis, pemphigus and other bullous diseases, rheumatic carditis, Goodpasture's syndrome, postcardiotomy syndrome, Sjogren's syndrome, polymyositis, dermatomyositis, and scleroderma; eye diseases such as uveitis or blinding Herpes stromal keratitis; liver disease; erhlichiosis or Lyme disease including Lyme arthritis; aberrant hematopoiesis; nephritis due to, for example, autosomal dominant polycystic kidney disease, diabetic nephropathy, IgA nephropathy, interstitial fibrosis, or lupus; as well as other disease states resulting from inappropriate inflammation, either local or systemic, for example, irritable or inflammatory bowel syndrome (Mazzucchelli et al., *J. Pathol.*, 178, 201 (1996)), psoriasis (Gillitzer et al., *Arch. Dermatol. Res.*, 284, 26 (1992); Yu et al., *Lab Investig.*, 71, 226 (1994)), delayed type hypersensitivity, Alzheimer's disease, chronic pulmonary inflammation, e.g., pulmonary alveolitis and pulmonary granuloma, gingival inflammation or other periodontal disease, and osseous inflammation associated with lesions of endodontic origin (Volejnikova et al., *Am. J. Pathol.*, 150, 1711 (1997)), hypersensitivity lung diseases such as hypersensitivity pneumonitis (Sugiyama et al., *Eur. Respir. J.*, 8, 1084 (1995)), and inflammation related to histamine release from basophils (Dvorak et al., *J. Allergy Clin. Immunol.*, 98, 355 (1996)), such as hay fever, histamine release from mast cells (Galli et al., *Ciba Foundation Symposium*, 147, 53(1989)), or mast cell tumors, types of type 1 hypersensitivity reactions (anaphylaxis, skin allergy, hives, allergic rhinitis, and allergic gastroenteritis); glomerulonephritis (Gesualdok et al., *Kidney International*, 51, 155 (1997)); inflammation associated with peritoneal dialysis (Sach et al., *Nephrol. Dial. Transplant*, 12, 315 (1997)); and pancreatitis.

Other indications falling within the scope of the invention include, but are not limited to, neoplasia, e.g., histocytoma, glioma, sarcoma, osteosarcoma, osteoma (Zheng et al., *J. Cell Biochem.*, 70, 121 (1998)), melanoma, Kaposi's sarcoma, small cell lung cancer, and ovarian carcinoma as well as myelosuppression and mucositis associated with chemotherapy; brain or spinal cord trauma, such as after disc surgery (Ghirnikar et al., *J. Neurosci. Res.*, 46, 727 (1996); Berman et al., *J. Immunol.*, 156, 3017 (1996)); gout; lung disease, e.g., due to respiratory syncicial virus infection of humans, cattle, pigs and the like, or lung injury (Lukacs et al., *Adv. Immunol.*, 62, 257 (1996)); strokes; Loeffler's syndrome; chronic eosinophilic pneumonia; pulmonary fibrosis; wound healing; bacterial infection, e.g., bacterial peritonitis or meningitis; granulomatous diseases such as Mycobacteriosis, Pneumocystosis, Histoplasmosis, Blastomycosis, Coccidiomycosis, Cryptococcosis, Aspergillosis, granulomatous enteritis, Candidiasis, foreign body granulomas and peritonitis, pulmonary granulomatosis, Wegener's granulomatosis (Del Papa et al., *Arthritis Rheum.*, 39, 758 (1996)), leprosy, syphilis, cat-scratch disease, schistosomiasis (Jacobs et al., *Am. J. Pathol.*, 150, 2033 (1997)), silicosis, sarcoidosis (Iida et al., *Thorax*, 52, 431 (1997); Car et al., *Am. J. Respir. Crit. Care Med.*, 149, 655 (1994)) and berylliosis; lethal endotoxemia (Zisman et al., *J. Clin. Invest.*, 99, 2832 (1997)); and indications associated with a weak inflammatory response, e.g., which occur in parasitic infection, e.g., Leishmaniasis (Moll, *Biol. Abs.*, 104, 21765 (1997)), trypanosome, *Mycobacterium leprae* or *Mycobacterium tuberculosis* infection, helminth infections, such as nematodes (round worms); (Trichuriasis, Enterobiasis, Ascariasis, Hookworm, Strongyloidiasis, Trichinosis, filariasis); trematodes (fluxes) (Schistosomiasis, Clonorchiasis), cestode (tape worms) (Echinococcosis, Taeniasis saginata, Cysticercosis); visceral works, visceral larva migrans (e.g., *Toxocara*), eosinophilic gastroenteritis (e.g., *Anisaki* spp., *Phocanema* ssp.), cutaneous larva migrans (*Ancylostoma braziliense, Ancylostoma caninum*), or fungal infection.

In addition, to prevent or treat indications associated with a weak inflammatory response, the agents of the invention, i.e., peptide 2, its variants, analogs and derivatives, may be employed as vaccine adjuvants.

The peptides of the invention may also be useful as contraceptives or to induce abortion, in acute respiratory distress syndrome, and diseases where steroids are routinely used (e.g., relapsing Beheers colitis and asthma).

Also included within the scope of the invention are indications associated with tumor necrosis factor α (TNFα), e.g., rheumatoid arthritis or endotoxemia, or indications associated with elevated levels of TNFα. These indications include, but are not limited to, endotoxic shock; Crohn's disease; fever, and flu-like symptoms; acute interstitial pneumonitis; septic and nonseptic shock; acute respiratory distress syndrome; thromboembolic conditions; bone resorption; arthritis; acute graft versus host disease; cerebral malaria; cachexia of tuberculosis or cancer; lung injury; and idiopathic fibrosis.

I. Identification of Therapeutic Agents Falling within the Scope of the Invention Agents useful in the practice of the invention include agents that inhibit or reduce (e.g., chemokine receptor antagonists), or increase, augment or enhance (e.g., chemokine receptor agonists), chemokine-induced activity, e.g., monocyte or macrophage recruitment. These agents can be identified by in vitro and in vivo assays, such as the assays described hereinbelow. It is recognized that not all agents falling within the scope of the invention can inhibit or enhance chemokine-induced activity in vitro and in vivo. The therapeutic agents of the invention may be direct receptor binding agonists and/or antagonists, or may act by a different mechanism, e.g., duplex formation of antisense nucleic acid with chemokine mRNA, or by more than one mechanism, so as to result in the alteration of chemokine-induced activity.

A. Peptides, Variants, Derivatives and Analogs

1. In Vitro Chemotaxis

To determine whether an agent inhibits a chemokine-induced activity, such as macrophage recruitment, varying amounts of the agent are mixed with cells in the presence of a known chemoattractant. For example, a range of known concentrations of an agent, e.g., a chemokine peptide, is incubated with a defined number (e.g., $10^4$-$10^6$) of human THP-1 monocyte cells in individual wells of the top compartment of a trans-well plate. Chemokine (such as MCP-1, MIP1α, IL8 or SDF-1α), at a concentration known to cause significant migration of THP-1 cells in the trans-well migration assay, is placed in the lower compartment (FIG. 1). Cells are then incubated at 37° C. for a period sufficient to allow migration, e.g., 4 hours. After incubation, the cells are gently removed from the top of the filter with a pipette, 20 μl of 20 mM EDTA in simple PBS is added into each top well, and incubated for 20 minutes at 4° C. The filter is carefully flushed with media using a gentle flow, and removed. A standard curve consisting of a two-fold dilution series of THP-1 cells (in 29 μl) is prepared to accurately quantify the number of cells that have migrated. Migrated cells are stained with 3 μl of MTT stock dye solution which is added directly into each well (5 mg/ml in RPMI-1640 without phenol red, Sigma Chemical Co.) and incubated at 37° C. for 4 hours. The media is carefully aspirated from each well, and the converted dye is solubilized by 20 μl of DMSO. Absorbance of converted dye is measured at a wavelength of 595 nm using an ELISA plate reader. The number of migrated cells in each well is then determined by interpolation of the standard curve (see also Imai et al., *J. Biol. Chem.*, 272, 15036 (1997)).

Any method suitable for counting cells can be used, for example, counting with a hemocytometer, incubation of the cells with MTT (see above), or FACS analysis. A negative control assay is also performed, using TGF-β or another non-chemokine chemoattractant (e.g., IL1β or TNFα). To assess whether the agent is cytotoxic, the same concentrations of agent are incubated with THP-1 cells. Agents which 1) are not cytotoxic at levels which inhibit migration, 2) are ineffective at inhibiting the negative control-induced migration, and 3) reduce or inhibit chemokine-induced THP-1 migration, are agents which fall within the scope of the invention.

Agents may also be screened in a chemotactic assay which employs human neutrophils, eosinophils, mast cells, basophils, platelets, lymphocytes or monocytes. For monocytes, 9 mls of fresh blood are transferred to a tube containing 1 ml of 3.8% sodium citrate, and left at room temperature for 15 minutes. Five mls of this anti-coagulated blood are carefully layered over 3.5 ml Polymorphprep® (Nycomed Pharma, Oslo), and centrifuged at 500 g for 35 minutes per the manufacturer's instructions. The top band at the sample/medium interface contains monocytes. The monocytes are carefully removed with a glass pipette, and reconstituted to the original volume (5 ml). The cells are washed with PBS plus 10% fetal calf serum, and centrifuged at 400 g for 10 minutes. The washing step is repeated three times before the cells are counted. Cells are resuspended at $1\times10^7$ cells/ml in RPMI-1640+10% fetal calf serum (FCS). The monocytes are cultured for two days at 37° C. in a humidified atmosphere of 5% $CO_2$.

On day 2, the cells are counted, spun down, and reconstituted to $1\times10^7$ cells/ml in Gey's balanced salt solution+1 mg/ml bovine serum albumin (BSA). Chemotaxis is induced in a 48 or 96-well disposable chemotaxis chamber fitted with a 5-8 µm polycarbonate filter for monocytes, neutrophils or eosinophils, or a 3 µm filter for lymphocytes (Uguccioni et al, *Eur. J. Immunol.,* 25, 64 (1995); Loetscher et al., *J. Exp. Med.,* 184, 569 (1996); Weber et al., *J. Immunol.,* 4166 (1995)) (PVP free, ChemoTX, Neuroprobe Inc., Cabin John, Md.). Twenty-nine µl of chemoattractant or control are added to the lower compartment of each well. The framed filter is aligned with the holes in the corner of the filter frame and placed over the wells. Two and one-half$\times10^5$ monocytes in 25 µl of Gey's balanced salt solution+1 mg/ml BSA are added to the upper compartment. The agent is dissolved in Milli Q water and then serially diluted in the Gey's balanced salt solution. In most cases, the serially diluted agent is added to the upper compartment of the chemotaxis chamber. The chamber is incubated at 37° C. in a humidified atmosphere of 5% $CO_2$ for 1.5 hours.

2. Enzyme Release

The release of N-acetyl-β-D-glucosaminidase from monocytes may be employed to determine whether a therapeutic agent inhibits a cytokine-associated activity. Samples of $1.2\times10^6$ monocytes in 0.3 ml of prewarmed medium (136 mM NaCl, 4.8 mM KCl, 1.2 mM $KH_2PO_4$, 1 mM $CaCl_2$, 20 mM Hepes, pH 7.4, 5 mM D-glucose, and 1 mg/ml fatty acid-free BSA) are pretreated for 2 minutes with cytochalasin B (2.7 mg/ml) and then stimulated with a chemokine in the presence or absence of the therapeutic agent. The reaction is stopped after 3 minutes by cooling on ice and centrifugation, and the enzyme activity is determined in the supernatant (Uguccioni et al., *Eur. J. Immunol.,* 25, 64 (1995)).

The release of elastase from neutrophils may also be employed to determine whether a therapeutic agent inhibits a cytokine-associated activity (Pereri et al., *J. Exp. Med.,* 1547 (1988); Clark-Lewis et al., *J. Biol. Chem.,* 269, 16075 (1994)).

3. Cytosolic Free $Ca^{2+}$ Concentration ($[Ca^{2+}]_i$) Changes

Monocytes, eosinophils, neutrophils and lymphocytes loaded with Fura-2 (0.1 nmol/$10^5$ cells) are stimulated with a chemokine in the presence or absence of the therapeutic agent, and $[Ca^{2+}]_i$-related fluorescence changes are recorded (Von Tschanner et al., *Nature,* 324, 369 (1986)). For example, to determine cytosolic $Ca^{2+}$ concentrations in monocytes, monocytes are incubated with 0.5 µM Fura-2/AM for 30 minutes at 37° C. in HEPES-buffered saline (145 mM NaCl, 5 mM KCl, 1 mM $MgCl_2$, 10 mM HEPES, and 10 mM glucose), pH 7.4, at 37° C., supplemented with 1% albumin (w/v) and 1 mM $CaCl_2$. After loading with Fura-2, the cells are centrifuged for 5 minutes at 300×g and then resuspended in buffer containing no added albumin, to a cell density of $1.5\times10^6$ cells/ml, and kept at room temperature until use. This protocol results in a cytosolic Fura-2 concentration of about 100 µM. Serial dilutions of chemokines in PBS plus 0.1% albumin (w/v) (sterile filtered) are added to aliquots (0.7 ml) of cell suspension. The Fura-2 fluorescence of the monocyte suspension is measured at 37° C. in a single excitation, single emission (500 nm) wavelength Perkin-Elmer LS5 fluorometer. $[Ca^{2+}]_i$ is calculated from changes in fluorescence measured at a single excitation wavelength of 340 nm.

$[Ca^{2+}]_i$ measurements in cells that are stably transformed with a molecularly cloned chemokine receptor which is not expressed in the corresponding non-transformed cells are performed essentially as described above. After loading with Fura-2/AM, cells ($1\times10^6$/ml) are kept in ice-cold medium (118 mM NaCl, 4.6 mM KCl, 25 mM $NaHCO_3$, 1 mM $KH_2PO_4$, 11 mM glucose, 50 mM HEPES, 1 mM $MgCl_2$, 1 mM $CaCl_2$, 0.1% gelatin (pH 7.4). Aliquots (2 ml) of cell suspension are prewarmed at 37° C. for 5 minutes in 3-ml plastic cuvettes, and fluorescence is measured in a fluorometer (Johnson Foundation Biomedical Group) with magnetic stirring and temperature controlled at 37° C. Excitation is set at 340 nm, and emission is set at 510 nm. $[Ca^{2+}]_i$ is calculated as described above.

For studies in monocytes on cross-desensitization of calcium responses, chemokines are added sequentially with a 2-minute interval, and $[Ca^{2+}]_i$ transients are recorded. The concentrations used in these types of studies vary for each chemokine and are set at levels known to induce the maximal response for $[Ca^{2+}]_i$ mobilization (see Forssmann et al., *FEBS Lett.,* 408, 211 (1997); Sozzani et al., *J. Leukoc. Biol.,* 57, 788 (1995); Berkhout et al., *J. Biol. Chem.,* 272, 16404 (1997)).

4. Chemokine Binding and Binding Displacement

In general, specific binding is calculated as the amount of labeled agent bound in the absence of cold competitor minus the amount of labeled agent bound in the presence of cold competitor. The amount of specific binding in the presence of varied amounts of cold competitor can be used to determine the association constant for the agent, as well as the number of binding sites on the cell for the agent, using, for example, Scatchard Analysis. The agent may be labeled by radiolabeling (e.g., iodination) or with a suitable biochemical tag (e.g., biotin) or by addition of a photoactivatable crosslinking group. Agents with an association constant lower than 100 µM (i.e., which bind more strongly than an agent with an association constant of 100 µM) and which have at least about 2,500, preferably at least about 10,000, and more preferably greater than 25,000, binding sites per cell for at least one cell type which expresses a chemokine receptor, fall under the scope of this invention. THP-1 cells have at least about 5,000 MCP-1 receptors/cell.

For example, monocytes are suspended in RPMI 1640 medium without bicarbonate containing 0.2% bovine serum albumin and 0.1% azide. Radiolabeled chemokine peptide is incubated with $1\text{-}2\times10^6$ cells, e.g., THP-1 cells, in the presence or absence of increasing concentrations of unlabeled chemokine (MCP-1, MCP-3, MCP-4, RANTES or MIP-1α)

for 15 minutes at 37° C. in a 96-well plate in a final volume of 0.2 ml (e.g., PBS+0.5% FCS). After the incubation, 0.5 ml of ice-cold wash buffer (20 mM Tris, 0.5 M NaCl, pH 7.4) is added, and cells are collected onto a polyethyleneimine-treated Whatman GF/C filter using a Brandall cell harvester. Filters are washed with 4 ml of cold wash buffer, and the radioactivity bound to the filters is counted in a γ-counter.

For competition studies, the $IC_{50}$ is calculated with a curve fitting program (GraFit, Erithacus Software, London), using a four-parameter logistic, $cpm_{bound} = cpm_{max}/(1+([L]/IC_{50})^s) + cpm_{ns}$, where $cpm_{max}$ represents the binding without competitor, [L] is the competitor concentration, $cpm_{ns}$ is the non-specific binding, and s is the slope factor. The $cmp_{bound}$ is corrected for "no cell" controls. To obtain the $K_d$ and capacity of binding specific binding, data from homologous displacement experiments are fitted into a single-site ligand binding equation using the GraFit best fit program.

Chemokine binding to cells stably transformed with a molecularly cloned chemokine receptor is performed essentially as described above except that radiolabeled agent is diluted with unlabeled chemokine. Cells are incubated with radiolabeled agent plus or minus unlabeled chemokines for 30 minutes at 37° C. (see also, Imai et al., supra; Sozzani et al. (1995), supra; Berkhout et al., supra; WO 97/22698).

5. Binding to the Duffy Antigen Receptor for Chemokines (DARC)

The affinity of the therapeutic agent to DARC may be determined by any method known in the art, e.g., the ability of the agent to inhibit the binding of radio-iodinated MCP-1 to red blood cells (see Example 3). Agents which bind to DARC with a lower association constant (i.e., stronger binding) than they bind to chemokine receptors (i.e., a DARC selectivity ratio of <1), and which bind to DARC with an association constant lower than 100 μM, preferably lower than 10 μM and more preferably lower than 1 μM, are useful in particular embodiments of the methods of the invention. In contrast, agents which do not bind DARC, or do not bind to DARC with an affinity that is greater than their affinity for chemokine receptors (i.e., a selectivity ratio >1), are useful in the practice of other embodiments of the methods of the invention.

6. Inhibition of the Co-Mitogenic Activity of Chemokines

Many chemokines are co-mitogenic with low concentrations of FCS, e.g., 50 ng/ml MCP-1+0.5% FCS is a mitogen for smooth muscle cells. Assays well known to the art for determination of DNA synthesis induced by any known chemokine plus a low concentration (<5%) of FCS on suitable cells (e.g., smooth muscle cells) in the presence and absence of the agent may be employed to screen agents for such inhibitory activity. See Porreca et al., J. Vasc. Res., 34, 58 (1997), the disclosure of which is incorporated by reference herein.

7. Anti-Lentiviral Activity

To prepare cell lines that are susceptible to lentiviral infection as a result of the expression of a particular chemokine receptor, a molecularly cloned chemokine receptor is introduced into a cell line that does not otherwise express the chemokine receptor, e.g., HeLa-MAGI (Kimpton and Emerman, J. Virol., 66(5), 3026 (1992)) or U373-MAGI (Harrington and Geballe, J. Virol., 67, 5939 (1993)) cells, by infection with a retroviral vector. Expression of the chemokine receptor on the cell surface is demonstrated by immunostaining live cells using antibody. Expression of the RNA encoding the receptor is demonstrated by RT-PCR analysis. HeLa-MAGI and U373-MAGI express β-galactosidase after lentiviral infection. Incubation of infected cells with X-gal results in the deposit of a blue stain in these cells.

Infection of the chemokine receptor-stably transformed cell lines with HIV in the presence or absence of agent is performed in 12-well plates with 10-fold serial dilutions of 300 μl of virus in the presence of 30 μg/ml DEAE-Dextran as described (Kimpton and Emerman, supra). Viral stocks are normalized by ELISA or $p24^{gag}$ (Coulter Immunology) or $p27^{gag}$ (Coulter Immunology) for HIV-1 and HIV-2/SIV, respectively, using standards provided by the manufacturer.

Two days after infection, cells are fixed and stained for β-galactosidase activity with X-gal. The cells are stained for 50-120 minutes at 37° C. The infectious titer is the number of blue cells per well multiplied by the dilution of virus and normalized to 1 ml.

For other methods useful to determine whether an agent inhibits lentiviral infection and/or replication, see also Cocchi et al., Science, 270, 1811 (1995), and WO97/22698.

8. Agonists

To determine whether an agent of the invention is a chemokine receptor agonist, varying amounts of a labeled form of the agent, e.g., biotinylated, are mixed with cells that express the receptor, e.g., THP-1 cells express receptors for MCP-1, MIP1α, SDF-1α and IL-8, while Jurkat cells express functional receptors for SDF-1. The affinity of the labeled agent for the cells is then determined. Agents that bind to receptors with a reasonable affinity and interact with the receptor by inducing signaling, are within the scope of the invention. While not encompassed by the term "agonist" or "antagonist", agents that bind to or near the receptor but elicit no response are also within the scope of the invention, and are termed "neutral" agents.

Agents with agonist activity may also be identified using the transwell migration assay, where the cells are placed in the upper compartment (see FIG. 1) in the absence of agent, and the agent, e.g. peptide 2[MCP-1], is placed at varying concentrations in the lower compartment in place of the chemokine. If the agent(s) have agonist activity, more cells are found in the lower compartment at the end of the assay in wells containing the agent(s) than in wells containing inactive control, i.e., agent or medium alone. Preferably, agents having agonist activity also stimulate migration of primary human cells, e.g., monocytes, in a transwell migration assay.

Moreover, weak agonists or neutral agonists (agents which bind to the receptor but do not inhibit binding of native chemokine and its subsequent signaling, nor do they induce signaling themselves) can be identified by screening the agents for ability to displace the binding of HIV gp120, specifically the V3 loop of gp120, to the surface of THP-1 cells or Jurkat cells. Cells are incubated with labeled (for example, radioiodinated) recombinant gp120 protein in an amount effective to bind to the virus receptor, in the presence and absence of various concentrations of the agent(s). Agents which reduce or abolish gp120 binding are agonists or neutral agonists within the scope of the invention.

9. In Vivo

A rapid method to determine whether an agent of the invention inhibits or augments an inflammatory response is to inject a selected chemokine into the skin of an animal in the presence or absence of an agent of the invention. At some later point in time, animals are sacrificed and the number of inflammatory cells in animals exposed to chemokine and the agent is compared to the number of inflammatory cells in animals exposed to chemokine alone, e.g., by quantitative immunofluorescence, relative to control animals.

B. Nucleic Acid Molecules of the Invention

1. Sources of the Nucleic Acid Molecules of the Invention

Sources of nucleotide sequences from which the present nucleic acid molecules encoding a chemokine peptide, a variant thereof or the nucleic acid complement thereof, include total or polyA+ RNA from any eukaryotic, preferably mammalian, cellular source from which cDNAs can be derived by methods known in the art. Other sources of the DNA molecules of the invention include genomic libraries derived from any eukaryotic cellular source. Moreover, the present DNA molecules may be prepared in vitro, e.g., by synthesizing an oligonucleotide of about 100, preferably about 75, more preferably about 50, and even more preferably about 40, nucleotides in length, or by subcloning a portion of a DNA segment that encodes a particular chemokine.

2. Isolation of a Gene Encoding a Chemokine

A nucleic acid molecule encoding a chemokine can be identified and isolated using standard methods, as described by Sambrook et al., *Molecular Cloning: A Laboratory Manual*, Cold Spring Harbor, N.Y. (1989). For example, reverse-transcriptase PCR (RT-PCR) can be employed to isolate and clone chemokine cDNAs. Oligo-dT can be employed as a primer in a reverse transcriptase reaction to prepare first-strand cDNAs from isolated RNA which contains RNA sequences of interest, e.g., total RNA isolated from human tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7-8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other eukaryotic chemokines. One primer is prepared which is predicted to anneal to the antisense strand, and another primer prepared which is predicted to anneal to the sense strand, of a DNA molecule which encodes a chemokine.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs.

Another approach to identify, isolate and clone cDNAs which encode a chemokine is to screen a cDNA library. Screening for DNA fragments that encode all or a portion of a cDNA encoding a chemokine can be accomplished by probing the library with a probe which has sequences that are highly conserved between genes believed to be related to the chemokine, e.g., the homolog of a particular chemokine from a different species, or by screening of plaques for binding to antibodies that specifically recognize the chemokine. DNA fragments that bind to a probe having sequences which are related to the chemokine, or which are immunoreactive with antibodies to the chemokine, can be subcloned into a suitable vector and sequenced and/or used as probes to identify other cDNAs encoding all or a portion of the chemokine.

As used herein, the terms "isolated and/or purified" refer to in vitro isolation of a DNA or polypeptide molecule from its natural cellular environment, and from association with other components of the cell, such as nucleic acid or polypeptide, so that it can be sequenced, replicated, and/or expressed. For example, "isolated chemokine nucleic acid" is RNA or DNA containing greater than 9, preferably 36, and more preferably 45 or more, sequential nucleotide bases that encode at least a portion of a chemokine, or a variant thereof, or a RNA or DNA complementary thereto, that is complementary or hybridizes, respectively, to RNA or DNA encoding the chemokine and remains stably bound under stringent conditions, as defined by methods well known in the art, e.g., in Sambrook et al., supra. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell. An example of isolated chemokine nucleic acid is RNA or DNA that encodes human MCP-1 and shares at least about 80%, preferably at least about 90%, and more preferably at least about 95%, sequence identity with the MCP-1 polypeptide having SEQ ID NO:16.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate tissue source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

3. Variants of the Nucleic Acid Molecules of the Invention

Nucleic acid molecules encoding amino acid sequence variants of a chemokine peptide are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the chemokine peptide.

Oligonucleotide-mediated mutagenesis is a preferred method for preparing amino acid substitution variants of a chemokine peptide. This technique is well known in the art as described by Adelman et al., *DNA*, 2, 183 (1983). Briefly, chemokine DNA is altered by hybridizing an oligonucleotide encoding the desired mutation to a DNA template, where the template is the single-stranded form of a plasmid or bacteriophage containing the unaltered or native DNA sequence of the chemokine. After hybridization, a DNA polymerase is used to synthesize an entire second complementary strand of the template that will thus incorporate the oligonucleotide primer, and will code for the selected alteration in the chemokine DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21-4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the chemokine, and the other strand (the original template) encodes the native, unaltered sequence of the chemokine. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-($\alpha$S) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-($\alpha$S) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a preselected DNA segment encoding peptide 3 (1-12)[MCP-1] having SEQ ID NO:1, having nucleotide substitutions which are "silent" (see FIG. 12). That is, when silent nucleotide substitutions are present in a codon, the same amino acid is encoded by the codon with the nucleotide substitution as is encoded by the codon without the substitution. For example, valine is encoded by the codon GTT, GTC, GTA and GTG. A variant of SEQ ID NO:79 at the tenth codon in the mature polypeptide (GT<u>C</u> in SEQ ID NO:79) includes the substitution of GT<u>T</u>, GT<u>A</u> or GT<u>G</u> for GT<u>C</u>. Other "silent" nucleotide substitutions in SEQ ID NO:76 which can encode peptide 3 (1-12) [MCP-1] having SEQ ID NO:1 can be ascertained by reference to FIG. 12 and page D1 in Appendix D in Sambrook et al., *Molecular Cloning: A Laboratory Manual* (1989). Nucleotide substitutions can be introduced into DNA segments by methods well known to the art. See, for example, Sambrook et al., supra. Likewise, nucleic acid molecules encoding other mammalian, preferably human, chemokines may be modified in a similar manner. Thus, nucleic acid molecules encoding at least a portion of, for example, MCP-2, MCP-3, MCP-4, MIP1$\alpha$ (SEQ ID NO:19), MIP1$\beta$ (SEQ ID NO:20), RANTES (SEQ ID NO:21), SDF1$\alpha$, IL8 (SEQ ID NO:23), GRO$\alpha$, eotaxin (SEQ ID NO:25), MIG, PF-4, I309, HCC-1, C10, CCR-2, ENA-78, GRO$\beta$, IP10, SDF1$\beta$, GRO$\alpha$, MIP3$\alpha$, TCA-3, CTAPIII, MARC/FYK, $\beta$-thromboglobulin, GCP-2, PBP, HC14, MDC, TECK, PARC, 6Ckine, Fractaline, DC-CK1, LIX, TARC, LARC, MIG, Ck$\beta$8, CCF18/MRP-2, CCIII, CK$\alpha$2, H1305, Dvic-1, DGWCC, TCA4, dendrokine, CC2/HCC1, CC3, and MIP1$\tau$, as well as virally encoded chemokines such as vMIP-I, vMIP-II and vMIP-III, or the complement thereto, may be modified so as to yield nucleic acid molecules of the invention having silent nucleotide substitutions, or to yield nucleic acid molecules having nucleotide substitutions that result in amino acid substitutions (see peptide variants hereinbelow).

C. In Vivo Studies

To further determine whether a particular agent is useful in the practice of the methods of the invention, an animal model is identified for a human disease. Transgenic animal models for human disease may also be employed to identify agents useful in the methods of the invention. For example, models of chemokine-induced macrophage recruitment associated with human atherosclerosis include, but are not limited to, mice with a homozygous deletion of the apolipoprotein E (apoE) gene, mice overexpressing human apoB and Watanabe heritable hyperlipidemic rabbits. Models for autoimmune disease include the collagen-induced arthritis in DBA/1 mice and myelin basic protein-induced experimental autoimmune encephalomyelitis. Models for osteoporosis include ovariectomized female rats, mice, monkeys, rats treated with heparin or with glucocorticoids as well as suspension-induced osteoporosis in rats. Models for HIV infection include infection of monkeys with SIV, SIV isolates, HIV or HIV isolates, SCID-Hu mice with HIV or HIV isolates, or rabbits with HIV or HIV isolates. Other animal models for lentiviral infection include cats infected with FIV, horses with EIAV, and goats infected with CAEV (which is also an animal model for arthritis).

The efficacy of an agent of the invention may be assessed by measuring the extent of inflammation, or the extent of macrophage infiltration of affected tissues. Macrophage infiltration can be detected by staining tissue sections with antibodies which specifically detect macrophages (e.g., mac-1 antiserum). Inflammation or other symptoms of disease may be detected by measuring appropriate clinical parameters, using techniques which are well known to those skilled in the art. For example, apoE knockout mice are treated with an agent, such as CRD-leu$_4$ile$_{11}$peptide 3, e.g., by intraperitoneal injection, for a period of twelve weeks, while control litter mates receive a suitable control peptide with no known biological activity. At the end of twelve weeks, the animals are sacrificed and the effect of the agent is assessed by measuring the reduction in macrophage recruitment into the vessel wall by quantitative immunohistochemistry using mac-1 antiserum, and by measuring the reduction in the extent of vascular lipid lesion formation by histochemistry using oil red O staining in accordance with Paigen, *Arteriosclerosis*, 10, 316 (1990).

Apo(a) transgenic mice develop lesions when fed a lipid-rich diet. These lesions do not contain any macrophages. In contrast, C57B16 inbred mice develop lipid lesions of similar size and severity to those in apo(a) transgenic mice, but these lesions are rich in infiltrating macrophage. Lesions of apo(a) mice, C57B16 mice, and 6 other strains of mice which develop lipid lesions rich with macrophage, were screened by quantitative immunofluorescence for levels of pro-inflammatory mediators, e.g., TNF-α, MCP-1, MIP-1α, IL1, ICAM-1, VCAM-1, and P-selectin. TNF-α, MIP-1α, IL1β, ICAM-1, VCAM-1 and P-selectin were all expressed at identical levels in the apo(a) mouse lesions and the C57B16 lesions. Thus, while these pro-inflammatory mediators may be necessary to infiltration, they are not sufficient alone. In marked contrast, MCP-1 was completely absent from the lesions of apo(a) mice, but expressed at high levels in lesions from all other mouse lines which had macrophage-rich lesions.

Confocal microscopic analysis of sections of blood vessel wall with lesions triple stained with antibodies specific for SM-α-actin (smooth muscle cells; IA4 antibody), macrophages (Mac-1 antibodies) and MCP-1 showed that MCP-1 is not exclusively expressed by macrophage. That is, both smooth muscle cells and macrophages expressed MCP-1. Thus, MCP-1 may be the missing "inflammatory mediator" in the apo(a) mouse model of atherosclerosis. These results suggest that the lack of MCP-1 in apo(a) mice lesions may not be a consequence of the absence of macrophages, but instead contribute to the cause of lack of monocyte infiltration. Moreover, these results provide evidence that the chemokine MCP-1 plays a role in atherosclerotic vascular inflammation. Thus, MCP-1 can provide the basis for analogs which block the recruitment activity of this chemokine.

Chemokines other than MCP-1 may also be involved in macrophage recruitment, inflammation and pathogenesis of atherosclerosis, and in other diseases associated with inappropriate proliferation. For example, MIP1α has been implicated in the inappropriate inflammation in multiple sclerosis. Thus, sequences analogous to peptide 2 and 3 from MIP1α may be particularly useful to treat or prevent multiple sclerosis. Therefore, when a particular chemokine is implicated in a particular disease, sequences from that particular chemokine may be especially useful to treat or prevent that disease. Preferred agents falling within the scope of the invention are inhibitors of signaling of more than one chemokine, and preferably of all chemokines. Thus, it may be preferable to prepare chemokine peptide analogs having sequences from a chemokine other than the one(s) associated with a particular disease process. Selection of a particular agent to treat a particular disease may be based on bioavailability, toxicity, DARC binding or other similar criteria.

Other models include, but are not limited to those reported by Lukacs (*Adv. Immunol.*, pp. 257-304, Academic Press (1996)), for lung injury; Lloyd et al. (*J. Leuko. Biol.*, 185, 1371 (1997)) and Tam et al. (*Kid. Int.*, 49, 715 (1996)), for nephritis; Volejnikova (*Am. J. Pathol.*, 150, 1711 (1997), for bone; Ghinikar et al. (*J. Neurosci. Res.* 46, 727 (1996)) and Ransoholf et al. (*J. Leuko. Biol.*, 62, 645 (1997)), for brain; Kaul et al. (*Am. J. Trop. Med. Hyg.*, 58, 240 (1995)), for malaria; Ajeubar et al. (*J. Leuko. Biol.*, 63, 108 (1998)), for peritonitis; Furukawa et al. (*Lupus*, 6, 193 (1997)), for systemic lupus; Suzuki et al. (*J. Heart & Lung Transpl.*, 16, 1141 (1967)), Abbott et al. (*Arch. Surg.*, 89, 645 (1964)), Corry et al. (*Transpl.*, 16, 343 (1973)), Dworkin et al. (*J. Heart Lung Transpl.*, 10, 591 (1991)), Laden et al. (*Arch. Path.*, 93, 240 (1972)) and Mitchell et al. (*Transpl.*, 49, 835 (1990)), for transplants; U.S. Pat. No. 5,661,132 for wound healing; Burhardt et al. (*Rheum. Int.*, 17, 91 (1997)) for autoimmunity; Elson et al. (*Gastroenter.*, 109, 1344 (1998)) for inflammatory bowel disease; Hayes et al. (*Arterio. Thromb. Vasc. Biol.*, 18, 397 (1998)) and Wang et al. (*Arterio. Thromb.*, 11, 1166 (1991)), for cardiovascular disease; Wegner et al. (*Science*, 247, 456 (1990) for eosinophilic infiltration into the lung; Brahn (*Ciinorth and Rel. Res.*, 265, 42 (1991)), Wooley (*Curr. Op. Rheum.*, 3, 407 (1991)) and Gay et al. (*Curr. Op. Rheum.*, 7, 199 (1995), SCID-human synovial implant model)) for rheumatoid arthritis); Beamer et al. (*Blood*, 86, 3220 (1998)), Nakaguma (*Int. J. Exp. Path.*, 76, 65 (1998)), Nanney et al. (*J. Invest. Dermat.*, 106, 1169 (1996)), Nickoff et al. (*AJP*, 146, 580 (1995)), Sundberg et al. (*Pathobiol.*, 65, 271 (1997)), and Wolf et al. (*Int. J. Dermat.*, 30, 448 (1998)) for psoriasis; and Conti et al. (*Blood*, 89, 4120 (1997)), Gonzalo et al. (*JCI*, 98, 2332 (1996)), Teiyeira et al. (*JCI*, 100, 1657 (1997)), Ceri et al. (*Allergy*, 52, 739 (1997)), Freed (*Eur. Res. J.*, 8, 1770 (1998)), Griffiths-Johnson et al. (*Meth. Enzy.*, 288, 241 (1991)), Herz et al. (*New Horizons in Allergy Immunoth.*, 25-32 Plenum Press, 1996) and Kane (*Eur. Resp. J.*, 7, 555 (1991)) for allergy.

II. Preparation of Agents Falling within the Scope of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a mRNA sequence encoding a chemokine is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for a chemokine, or portions thereof, a portion of the preselected DNA may be untranscribed, serving a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding a chemokine or its complement, by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. For mammalian gene therapy, it is desirable to use an efficient means of precisely inserting a single copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding the chemokine or its complement, which host cell may or may not express significant levels of autologous or "native" chemokine.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular chemokine, e.g., by immunological means (ELISAs and Western blots) or by assays described hereinabove to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the peptide products of the introduced preselected DNA sequences or evaluating the phenotypic changes brought about by the expression of the introduced preselected DNA segment in the host cell.

B. Peptides, Peptide Variants, and Derivatives Thereof

The present isolated, purified chemokine peptides, peptide variants or derivatives thereof, can be synthesized in vitro, e.g., by the solid phase peptide synthetic method or by recombinant DNA approaches (see above). The solid phase peptide synthetic method is an established and widely used method, which is described in the following references: Stewart et al., *Solid Phase Peptide Synthesis*, W.H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48-267; Bavaay and Merrifield, "The Peptides," eds. E. Gross and F. Meienhofer, Vol. 2 (Academic Press, 1980) pp. 3-285; and Clark-Lewis et al., *Meth. Enzmmol.*, 287, 233 (1997). These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given chemokine peptide can be readily prepared. For example, amides of the chemokine peptide or chemokine peptide variants of the present invention may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the chemokine peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the peptide or peptide variant. Other amino-terminal modifications include aminooxypentane modifications (see Simmons et al., *Science*, 276, 276 (1997)).

In addition, the amino acid sequence of a chemokine peptide can be modified so as to result in a chemokine peptide variant. The modification includes the substitution of at least one amino acid residue in the peptide for another amino acid residue, including substitutions which utilize the D rather than L form, as well as other well known amino acid analogs, e.g., unnatural amino acids such as α,α-disubstituted amino acids, N-alkyl amino acids, lactic acid, and the like. These analogs include phosphoserine, phosphothreonine, phosphotyrosine, hydroxyproline, gamma-carboxyglutamate; hippuric acid, octahydroindole-2-carboxylic acid, statine, 1,2,3,4-tetrahydroisoquinoline-3-carboxylic acid, penicillamine, ornithine, citruline, α-methyl-alanine, para-benzoyl-phenylalanine, phenylglycine, propargylglycine, sarcosine, ε-N,N,N-trimethyllysine, ε-N-acetyllysine, N-acetylserine, N-formylmethionine, 3-methylhistidine, 5-hydroxylysine, ω-N-methylarginine, and other similar amino acids and imino acids and tert-butylglycine.

One or more of the residues of the peptide can be altered, so long as the peptide variant is biologically active. For example, for peptide 3[MCP-1] variants, e.g., Ser$_7$peptide 3(1-12)[MCP-1], it is preferred that the variant has at least about 10% of the biological activity of the corresponding non-variant peptide, e.g., a peptide having SEQ ID NO:1. Conservative amino acid substitutions are preferred—that is, for example, aspartic-glutamic as acidic amino acids; lysine/arginine/histidine as basic amino acids; leucine/isoleucine, methionine/ valine, alanine/valine as hydrophobic amino acids; serine/glycine/alanine/threonine as hydrophilic amino acids. Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide can readily be determined by assaying the specific activity of the peptide variant. Assays are described in detail herein.

Conservative substitutions are shown in FIG. 13 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

The invention also envisions peptide variants with non-conservative substitutions. Non-conservative substitutions entail exchanging a member of one of the classes described above for another.

Acid addition salts of the peptide or variant peptide or of amino residues of the peptide or variant peptide may be prepared by contacting the peptide or amine with one or more equivalents of the desired inorganic or organic acid, such as, for example, hydrochloric acid. Esters of carboxyl groups of the peptides may also be prepared by any of the usual methods known in the art.

Moreover, it is also envisioned that the agents of the invention, e.g., chemokine peptides, are modified in a manner that increases their stability in vivo, e.g., their half-life or bioavailability. These modified agents are termed "derivatives." Methods to prepare such derivatives are well known to the art. One method to stabilize peptides is to prepare derivatives which are cyclized peptides (see EPA 471,453 (amide bonds), such as that between lysine and aspartic acid side chains; EPA 467,701 (disulfide bonds); EPA 467,699 (thioether bonds). Other modifications which may increase in vivo stability are disclosed in Jameson et al. (*Nature*, 368, 744 (1994)); U.S. Pat. No. 4,992,463; U.S. Pat. No. 5,596,078 and U.S. Pat. No. 5,091,396. A preferred embodiment of the invention is a chemokine peptide or variant that has been cyclized by addition of one or more cysteine residues to the N and/or C terminus of the peptide, as well as peptides which are constructed of the reverse sequence (i.e., reading C-terminal to N-terminal) of D-form amino acids. A more preferred embodiment of this invention is a peptide which is both cyclized and constructed with the reverse sequence of D-form amino acids, i.e., a CRD derivative.

C. Chemokine Analogs

Chemokine analogs have properties analogous to those of the corresponding peptide. These analogs can be referred to as "peptide mimetics" or "peptidomimetics" (Fauchere, J. (1986) *Adv. Dru Res.*, 15:29; Veber and Freidinger (1985) TINS p. 392; and Evans et al. (1987) *J. Med. Chem,* 30:1229, which are incorporated herein by reference) and can be developed with the aid of computerized molecular modeling. These analogs include structures having one or more peptide linkages optionally replaced by a linkage selected from the group consisting of: —CH$_2$NH—, —CH$_2$S—, —CH$_2$—CH$_2$—, —CH=CH-(cis and trans), —CH=CF-(trans), —COCH$_2$—, —CH(OH)CH$_2$ and —CH$_2$SO—, by methods known in the art and further described in the following references: Spatola, A. F. in "Chemistry and Biochemistry of Amino Acids, Peptides, and Proteins," B. Weinstein, eds. Marcel Dekker, New York, P. 267 (1983); Spatola, A. F., Vega Data (March 1983), Vol. 1, Issue 3, "Peptide Backbone Modifications" (general review); Morley, J. S., *Trends Pharm. Sci.* (1980) pp. 463-468 (general review); Hudson, D. et al., *Int. J. Pept. Prot. Res.* (1979) 14:177-185 (—CH$_2$NH—, CH$_2$CH$_2$—); Spatola, A. F. et al., *Life Sci.* (1986) 38:1243-1249 (—CH$_2$—S); Hann, M. M., *J. Chem. Soc.* Perkin Trans 1(1982) 307-314 (—CH—CH—, cis and trans); Almquist, R. G. et al., *J. Med. Chem.* (1980) 23:1392-1398 (—COCH$_2$—); Jennings-White, C. et al., *Tetrahedron Lett.* (1982) 23:2533 (—COCH$_2$—); Szelke, M. et al. European Appln. EP 45665 (1982) CA; 97:39405 (1982) (—CH(OH)CH$_2$—); Holladay, M. W. et al., *Tetrahedron Lett.* (1983) 24:4401-4404 (—C(OH)CH$_2$—); and Hruby, V. J., *Life Sci.* (1982) 31:189-199 (—CH$_2$S—); each of which is incorporated herein by reference. A particularly preferred non-peptide linkage is —CH$_2$NH—. Such analogs may have greater chemical stability, enhanced pharmacological properties (half-life, absorption, potency, efficacy, etc.), altered specificity (e.g., a broad-spectrum of biological activities), reduced antigenicity, and be economically prepared. Labeling of analogs usually involves covalent attachment of one or more labels, directly or through a spacer (e.g., an amide group), to non-interfering positions(s) on the analog that are predicted by quantitative structure-activity data and/or molecular modeling. Such non-interfering positions generally are positions that do not form direct contacts with the macromolecule(s) to which the analog binds to produce the therapeutic effect. Systematic substitution of one or more amino acids of a consensus sequence with a D-amino acid of the same type (e.g., D-lysine in place of L-lysine) may also be used to generate more stable peptides.

1. Isosteres of Chemokine Tripeptides (a Compound of Formula (IV))

A compound of formula (IV), wherein Z=CH$_3$; R=indolyl; Y=O; and X=CH$_3$, can be prepared from N-tBOC-NinBOC-L-tryptophan-OH and cyclohexenone. For example, 2-cyclohexen-1-one (Aldrich C10,281-4) can be reacted with lithium dimethylcuprate in the presence of trimethylsilyl chloride (Aldrich 38,652-9) (Reaction 1) to trap the enolate intermediate. Lithium dimethylcuprate is prepared from methyllithium and a copper (I) salt in a 2:1 stoichiometry, prior to use in the reaction, by methods well known to those skilled in the art (e.g., House et al., *J. Org. Chem.*, 40, 1460 (1975)). The addition of α-β unsaturated ketones by organocuprates is described, for example, in House et al., *J. Org. Chem.*, 31, 3128 (1966). Similarly, capture of the enolate by trimethyl silyl chloride is described in House et al., *J. Org. Chem.*, 36, 2361 (1971). The trapped enolate is then resolved to the α-iododerivative, for example, by addition of molecular iodine in the presence of acetoxy-silver and tetrabutylammonium fluoride, according to the method of Rubottom (*J. Org. Chem.*, 44, 1731 (1979)) to give the trans-disubstituted cyclohexanone of formula (VI).

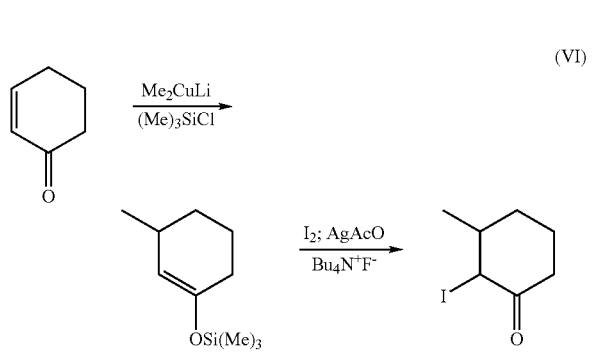

Conversion of the iodide of formula (VI), to a secondary alcohol, and formation of an ester, for example, with acetic anhydride yields a compound of formula (VIIb).

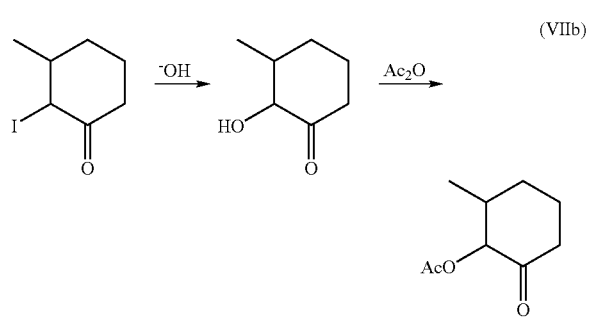

A compound of formula (VIIb) can alternatively be prepared by conversion of the above trimethylsilyl ether enolate to the α-hydroxy ketone followed by formation of the ester, using procedures which are well known in the art.

A compound of formula (VIIb) can be alkylated, for example, with vinyl magnesium bromide under standard conditions, and dehydrated (for example, in the presence of molecular iodine and heat) to yield a diene of formula (VIII):

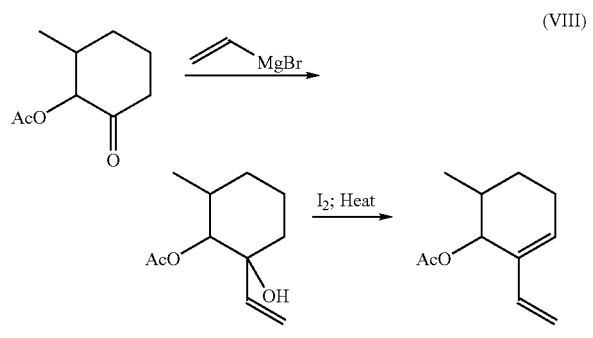

Diels-Alder reaction between the diene of formula (VIII) and ethyl acrylate (Aldrich E970-6) gives a stereospecific and regiospecific product of formula IX. For example, the cyclization reaction can be performed by mixing the compound of formula (VIII) and ethyl acrylate in a sealed tube and heating, essentially as described by Green et al. (*Adv. Pest Control Res.*, 3, 129 (1960)).

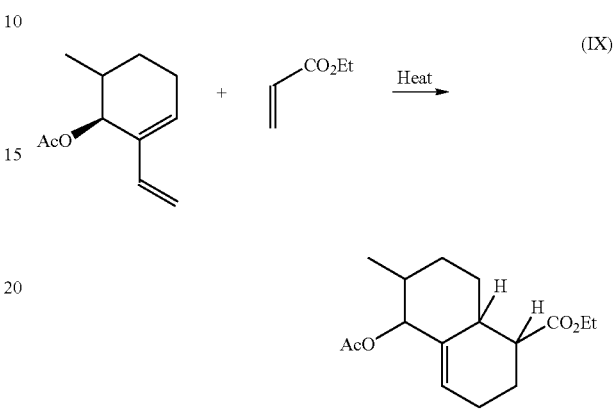

Oxidative cleavage of the double bond in a compound of formula (IX) gives a diacid of formula (X). Such an oxidative cleavage may conveniently be carried out by ozonolysis or by oxidation with an acid chromate. For example, using $CrO_3$ in acid, the compound of formula (X) may be prepared, essentially as described by Eschenmoser & Winter, *Science*, 196, 1410 (1977).

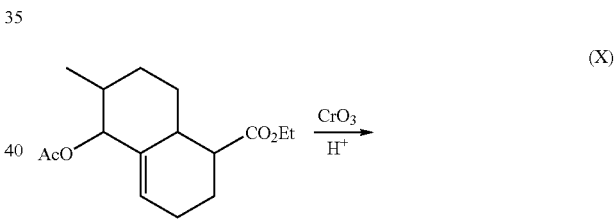

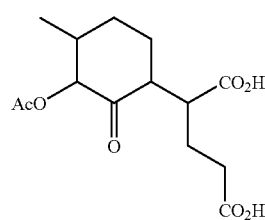

Activation of the diacid with $POCl_5$ and subsequent reaction with dimethylamine gives a di-amide of formula (XI).

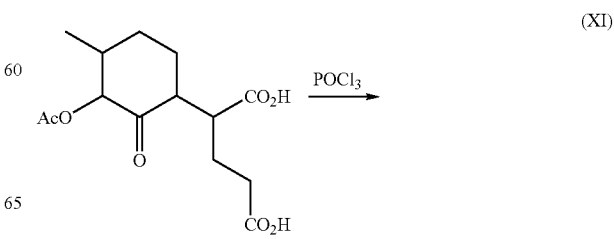

-continued

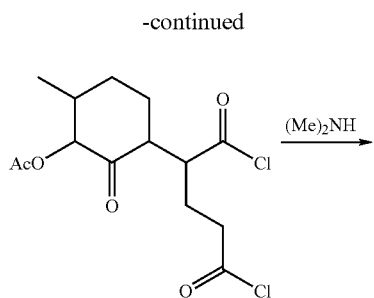

Hydrolysis of the acetoxy group of a compound of formula (XI) followed by formation of the mesylate (or other suitable leaving group) and addition of sodium iodide in THF gives a compound of formula (XIb).

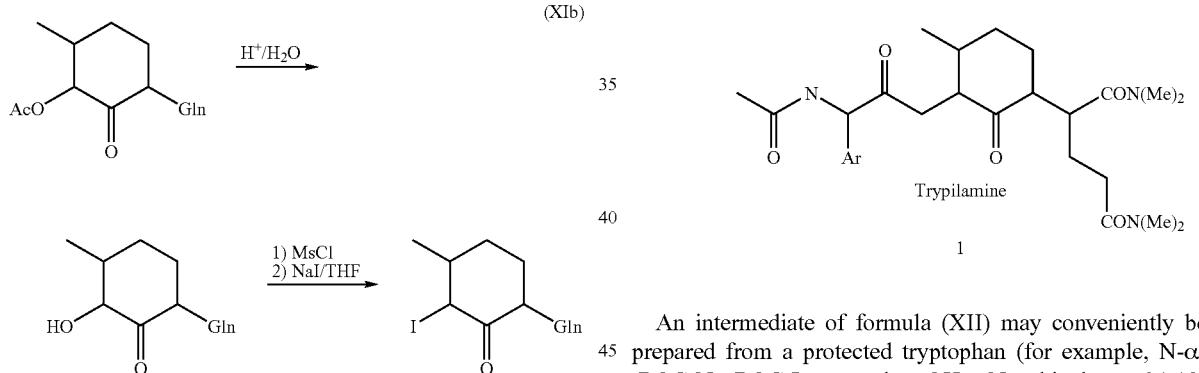

Reaction of a compound of formula (XI) and a compound of formula (XII) in the presence of anhydrous potassium carbonate in dry DMF, essentially as described by Lygo and Rudd (*Tetrahedron Lett.*, 36, 3577 (1995)) followed by removal of the sulfone, for example, using $SmI_2$, gives a compound of formula (XII) which can be deprotected and acylated to give a compound of formula (IV) wherein $R^2$ and $R^3$ are $NMe_2$.

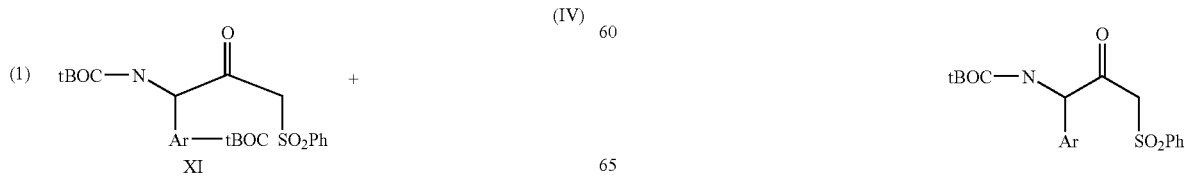

-continued

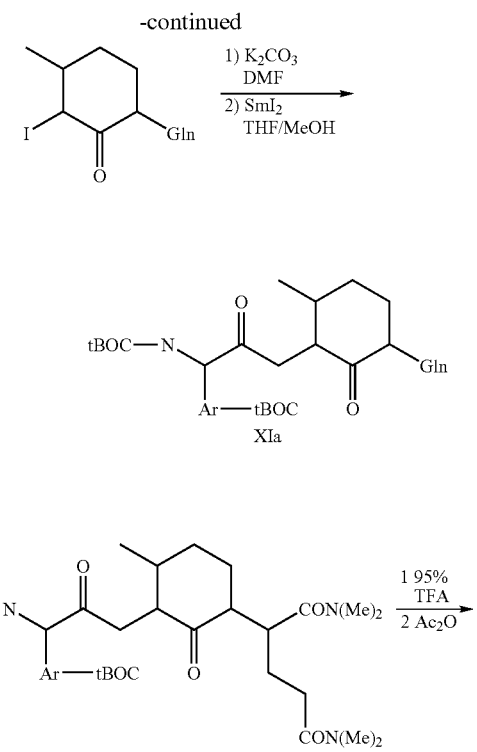

An intermediate of formula (XII) may conveniently be prepared from a protected tryptophan (for example, N-α-tBOC-N$_{in}$tBOC-L-tryptophan-OH; Novabiochem 04-12-0201) by reaction with the dianion derived of phenylmethylsulfone.

Ar=N-tBOC-Indolyl

A preferred synthesis for a compound of formula (IV) is:

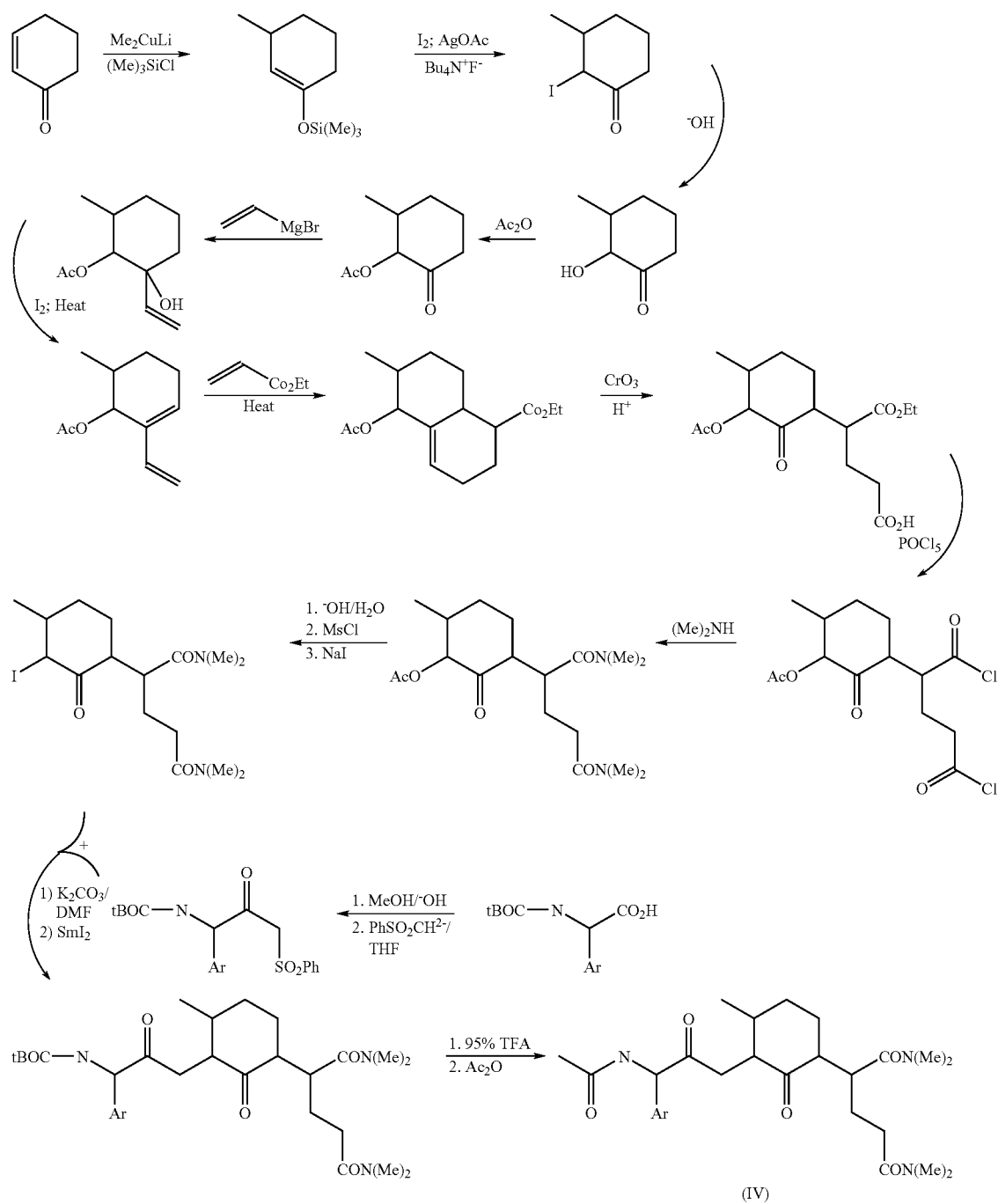

Thioketone derivatives (Y=S) may be synthesized by insertion of an additional reaction, in which the β-ketosulfone derivative of protected tryptophan is converted to the thioketone derivative. For example, reaction with a dithiol, such as 1,2-ethanedithiol, forms a thioacetal which can be hydrolyzed in the presence of $H_2S$ under anhydrous conditions, to yield the thioketone. The conversion may also be carried out using [2,4-bis(4-methoxy-phenyl)-1,3-dithia-2,4-diphosphetane-2,4 disulfide] (Lawesson's Reagent). Reaction of the thioketone derivative with the compound of formula (XI) gives a compound of formula (I) wherein Y=S.

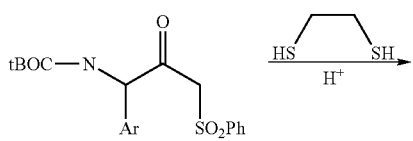

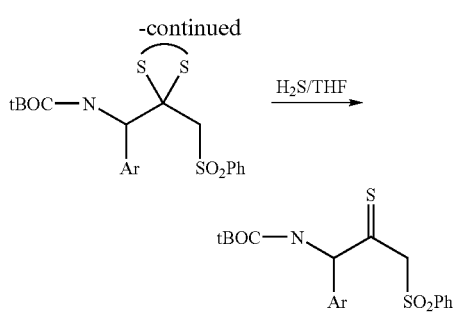

Aryl substituents other than indolyl require preparation of suitably protected β-ketosulfone derivatives of the appropriate amino acid. Where the amino acid is readily available, the reaction can be performed using the appropriate tBOC or Fmoc protected amino acid (phenylalanine and tyrosine, respectively), for example, from Novabiochem. When the amino acid is not readily available (e.g., R=coumaryl), the suitably protected amino acid must first be prepared by methods well established in the art for synthesis of non-standard amino acids (for example, see Yuan and Hruby, *Tetrahedron Lett.*, 38, 3853 (1997)).

As illustrated below, a compound of formula (V) can conveniently be prepared from an ester of formula 13. Deprotonation with lithium diisopropylamide followed by alkylation with bromide 14 gives a compound of formula 15. Selective reduction of the ester, for example with diisobutylaluminum hydride, gives an aldehyde of formula 16, which can be converted to the difluoroalkene 17 by a Wittig reaction with $PPh_3=CF_2$ (Hayashi et al., *Chemistry Letters*, 1980, pages 935-938).

Aldehyde 18 can be converted to bromide 19 using a procedure similar to that described in Visweswariah et al., *Synthesis*, 1982, pages 309-310, by treatment with phenyltrimethylammonium tribromide, followed by formation of the acetal under standard conditions. Conversion of the bromide to the corresponding alkyllithium by treatment with n-butyllithium, followed by reaction with difluoride 17, yields a compound of formula 20 (*Chemistry Letters*, 1980, pages 935-940). Deprotection under acidic conditions gives aldehyde 21, which can be reacted with $PPh_3=CF_2$ to give trifluoride 22. Subsequent treatment of 22, with the alkyllithium derived from bromide 23 yields a compound of formula (V). It will be understood by one skilled in the art that a variety of other known protecting groups can be utilized in the above procedures and that certain protecting groups may be preferred over others depending on the structure of the groups $R_4$-$R_8$.

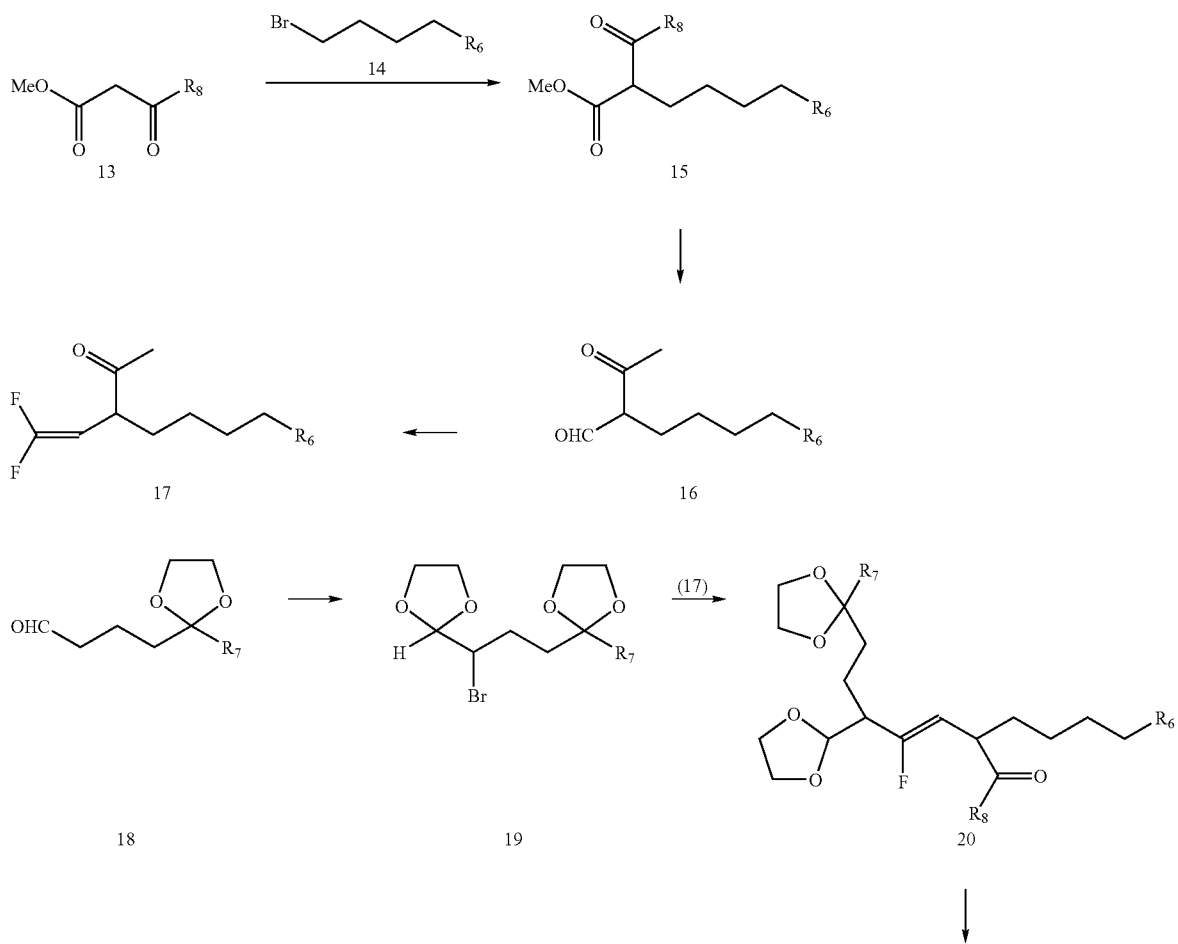

-continued

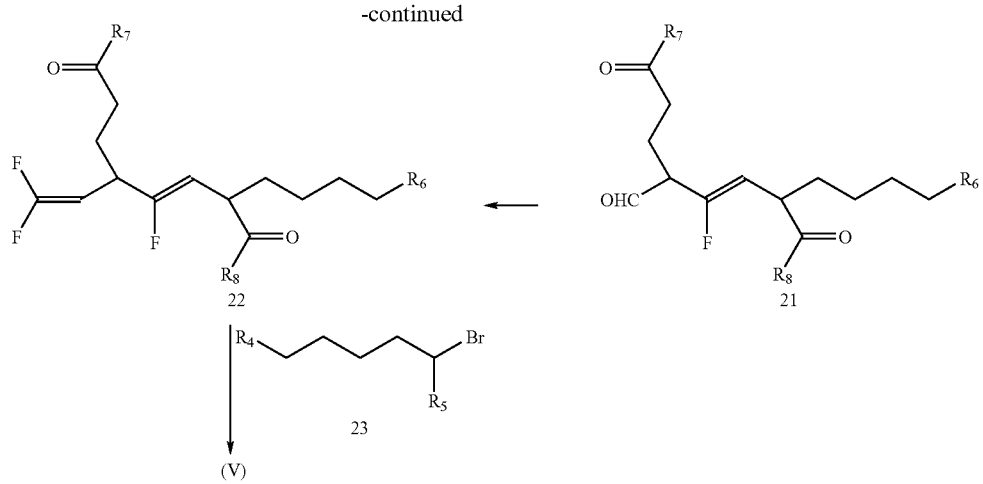

Other useful chemokine analogs may be identified by the methods described hereinabove. In particular, chemokine analogs that are orally bioavailable, and stable and potent inhibitors of chemokine activity are preferred.

D. Targeting of the Therapeutic Agent

Chemokine peptides, variants, analogs or derivatives thereof may be targeted to a specific therapeutic site by linking the therapeutic agent to a moiety that specifically binds to a cellular component, e.g., antibodies or fragments thereof, lectins, transferrin (for liver targeting) and small molecule drugs, so as to form a therapeutic conjugate. Targeting of the therapeutic agents of the invention can result in increased concentration of the therapeutic agent at a specific anatomic location. Moreover, the linking of a therapeutic agent of the invention to a binding moiety may increase the stability of the therapeutic agent in vivo. For example, an anti-CD4 mimetic that binds to the CD4 receptor may be linked to a therapeutic agent of the invention so as to result in a therapeutic conjugate, a portion of which binds to the HIV co-receptor. This may enhance the ability to target the therapeutic agent to a particular cell type and thus block HIV infection of that cell type.

For neoplasia, anti-tumor antibodies such as NR-LU-10 (anti-carcinoma), NR-ML-5 (anti-melanoma), or anti-CD45 (anti-lymphoma), may be useful to localize the therapeutic agent to a particular type of tumor. For infectious disease, antibodies which recognize a pathogen-specific epitope, such as mAb 17.41 (*Cryptosporidium parvum*), may be employed. To target to joints for treating rheumatoid arthritis, anti-synovium or chondroitin sulfate (e.g., Catalog No. C8035, Sigma Chemical Co., St. Louis, Mo.) antibodies can be linked to a therapeutic agent of the invention). To treat or prevent asthma or pneumonia, antibodies to the bronchial epithelium may be useful to prepare immunoconjugates for use in the methods of the invention.

Other antibodies useful in targeting a therapeutic agent of the invention to a specific site or cell type include antibodies specific for blood vessels or lymphatics (e.g., Ulex europaeus-I lectin, Catalog No. U4754, Sigma Chemical Co., St. Louis, Mo.), blood clots or platelets (e.g., Catalog Nos. F9902, F4639, F2506, F8512, Sigma Chemical Co., St. Louis, Mo.), T cells (e.g., Catalog Nos. C7048 (CD3); C1805 (CD4); C7173 (CD5); and C7298 (CD7), Sigma Chemical Co., St. Louis, Mo.), brain (e.g., Catalog Nos. S2644 and S2407, Sigma Chemical Co., St. Louis, Mo.), tumors (e.g., Catalog No. C2331, Sigma Chemical Co., St. Louis, Mo.), epithelial cells (e.g., Catalog Nos. E6011 and C1041, Sigma Chemical Co., St. Louis, Mo.), fibroblasts (e.g., Catalog Nos. F4771 and V4630, Sigma Chemical Co., St. Louis, Mo.), macrophage (e.g., Catalog No. M1919, Sigma Chemical Co., St. Louis, Mo.), stomach lumen (e.g., Catalog No. M5293, Sigma Chemical Co., St. Louis, Mo.), neutrophils (e.g., Catalog Nos. N1890 and N1765, Sigma Chemical Co., St. Louis, Mo.), tendons (e.g., Catalog No. E4013, Sigma Chemical Co., St. Louis, Mo.), skin (e.g., Catalog No. K4252, Sigma Chemical Co., St. Louis, Mo.) mammary tissue or epithelium (e.g., Catalog No. C6930, Sigma Chemical Co., St. Louis, Mo.) and skeletal muscle (e.g., Catalog Nos. D8281 and D1033, Sigma Chemical Co., St. Louis, Mo.).

To prepare immunoconjugates useful for targeting a malignant or virus-infected cell, an antibody or fragment thereof having a specificity for a surface antigen on a malignant cell or virus-infected is attached to a therapeutic agent of the invention. Preferably, a chemokine peptide or variant thereof is attached via peptide bonds to the carboxy termini regions, e.g., CH3, of antibody heavy chains. The immunoconjugates can be prepared by genetic engineering techniques, i.e, by forming a nucleic acid construct encoding the chimeric immunoconjugate. Preferably, the gene construct encoding the immunoconjugate includes, in 5' to 3' orientation, a DNA segment which encodes a heavy chain variable region, a DNA segment encoding the heavy chain constant region, and a DNA segment coding for the chemokine peptide, peptide variant, or repeats thereof. The fused gene is inserted into an expression vector for transfection of the appropriate recipient cells where it is expressed. The hybrid chain can be combined with a light (or heavy) chain counterpart to form monovalent and divalent immunoconjugates.

The heavy chain constant region for the conjugates can be selected from any of the five isotypes: alpha, delta, epsilon, gamma or mu. Heavy chains or various subclasses (such as the IgG subclasses 1-4) can be used. The light chains can have either a kappa or lambda constant chain. DNA sequences for these immunoglobulin regions are well known in the art (see, e.g., Gillies et al., *J. Immunol. Meth.*, 125, 191 (1989)).

In preferred embodiments, the variable region is derived from an antibody specific for the target antigen (an antigen associated with a diseased cell such as a cancer cell or virus-infected cell), and the constant region includes the CH1, CH2 and CH3 domains. The gene encoding the chemokine peptide or variant is joined, e.g., by appropriate linkers, e.g., by DNA encoding $(Gly_4-Ser)_3$ in frame to the 3' end of the gene encoding the constant region (e.g., CH3 exon), either directly or through an intergenic region. In certain embodiments, the intergenic region can comprise a nucleotide sequence coding for a proteolytic cleavage site. This site, interposed between the immunoglobulin and the chemokine peptide or variant, can be designed to provide for proteolytic release of the chemokine peptide or variant at the target site. For example, it is well known that plasmin and trypsin cleave after lysine and arginine residues at sites that are accessible to the proteases. Many other site-specific endoproteases and the amino acid sequences they attack are well known.

The nucleic acid construct can include the endogenous promoter and enhancer for the variable region-encoding gene to regulate expression of the chimeric immunoglobulin chain. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. Alternatively, the gene coding for the variable region can be obtained apart from endogenous regulatory elements and used in an expression vector which provides these elements.

Variable region genes can be obtained by standard DNA cloning procedures from cells that produce the desired antibody. Screening of the genomic library for a specific functionally rearranged variable region can be accomplished with the use of appropriate DNA probes such as DNA segments containing the J region DNA sequence and sequences downstream. Identification and confirmation of correct clones are then achieved by DNA sequencing of the cloned genes and comparison of the sequence to the corresponding sequence of the full length, properly spliced mRNA.

Genes encoding appropriate variable regions can be obtained generally from Ig-producing lymphoid cells. For example, hybridoma cell lines producing Ig specific for tumor associated antigens or viral antigens can be produced by standard somatic cell hybridization techniques. These Ig-producing cell lines provide the source of variable region genes in functionally rearranged form. The variable region genes are typically of murine origin because the murine system lends itself to the production of a wide variety of Igs of desired specificity.

The DNA fragment containing the functionally rearranged variable region gene is linked to a DNA fragment containing the gene encoding the desired constant region (or a portion thereof). Ig constant regions (heavy and light chain) can be obtained from antibody-producing cells by standard gene cloning techniques. Genes for the two classes of human light chains and the five classes of human heavy chains have been cloned, and thus, constant regions of human origin are readily available from these clones.

The fused gene encoding the hybrid IgH chain is assembled or inserted into expression vectors for incorporation into a recipient cell. The introduction of gene construct into plasmid vectors can be accomplished by standard gene splicing procedures.

The chimeric IgH chain can be co-expressed in the same cell with a corresponding L chain so that a complete immunoglobulin can be expressed and assembled simultaneously. For this purpose, the heavy and light chain constructs can be placed in the same or separate vectors.

Recipient cell lines are generally lymphoid cells. The preferred recipient cell is a myeloma (or hybridoma). Myelomas can synthesize, assemble, and secrete immunoglobulins encoded by transfected genes and they can glycosylate polypeptide. A particularly preferred recipient cell is the Sp2/0 myeloma which normally does not produce endogenous immunoglobulin. When transfected, the cell will produce only Ig encoded by the transfected gene constructs. Transfected myelomas can be grown in culture or in the peritoneum of mice where secreted immunoconjugate can be recovered from ascites fluid. Other lymphoid cells such as B lymphocytes can be used as recipient cells.

There are several methods for transfecting lymphoid cells with vectors containing the nucleic acid constructs encoding the chimeric Ig chain. A preferred way of introducing a vector into lymphoid cells is by spheroblast fusion (see Gillies et al., Biotechnol., 7, 798-804 (1989)). Alternative methods include electroporation or calcium phosphate precipitation.

Other useful methods of producing the immunoconjugates include the preparation of an RNA sequence encoding the construct and its translation in an appropriate in vivo or in vitro system.

Methods for purifying recombinant immunoglobulins are well known. For example, a well known method of purifying antibodies involves protein A purification because of the propensity of protein A to bind the Fc region of antibodies. The antigen binding activity of the purified immunoconjugates can then be measured by methods well known to the art, such as described in Gillies et al. (J. Immunol. Methol., 125, 191 (1989)). For example, immunoconjugate activity can be determined using antigen-coated plates in either a direct binding or competition assay format.

In particular, it is preferred that humanized antibodies are prepared and then assayed for their ability to bind antigen. Methods to determine the ability of the humanized antibodies to bind antigen may be accomplished by any of numerous known methods for assaying antigen-antibody affinity. For example, the murine antibody NR-LU-13 binds an approximately 40 kilodalton glycoprotein expressed on numerous carcinomas. This antigen has been characterized in Varki et al., Cancer Res., 44, 681 (1984); Okabe et al., Cancer Res., 44, 5273 (1989). Thus, it is routine to test the ability of humanized antibodies to bind the NR-LU-13 antigen. Moreover, methods for evaluating the ability of antibodies to bind to epitopes of this antigen are known.

Humanized antibodies (or fragments thereof) are useful tools in methods for therapeutic purposes. When determining the criteria for employing humanized antibodies or antibody conjugates for in vivo administration for therapeutic purposes, it is desirable that the general attainable targeting ratio is high and that the absolute dose of therapeutic agent delivered to the tumor is sufficient to elicit a significant tumor response. Methods for utilizing the humanized antibodies can be found, for example, in U.S. Pat. Nos. 4,877,868, 5,175,343, 5,213,787, 5,120,526, and 5,202,169.

To target vascular smooth muscle cells (VSMC), VSMC binding proteins, e.g., polypeptides or carbohydrates, proteoglycans and the like, that are associated with the cell membranes of vascular smooth muscle cells can be employed to prepare therapeutic conjugates. In a preferred embodiment, the binding moiety is exemplified by chondroitin sulfate proteoglycans (CSPGs) synthesized by vascular smooth muscle cells and pericytes, and a discrete portion (termed an epitope herein) of the CSPG molecule having an apparent molecular weight of about 250 kD is especially preferred. The 250 kD target is an N-linked glycoprotein that is a component of a larger 400 kD proteoglycan complex. In one presently preferred embodiment of the invention, a vascular smooth muscle binding protein is provided by NR-AN-01 monoclonal antibody (a subculture of NR-ML-05) that binds to an epitope in a vascular smooth muscle CSPG target molecule. The monoclonal antibody designated NR-ML-05 reportedly binds a 250 kD CSPG synthesized by melanoma cells (Morgan et al., U.S. Pat. No. 4,897,255). Smooth muscle cells and pericytes also reportedly synthesize a 250 kD CSPG as well as other CSPGs. NR-ML-05 binding to smooth muscle cells has been disclosed (Fritzberg et al., U.S. Pat. No. 4,879,225). Subculture NR-ML-05 No. 85-41-4I-A2, freeze # A2106, has been deposited with the American Type Culture Collection, Rockville, Md. and granted Accession No. HB-9350. NR-ML-05 is the parent of, and structurally and functionally equivalent to, subclone NR-AN-01, disclosed herein. It will be recognized that NR-AN-01 is just one example of a vascular smooth muscle binding protein that specifically associates with the 400 kD CSPG target, and that other binding proteins associating with this target and other epitopes in this target are also useful in the therapeutic conjugates and methods of the invention.

It will be recognized that the inventors also contemplate the utility of human monoclonal antibodies or "humanized" murine antibody as a vascular smooth muscle binding protein in the therapeutic conjugates of their invention. For example, murine monoclonal antibody may be "chimerized" by genetically recombining the nucleotide sequence encoding the murine Fv region (i.e., containing the antigen binding sites) with the nucleotide sequence encoding a human constant domain region and an Fe region, e.g., in a manner similar to that disclosed in European Patent Application No. 0,411,893 A2. Humanized vascular smooth muscle binding partners will be recognized to have the advantage of decreasing the immunoreactivity of the antibody or polypeptide in the host recipient, which may thereby be useful for increasing the in vivo half-life and reducing the possibility of adverse immune reactions. See also, N. Lonberg et al. (U.S. Pat. Nos. 5,625,126; 5,545,806; and 5,569,825); and Surani et al. (U.S. Pat. No. 5,545,807).

Useful binding peptides for cancer treatment embodiments of the present invention include those associated with cell membrane and cytoplasmic epitopes of cancer cells and the like. These binding peptides localize to the surface membrane of intact cells and internal epitopes of disrupted cells, respectively, and deliver the therapeutic agent for assimilation into the target cells. Minimal peptides, mimetic organic compounds and human or humanized antibodies that localize to the requisite tumor cell types are also useful as binding peptides of the present invention. Such binding peptides may be identified and constructed or isolated in accordance with known techniques. Preferred binding peptides of these embodiments of the present invention bind to a target epitope with an association constant of at least about $10^{-6}$.

Methods useful to prepare antibody-peptide conjugates are well known to the art. See, for example U.S. Pat. No. 5,650,150, the disclosure of which is incorporated by reference herein. Representative "coupling" methods for linking the therapeutic agent through covalent or non-covalent bonds to the targeting moiety include chemical cross-linkers and heterobifunctional cross-linking compounds (i.e., "linkers") that react to form a bond between reactive groups (such as hydroxyl, amino, amido, or sulfhydryl groups) in a therapeutic agent and other reactive groups (of a similar nature) in the targeting moiety. This bond may be, for example, a peptide bond, disulfide bond, thioester bond, amide bond, thioether bond, and the like. In one illustrative example, conjugates of monoclonal antibodies with drugs have been summarized by Morgan and Foon (Monoclonal Antibody Therapy to Cancer: Preclinical Models and Investigations, *Basic and Clinical Tumor Immunology*, Vol. 2, Kluwer Academic Publishers, Hingham, Mass.) and by Uhr, *J. of Immunol.* 133:i-vii, 1984). In another illustrative example where the conjugate contains a radionuclide cytostatic agent, U.S. Pat. No. 4,897,255, Fritzberg et al., incorporated herein by reference, is instructive of coupling methods that may be useful. In one embodiment, the therapeutic conjugate contains a vascular smooth muscle binding protein coupled covalently to a chemokine peptide or variant. In this case, the covalent bond of the linkage may be formed between one or more amino, sulfhydryl, or carboxyl groups of the vascular smooth muscle binding protein and the chemokine peptide or variant.

In a preferred embodiment of the invention, an antibody conjugate is used in pretargeting methods. Essentially, such pretargeting methods are characterized by an improved targeting ratio or increased absolute dose to the target cell sites in comparison to conventional cancer diagnosis or therapy. A general description of pretargeting methods may be found in U.S. Pat. Nos. 4,863,713, 5,578,287, and 5,630,996. Typical pretargeting approaches are summarized below.

Pretargeting methods are of two general types: three-step pretargeting methods and two-step pretargeting methods. A three-step pretargeting protocol includes the administration of a targeting moiety-ligand conjugate, which is allowed to localize at a target site and to dilute in the circulation. This is followed by administration of an anti-ligand which binds to the targeting moiety-ligand conjugate and clears unbound targeting moiety-ligand conjugate from the blood, as well as binds to targeting moiety-ligand conjugate at the target site. Thus, the anti-ligand fulfills a dual function by clearing targeting moiety-ligand conjugate not bound to the target site as well as attaches to the target site to form a targeting moiety-ligand: anti-ligand complex. Finally, a therapeutic agent-ligand conjugate that exhibits rapid whole body clearance is administered.

When the therapeutic agent-ligand conjugate in circulation comes into close proximity to the targeting moiety-ligand: anti-ligand complex bound to the target site, the anti-ligand portion of the complex binds to the ligand portion of the circulating therapeutic agent-ligand conjugate, thus producing a targeting moiety-ligand:anti-ligand:ligand-therapeutic agent "sandwich" at the target site. Furthermore, because the unbound therapeutic agent is attached to a rapidly clearing ligand (rather than a slowly clearing targeting moiety, such as antibody or antibody fragment), this technique provides decreased non-target exposure to the active agent.

Alternatively, two-step pretargeting methods eliminate the step of administering the above identified anti-ligand. These "two-step" procedures feature targeting moiety-ligand or targeting moiety-anti-ligand administration, followed by the administration of a therapeutic agent which is conjugated to the opposite member of the ligand/anti-ligand pair.

As an optional step in the two-step pretargeting method, ligand or anti-ligand, designed specifically to provide a clearance function, is administered to facilitate the clearance of circulating targeting moiety-ligand or targeting moiety-anti-ligand. Thus, in the two-step pretargeting approach, the clearing agent does not become bound to the target cell population, either directly or through the previously administered target cell bound targeting moiety-anti-ligand or targeting moiety-ligand conjugate.

A targeting moiety in a pretargeting method binds to a defined target cell population, such as tumor cells. Preferred targeting moieties useful in this regard are antibodies (polyclonal or monoclonal), such as human monoclonal antibodies, or "humanized" murine or chimeric antibodies. Some examples of humanized antibodies include those that are CHO produced, produced in hosts such as plant (for example corn, soybean, tobacco, and the like), insect, mammalian, yeast, and bacterial. The humanized antibodies may be those that bind to the antigen bound by antibody NR-LU-13. Preferably, the humanized antibody may not possess N-linked glycosylation or its N-linked glycosylation has been modified post expression to reduce immunogenicity or toxicity.

Ligand/anti-ligand pairs suitable for use in targeting protocols include biotin/avidin or streptavidin, haptens and epitopes/antibody, fragments or analogs thereof, including mimetics, lectins/carbohydrates, zinc finger proteins/dsDNA fragments, enzyme inhibitors/enzymes; and analogs and derivatives thereof. Preferred ligands and anti-ligands bind to each other with an affinity of at least about $K_A \geqq 10^9 M^{-1}$ or $K_D \leqq 10^{-9} M$. Biotin/avidin or streptavidin is a preferred ligand/anti-ligand pair.

In general, such pretargeting methods preferably include the administration of an anti-ligand that provides a clearance function. The clearance is probably attributable to cross-linking and/or aggregation of conjugates that are circulating in the blood, which leads to complex/aggregate clearance by the recipient's RES (reticuloendothelial system). The anti-ligand clearance of this type is preferably accomplished with a multivalent molecule. However, a univalent molecule of sufficient size to be cleared by the RES on its own could also be employed.

Alternatively, receptor-based clearance mechanisms, e.g., Ashwell receptor or other receptors, may be exploited by addition of hexose residues, such as galactose or mannose residues, to provide for clearance of the anti-ligand, anti-ligand conjugate or humanized antibody via the liver. Such clearance mechanisms are less dependent upon the valency of the clearing agent than the RES complex/aggregate clearance mechanisms described above.

For example, if the targeting moiety-ligand or targeting moiety-anti-ligand has been derivatized to provide for clearance (i.e., addition of a hexose residue) a clearing agent should not be necessary. Preferred clearing agents are disclosed in U.S. Pat. Nos. 5,624,896 and 5,616,690; as well as PCT Application Publication Number WO 95/15978.

One skilled in the art, based on the teachings herein and the applications referenced herein, can readily determine an effective therapeutic effective dosage and treatment protocol. This will depend upon factors such as the particular selected therapeutic agent, route of delivery, the type of target site(s), affinity of the targeting moiety for target site of interest, any cross-reactivity of the targeting moiety with normal tissue, condition of the patient, whether the treatment is effected alone or in combination with other treatments, among other factors.

For example, in the case of humanized antibody-avidin or streptavidin conjugates in pretargeting strategies, a suitable dosage ranges from about 10 to about 2500 mg, more preferably from about 50 to 1500 mg, and most preferably from about 100 to 800 mg. The dosage of the ligand-therapeutic agent conjugate, generally ranges from about 0.001 to about 10 mg and more preferably from about 0.1 to 2 mg.

In general, such pretargeting methods include the administration of a clearing agent. The dosage of the clearing agent is an amount which is sufficient to substantially clear the previously administered conjugate from the circulation, i.e., at least about 50%, more preferably at least about 90%, and most preferably approaching or at 100%. In general, the clearing agent is administered several days after administration of the humanized antibody-streptavidin conjugate, preferably about 1 to 5 days after, more preferably at least about 1 to 2 days after. Generally, the determination of when to administer the clearing agent depends on the target uptake and endogenous clearance of targeting moiety conjugate. Particularly preferred clearing agents are those which provide for Ashwell receptor mediated clearance, such as galactosylated proteins, e.g., galactosylated biotinylated human serum albumin (HSA) and small molecule clearing agents containing galactose and biotin. In the case of HSA based clearing agents, a typical dosage of the clearing agent will range from about 100 to 1000 mg, and more preferably about 200-500 mg. If a clearing agent is administered, the ligand-therapeutic agent conjugate is preferably administered about 2 to 12 hours after.

The conjugates may be administered by known methods of administration. Known methods of administration include, by way of example, intraperitoneal injection, intravenous injection, intramuscular injection, intranasal administration, among others. Intravenous administration is generally preferred.

III. Indications Amenable to Treatment by the Agents of the Invention

The agents of the invention are useful to treat a mammal afflicted with, to inhibit in a mammal at risk of, or to augment in a mammal at risk of, an indication associated with chemokine-induced activity, such as aberrant or pathological inflammatory processes. The chemokines participate in a broad range of inflammatory processes, both physiological and pathological. Thus, broad specificity chemokine inhibitors may be useful to treat or prevent a wide range of inflammatory diseases. Moreover, the use of rationally designed chemokine inhibitors, i.e., inhibitors with relative specificity for various chemokines, may reduce or inhibit side-effects associated with chronic therapies of broad spectrum chemokine inhibitors. Thus, these inhibitors may be designed to treat particular diseases, thereby minimizing side effects resulting from disrupting unrelated physiological processes.

Atherosclerosis. Development of atherosclerosis is a complex process involving smooth muscle cells, endothelial cells and inflammatory cells, and, in particular, monocyte-derived tissue macrophages, B or T cells. Once endothelial cells are activated, they express adhesion molecules important for the extravasation of inflammatory cells. For example, in the TGFβ1 knockout (−/−) mouse, the absence of this cytokine resulted in endothelial cell activation. The activated endothelial cells express, among other adhesion molecules, E-selectin, P-selectin, and ICAM-1, which in turn participate in the extravasation of leukocytes. Potent pro-inflammatory cytokines were also expressed at the sites of incipient vascular lesions. TNF-α, IL-1, as well as several chemokines including IL-8 and MCP-1, have been detected at elevated levels in atherosclerotic lesions. Results described hereinabove show that the chemokine MCP-1 in particular plays a role in atherosclerotic vascular inflammation.

It is now well accepted that the acute stability of vascular lesions is a more important determinant of short-term, e.g., less than several years, risk of myocardial infarction than is total plaque burden. The degree of macrophage infiltration is probably the major determinant of relative plaque stability. At least two factors contribute to plaque stability: macrophages secrete an excess of matrix-degrading enzymes (such as the matrix metalloproteinases) over their inhibitors, resulting in the loss of extracellular matrix (ECM) in the macrophage-rich shoulder and fibrous cap regions, a common feature of unstable or ruptured plaques; and macrophage-derived foam cells become necrotic, possibly in response to toxic oxidative metabolites of lipids, resulting in a lipid-filled extracellular pool which further destabilizes the local vessel wall architecture.

Inhibitors of chemokine action, and in particular inhibitors of MCP-1, may improve plaque stability and thus rapidly reduce the risk of myocardial infarction, without necessarily reducing the total atherosclerotic plaque burden. In particular, the agents of the invention may decrease lipid lesion formation and/or lipid lesion progression as well as increasing plaque stability (Boring et al., Nature, 394, 894 (1998)). Thus, agents of the invention, e.g., peptide 3(1-12)[MCP-1] (SEQ ID NO:1), KQK, peptide 3[7-12] (SEQ ID NO:9), as well as variants, e.g., $Leu_4Ile_{11}$peptide 3(1-12)[MCP-1] (SEQ ID NO:14), or derivatives thereof, may be useful to treat and/or prevent unstable angina pectoris, atherosclerosis, as well as other diseases characterized by local or systemic vasculitis, as well as the symptoms and diseases which occur secondarily to the vessel wall inflammation such as myocardial infarction.

Moreover, the agents of the invention are also useful in combination with lipid lowering agents, such as the statins, or TGF-beta elevating agents (see, for example, WO 96/40098, the disclosure of which is incorporated by reference herein).

Osteoporosis. Low bone mineral density, often categorized as osteoporosis, results from an imbalance between bone matrix deposition by osteoblasts and its subsequent resorption by osteoclasts. The balance between these two dynamic processes determines bone density. One strategy to increase bone density has been the use of analogs of tamoxifen, such as raloxifene, which mimic the effects of estrogen on bone and thus, promote osteoblast differentiation (increasing bone matrix deposition) and inhibit osteoclast recruitment (decreasing resorption). An alternative strategy is to decrease matrix resorption by directly inhibiting the mechanism by which osteoclasts are recruited to the bone. Measurement of bone matrix degradation products (such as the N-terminal and C-terminal telopeptides of collagen as well as pyridinium cross-links) in plasma and urine confirm that bone resorption is increased in osteoporosis, and hence inhibition of osteoclast activity is likely to prove an effective therapeutic strategy.

Unlike osteoblasts, which are locally derived, osteoclasts are continuously recruited to bone as precursor cells which circulate in the monocyte fraction, and which may be identical to monocytes. Once recruited, the precursors differentiate into osteoclasts which then resorb matrix until they die by apoptosis. Thus, the number of osteoclasts in bone tissue (and hence the osteoclast activity) can be rapidly regulated by modulating the osteoclast recruitment process.

A number of lines of evidence now suggest that the monocyte recruitment into bone is a molecular parallel of the pathological monocyte recruitment into the blood vessel wall that occurs during atherogenesis. In particular, the chemokine MCP-1 is implicated in both processes. Thus, MCP-1 inhibitors may act to reduce monocyte recruitment and thus decrease osteoclast recruitment and/or decrease the number of cells differentiating into osteoclasts, which would result in a rapid increase in bone density, for example, over a period of weeks rather than years. The ability of the present therapeutic agents to increase bone density contrasts with existing drugs which prevent a further decrease in bone density but do not increase bone density. Therefore, peptide 3, e.g., peptide 3(7-12)[MCP-1], and variants (e.g., $Leu_4Ile_{11}$peptide 3(1-12)[MCP-1]) and derivatives (e.g., $CRD-Cys_{13}Leu_4Ile_{11}$peptide 3(3-12)[MCP-1]) thereof, may be useful to inhibit or prevent low bone density. In particular, derivatives with specificity for CC chemokines, such as $CRD-Cys_{13}Leu_4Ile_{11}$peptide 3(3-12)[MCP-1], are preferred agents for the treatment of osteoporosis.

HIV Infection and AIDS. In addition to the CD4 receptor, additional cell surface molecules (termed co-receptors) are required for the productive infection of a cell by HIV isolates. HIV isolates can be divided into two subtypes, which depend on whether they can infect monocyte/macrophages (M-tropic strains) or helper T lymphocytes (T-tropic strains). Experiments with chemokine ligands suggest that the chemokine receptors function as the HIV co-receptors: MIP1α and RANTES inhibited the infection of monocytes with M-tropic strains (but not infection of T-cells by T-tropic strains), while SDF-1 inhibited T cell infection (but not monocyte infection). Further molecular analyses confirmed that the MIP1α/RANTES receptor CCR-5 is the HIV co-receptor on monocytes while the SDF-1 receptor CXCR-4 (also termed LESTR and fusin) is the co-receptor on T-cells. Early in infection, M-tropic virus predominates, a virus which is non-syncytium forming, less virulent and does not deplete T-cells. At a later time, selection favors conversion to the more virulent, syncytium forming T-tropic strain, a strain which depletes helper T cells and leads to acquired immunodeficiency (AIDS). It is possible that the virions can use other chemokine receptors, although at lower efficiency. Thus, to provide an effective agent to inhibit HIV, the agent preferably inhibits virus binding to more than one receptor, i.e., an agent would have to have broad specificity for chemokine receptors.

Genetic studies have identified a mutation in CCR5 which renders individuals essentially immune to HIV infection. This mutation, termed CCR5Δ32, results in a truncated mRNA for CCR-5. The expression of the truncated CCR-5 does not produce any detectable CCR-5 protein on the cell surface. Individuals homozygous for this deficiency have been reported to be entirely resistant to HIV infection, even under exposure to extremely high viral challenge, although there is now a single report of a homozygous mutant individual seropositive for HIV infection. Thus, these observations demonstrate that effective blockade of the CCR-5 receptor may effectively prevent infection. Moreover, CCR-5 mediated chemokine signaling does not have a crucial role in normal physiology, since CCR-5Δ32 homozygotes have no detectable phenotype other than HIV resistance.

Therefore, inhibitors of chemokine receptors, such as peptide 3, its variants, analogs or derivatives, may inhibit HIV infection as these agents have broad specificity. As described hereinbelow (Example 5), peptide 3[MCP-1] inhibited HIV binding and infection of Jurkat cells and macrophage. A preferred agent to prevent or inhibit HIV infection and/or replication is $CRD-Cys_{13}Leu_4Ile_{11}$peptide 3(3-12)[MCP-1]. In particular, peptide 3, its variants, analogs or derivatives, e.g., $CRD-Cys_{13}Leu_4Ile_{11}$peptide 3(3-12)[MCP-1], may be especially useful to inhibit infection of M-tropic strains of HIV.

Peptide 2, its variants, analogs or derivatives, are also useful to prevent or inhibit HIV infection and/or replication, as peptide 2 inhibited HIV replication in T cells and macrophage. Preferred therapeutic agents have decreased Duffy binding and increased co-receptor affinity (in at least about the nM range) (see Example 5) relative to the corresponding chemokine or peptide having the native or wild-type sequence. Preferably, Peptide 2, its variants, analogs or derivatives, e.g., LRD derivatives, are useful to inhibit T-tropic strains of HIV.

Thus, a combination of peptide 3, its variants, analogs or derivatives, and peptide 2, its variants, analogs or derivatives, may be particularly useful to prevent or treat HIV infection.

Thus, these agents are useful for the treatment, as well as the prevention, of both HIV seropositives and of progression of seropositive patients to AIDS, when used, either alone, in combination, or in combination with other anti-viral therapies. When used in combination, it is preferred that an infected individual is pre-treated with viral inhibitors (such as a cocktail of reverse transcriptase and viral protease inhibitors) and then given doses of a general chemokine inhibitor, preferably peptide 3, peptide 2, their variants or derivatives, more preferably peptide 2[MIP1α], its analogs or derivatives. Moreover, since resistance to other therapies (such as protease inhibitors or reverse transcriptase inhibitors) arise because of viral replication, agents which reduce virus infectivity may drastically increase the success of these existing therapies. Specifically, unlike all currently exploited therapeutic targets such as reverse transcriptase or the viral protease, chemokine agonists and/or antagonists target the susceptible cell rather than the virus itself. Although the virus can rapidly mutate to generate strains resistant to the virus-targeted agents, cells mutate less readily and are under less or no selective pressure to mutate. The extent to which the mutations in the HIV virus must occur to circumvent the use of a chemokine co-receptor is likely to be much greater than the mutations necessary to render a reverse transcriptase resistant to a reverse transcriptase inhibitor. Thus, the administration of chemokine analogs is likely to prove effective either alone or in combination with the virus-targeted therapies. Furthermore, chemokine inhibitors may have limited side effects in vivo, i.e., limited physiological impact, and therefore have a good therapeutic index when used in vivo.

Malaria. Malaria is caused by intracellular parasites of the plasmodium group. The main cellular target of the parasite is the red blood cell, and the mechanism of infection involves interaction of a plasmodium surface protein and the Duffy Antigen Receptor for Chemokines (DARC) for at least one common plasmodium species, *P. vivax*. Studies have indicated that normal surface presentation of DARC on the red blood cell surface is necessary for *plasmodium* entry. Consequently, inhibitors of DARC function may be useful antimalarial agents. Hence, peptide 3, or preferably a derivative showing higher affinity DARC binding such as $Ser_7Glu_8Glu_9$peptide 3(1-12)[MCP-1], or more preferably, a peptide which shows high affinity DARC binding and does not inhibit chemokine activity such as peptide 2[MCP-1], peptide 2[MGSA], or peptide 2[IL-8] are examples of agents falling under the scope of this invention which are useful for the prevention and treatment of malaria. Peptide 2, peptide 2 variants and derivatives are proinflammatory agents. Thus, these agents are useful to augment inflammatory responses, in particular weak inflammatory responses which are often associated with persistent infections such as parasitic infection, e.g., intracellular parasites.

Psoriasis. Psoriasis is an inflammatory disorder that is associated with MCP-1 and monocyte recruitment. Topical application of a therapeutic agent of the invention, e.g., peptide 3, is preferred to prevent or treat psoriasis as this delivery method reduces bioavailability problems. Derivatives of the therapeutic agents of the invention, e.g., CRD peptides, which are administered topically may exhibit enhanced bioavailability relative to non-derivatized counterparts.

Autoimmune Diseases. Autoimmune diseases, such as multiple sclerosis, Crohn's disease, rheumatoid arthritis and systemic lupus erythematosus, are characterized by inappropriate activation of the immune system, orchestrated by autoreactive leukocytes. Although it remains unclear what factors lead to the initial inappropriate recognition of self-antigens, a number of pro-inflammatory cytokines have been implicated in the continuing inflammation which underlies the tissue destruction that, in turn, leads to the morbidity and mortality associated with these diseases. Of these inflammatory cytokines, TNF-α and the chemokines (in particular MIP-1α) have been implicated.

For example, elevated MIP-1α expression is detected in experimental autoimmune encephalomyelitis, a model of T-cell mediated autoimmune disease with some common characteristics to human multiple sclerosis. Elevated MIP1α activity is also detected in the cerebrospinal fluid of patients with multiple sclerosis. Antibody therapy to reduce chemokine levels has been shown to be effective in animal models of autoimmune diseases, but this method only lowers chemokine levels for a short period, and is unlikely to be useful in human therapy. In contrast, a general antagonist of chemokine signaling is likely to suppress the inappropriate inflammation indefinitely. Thus, peptide 3, its derivatives and variants, may be useful to prevent and/or treat autoimmune disorders including, but not limited to, type I diabetes, multiple sclerosis, rheumatoid arthritis and systemic lupus erythematosus.

Moreover, different chemokine expression patterns may be associated with different autoimmune disorders, and hence each autoimmune disease may require a different derivative or variant of peptide 3. For example, MIP1α may play a central role in multiple sclerosis. MIP1α is a CC chemokine. Thus, the administration of a CC-selective agent of the invention can be used to treat multiple sclerosis (e.g., $Leu_4Ile_{11}$peptide 3(1-12)[MCP-1] or $Ser_7Glu_8Glu_9$peptide 3(1-12)[MCP-1]).

Wound Healing. Following wounding, there is a complex process of wound healing involving recruitment and proliferation of different cell types, elaboration of matrix, and increased immune surveillance. In the fetus (where increased immune surveillance is not required) this wound healing process leads to complete restoration of the normal tissue architecture (e.g., normal dermal architecture is restored after incisional wounding). In marked contrast, in the adult, incisional wounding results in a wound healing process that does not restore normal dermal architecture. Matrix is elaborated in excess amounts and in inappropriate spatial organization. The result is a scar. In some cases, such as in children following severe wounding such as from burns, the scars are hypertrophic having huge excess of matrix deposition and are particularly disfiguring.

In adults, the risk of infection following wounding is high. Leukocytes, particularly neutrophils, are recruited rapidly to the wound site, while monocyte/macrophages appear several days after wounding, resulting in a rapid formation of granulomatous tissue. Studies with antibodies have suggested that CXC chemokines such as IL-8 play an important role in neutrophil attraction to the wound site, and that inhibition of IL-8 production reduces both neutrophil accumulation and subsequent scarring. Experiments blocking CC chemokines have similarly shown that they have a role in the attraction of macrophages to the wound site, and these cells may also promote rapid healing at the expense of wound quality. Hence inhibition of either CXC or CC chemokines, or both, may result in a decrease in the wound-induced inflammatory reaction, and in turn promote a balance between fast healing and good restoration of dermal architecture.

To prevent or reduce scarring and/or enhance wound healing, a preferred embodiment of the invention is the topical application of a therapeutic agent of the invention that inhibits chemokine action at the site of the wound. Thus, a broad spectrum chemokine inhibitor, such as peptide 3(1-12)[MCP-1], $Leu_4Ile_{11}$peptide 3(1-12)[MCP-1], CRD-$Leu_4$-

Ile₁₁peptide 3[MCP-1] or WVQ, or combinations thereof may be administered. Alternatively, a selective inhibitor of IL-8, such as KEN, or a selective inhibitor of MCP-1, such as KQK, as well as combinations thereof may be administered. In addition, a combination of a broad spectrum inhibitor and a selective inhibitor may be administered. In this way, the various components of the wound-induced inflammatory process may be controlled as desired and the wound may be allowed to heal more slowly (under conditions where it is protected from infection, e.g., by simultaneous use of antibiotics) but with enhanced recovery of dermal architecture. See U.S. Pat. No. 5,202,118 for methods to determine the efficacy of an agent to treat or enhance wound healing.

Hypertension. Hypertension is a risk factor for atherosclerosis. To determine whether an agent of the invention is useful to inhibit or treat hypertension, a rabbit model is employed. New Zealand white rabbits are fed an atherogenic diet for three weeks to induce plaque formation. One half of each group of rabbits is administered an agent of the invention. Aortic coarctation is created in one group of the rabbits by wrapping a Dacron band around the midportion of the descending thoracic aorta (stenosis group). Another group of rabbits undergo the banding technique without aortic constriction. Yet another group of rabbits serve as nonoperated controls. Monocyte binding to the aortic endothelial surface is determined with epifluorescent microscopy on standard aortic segments proximal and distal to the band. Immunohistochemistry is performed using the following antibodies: VCAM-1, RAM11, CD11b, and factor VIII. In rabbits that did not receive the agent, hypertensive regions of the aorta proximal to the stenosis, monocyte adhesion and endothelial VCAM-1 expression are increased, with intimal thickening and accumulation of macrophage. In agent-treated rabbits, monocyte adhesion and endothelial VCAM-1 expression, intimal thickening and accumulation of macrophage are decreased relative to non-agent-treated rabbits.

Tuberculosis. Infection with *Mycobacterium tuberculosis* is an example of a disease where the monocyte/macrophage is responsible for attempting to clear the pathogen from the host tissue (in this case the lung) but where the immune response is often insufficient. As a consequence, even when antibiotics are used, *M. tuberculosis* infection can persist, clinically or sub-clinically as the body fails to clear the entire pathogen load.

Thus, diseases such as tuberculosis are amenable to therapy by agents which augment the existing immune reaction to recruit additional monocytes to the target tissue. Agents which illicit a systemic inflammation are less useful because the systemic inflammation has side effects (e.g., nausea, high temperature, lethargy, etc.). Thus, agents which bind to DARC with high affinity, may be useful as these agents may augment an existing inflammatory reaction but do not result in systemic inflammation. Since DARC normally acts to limit the extent of a local inflammatory reaction by sequestering locally produced chemokines, agents which reduce or block the capacity for DARC to sequester the chemokines may augment the desired response. Thus, one embodiment of the invention is the administration of a DARC binding agent, e.g., peptide 2[MCP-1], either locally to the lungs or systemically, to reduce or inhibit DARC sequestration of chemokines. Increased local chemokine levels can augment monocyte recruitment, and the resultant increase in the number of tissue macrophages may aid clearance of *M. tuberculosis* and reduce or prevent chronic infection.

The agent of the invention may be administered either alone, or more preferably, in combination with antibiotics or other drugs which have been shown to inhibit the growth of *M. tuberculosis*, but which when used singly may not prevent or abolish chronic infection.

Agents such as peptide 2[MCP-1] which augment existing immune reactions may also be useful for reduction or elimination of other chronic or parasitic infections, e.g., leishmania, trypanosomes, leprosy, and the like.

Basophil-mediated diseases. Asthma is a disease characterized by hyper-reactive airways and chronic inflammation resulting from an influx of many cell types and inflammatory mediators. The interaction and causal effects of all the inflammatory mediators in asthma is not entirely understood. MCP-1 can play a role in asthma through several different effector functions such as: monocyte recruitment, basophil recruitment, lymphocyte recruitment, monocyte activation or by triggering the release of histamine from basophils or resident mast cells (Bischoff et al., *J. Exp. Med.,* 175(5), 1271 (1992)). Inhibition of these processes are likely to reduce the severity of the disease. Allergic diseases, like asthma, are manifested through a complex interaction of inflammatory mediators including monocytes/macrophages, lymphocytes and histamine release from mast cells and basophils.

A preferred mode for administration of a therapeutic agent of the invention to treat or inhibit the symptoms associated with asthma is by inhalation. As red blood cells are not normally present in the respiratory tract, the DARC specificity of the therapeutic agent is less important for administration to the respiratory tract than for other modes of administration.

Endotoxemia. Endotoxemia is an acute systemic illness often mediated by LPS, a major component in the cell wall of gram-negative bacteria. LPS stimulates the release of proinflammatory cytokines. MCP-1 and MCP-2 are expressed in endotoxemia and exert their effect by recruiting leukocytes to target organs. The intraperitoneal administration of recombinant murine MCP-1 to LPS-challenged mice protected them from endotoxic lethality (Zisman et al., *J. Clin. Invest.,* 99, 2832 (1997)). Thus, preferred peptides for use in this embodiment of the invention are MCP-1 and MCP-2 peptides.

Myocardial Infarction/Acute Ischemia. Myocardial infarction is the result of acute closure of a coronary vessel usually due to thrombosis secondary to rupture of an atherosclerotic plaque. The damage to the adjacent myocardium and resultant heart failure is secondary to the period of ischemia and the damage caused during the reperfusion period. Reperfusion injuries are associated with increased oxygen free radicals and inflammatory mediators. MCP-1 is up-regulated during the reperfusion period and is a key inflammatory mediator (Kumar et al., *Circulation,* 90, 1427 (1994); Kumar et al., *Circulation,* 95, 693 (1997)). Inhibition of MCP-1 and the resultant inflammatory input may decease damage to the myocardium during recovery and reduce the incidence of heart failure.

Rheumatoid Arthritis. Rheumatoid arthritis is a multi-systemic inflammatory disease involving primarily the joints but also the skin, blood vessels, heart, lung and muscle. The characteristic pathology of rheumatoid arthritis involves the accumulation of non-suppurative inflammatory cell infiltrate consisting of macrophages and lymphocytes within the joint. MCP-1 is produced by both synovial cells and infiltrating monocyte/macrophages in rheumatoid arthritis and is thought to contribute to the accumulation of inflammatory cells within the joint. The ability of native MCP-1 and an antagonist of MCP-1 residues 9-76 of native MCP-1) have been assessed in the MRL-lpr model of chronic arthritis. Treatment with the antagonist MCP-1 (9-76) but not native MCP-1 resulted in a reduction of the symptoms and histopathology of chronic arthritis in this model (Gong et al., *J. Exp. Med.,* 186, 131 (1997); Plater-Zyberk et al., *Immunol. Lett.*, 51, 117 (1997); Wilder, *Clin. Rheumat.*, 10, 259 (1996)). Thus, peptide 3, its variants, analogs and derivatives may be especially useful to treat or prevent rheumatoid arthritis.

Contraception. Knockout mice for the CXCR4 chemokine receptor exhibit embryonic lethality. Agents of the invention have been identified which block the CXCR4 receptor (see Example 5) and other chemokine receptors. Thus, the agents of the invention may be useful in inducing abortion or providing contraception. Blockade of the CXCR4 receptor could provide an alternative to traditional contraceptives and could be used post-coitus.

IV. Dosages, Formulations and Routes of Administration of the Agents of the Invention The therapeutic agents of the invention, including a compound of formula (I)-(V), including their salts, are preferably administered so as to achieve serum levels of about 0.01 pM to about 100 nM, more preferably at doses of about 0.01 pM to about 5 nM, and even more preferably at doses of about 0.1 pM to about 2 nM, of the therapeutic agent. To achieve these levels, the agent may be administered at dosages of at least about 0.01 to about 100 mg/kg, more preferably about 0.1 to about 50 mg/kg, and even more preferably about 0.1 to about 30 mg/kg, of body weight, although other dosages may provide beneficial results. The amount administered will vary depending on various factors including, but not limited to, the agent chosen, the disease, whether prevention or treatment is to be achieved, and if the agent is modified for bioavailability and in vivo stability.

Administration of sense or antisense nucleic acid molecule may be accomplished through the introduction of cells transformed with an expression cassette comprising the nucleic acid molecule (see, for example, WO 93/02556) or the administration of the nucleic acid molecule (see, for example, Felgner et al., U.S. Pat. No. 5,580,859, Pardoll et al., *Immunity*, 3, 165 (1995); Stevenson et al., *Immunol. Rev.*, 145, 211 (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)). Pharmaceutical formulations, dosages and routes of administration for nucleic acids are generally disclosed, for example, in Felgner et al., supra.

The amount of therapeutic agent administered is selected to treat a particular indication. For example, to treat malaria, higher doses of peptide 2, its variants or derivatives, may be administered, while smaller doses of peptide 2, its variants or derivatives, are useful to prevent or inhibit HIV infection. The therapeutic agents of the invention are also amenable to chronic use for prophylactic purposes, preferably by systemic administration.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated.

One or more suitable unit dosage forms comprising the therapeutic agents of the invention, which, as discussed below, may optionally be formulated for sustained release, can be administered by a variety of routes including oral, or parenteral, including by rectal, buccal, vaginal and sublingual, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Formulations suitable for vaginal administration may be presented as pessaries, tampons, creams, gels, pastes, douches, lubricants, foams or sprays containing, in addition to the active ingredient, such carriers as are known in the art to be appropriate. Formulations suitable for rectal administration may be presented as suppositories.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, poly-esters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydro-gel), polyvinylidene chloride, poly(ethylene terephthalate), butyl rubber, epichlorohydrin rubbers, ethylenevinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols, as well as in toothpaste and mouthwash, or by other suitable forms, e.g., via a coated condom. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. No. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-25% by weight.

When desired, the above-described formulations can be adapted to give sustained release of the active ingredient employed, e.g., by combination with certain hydrophilic polymer matrices, e.g., comprising natural gels, synthetic polymer gels or mixtures thereof.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; mouthwashes comprising the composition of the present invention in a suitable liquid carrier; and pastes and gels, e.g., toothpastes or gels, comprising the composition of the invention.

The formulations and compositions described herein may also contain other ingredients such as antimicrobial agents, or preservatives. Furthermore, the active ingredients may also be used in combination with other therapeutic agents, for example, oral contraceptives, bronchodilators, anti-viral agents, steroids and the like.

Sustained Released Dosage Forms

Sustained release dosage forms of the invention may comprise microparticles and/or nanoparticles having a therapeutic agent dispersed therein. The therapeutic dosage forms of this aspect of the present invention may be of any configuration suitable for sustained release. Preferred sustained release therapeutic dosage forms exhibit one or more of the following characteristics:

microparticles (e.g., from about 0.5 micrometers to about 100 micrometers in diameter, with about 0.5 to about 2 micrometers more preferred; or from about 0.01 micrometers to about 200 micrometers in diameter, preferably from about 0.5 to about 50 micrometers, and more preferably from about 2 to about 15 micrometers) or nanoparticles (e.g., from about 1.0 nanometer to about 1000 nanometers in diameter, with about 50 to about 250 nanometers being more preferred; or from about 0.01 nanometer to about 1000 nanometers in diameter, preferably from about 50 to about 200 nanometers), free flowing powder structure;

biodegradable structure designed to biodegrade over a period of time preferably between from about 0.5 to about 180 days, preferably from about 1-3 to about 150 days, or from about 3 to about 180 days, with from about 10 to about 21 days more preferred; or non-biodegradable structure to allow therapeutic agent diffusion to occur over a time period of between from about 0.5 to about 180 days, more preferably from about 30 to about 120 days; or from about 3 to about 180 days, with from about 10 to about 21 days preferred;

biocompatible with target tissue and the local physiological environment into which the dosage form to be administered, including yielding biocompatible biodegradation products;

facilitate a stable and reproducible dispersion of therapeutic agent therein, preferably to form a therapeutic agent-polymer matrix, with active therapeutic agent release occurring by one or both of the following routes: (1) diffusion of the therapeutic agent through the dosage form (when the therapeutic agent is soluble in the shaped polymer or polymer mixture defining the dimensions of the dosage form); or (2) release of the therapeutic agent as the dosage form biodegrades; and/or for targeted dosage forms, capability to have, preferably, from about 1 to about 10,000 binding protein/peptide to dosage form bonds and more preferably, a maximum of about 1 binding peptide to dosage form bond per 150 square angstroms of particle surface area. The total number of binding protein/peptide to dosage form bonds depends upon the particle size used. The binding proteins or peptides are capable of coupling to the particles of the therapeutic dosage form through covalent ligand sandwich or non-covalent modalities as set forth herein.

Nanoparticle sustained release therapeutic dosage forms are preferably biodegradable and, optionally, bind to the vascular smooth muscle cells and enter those cells, primarily by endocytosis. The biodegradation of the nanoparticles occurs over time (e.g., 30 to 120 days; or 10 to 21 days) in prelysosomic vesicles and lysosomes. Preferred larger microparticle therapeutic dosage forms of the present invention release the therapeutic agents for subsequent target cell uptake with only a few of the smaller microparticles entering the cell by phagocytosis. A practitioner in the art will appreciate that the precise mechanism by which a target cell assimilates and metabolizes a dosage form of the present invention depends on the morphology, physiology and metabolic processes of those cells. The size of the particle sustained release therapeutic dosage forms is also important with respect to the mode of cellular assimilation. For example, the smaller nanoparticles can flow with the interstitial fluid between cells and penetrate the infused tissue. The larger microparticles tend to be more easily trapped interstitially in the infused primary tissue, and thus are useful to therapeutic agents.

Preferred sustained release dosage forms of the present invention comprise biodegradable microparticles or nanoparticles. More preferably, biodegradable microparticles or nanoparticles are formed of a polymer containing matrix that biodegrades by random, nonenzymatic, hydrolytic scissioning to release therapeutic agent, thereby forming pores within the particulate structure.

Polymers derived from the condensation of alpha hydroxycarboxylic acids and related lactones are preferred for use in the present invention. A particularly preferred moiety is formed of a mixture of thermoplastic polyesters (e.g., polylactide or polyglycolide) or a copolymer of lactide and glycolide components, such as poly(lactide-co-glycolide). An exemplary structure, a random poly(DL-lactide-co-glycolide), is shown below, with the values of x and y being manipulable by a practitioner in the art to achieve desirable microparticle or nanoparticle properties.

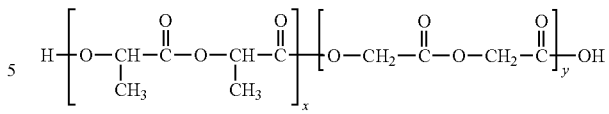

Other agents suitable for forming particulate dosage forms of the present invention include polyorthoesters and polyacetals (*Polymer Letters*, 18:293 (1980) and polyorthocarbonates (U.S. Pat. No. 4,093,709) and the like.

Preferred lactic acid/glycolic acid polymer containing matrix particles of the present invention are prepared by emulsion-based processes, that constitute modified solvent extraction processes, see, for example, processes described by Cowsar et al., "Poly(Lactide-Co-Glycolide) Microcapsules for Controlled Release of Steroids," *Methods Enzymology*, 112:101-116, 1985 (steroid entrapment in microparticles); Eldridge et al., "Biodegradable and Biocompatible Poly(DL-Lactide-Co-Glycolide) Microspheres as an Adjuvant for Staphylococcal Enterotoxin B Toxoid Which Enhances the Level of Toxin-Neutralizing Antibodies," *Infection and Immunity* 59:2978-2986, 1991 (toxoid entrapment); Cohen et al., "Controlled Delivery Systems for Proteins Based on Poly(Lactic/Glycolic Acid) Microspheres," *Pharmaceutical Research,* 8(6):713-720, 1991 (enzyme entrapment); and Sanders et al., "Controlled Release of a Luteinizing Hormone-Releasing Hormone Analogue from Poly(D,L-Lactide-Co-Glycolide) Microspheres," *J. Pharmaceutical Science,* 73(9): 1294-1297, 1984 (peptide entrapment).

In general, the procedure for forming particle dosage forms of the present invention involves dissolving the polymer in a halogenated hydrocarbon solvent, dispersing a therapeutic agent solution (preferably aqueous) therein, and adding an additional agent that acts as a solvent for the halogenated hydrocarbon solvent but not for the polymer. The polymer precipitates out from the polymer-halogenated hydrocarbon solution onto droplets of the therapeutic agent containing solution and entraps the therapeutic agent. Preferably the therapeutic agent is substantially uniformly dispersed within the sustained release dosage form of the present invention. Following particle formation, they are washed and hardened with an organic solvent. Water washing and aqueous nonionic surfactant washing steps follow, prior to drying at room temperature under vacuum.

For biocompatibility purposes, particulate dosage forms, characterized by a therapeutic agent dispersed in the matrix of the particles, are sterilized prior to packaging, storage or administration. Sterilization may be conducted in any convenient manner therefor. For example, the particles can be irradiated with gamma radiation, provided that exposure to such radiation does not adversely impact the structure or function of the therapeutic agent dispersed in the therapeutic agent-polymer matrix or the binding protein/peptide attached thereto. If the therapeutic agent or binding protein/peptide is so adversely impacted, the particle dosage forms can be produced under sterile conditions.

Release of the therapeutic agent from the particle dosage forms of the present invention can occur as a result of both diffusion and particle matrix erosion. The biodegradation rate directly effects the kinetics of therapeutic agent release. The biodegradation rate is regulable by alteration of the composition or structure of the sustained release dosage form. For example, alteration of the lactide/glycolide ratio in preferred dosage forms of the present invention can be conducted, as described by Tice et al., "Biodegradable Controlled-Release Parenteral Systems," *Pharmaceutical Technology*, pp. 26-35, 1984; by inclusion of agents that alter the rate of polymer hydrolysis, such as citric acid and sodium carbonate, as described by Kent et al., "Microencapsulation of Water Soluble Active Polypeptides," U.S. Pat. No. 4,675,189; by altering the loading of therapeutic agent in the lactide/glycolide polymer, the degradation rate being inversely proportional to the amount of therapeutic agent contained therein, by judicious selection of an appropriate analog of a common family of therapeutic agents that exhibit different potencies so as to alter said core loadings; and by variation of particle size, as described by Beck et al., "Poly(DL-Lactide-Co-Glycolide)/Norethisterone Microcapsules: An Injectable Biodegradable Contraceptive," *Biol. Reprod.*, 28:186-195, 1983, or the like. All of the aforementioned methods of regulating biodegradation rate influence the intrinsic viscosity of the polymer containing matrix, thereby altering the hydration rate thereof.

The preferred lactide/glycolide structure is biocompatible with the mammalian physiological environment. Also, these preferred sustained release dosage forms have the advantage that biodegradation thereof forms lactic acid and glycolic acid, both normal metabolic products of mammals.

Functional groups required for binding of the protein/peptide to the particle dosage form are optionally included in or on the particle matrix and are attached to the non-degradable or biodegradable polymeric units. Functional groups that are useful for this purpose include those that are reactive with peptides, e.g., carboxyl groups, amine groups, sulfhydryl groups and the like. Preferred binding enhancement moieties include the terminal carboxyl groups of the preferred (lactide-glycolide) polymer containing matrix or the like.

To employ the therapeutic agents of the invention to enhance the immunological response of a particular immunogen, e.g., the *Haemophilis influenza* type b (Hib) capsular polysaccharide (polyribosylribitol phosphate, PRP), the agents may be conjugated to the immunogen. Thus, for example, peptide 2(1-15)[MCP-1] may be covalently linked to PRP through a 6 carbon spacer molecule derived from adipic acid dihydrazide (see Gordon, Patent 83/4939, Republic of South Africa, 1984), and administered in a manner similar to that described in Eskola et al., *Lancet*, 1, 1184 (1985). The use of nucleic acid molecules to prepare vaccines is described in, for example, Felgner et al., supra and Stevenson et al., supra.

A vaccine of the invention may also comprise cells or viruses having nucleic acid encoding the immunogen and a peptide or variant peptide of the invention or its complement, optionally as a fusion protein.

For a general description of vaccine principles and practice, see Ada, In: *Fundamental Immunology*, 2$^{nd}$ ed., Raven Press Ltd., N.Y., pp. 985-1030 (1989).

V. Detection of the Peptides of the Invention in Physiological Fluid

Analysis of peptide 3 in blood and urine was performed on a semi-permeable surface (SPS) HPLC column (restricted access media). Serum or other protein-containing samples can be injected directly onto an SPS column (e.g., SPS-C18 with a column size of 4.6 mm×250 mm; using a mobile phase: A: 0.1% TFA in water, B: 0.1% TFA in acetonitrile: 0-5 min—5% B, 5-30 min—60% B, 30-40 min—5% B detector; 215 nm). The outer phase of the column forms a semipermeable surface that prevents large molecules from reaching the inner phase. Small molecules penetrate the semipermeable surface and interact with the inner reversed phase.

Standards of peptide 3 (range of 1.5 µg/ml to 1000 µg/ml) in PBS were injected and a standard curve was created. 20 µl of serum and urine were injected and the areas under the peptide 3 peaks were obtained. The concentration was then calculated from the standard curve. This method can detect at least about 20 µg/ml of a peptide in physiological fluid samples.

The invention will be further described by, but is not limited to, the following examples.

Example 1

Identification and Characterization of Pan-Chemokine Peptide Inhibitors

Based on an alignment of MCP-1 sequences from different species, three regions in MCP-1 were identified which were conserved between all the species examined. Three purified (>95% purity) peptides (12-15mers) were prepared which had the greatest sequence homology between the human and mouse MCP-1 sequences (Table 1). These peptides were screened for their ability to inhibit hMCP-1 induced THP-1 migration. Similarly, the sequences of *Xenopus laevis* TGF-beta1 and TGF-beta3 and human TGF-beta1 and TGF-beta3 were compared, and 3 regions (each 10 mer) of perfect homology were identified. These peptides were termed "betatides".

For this assay, THP-1 cells were maintained at a density of $4 \times 10^5$ cells per ml in RPMI-1640 supplemented with 10% fetal calf serum+20 µM 2-mercaptoethanol. Chemotaxis was induced in a 96-well disposable chemotaxis chamber fitted with a 5 µM polycarbonate filter (PVP free, ChemoTX, Neuroprobe Inc., Cabin John). Twenty-nine µl of chemoattractant (recombinant human chemokine; 50 ng/ml, i.e., 5.9 nM) or control (100 ng/ml TGFβ) was added to the lower compartment of each well. The framed filter was aligned with the holes in the corner of the filter frame and placed over the wells. Five×$10^4$ THP-1 cells in 25 µl of RPMI-1640 culture media were added to the upper compartment. Peptides were dissolved in Milli Q water and then serially diluted in culture medium. In most cases, the serially diluted peptides were added to the upper compartment of the chemotaxis chamber. The chamber was incubated at 37° C. in a humidified atmosphere of 5% $CO_2$ for 4 hours.

After incubation, the cells were gently removed from the top of the filter with a pipette, 20 µl of 20 mM EDTA in PBS was added into each top well, and the mixture was incubated for 20 minutes at 4° C. The filter was then carefully flushed with media using a gentle flow, and removed. A standard curve was prepared to accurately quantify the number of THP-1 cells that had migrated. The curve was based on a two-fold dilution series of THP-1 cells (top standard 100,000 cells in 29 µl). Cells which had migrated, and in separate wells, the cells in the standards, were stained with 3 µl of MTT stock solution which was added directly into each well (5 mg/ml in RPMI 1640 without phenol red, Sigma Chemical Co.) and incubated at 37° C. for 4 hours. The media was carefully aspirated from each well, and the converted dye was solubilized by 20 µl of DMSO. Absorbance of converted dye was measured at a wavelength of 595 nM using an ELISA plate reader. The number of cells that had migrated in each well was determined by interpolation of the standard curve.

Peptide 1[MCP-1] (see Table 1; SEQ ID NO:2), i.e., the N-terminal peptide of human MCP-1, was only weakly active in the migration assay ($ED_{50}$>100 µM; 10% inhibition at 100 µM, p=0.27). Peptide 2[MCP-1] (Table 1; SEQ ID NO:3) was also a weak inhibitor of chemokine-induced migration ($ED_{50}$>100 μM; 19% inhibition at 100 μM, p=0.09). Thus, in the presence of a strong agonist, i.e., MCP-1, peptide 2[MCP-1] having SEQ ID NO:3, a weak agonist, displaces MCP-1 from its receptor. However, in the absence of a strong agonist, i.e., MCP-1, peptide 2[MCP-1] exhibited weak agonist properties, i.e., peptide 2[MCP-1] stimulated chemotaxis. Surprisingly, peptide 2(1-15)[SDF1α] had potent pan-chemokine antagonist properties.

Figure 2:
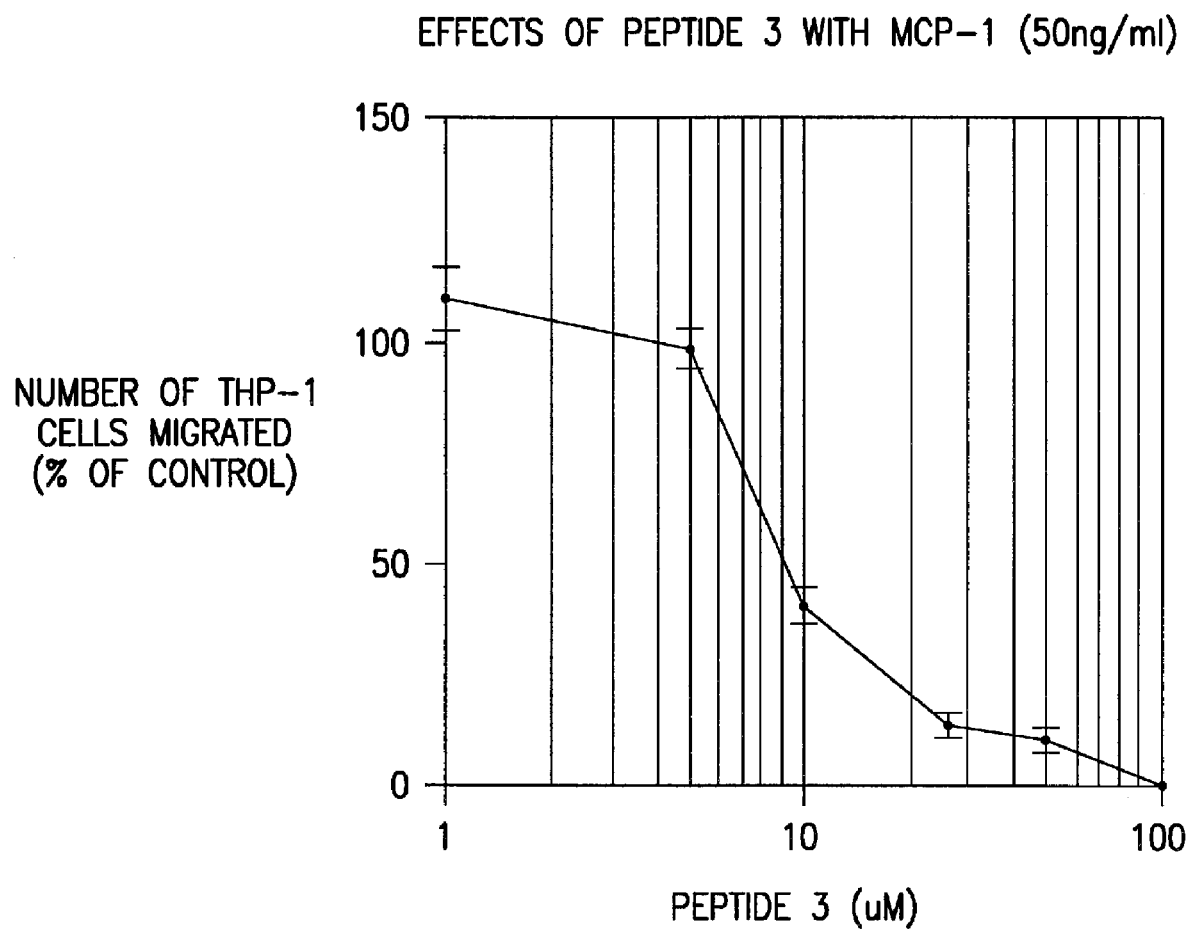
FIG. 2 shows a dose-response curve for the peptide 3 (SEQ ID NO:1) inhibition of MCP-1-induced THP-1 cell migration.

In contrast, peptide 3(1-12)[MCP-1] (Table 1; SEQ ID NO:1) was a highly effective inhibitor of MCP-1 induced THP-1 migration with a dose giving 50% inhibition ($ED_{50}$) of 8±1 μM (n=4). A typical dose response curve is shown in FIG. 2. At concentrations above 50 μM, peptide 3(1-12)[MCP-1] having SEQ ID NO:1 abolished all of the MCP-1 induced THP-1 migration.

MCP-1 induced migration by direct receptor antagonism. To confirm this observation, the binding affinity of an N-terminally biotinylated derivative of peptide 3(1-12)[MCP-1] (SEQ ID NO:1) was determined. This derivative bound to the surface of THP-1 cells with a ka of about 10 μM.

Peptide 3(1-12)[MCP-1] (SEQ ID NO:1) also inhibited other functions of MCP-1, which may be mediated by different combinations of receptors. MCP-1 has been reported to be a weak co-mitogen with 0.5% fetal calf serum for cultured smooth muscle cells. It was found that 100 μM peptide 3(1-12)[MCP-1] (SEQ ID NO:1) completely abolished the co-mitogenic effect of MCP-1 for cultured smooth muscle cells, also consistent with the hypothesis that peptide 3(1-12)[MCP-1] (SEQ ID NO:1) is an MCP-1 receptor antagonist. The observation that peptide 3(1-12)[MCP-1] (SEQ ID

TABLE 1

Alignment of Chemokine Sequences

```
                                                                                          (SEQ ID NO:16)
AQPDAINAPV TCCYNFTNRK ISVQRLASYR RITSSKCPKE AVIFKTIVAK EICADPKQKW VQDSMDHLDK QTQTPKT    hMCP1
*****.***. **** **  .  *    ** **. *****.**** ** * *  . . *.***** * **      **.
                                                                                          (SEQ ID NO:26)
AQPDAVNAPL TCCYSPTSKM IPMSRLESYK RITSSRCPKE AVVFVTKLKR EVCADPKKEW VQTYIKNLDR NQMR.....  mMCP1

Peptide 1              Peptide 2              Peptide 3

(SEQ ID NO:17)
AQPDSVSIPI TCCPNVINRK IPIQRLESYR RITNIQCPKE AVIFKTKRGK EVCADPKERW VRDSNKHLDQ IFQNLKP    hMCP2
                                                                                          (SEQ ID NO:18)
AQPVGINTST TCCYRFINKK IPKQRLESYR RTTSSHCPRE AVIFKTKLDK EICADPTQKW VQDFMKHLDK KTQTPKL    hMCP3

(SEQ ID NO:19)
SASLAADTPT ACCFSYTSRQ IPQNFIADYF E-TSSQCSKP GVIFLTKRSR QVCADPSEEW VQKYVSDLEL SA           hMIP1a
                                                                                          (SEQ ID NO:20)
SAPMGSDPPT ACCFSYTARK LPRNFVVDYY E-TSSLCSQP AVVFQTKRSK QVCADPSESW VQEYVYDLEL N            hMIP1b (SEQ ID NO:21)
SAPMGSDPPT ACCFSYTARK LPRNFVVDYY E-TSSLCSQP AVVFQTKRSK QVCADPSESW VQEYVYDLEL N             RANTES (SEQ ID NO:25)
   HPGIPS ACCYNFTNKK ISFQRLKSYK IITSSKCPQT AIVFEIKPDK MICADPKxxW VQDAKKYLDQ ISQxTKP     Eotaxin (SEQ ID NO:23)
LPRSAKELRC QCIKTYSKPF HPKFIKELRV IESGPHCANT EIIVRLSDGR ELCLDPKENW VQRVEKFLKR AENS          hIL-8

(SEQ ID NO:56)
   GKPVSLSY RCPCRFFESH IARANVKHLK ILNTPNCALQ IVARLKNNNR QVCIDPKLKW IQEYEKALNK            hSDF1b

.......... .C...F.... I......... ..T...C... AVI......K .VCADP...W VQ.....L..  .....   CONSENSUS
```

To determine whether the peptides were MCP-1 receptor antagonists, the peptides were introduced with the chemokine in the lower compartment (as opposed to with the cells in the upper compartment in the experiments described above; in the trans-well THP-1 migration assay. Under these conditions, peptide 1[MCP-1] having SEQ ID NO:2 was a more efficient inhibitor of MCP-1 induced chemokine migration that it had been when it was incubated with the cells, inhibiting 48% of the MCP-1 induced migration at 100 μM compared to 10% inhibition when peptide 1[MCP-1] (SEQ ID NO:2) was incubated With the cells. This result is consistent with published reports which show that peptide 1[MCP-1] (SEQ ID NO:2) and its derivatives act by disrupting the MCP-1 dimer, forming inactive monomers. Peptide 1[MCP-1] (SEQ ID NO:2) is not, therefore, a classical receptor-level antagonist of MCP-1 function. In marked contrast, peptide 3(1-12)[MCP-1] having SEQ ID NO:1 was much less effective when incubated with the chemokine than with the cells (17% inhibition at 100 μM compared with >99% inhibition), suggesting that a peptide having SEQ ID NO:1 inhibits NO:1) completely inhibits different responses to MCP-1 in different cell types suggests that peptide 3 may be a general antagonist of all chemokine receptors capable of binding and signaling in response to MCP-1.

To investigate the receptor specificity of peptide 3 inhibition, the $ED_{50}$ was determined for peptide 3(1-12)[MCP-1] (SEQ ID NO:1) inhibition of THP-1 migration induced by chemokines which signal through different receptors than MCP-1 receptors. Representative chemokines included a beta-chemokine ("CC"), MIP-1α, and two alpha-chemokines ("CXC"), IL-8 and SDF-1α. Additionally, to determine the specificity of peptide 3(1-12)[MCP-1] (SEQ ID NO:1) for chemokine receptors, TGF-beta was selected as a migration-inducing agent unrelated to the chemokine family, and as an agent which elicits a biological activity by signaling through identified, unrelated receptors.

Peptide 3(1-12)[MCP-1] (SEQ ID NO:1) inhibited the THP-1 migration induced response to all four of the selected chemokines, with the order of potency: MIP-1α≧MCP-1>SDF1α≧IL-8 (see Table 2). In contrast, peptide 1[MCP-1]

(SEQ ID NO:2) or peptide 2(1-15)[MCP-1] (SEQ ID NO:3) did not inhibit migration in response to any of these chemokines by more than 20%, even at 100 μM (Table 2).

TABLE 2

(a) ED$_{50}$ for inhibition of THP-1 migration

| PEPTIDE | ED$_{50}$ (μM) versus | | | | |
|---|---|---|---|---|---|
| | MCP-1 | MIP1α | IL8 | SDF-1α | TGFβ1 |
| Peptide 1 (SEQ ID NO: 2) | n.s.[b] | n.s.[b] | n.s. | n.s. | n.s. |
| Peptide 2 (SEQ ID NO: 3) | n.s. | n.s. | n.s. | n.s. | n.s. |
| Peptide 3[a] (SEQ ID NO: 1) | 8 ± 1 | 8 ± 1 | 14 ± 1 | 10 ± 0 | n.s. |

(b) Extent of inhibition of THP-1 migration at 100 μM

| PEPTIDE | % inhibition at 100 μM versus | | | | |
|---|---|---|---|---|---|
| | MCP-1 | MIP1α | IL8 | SDF-1α | TGFβ1 |
| Peptide 1 (SEQ ID NO: 2) | n.s.[b] | n.s.[b] | n.s. | n.s. | n.s. |
| Peptide 2 (SEQ ID NO: 3) | n.s. | n.s. | n.s. | n.s. | n.s. |
| Peptide 3 (SEQ ID NO: 1) | 112 | 99 | 103 | 107 | n.s. |

(c) Extent of inhibition of human monocyte migration at 100 μM

| PEPTIDE | % inhibition at 100 μM versus | | | | |
|---|---|---|---|---|---|
| | MCP-1 | MIP1α | IL8 | SDF-1α | TGFβ1 |
| Peptide 1 (SEQ ID NO: 2) | n.s. | n.s. | n.s. | n.s. | n.s. |
| Peptide 2 (SEQ ID NO: 3) | 23 | n.s. | n.s. | n.s. | n.s. |
| Peptide 3 (SEQ ID NO: 1) | 108 | 120 | 106 | 108 | n.s. |

[a] mean ± SEM of at least three determinations
[b] Peptide 1 caused significant inhibition only when added to the lower compartment
n.s. = no statistically significant inhibition (p > 0.05)

Furthermore, peptide 3(1-12)[MCP-1] having SEQ ID NO:1 (as well as peptide 1[MCP-1] (SEQ ID NO:2) and peptide 2(1-15)[MCP-1] (SEQ ID NO:3)) did not significantly inhibit THP-1 migration induced by TGF-beta even at 100 μM. Taken together, these results demonstrated that peptide 3(1-12)[MCP-1] (SEQ ID NO:1) is a general and specific inhibitor of chemokine signaling. Although peptide 3(1-12)[MCP-1] (SEQ ID NO:1) shows weak selectivity for CC chemokines over CXC chemokines, nevertheless, at 100 μM, peptide 3(1-12)[MCP-1] (SEQ ID NO:1) inhibits >99% of the migration induced by any of the chemokines of either chemokine family tested (Table 2). Thus, although MCP-1 signals through multiple related receptors, peptide 3(1-12)[MCP-1] (SEQ ID NO:1) blocks all of the receptors which participate in the chemotactic and mitogenic signaling pathways elicited by MCP-1.

To exclude the possibility that peptide 3 (1-12)[MCP-1] (SEQ ID NO:1) was more effective on THP-1 cells than primary human monocytes, the effect of peptide 3(1-12)[MCP-1] (SEQ ID NO:1) on the chemokine-induced migration of freshly prepared peripheral blood monocytes from 3 donors was tested. Similar to the results for THP-1 cells, 100 μM of peptide 3(1-12)[MCP-1] (SEQ ID NO:1), but not peptide 1 [MCP-1] (SEQ ID NO:2) or peptide 2(1-15)[MCP-1] (SEQ ID NO:3), inhibited all or almost all (>95%) of the migration induced with each of the four chemokines, but did not affect TGF-beta induced migration. Thus, peptide 3(1-12) [MCP-1] (SEQ ID NO:1) is an inhibitor of a broad range of pro-inflammatory chemokines which act on a wide range of target cells (smooth muscle cells, THP-1, Jurkat T-cell line and primary human monocytes). Note that in contrast to THP-1 cells, peptide 2(1-15)[MCP-1] (SEQ ID NO:3) inhibition of MCP-1 induced migration of primary human monocytes (20%) was statistically significant (Table 2).

Example 2

Characterization of Fragments and Variants of Peptide 3(1-12)[MCP-1] and Peptide 2 [MCP-1]

To determine whether a fragment of peptide 3 has biological activity and selectivity, two 6mer "half-peptides" were analyzed (Table 3): EICADP (SEQ ID NO:8), corresponding to peptide 3(1-6)[MCP-1], and KQKWVQ (SEQ ID NO:9), corresponding to peptide 3(7-12)[MCP-1]. Peptide 3(7-12) [MCP-1] (SEQ ID NO:8) was as potent an inhibitor of CC chemokine signaling as peptide 3(1-12)[MCP-1] (SEQ ID NO:1), but was noticeably more potent as an inhibitor of CXC chemokines (Table 4). In contrast, peptide 3(1-6)[MCP-1] (SEQ ID NO:8) was much less potent as an inhibitor than peptide 3(1-12)[MCP-1] (SEQ ID NO:1).

TABLE 3

| NAME | SEQUENCE | SOURCE |
|---|---|---|
| Peptide 1 family | | |
| Pep1 | AQPDAINAPVTCC (SEQ ID NO:2) | Residues 1-13 of mature hMCP-1 |
| Peptide 2 family | | |
| Pep2(1-15)[MCP1] | SYRRITSSKCPKEAV (SEQ ID NO:3) | Residues 28-42 of mature hMCP-1 |
| Pep2(1-15)[SDF1] | HLKILNTPNCALQIV (SEQ ID NO:4) | Residues 26-40 of mature hSDF-1β |
| Pep2(1-14)[MIP1α] | ]DYFETSSQCSKPGV (SEQ ID NO:5) | Residues 28-41 of mature hMIP1α |
| Pep2(1-16)[IL8] | ELRVIESGPHCANTEI (SEQ ID NO:6) | Residues 27-42 of mature hIL-8 |

TABLE 3-continued

| NAME | SEQUENCE | SOURCE |
| --- | --- | --- |
| Peptide 3 family | | |
| Pep3(1-12)[MCP-1] | EICADPKQKWVQ (SEQ ID NO:1) | Residues 50-61 of mature hMCP-1 |
| Pep3(3-12)[MCP-1] | CADPKQKWVQ (SEQ ID NO:7) | Residues 52-61 of mature hMCP-1 |
| Pep3(1-6)[MCP-1] | EICADP (SEQ ID NO:8) | Residues 50-55 of mature hMCP-1 |
| Pep3(7-12)[MCP-1] | KQKWVQ (SEQ ID NO:9) | Residues 56-61 of mature hMCP-1 |
| Leu$_4$Pep3 (1-12)[MCP-1] | EICLDPKQKWVQ (SEQ ID NO: 10) | Mutant of peptide 3 |
| Ser$_7$Pep3 (1-12)[MCP-1] | EICADPSQKWVQ (SEQ ID NO:11) | Mutant of peptide 3 |
| Ser$_7$Glu$_8$Glu$_9$Pep3 (1-12)[MCP-1] | EICADPSEEWVQ (SEQ ID NO:12) | Residues 50-61 of mature hMIP1α |
| Ile$_{11}$Pep3 (1-12)[MCP-1] | EICADPKQKWIQ (SEQ ID NO:13) | Mutant of peptide 3 |
| Leu$_4$Ile$_{11}$Pep3 (1-12)[MCP-1] | EICLDPKQKWIQ (SEQ ID NO:14) | Mutant of peptide 3 |
| Unrelated control peptide | | |
| Peptide C | CPSLEDSFIQVA (SEQ ID NO:15) | C-terminus of h Apo(a)RG-C protein |
| D-ala-peptide 3(1-12)[MCP-1] | | |

TABLE 4

Effect of Mutant Sequence Peptide 3 Derivatives on THP-1 Migration

| PEPTIDE | ED$_{50}$ (µM) versus | | | | |
| --- | --- | --- | --- | --- | --- |
| | MCP1 | MIP1α | IL8 | SDF1α | TGFβ1 |
| Peptide 3 (SEQ ID NO: 1) | 8 | 8 | 14 | 10 | n.s. |
| Peptide 3[3-12] (SEQ ID NO: 7) | 8 | 7 | 9 | 9 | n.s. |
| Peptide 3[1-6] (SEQ ID NO: 8) | 33 | 25 | 17 | 19 | n.s. |
| Peptide 3[7-12] (SEQ ID NO: 9) | 7 | 5 | 6 | 6 | n.s. |
| Leu$_4$peptide 3 (SEQ ID NO: 10) | 8 | 7 | 3 | 3 | n.s. |
| Ser$_7$peptide 3 (SEQ ID NO: 11) | 7 | 6 | 3 | 4 | n.s. |
| Ile$_{11}$peptide 3 (SEQ ID NO: 13) | 6 | 4 | 2 | 7 | n.s. |
| Leu$_4$Ile$_{11}$peptide 3 (SEQ ID NO: 14) | 2 | 1 | 3 | 3 | n.s. |
| Ser$_7$Glu$_8$Glu$_9$pep3 (SEQ ID NO: 12) | 7 | 2 | 9 | 5 | n.s. |
| WVQ | 8 | <1 | <1 | <1 | n.s. |
| KQK | 7 | n.s. | n.s. | n.s. | n.s. |
| SEE | n.s. | 6 | n.s. | n.s. | n.s. |

Peptide 3(7-12)[MCP-1] (SEQ ID NO:9) showed essentially no selectivity, inhibiting migration by all chemokines tested with an ED$_{50}$ in the range of 7-9 µM. Peptide 3(1-6)[MCP-1] (SEQ ID NO:8) was much less efficient at inhibiting the CC chemokines (ED$_{50}$ of about 30 µM) but only slightly less efficient at inhibiting CXC chemokines (18 µM) compared with peptide 3(1-12)[MCP-1] (SEQ ID NO:1). The selectivity ratio is defined as the average ED$_{50}$ for MCP-1 and MIP1α divided by the average ED$_{50}$ for IL-8 and SDF1α. Selectivity ratios of greater than 1 indicate greater inhibition of CC chemokines relative to CXC chemokines; selectivity ratios of less than 1 indicate greater inhibition of CXC chemokines relative to CC chemokines; and a selectivity ratio of 1 indicates that both families of cytokines are inhibited to the same extent. Hence, although it is overall a markedly weaker inhibitor of chemokine signaling, peptide 3(1-6) [MCP-1] (SEQ ID NO:8) showed a 2-fold selectivity for CXC chemokines. Thus, peptide 3(1-6)[MCP-1] (SEQ ID NO:8) is a preferred inhibitor of the CXC chemokines, with a selectivity ratio of 0.7, while peptide 3(7-12)[MCP-1] (SEQ ID NO:9) is a preferred inhibitor of both classes of chemokines, with a selectivity ratio of 1.1. The selectivity ratio for peptide 3(1-12)[MCP-1] (SEQ ID NO:1) is 1.5.

Peptide 3(3-12)[MCP-1] (SEQ ID NO:7) had very similar properties to peptide 3(1-12)[MCP-1] (SEQ ID NO:1). This result suggested that the glutamate (E) and isoleucine (I) residues at positions 1 and 2 of the peptide 3(1-12)[MCP-1] (SEQ ID NO:1) sequence, which are not conserved in chemokine sequences other than MCP-1, are unimportant for receptor binding. Alignment of all human chemokine sequences in the peptide 3 region indicate a common conserved motif present in almost all chemokines whether of the alpha or beta subfamily (Table 3). This motif is: Cx$_1$DPx$_2$x$_3$x$_4$Wx$_5$Q.

Furthermore, there is a pattern of amino acids in the variable positions $x_1$ through $x_5$ which suggests that the nature of the amino acid at these positions may play a role in determining the selectivity of receptor binding. For example, in the CC chemokine family, position $x_1$ is usually occupied by alanine (A), whereas this position in commonly leucine (L) in the CXC chemokines except in SDF1 (Isoleucine (I) in SDF-1). To test this hypothesis, the selectivity of $Leu_4$peptide 3(1-12)[MCP-1] (SEQ ID NO:10) was compared to peptide 3(1-12)[MCP-1] (SEQ ID NO:1). While $Leu_4$peptide 3(1-12)[MCP-1] (SEQ ID NO:10) showed an approximately 4-fold increase in potency as an inhibitor of CXC chemokines compared with ala-containing peptide 3(1-12)[MCP-1] (SEQ ID NO:1), there was no decrease in the potency of CC chemokine inhibition (Table 4). Thus, $Leu_4$peptide 3(1-12)[MCP-1] (SEQ ID NO:10) showed some CXC selectivity (a selectivity ratio of 0.37) and was the most CXC selective of all the derivatives tested other than the tripeptides (see below).

As noted for position $x_1$ above, only three different amino acids appear at position $x_5$ (Table 1). Most chemokines have valine (V) at position $x_5$ as do the CXC chemokines IL-8 and MIP. In contrast, SDF-1 and IP10 have isoleucine (I) at this position, while ENA78 is the only chemokine with leucine (L) at this position. The results showed that $Ile_{11}$peptide 3(1-12)[MCP-1] (SEQ ID NO:13) showed some CXC selectivity, though not as marked as $Leu_4$peptide 3(1-12)[MCP-1] (SEQ ID NO:10) (a selectivity ratio of 0.9), but surprisingly showed the greatest selectivity for IL-8 (which has valine at this position) not SDF-1. This analog was the most selective inhibitor of IL-8 signaling other than the tripeptides, i.e., the analog had a selectivity of IL-8 over other chemokines by about 3 fold.

An analog having both the $Leu_4$ and $Ile_{11}$ substitutions did not show any greater specificity as an inhibitor of CXC chemokines than either single mutant $Leu_4$peptide 3(1-12)[MCP-1] (SEQ ID NO:10) or $Ile_{11}$peptide 3(1-12)[MCP-1] (SEQ ID NO:13) (Table 6). However, $Leu_4Ile_{11}$peptide 3(1-12)[MCP-1] (SEQ ID NO:14) was approximately 5-fold more potent as an inhibitor of CC chemokines than peptide 3(1-12)[MCP-1] (SEQ ID NO:1), or the single mutants $Leu_4$peptide 3(1-12)[MCP-1] (SEQ ID NO:10) or $Ile_{11}$peptide 3(1-12)[MCP-1] (SEQ ID NO:13). Thus, $Leu_4Ile_{11}$peptide 3(1-12)[MCP-1] (SEQ ID NO:14) was a more potent general chemokine inhibitor, with an average $ED_{50}$ of 2.3 μM compared with 10 μM for peptide 3(1-12)[MCP-1] (SEQ ID NO:1). Furthermore, the $Leu_4Ile_{11}$peptide 3(1-12)[MCP-1] (SEQ ID NO:14) unexpectedly preserved the modest CC selectivity of peptide 3(1-12)[MCP-1] (SEQ ID NO:1) with a selectivity ratio of 2.0. Surprisingly, therefore, the $Leu_4Ile_{11}$peptide 3(1-12)[MCP-1] (SEQ ID NO:14) was approximately 5-fold more potent as an inhibitor of MCP-1 signaling than peptide 3(1-12)[MCP-1] (SEQ ID NO:1), despite the fact that peptide 3(1-12)[MCP-1] (SEQ ID NO:1) contains the cognate sequence from human MCP-1. Moreover, it was found that the $Leu_4Ile_{11}$peptide 3(3-12)[MCP-1] (SEQ ID NO:27), like $Leu_4Ile_{11}$peptide 3(1-12)[MCP-1] (SEQ ID NO:14), was a higher affinity peptide analog of peptide 3(1-12)[MCP-1] (SEQ ID NO:1).

For positions $x_2$ through $x_4$, all chemokines described to date have at least one charged amino acid in this tripeptide region (Table 1). Many chemokines have two basic residues occupying $x_2$ and $x_4$ (e.g., KQK in MCP-1, KER in MCP-2 and KLK in SDF-1) while others have two acidic residues (e.g., SEE in MIP1α, SES in MIP1β, and SES in RANTES). A recent report (*Nature Med.,* 3, 367 (1997)) suggested that the charge in the extracellular loops of the chemokine receptors may be an important determinant of ligand specificity, e.g., CXCR4 which binds SDF-1 is negatively charged, while CCR5, which binds MIP1α, MIP1β and RANTES is positively charged. Thus, residues $x_2$-$x_4$ may play an important role in receptor specificity.

To test this hypothesis, several variants were prepared: $Ser_7$peptide 3(1-12)[MCP-1] (SEQ ID NO:11) substitutes the positively charged K residue present in MCP-1, MCP-2, Eotaxin, IL-8 and SDF-1 with the hydroxylated S residue present in MIP-1α, MIP1β and RANTES. However, this alteration did not markedly alter the selectivity. In particular, this alteration did not decrease the potency of inhibition of MCP-1 signaling, nor increase the potency of inhibition of MIP1α signaling (Table 4). The only detectable change was a modest shift from the moderate CC selectivity of peptide 3(1-12)[MCP-1] (SEQ ID NO:1) to a moderate CXC selectivity of the $Ser_7$peptide 3(1-12)[MCP-1] (SEQ ID NO:11) variant (a selectivity ratio of 0.5). Another variant, $Ser_7Glu_8Glu_9$peptide 3(1-12)[MCP-1] (SEQ ID NO:12) which converts the peptide from being the cognate of the MCP-1 sequence to the cognate of the MIP1α sequence, resulted in a more selective MIP1α inhibitor, although the selectivity ratio for MIP1α versus all other chemokines was only about 3 fold.

None of the peptide 3(1-12)[MCP-1] variants had any detectable activity as an inhibitor of TGF-beta induced migration of THP-1 cells, even at 100 μM (Table 4). Thus, all these variants were highly selective inhibitors of chemokine-induced signaling. There were no substitutions which altered an amino acid residue in peptide 3(1-12)[MCP-1] to any other amino acid regions found in the chemokine sequences described above which markedly reduced the potency of the general chemokine inhibition observed. However, certain alterations resulted in a marked shift in selectivity. For example, the CC selectivity of peptide 3(1-12)[MCP-1] (SEQ ID NO:1) can be converted to CXC selectivity by mutating A to L at position 4 ($x_1$) or by mutating V to I at position 11 ($x_5$). In particular, two variants had greater than 3-fold selectivity for one chemokine over the average $ED_{50}$ for all the others, i.e., $Ile_{11}$peptide 3(1-12)[MCP-1] (SEQ ID NO:13) had weak overall selectivity for IL8 inhibition and $Ser_7Glu_8Glu_9$peptide 3(1-12)[MCP-1] (SEQ ID NO:12) had weak overall selectivity for MIP1α.

In summary, although peptide 3(1-12)[MCP-1] variants varied to a small extent in their $ED_{50}$s and their specificity for either the α family or β family of chemokines, nevertheless, they were all similar to peptide 3(1-12)[MCP-1] (SEQ ID NO:1). The results in Table 6 showed that peptide 3(1-12)[MCP-1] (SEQ ID NO:1) and peptide 3(1-12)[MCP-1] variants inhibited migration induced by MCP-1, MIP1α, IL8 and SDF1α chemokines to a similar extent. While some peptides or peptide variants showed slight preference for CC chemokines, others showed slight preference for CXC chemokines but in no case did the CC-specificity exceed two-fold. Peptide 3(1-12)[MCP-1] (SEQ ID NO:1), peptide 3(1-6)[MCP-1] (SEQ ID NO:8) and peptide 3(7-12)[MCP-1] (SEQ ID NO:9) also showed no significant CC or CXC selectivity.

Example 3

Identification and Characterization of Chemokine Sequences that are Functional Agonists The results described above, that peptide 2(1-15)[MCP-1] (SEQ ID NO:3) did not inhibit MCP-1 activity in the THP-1 migration assay, did not exclude the possibility that peptide 2(1-15)[MCP-1] (SEQ ID NO:3) associates with the MCP-1 receptor and either fails to inhibit MCP-1 binding and signaling, or acts as an agonist, preventing binding of MCP-1 but transducing an MCP-1 like signal. To determine whether peptide 2(1-15)[MCP-1] (SEQ ID NO:3) binds to chemokine receptors, THP-1 cells were mixed with a biotinylated derivative of peptide. Peptide 2(1-15)[MCP-1] (SEQ ID NO:3) was found to bind to THP-1 cells with a reasonable affinity (kD=1.9 µM), suggesting that peptide 2(1-15)[MCP-1] (SEQ ID NO:3) was able to interact with chemokine receptors without inhibiting chemokine signaling (a neutral binding agent).

Unlike peptide 3, which represents a region that is relatively conserved between chemokines, there is much less marked sequence similarity in the peptide 2 region of chemokines. Thus, peptide 2, derivatives or variants thereof, may possess more chemokine-specific effects. To test this hypothesis, the binding of biotinylated peptide 2(1-15) [MCP-1] (SEQ ID NO:3) to two different cell types, i.e., THP-1 cells and Jurkat cells, was compared. THP-1 cells express receptors for MCP-1, MIP1α, SDF-1α and IL-8 while Jurkat cells express functional receptors for SDF-1 only. Peptide 2(1-15)[MCP-1] (SEQ ID NO:3) bound to Jurkat cells with a similar kD (3 µM) to THP-1 cells (1.9 µM). This observation suggests that, surprisingly, peptide 2(1-15) [MCP-1] was able to bind to a number of different chemokine receptors, although the sequence of peptide 2(1-15)[MCP-1] (SEQ ID NO:3) shows little homology to the equivalent region from SDF-1.

The functional agonist properties of peptide 2(1-15)[MCP-1] (SEQ ID NO:3) were characterized by incubating THP-1 cells with varying concentrations of peptide 2(1-15)[MCP-1] (SEQ ID NO:3) in a migration assay. Peptide 2(1-15)[MCP-1] (SEQ ID NO:3) had weak agonist activity (promoting migration with an $ED_{50}$ of about 10 µM) with maximal migration at 100 µM, which was approximately 10% of that induced by MCP-1. Thus, at high concentrations (>20 µM) peptide 2(1-15)[MCP-1] (SEQ ID NO:3), variants or derivatives thereof, may be useful for applications which require weak MCP-1 agonist activity (for example, for the therapy of parasitic infections where increased macrophage activity is desirable). Moreover, at lower concentrations (>1 µM but <20 µM), peptide 2, peptide 2 variants or derivatives may be useful as a neutral binding agent which may affect binding of non-MCP-1 proteins to the chemokine receptors. For example, peptide 2, derivatives or variants thereof, may be useful to prevent or inhibit HIV binding to chemokine receptors without inhibiting desirable chemokine signaling.

Example 4

Identification, Preparation and Characterization of Therapeutic Agents of the Invention for In Vivo Use A. Derivatives Peptides are generally susceptible to chemical or enzymatic hydrolysis. In particular, peptides are not normally bioavailable by the oral route since they are not stable in the acid and proteolytic environment of the stomach. Thus, chemical or enzymatic hydrolysis leads to a very short in vivo half-life for peptides. To extend the half-life of agents susceptible to hydrolysis, in vitro active agents are modified in a manner that results in a derivative which may be orally bioavailable, have improved pharmacokinetics, and the administration of which may achieve concentrations in blood that inhibit chemokine activity. For example, cyclic-reverse-D (CRD) peptides may be prepared. CRD peptides are prepared by synthesizing the reverse sequence of the peptide (C-terminal to N-terminal) using the opposite stereoisomer (D-amino acids in place of L amino acids). The resulting peptide is then cyclized via N- and C-terminal cysteine residues. These derivatives retain a very similar steric arrangement of atoms to non-CRD peptide, but are not subject to enzymatic hydrolysis. Other derivatives which may exhibit an extended half-life in vivo include thienyl or pyridyl derivatives (e.g., U.S. Pat. No. 4,992,463; U.S. Pat. No. 5,091,396).

Figure 4:
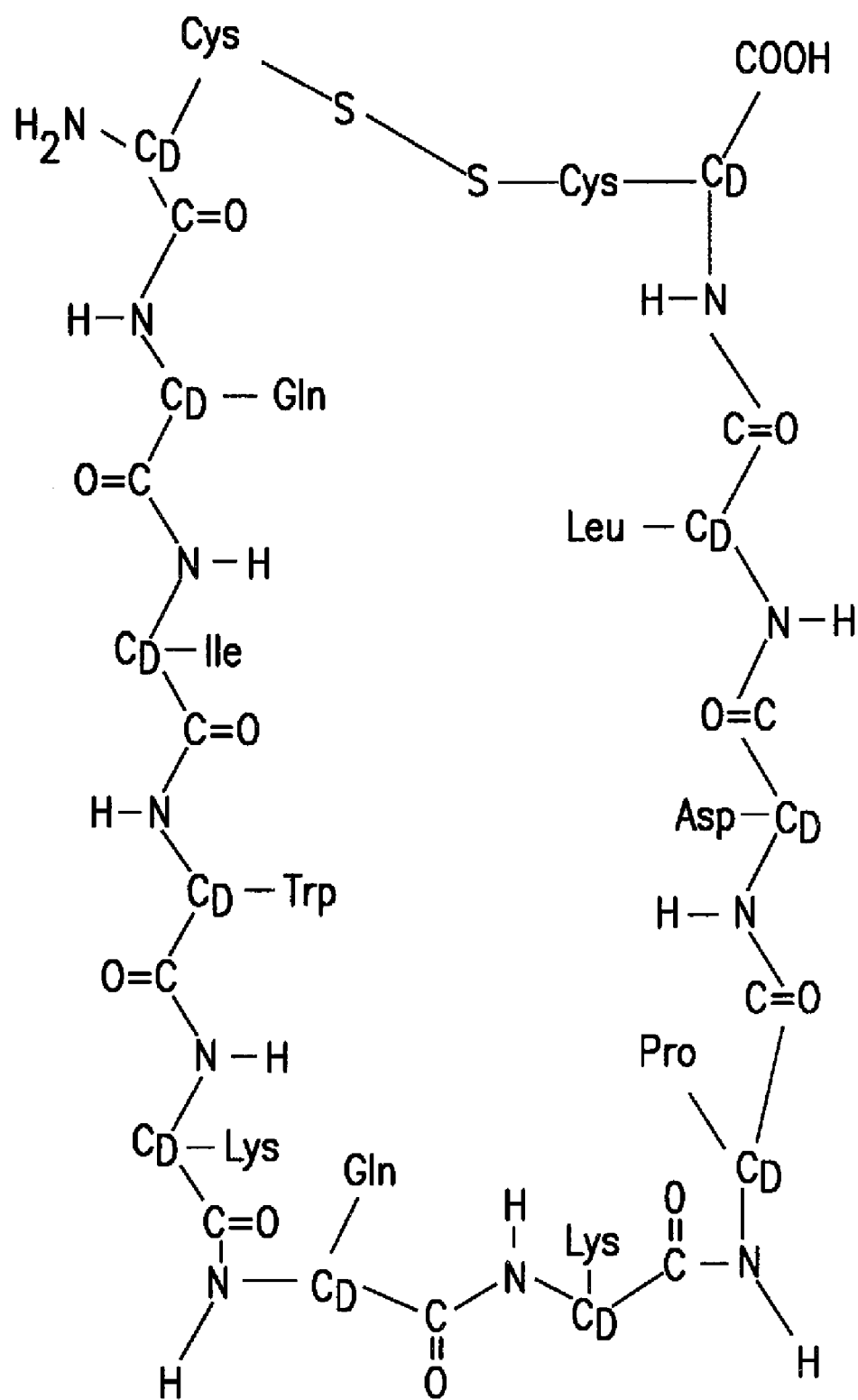
FIG. 4 shows the structure of CRD-Cys$_{13}$leu$_4$ile$_{11}$peptide 3[MCP-1] (3-12)[MCP-1], which is cyclized via disulphide bonds. The main chain α carbons are indicated by $C_D$ which indicates that the D form of the amino acid is present.
Figure 5:
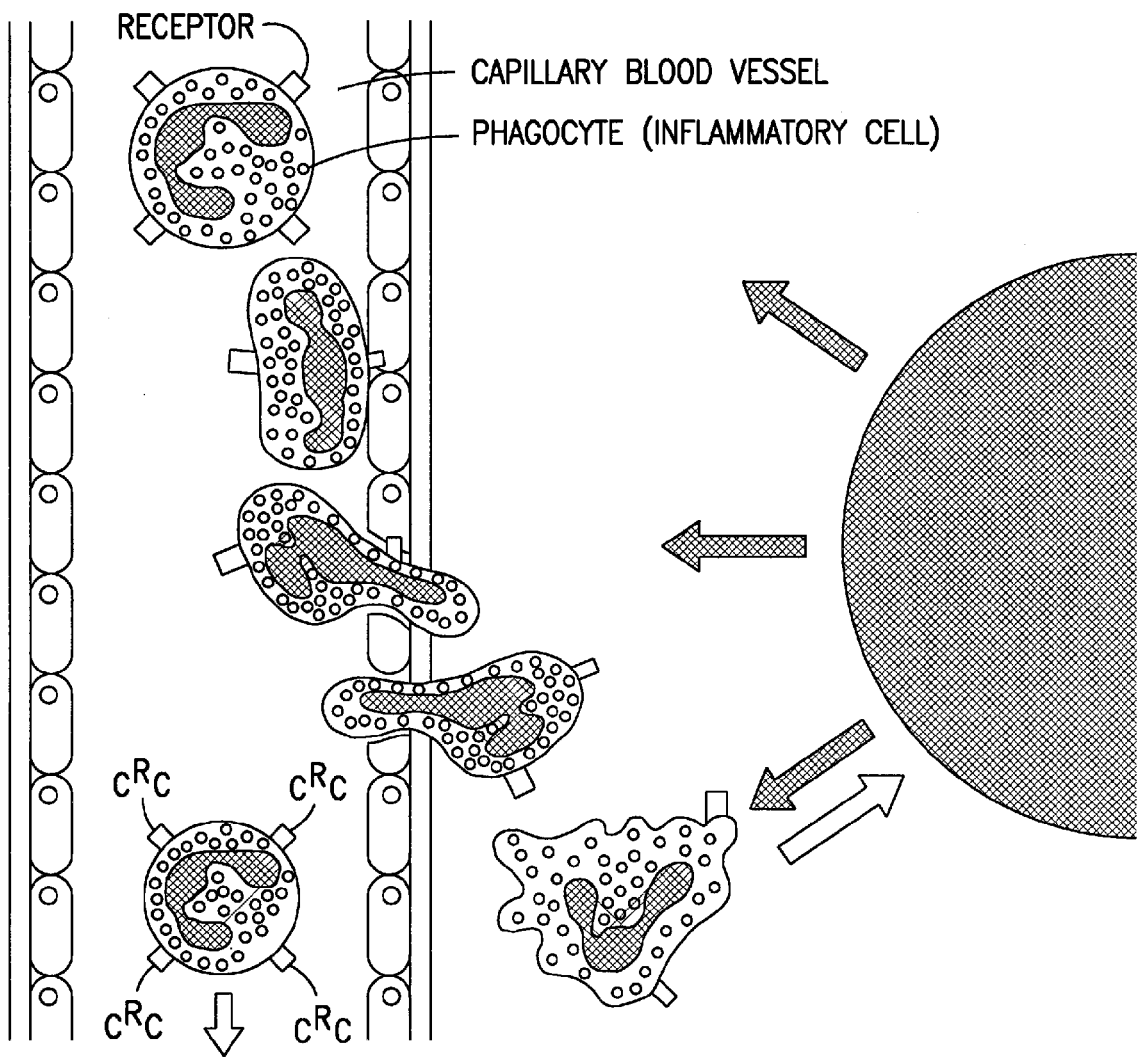
FIG. 5 depicts a schematic of inhibition of cell migration via binding of a therapeutic agent of the invention to a chemokine receptor. $C^RC$=a therapeutic agent of the invention. Chemokine receptors are shown as blackened rectangles.
Figure 6:
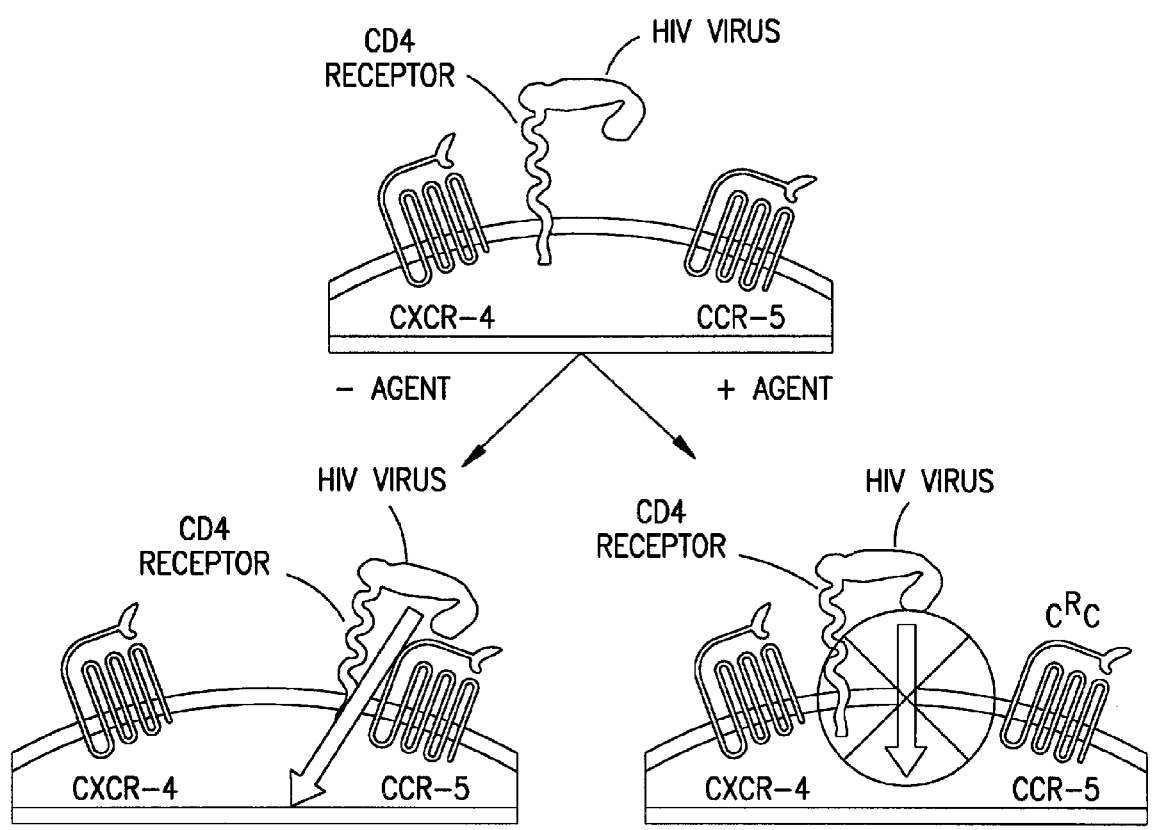
FIG. 6 depicts a schematic of the inhibition of HIV entry by an agent of the invention.
Figure 7A:
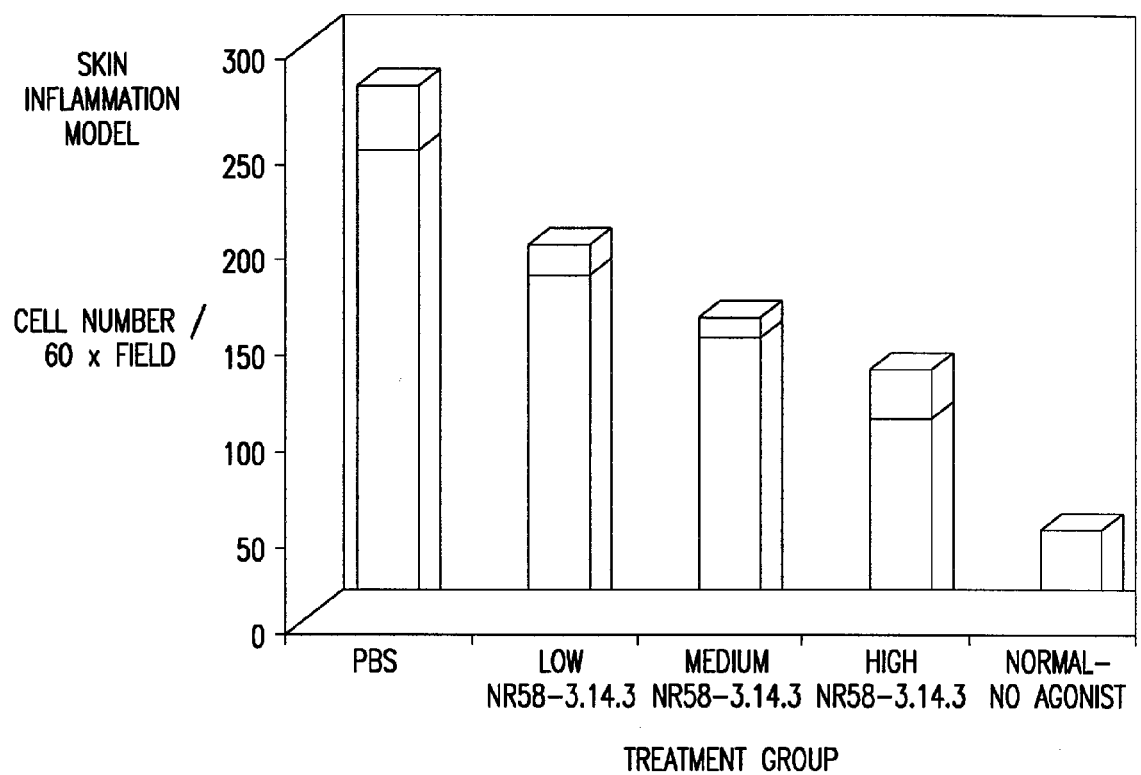
FIG. 7 shows the dose-dependent inhibition of inflammation (A) and endotoxemia (B) in animal models by peptide 3 (CRD-Cys$_{13}$Leu$_4$Ile$_{11}$ peptide 3(3-12) [MCP-1]=NR58-3.14.3).
Figure 7B:
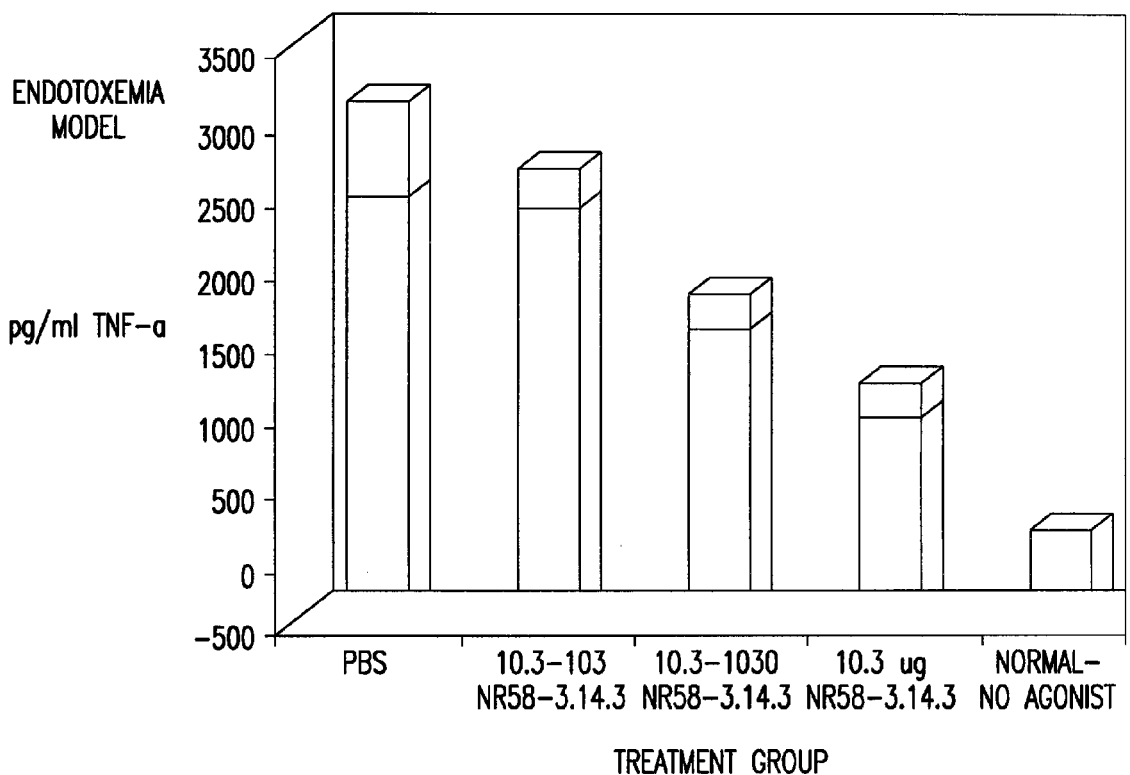
Figure 8:
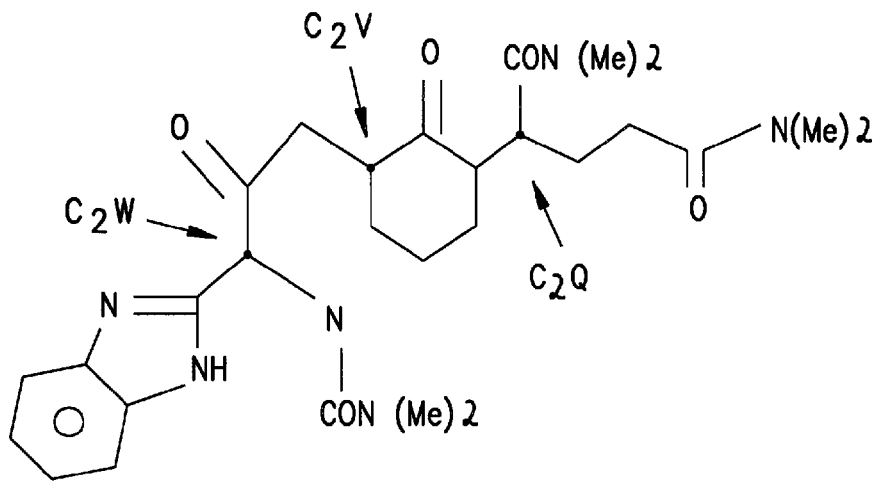
FIG. 8 shows a preferred analog of peptide WVQ.

For example, to prepare a peptide 3 derivative, peptide 3(3-12)[MCP-1] was modified according to Jameson et al. (Nature, 368, 744 (1994)), which yielded CRD-$Cys_{13}Leu_4Ile_{11}$peptide 3(3-12)[MCP-1] (FIG. 4). CRD-$Cys_{13}Leu_4Ile_{11}$peptide 3(3-12)[MCP-1], which had very similar properties to peptide 3(1-12)[MCP-1] (SEQ ID NO:1) in the in vitro assays described hereinabove, was found to be stable against both acid hydrolysis (<10% degradation at pH 2.0 for 2 hrs at 37° C.) and enzymatic destruction (5 units trypsin for 2 hrs at 37° C.). CRD-$Cys_{13}Leu_4Ile_{11}$peptide 3(3-12)[MCP-1] was also resistant to hydrolysis in vivo and allowed therapeutically useful plasma concentrations to be achieved (>10 µM 24 hours after a single intraperitoneal dose of 1 mg of CRD-$Cys_{13}Leu_4Ile_{11}$peptide 3(3-12)[MCP-1] in 250 µl saline).

Cyclic-reverse D (CRD), linear reverse-D (LRD), cyclic forward L (CFL), and linear forward L (LFL) (i.e., the standard form of peptides) derivatives of $Leu_4Ile_{11}$peptide 3 were prepared and their MCP-1 inhibitory activity in the THP-1 transwell assay determined. The results were

| | |
|---|---:|
| LFL-$Leu_4Ile_{11}$peptide 3 | 1-5 µM |
| LRD-$Leu_4Ile_{11}$peptide 3 | 200-400 nM |
| CFL-$Cys_{13}Leu_4Ile_{11}$peptide 3 | 500-700 nM |
| CRD-$Cys_{13}Leu_4Ile_{11}$peptide 3 | 50-100 nM |

These results show, somewhat surprisingly, that both cyclization and reverse-D derivatization independently improve activity. This improvement is then additive in the CRD derivative. Thus, cyclization improved affinity by constraining the conformations of the peptide. However, it was not expected that the reverse-D derivatization would be so beneficial, possibly by increasing stability of the molecule.

CRD-$Cys_{13}Leu_4Ile_{11}$peptide 3(3-12)[MCP-1] was found to be a very potent inhibitor of MCP-1 induced THP-1 migration ($ED_{50}$ of about 1 nM). This increased potency compared to the parent $Leu_4Ile_{11}$peptide 3(1-12)[MCP-1] (SEQ ID NO:14) may reflect increased stability, even in vitro, or it may reflect the increased conformational stability of the peptide. Moreover, this compound binds to the signaling receptor with the same affinity as native full-length MCP-1 but does not signal.

To determine if CRD-$Leu_4Ile_{11}Cys_{13}$peptide 3(3-12) [MCP-1] inhibited or enhanced the proliferation of T or B cells to conconavalin A or tetanus toxoid in culture, proliferation of CD4 T cells and B cells was assessed by CFSE-FITC cell labeling. 50 ng of CRD-$Leu_4Ile_{11}Cys_{13}$peptide 3(3-12) [MCP-1] inhibited ConA proliferation of CD4 T cells by 50% and 5 ng of CRD-$Leu_4Ile_{11}Cys_{13}$peptide 3(3-12) [MCP-1] reduced ConA proliferation of CD4 T cells by <3%. CRD-$Leu_4Ile_{11}Cys_{13}$peptide 3(3-12)[MCP-1] had no effect on proliferation of B cells to tetanus toxoid.

Computer modeling was employed to determine whether specific amino acid replacements affected the conformation of the peptide derivative CRD-$Leu_4Ile_{11}Cys_{13}$peptide 3(3-12)[MCP-1]. The peptide sequence was entered into Hyper-Chem 5.0 (HyperCube). A minimum energy conformation was sought using the Amber Force Field parameters and the Polak-Ribiere algorithm. The initial model was manipulated both by molecular dynamics simulations (300° K., 2 nsec) and manual sidechain rotations, followed by geometry optimization, until an apparent global minimum energy conformation was reached. Convergence criterion was <0.01 Kcal/mol Å. A conformation was obtained using this procedure with an energy of about 213.4 kcal/mol.

To test the sensitivity of the model peptide to perturbations, each of the residues except the terminal cysteines forming the disulfide bond was mutated individually from D to L, and the geometry re-optimized, starting with the minimum conformation of the all D peptide. For these perturbations each mutant was first run through the geometry optimization routine, then a molecular dynamics simulation, then another geometry optimization. The resulting mutant peptides were compared to the all-D form by overlaying the disulfide bond and one adjacent atom, and visually assessing the difference between the peptide backbones. The overall conformation was insensitive to change of chirality at positions 2, 3, 4, 8, 9, and 10, but was sensitive to change of chirality at positions 5, 6, and 7. Generally, changes in sidechain position were minor except when the backbone conformation changed significantly. Energies for the mutants varied from −187.9 to −226.1 Kcal/mol, but the energy change (from −213.4 for the starting conformation) did not correlate with conformational change.

In addition, the effect of modifying the aspartate residue at position 9 was examined by converting it sidechain carboxyl group to the D-alanyl amide. A minimum energy conformation of the modified peptide was sought using the same routine as for the chiral mutants, starting from the same minimum energy conformation. Condensation of D-alanine to the residue 9 sidechain carboxyl caused a major change in the conformation of the peptide. This is consistent with the in vitro monocyte migration data which demonstrated a significant loss in biological activity of the D-ala peptide relative to CRD-Leu$_4$Ile$_{11}$Cys$_{13}$peptide 3(3-12)[MCP-1].

Molecular modeling indicated that L-Leu-CRD-Leu$_4$Ile$_{11}$Cys$_{13}$peptide 3(3-12)[MCP-1], which is CRD-Leu$_4$Ile$_{11}$Cys$_{13}$peptide 3(3-12)[MCP-1] with the D-Leu replaced with an L-Leu, should result in very little change to the conformation of the peptide backbone. In vitro migration studies with the L-Leu-derivative showed that it retained functional activity as well. Thus, to select for particular amino acid substitutions which retain the conformation of a biologically active molecule of the invention, molecular modeling may be employed.

The following D-amino acid to L-amino acid changes had no significant impact on the structure of the peptide backbone as assessed by modeling.

| Amino Acid | Position | kcal/mole |
|---|---|---|
| GLN | 2 | −205.5 |
| ILE | 3 | −202.4 |
| TRP | 4 | −222.0 |
| PRO | 8 | −226.1 |
| LEU | 10 | −211.9 |

The following D-amino acid to L-amino acid changes had a significant impact on the structure of the peptide backbone as assessed by this technique.

| Amino Acid | Position | kcal/mole |
|---|---|---|
| LYS | 5 | −200.1 |
| GLN | 6 | −211.6 |
| LYS | 7 | −187.9 |
| ASP | 9 | −214.9 |

B. DARC Binding

A further consideration for bioavailability is non-specific binding of the therapeutic agent. Red blood cells have a signaling-deficient chemokine receptor or binding protein, termed the Duffy Antigen Receptor for Chemokines (DARC). Although it does not signal, this receptor has a high affinity for chemokines (10 nM) and may play a role in clearing them from the circulation. Unfortunately, any chemokine receptor antagonist which has a high affinity for DARC may be sequestered by the huge pool of binding sites on red blood cells, and hence unavailable to inhibit productive chemokine signaling in other tissues. Similarly, agonists which bind DARC with high affinity are unavailable to productively signal through specific chemokine receptors. For in vivo use, an agent of the invention preferably has some affinity for DARC, since peptides which do not bind to DARC are rapidly cleared at first pass by glomerular filtration. Thus, preferred agents have DARC binding (affinity constant) in the range 100 nM to 1 mM, more preferably in the range 1 μM to 100 μM and even more preferably in the range of 10 to 100 μM.

Although the interaction of chemokines with DARC is high affinity (5-10 nM association constant), kinetically the interaction is characterized by extremely rapid on and off rates. Consequently, incubation with labeled chemokine leads to saturation of the DARC binding sites, but most of the bound label is lost within minutes of removing the unbound label (>90% loss within 3 minutes). As a result, it is difficult to directly determine the binding of peptides to DARC by assaying direct binding of biotinylated peptide, since the rapid off rates make determination of the amount of bound label impossible or inaccurate.

To overcome this difficulty, the ka for association of DARC with peptide 3(1-12)[MCP-1] (SEQ ID NO:1) and peptide 2(1-15)[MCP-1] (SEQ ID NO:3) was estimated by incubating red blood cells expressing DARC with $^{125}$I-labeled MCP-1 in the presence of varying concentrations of peptide. After binding has reached equilibrium (30 minutes at 37° C.), the cells are separated from the unbound label by centrifugation for 5 minutes through a sucrose gradient. Counts associated with the cells are then determined by gamma-counting scintigraphy. In the absence of all peptides, the association constant for $^{125}$I-labeled MCP-1 on human red blood cells was 5.45 nM, a value which is in accord with a previous report. Furthermore, Scatchard analysis confirms the presence of a single high affinity binding site with 500-1000 copies per cell, consistent with the known properties of DARC. Thus, determination of $^{125}$I-MCP-1 binding to red blood cells in this assay in the presence of various concentrations of the peptide(s) allows the association constant of the peptide for DARC to be accurately estimated.

The DARC specificity ratio is also determined. The DARC specificity ratio is defined as the estimated ka for association with DARC divided by the ED$_{50}$ for biological activity. A DARC specificity ratio greater than 1 indicates that a peptide associates poorly with DARC and is bioavailable for modulating chemokine signaling, either as an antagonist or agonist.

A DARC specificity ratio of about 1 indicates that the peptide binds DARC and the THP-1 signaling receptors with similar affinity. Thus, it may be difficult to achieve biologically active (as a chemokine inhibitor) concentrations of these peptides in vivo without further modifications of the peptide. A DARC specificity ratio less than 1 indicates much higher affinity for DARC than for chemokine signaling receptors.

Peptide 1[MCP-1] (SEQ ID NO:2)(which does not bind to chemokine receptors but functions in a dominant negative fashion) showed no binding to DARC (estimated ka >100 µM). In marked contrast, the weak agonist peptide 2(1-15)[MCP-1] (SEQ ID NO:3) showed high affinity binding to DARC. The association constant for peptide 2(1-15)[MCP1] (SEQ ID NO:3) for chemokine receptors on THP-1 cells was estimated at 2 µM using competition binding analysis. However, this peptide had an affinity for DARC of less than 500 nM, also assessed by competition binding analysis, using red blood cells. Thus, peptide 2(1-15)[MCP1] (SEQ ID NO:3) binds to THP-1 cell chemokine receptors, although it does not inhibit signaling through the receptors, and it binds DARC even more strongly (DARC selectivity ratio=0.1-0.2). Thus, peptide 2 is a preferred therapeutic agent for the treatment or prevention of malaria (an action requiring DARC inhibition, but not modulation of chemokine signaling).

Peptides, such as peptide 2(1-15)[MCP-1] (SEQ ID NO:3) which have very high affinity for the DARC receptor, may have strong biological agonist activity in vivo (although they are only weak agonists or neutral agonists in vitro). Moreover, peptide 2, variants and derivatives thereof may be strongly pro-inflammatory in vivo, or strongly exacerbate existing inflammation by preventing DARC from performing the function of binding chemokines. If DARC functions as a sink to remove chemokines from the circulation, then the concentration of chemokines may be markedly increased by the presence of peptide 2. Under conditions where chemokines are being made a released into the circulation (e.g., during inflammation), peptide 2 may exacerbate that inflammation, allow the inflammation to persist longer than in the absence of the peptide or otherwise change the qualitative nature of the inflammatory reaction. For these reasons, peptides with a low DARC specificity ratio are useful for the treatment of conditions which require improved immune function, or conditions which are characterized by a pathologically inadequate inflammatory response.

MIP1-α has previously been shown to be the only chemokine which does not bind with significant affinity to DARC. Peptide 2(1-9)[MCP-1] had a Duffy affinity of about 50 µM while peptide 2(1-14)[MIP1-α] (SEQ ID NO:5) was a potent receptor binding agent for the MIP1-α receptor and had excellent specificity over DARC. That is, peptide 2(1-14)[MIP1α] (SEQ ID NO:5) did not bind to DARC (association constant >50 µM) but bound strongly to chemokine receptors on THP-1 cells (association constant 100-900 nM; number of binding sites is about 150,000 per cell). Moreover, this agent did not inhibit THP-1 cell migration induced by MCP-1, MIP1α, IL-8, or SDF1α. Thus, this latter agent may be particularly useful as a neutral chemokine receptor binding agent in vivo, highly selective over DARC.

Peptide 3(1-12)[MCP-1] (SEQ ID NO:1) also binds to DARC, although it binds to DARC with only a similar affinity to which it binds to the chemokine receptors (low µM concentration range). Leu$_4$ile$_{11}$peptide 3(1-12)[MCP-1] (SEQ ID NO:14) had essentially no DARC binding capacity, while inhibiting MCP1 induced migration at concentrations around 1 µM. Thus, peptide 3 derivatives, such as leu$_4$ile$_{11}$peptide 3(1-12)[MCP-1] (SEQ ID NO:14) may achieve antagonist properties in vivo.

The shorter fragments of peptide 3[MCP-1] (e.g., peptide 3(7-12)[MCP-1] (SEQ ID NO:9)) showed progressively higher DARC specificity ratios (about 3.0 for peptide 3(7-12)[MCP-1] (SEQ ID NO:9) versus 1.0 for peptide 3(1-12)[MCP-1] (SEQ ID NO:1)), indicating that where chemokine signaling receptor specificity is desired, shorter peptide fragments which retain full chemokine antagonist or agonist activity are in general to be preferred over the full length peptides.

Peptide 3(1-12)[MCP-1] (SEQ ID NO:1) (DARC specificity ratio=1.00) is unlikely to be useful as a pan-chemokine inhibitor in vivo, whereas the Leu$_4$Ile$_{11}$peptide 3[MCP-1] (SEQ ID NO:14) (DARC specificity ratio=37.83), or its derivatives such as CRD-Cys$_{13}$Leu$_4$Ile$_{11}$peptide 3(3-12)[MCP-1], which bound only weakly to DARC (association constant=90 µM) but bound very strongly to chemokine receptors on THP-1 cells (association constant=100-500 nM; number of binding sites is about 150,000 per cell), are a preferred embodiment for the treatment or prevention of atherosclerosis, osteoporosis, and autoimmune diseases, and HIV infection (chemokine signaling receptor binding functions). Moreover, CRD-Cys$_{13}$Leu$_4$Ile$_{11}$peptide 3(3-12)[MCP-1] inhibited THP-1 cell migration induced by MCP-1, MIP1α, IL-8, and SDF1, with very similar ED$_{50}$s.

CRD-peptide 2(1-15)[MCP-1] has more functional potency, less Duffy binding activity compared with the LFL derivative. LRD peptide 2(1-15)[MCP-1] had approximately a 100-fold decrease in Duffy binding (25 µM versus 100 µM for LFL).

An alternative approach to preparing agents that are bioavailable is the preparation of non-peptide analogs of chemokines. A preferred non-peptide analog of the invention includes an isostere of WIQ, e.g., a compound of formula (IV), wherein Z=CH$_3$; Y=O; X=CH$_3$; and Ar=indolyl. This compound did not bind to DARC (association constant=>30 µM) but bound very strongly to chemokine receptors to THP-1 cells (association constant=100 nM-1 µM; number of binding sites is about 150,000 per cell). This agent inhibited THP-1 cell migration induced by MCP-1, MIP1α, IL-8 and SDF1α with very similar ED$_{50}$s.

TABLE 5

| PEPTIDE | SEQUENCE | | CC SPECIFICITY[a] | DUFFY SELECTIVITY[b] | AVERAGE ED$_{50}$ (µM)[c] |
|---|---|---|---|---|---|
| Pep2[MCP1] | SYRRITSSKCPKEAV | (SEQ ID NO:3) | — | 0.18[d] | 2[e] |
| Pep2[SDF1] | HLKILNTPNCALQIV | (SEQ ID NO:4) | — | <1[d] | 1-10[e] |
| Pep2[MIP1α] | DYFETSSQCSKPGV | (SEQ ID NO:5) | — | >100[d] | 1-10[e] |
| Pep2[IL8] | ELRVIESGPHCANTEI | (SEQ ID NO:6) | — | <1[d] | 1-10[e] |

TABLE 5-continued

| PEPTIDE | SEQUENCE | | CC SPECIFICITY[a] | DUFFY SELECTIVITY[b] | AVERAGE ED$_{50}$ (μM)[c] |
|---|---|---|---|---|---|
| Pep3 | EICADPKQKWVQ | (SEQ ID NO:1) | 1.5 | 1.00 | 10 |
| Pep3[3-12] | CADPKQKWVQ | (SEQ ID NO:7) | 1.2 | 1.21 | 8 |
| Pep3[1-6] | EICADP | (SEQ ID NO:8) | 0.7 | 5.32 | 24 |
| Pep3[7-12] | KQKWVQ | (SEQ ID NO:9) | 1.0 | 2.94 | 6 |
| Leu$_4$pep3 | EICLDPKQKWVQ | (SEQ ID NO:10) | 0.4 | n.d. | 5 |
| Ser$_7$pep3 | EICADPSQKWVQ | (SEQ ID NO:11) | 0.5 | 2.00 | 5 |
| Ile$_{11}$pep3 | EICADPKQKWIQ | (SEQ ID NO:12) | 0.9 | n.d. | 5 |
| Leu$_4$Ile$_{11}$pep3 | EICLDPKQKWIQ | (SEQ ID NO:13) | 2.0 | 37.83 | 2 |
| Ser$_7$Glu$_8$Glu$_9$ | EICADPSEEQVQ | (SEQ ID NO:2) | 1.6 | 0.59 | 6 |
| — | KQK | | >100 | 22.34 | 6[f] |
| Pep3[10-12] | WVQ | | 1.1 | 24.81 | 2 |
| — | WIQ | | 1.0 | n.d. | 2 |
| — | SEE | | >100 | | n.d. 0.8[f] |
| — | KLK | | <0.1 | | n.d. 0.1-10[f] |
| — | KEN | | <0.1 | | n.d. 0.1-10[f] |
| CRD-Cys$_{13}$pep3[3-12] | -CQVWKQKPDAC-- | | n.d. | 8.82 | 0.8 |
| LRD-Cys$_{13}$Leu$_4$Ile$_{11}$pep3[3-12] | CQIWKQKPDLC | | n.d. | 4.59 | 1 |
| CRD-Cys$_{13}$Leu$_4$Ile$_{11}$pep3[3-12] | -CQIWKQKPDLC-- | | n.d. | >100 | 0.1 |

Footnotes
a 'CC-specificity' is the average inhibitory ED$_{50}$ versus SDF1 and IL8 divided by average inhibitory ED$_{50}$ versus MCP-1 and MIP1α.
b 'Duffy selectivity' is the estimated ka for binding to red blood cells divided by average inhibitory ED$_{50}$ versus each of the chemokines (except for peptide 2; see footnote d below).
c 'Average ED$_{50}$' is the average inhibitory ED$_{50}$ for inhibition of THP-1 migration induced by each of the chemokines (except for peptide 2; see footnote e below).
dFor the peptide 2 family, the 'average ED$_{50}$' is the estimated ka for binding to THP-1 cells.
eFor the peptide 2 family, the 'Duffy selectivity' is calculated as the ka for binding to red blood cells divided by the ka for binding THP1-1 cells.
fFor tripeptide derivatives so marked, the peptide is highly specific for one of the four exemplary chemokines. In these cases, the ED$_{50}$ shown is for inhibition of that chemokine.
n.d. = not determined.
Abbreviations
CRD = Cyclic reverse-D derivative
LRD = Linear reverse-D derivative
CFL = Cyclic derivative of standard L-form peptide
LFL = Standard, linear L-form peptide [NB; all peptides are LFL unless stated otherwise]
Amino acids in italics are D-form amino acids, all others are L-form
-- = Cyclization linking two cysteines so marked Example 5

Anti-HIV Activity of the Agents of the Invention

Figure 3:
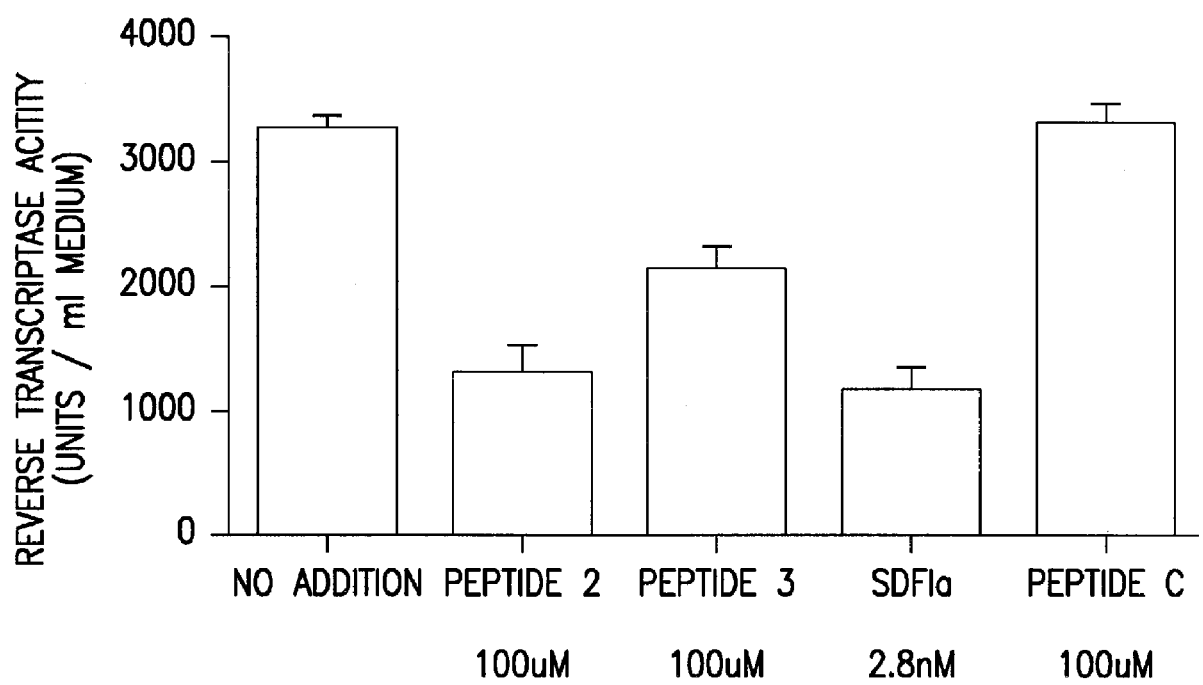
FIG. 3 shows the reverse transcriptase activity present in the culture medium at day 21 after infection of Jurkat cells with a T-tropic HIV. Peptides were added on day 0, one hour prior to infection of the cells with HIV isolate. The full length chemokine SDF-1α was used as a positive control.

To demonstrate that the agents of the invention inhibit HIV binding and infection of cells, human T-cell derived Jurkat cells were incubated with an infectious T-tropic HIV isolate in the presence of (i) no inhibitor, (ii) peptide C (Table 5) as an inactive control peptide, (iii) 100 μM peptide 3(1-12)[MCP-1] (SEQ ID NO:1), or (iv) 100 ng/ml SDF-1, which should bind to and block all CXCR-4 receptors. After 3 weeks in culture, viral replication was assessed by a reverse transcriptase assay of the culture medium. Peptide 3(1-12)[MCP-1] (SEQ ID NO:1) was found to be an effective inhibitor of Jurkat cell infection by HIV (FIG. 3).

Since peptide 2(1-15)[MCP1] (SEQ ID NO:3) binds to chemokine receptors on the surface of Jurkat cells and THP-1 cells, but does not inhibit productive signaling by chemokines, it is possible that peptide 2(1-15)[MCP-1] (SEQ ID NO:3) binds and inhibits an epitope used by HIV for cell entry but not by MCP-1 for signaling. To test this hypothesis, the same HIV infection assay described above was employed to test whether peptide 2(1-15)[MCP-1] (SEQ ID NO:3) inhibits HIV infection of Jurkat cells. At 100 μM, peptide 2(1-15)[MCP-1] (SEQ ID NO:3) was more effective than peptide 3(1-12)[MCP-1] (SEQ ID NO:1), and as effective as SDF1α, in preventing virus entry.

Peptide 2 derivatives (FIG. 10) are better inhibitors of Jurkat T cell infection by HIV (a CXCR4 mediated event) than peptide 3 derivatives, while surprisingly peptide 3 is a better inhibitor of THP-1 cell infection (a CCR-5 mediated event). Thus, combinations of peptide 2 and peptide 3 may be particularly useful for anti-HIV therapy, e.g., to inhibit productive infections by both M-tropic and T-tropic isolates.

Moreover, as LRD peptide 2(1-15)[MCP-1] had a 100 nM affinity constant or lower for CCR5/CXCR4 and a 100 fold decrease in Duffy binding relative to LFL peptide 2[MCP-1], LRD derivatives may be more efficacious than their LFL counterparts (25 µM versus 100 µM for LFL).

Current therapies for inhibition of HIV focus on the virus, for example reverse transcriptase inhibitors or viral protease inhibitors. These therapies are only effective for a limited period. In each case, the efficacy is reduced because the virus is undergoing rapid replication, and there is selection in favor of mutants which are resistant to the inhibitors. Although combination therapies are more effective, they are unlikely to result in clearance of the virus from an infected individual. Eventually, mutant virus will arise which circumvents the drug cocktail and progression will again occur in the now drug-resistant individual. Thus, strategies which are based on co-receptor inhibition target a host protein, rather than a virus protein, may have increased efficacy as more extensive mutations in the virus may be necessary to circumvent an inhibited co-receptor. Indeed, the resistance to infection of CCR-5Δ32 homozygotes suggests that the virus cannot readily adapt to use of an alternative co-receptor, at least while the virus population is small.

Preferably, a Ser10 variant of peptide 2(1-15)[MCP-1] (SYRRITSSKSPKEAV), or its LRD $Cys_0Ser_{10}Cys_{16}$ derivative (cvaekpsksstirrysc) or CRD derivative, is employed. DARC binding of SYRRITSSKSPKEAV is in the range 20 µM to 100 µM and activity in the range 1-100 nM as an anti-HIV agent.

Example 6

Rapid Screening Method for Infectivity

Current assays for HIV infection in vitro are time consuming and lack reproducibility. For example, infection is often monitored by the production of viral reverse transcriptase (RT) activity using a radiolabelled RT substrate. Unfortunately, RT production is low, even when a laboratory adapted HIV strain is used to infect a high permissive line such as the Jurkat human T cell line. As a result, it is necessary for the infected cells to be cultured for two or more weeks to allow sufficient infection to occur for RT production be measurable. In addition to being time consuming, this assay has a number of other disadvantages: most importantly, it relies on multiple rounds of secondary infection to increase the viral titer sufficiently for RT activity to become detectable. As a result, small differences in primary infection are magnified, and since primary infection frequency is low, stochastic differences between identically treated wells become significant. The assay therefore requires many replicate wells for each analysis, with as many as 24 replicates being routinely used. For example, in a typical assay groups of 24 wells of Jurkat cells in 96-well plates are infected with replicate aliquots of HIV virus stock, with one group receiving treatment with peptide 2 as a chemokine co-receptor inhibitor, another group receiving SDF-1α (the CXCR-4 natural ligand) and a third group is untreated. After three weeks, the cells were harvested and RT activity measured. The co-efficient of variation in the untreated wells was 37%. As a result, although peptide 2 inhibited RT activity by 75%, this was significant only with p=0.02 because of the high well to well variability. This necessitates the use of many replicate making the assay cumbersome for screening purposes.

An alternative method is to use direct visualization of the HIV proteins, for example, by immunofluorescence microscopy. Unfortunately, even the most highly expressed HIV proteins (such as p24gag) are present at fairly low levels in cells. Thus, direct detection the earliest stages after infection has been difficult and error prone. Therefore, the following method was employed to enhance the sensitivity of immunofluorescence, allowing the number of HIV infected cells to be accurately determined between 24 hours and 72 hours after infection. Furthermore, the signal to noise ratio of this technique allows automated counting of the infected cells using image analysis software.

For THP-1 cells, the cells are adhered to glass multiwell slides (for example, 16-well chamber slides; Nunc) using PMA and hydrocortisone. The cells are then exposed to virus in the chamber slide in the presence of various test agents. For non-adherent cells such as Jurkat cells, infections are carried out in, for example, 96-well culture plates as for RT assays, but prior to analysis the cells are attached to glass slides using a cyrospin apparatus in accordance with the manufacturer's instructions. The infected cells on the glass slides are fixed between 24 hours and 72 hours after infection, for example, by immersing the slides in ice cold acetone for 90 seconds. Other methods of fixation compatible with quantitative immunofluorescence may also be used (see *J. Histochem. Cytochem.*, 44, 1043 (1997) for a discussion of quantitative immunofluorescence procedures). Following fixation, non-specific binding of proteins to the cells is blocked, e.g., by incubation in 3% w/v fatty acid free bovine serum albumin in phosphate buffered saline (3% FAF-BSA in PBS) for 30 minutes at room temperature. Alternatively, other blocking solutions (e.g., 5% sucrose, 5% Tween-20 in PBS) may be used. The blocked sections are then stained for HIV protein, for example, using a specific antiserum to p24gag. Slides are incubated with the antiserum at a suitable concentration (usually in the range 1-100 µg/ml of specific IgG) in 3% FAF-BSA in PBS. Antibodies to other HIV antigens may be used, although relatively highly expressed antigens such as p24gag are preferred.

This incubation should be left on for at least 16 hours. Traditional immunofluorescence procedures use primary antibody incubation periods typically 1-2 hours in length, but longer incubation increases signal without increasing background (*J. Histochem. Cytochem.*, 44, 1043 (1997)). The incubation may be left on for up to 36 hours without deleterious effects on the signal to noise ratio. Unbound antibody is then washed off. Typically, this involves 3×3 minute washes in PBS, although other washing regimens may be used (see *J. Histochem. Cytochem.*, 44, 1043 (1997)) for a comparison of washing methods). Normally, second antibody labelled with an appropriate fluorophore is then used to detect the unbound primary antibody. However, to prevent primary antibody from falling off the antigen, primary antibody is post-fixed to the section. This may be achieved, for example, by incubating the slide in freshly prepared 4% paraformaldehyde in PBS for 10 minutes at room temperature. After three further washes, e.g., 3×3 minutes in PBS, the slides are exposed to a secondary antibody specific for the species of the primary antibody coupled to an appropriate fluorophore (for example, antirabbit-IgG FITC conjugate at 1-100 µg/ml). A non-specific nuclear stain should be included in this incubation. For example, Hoescht 33342 at 1-100 ng/ml could be used, or propidium iodide at 1-100 ng/ml. This incubation is for a minimum of about 4 hours, preferably at least 8 hours and may be left up to 24 hours without detrimental effect on the signal to noise ratio. Slides are then washed, for example, 3×3 minutes in PBS, to remove unbound second antibody and mounted with a suitable mounting medium such as Citifluor AF1. Slides are left at least about 18 hours after mounting but less than about 72 hours in a dark box following mounting prior to analysis.

Analysis may be performed manually using any suitable microscope with epifluorescence visualization capability and appropriate filter sets to allow examination of the fluorescence of the secondary antibody fluorophore selected (e.g., FITC) and the non-specific nuclear staining selected (e.g., Hoescht 33342) separately. The number of cells in each field of view is determined by counting nuclei using filters to visualize the non-specific nuclear stain. The number of cells infected with HIV in the same field of view is then determined by switching the filter set to visualize the fluorophore coupled to the secondary antibody. In each case, the number of cells may be determined by manual counting. Alternatively, image analysis software (for example, OpenLab software: Improvision, U.K.) may be used to apply a consistent threshold to each image and count the number of separate objects above that threshold. Deagglomeration algorithms, standard in the field of image analysis, may be applied if required according to the density of the cells on the slides. Provided that constant set of illumination conditions are used during image acquisition and that a constant threshold is applied, the fraction of HIV stained cells may be rapidly and accurately determined without reference to subjective considerations.

Figure 11:
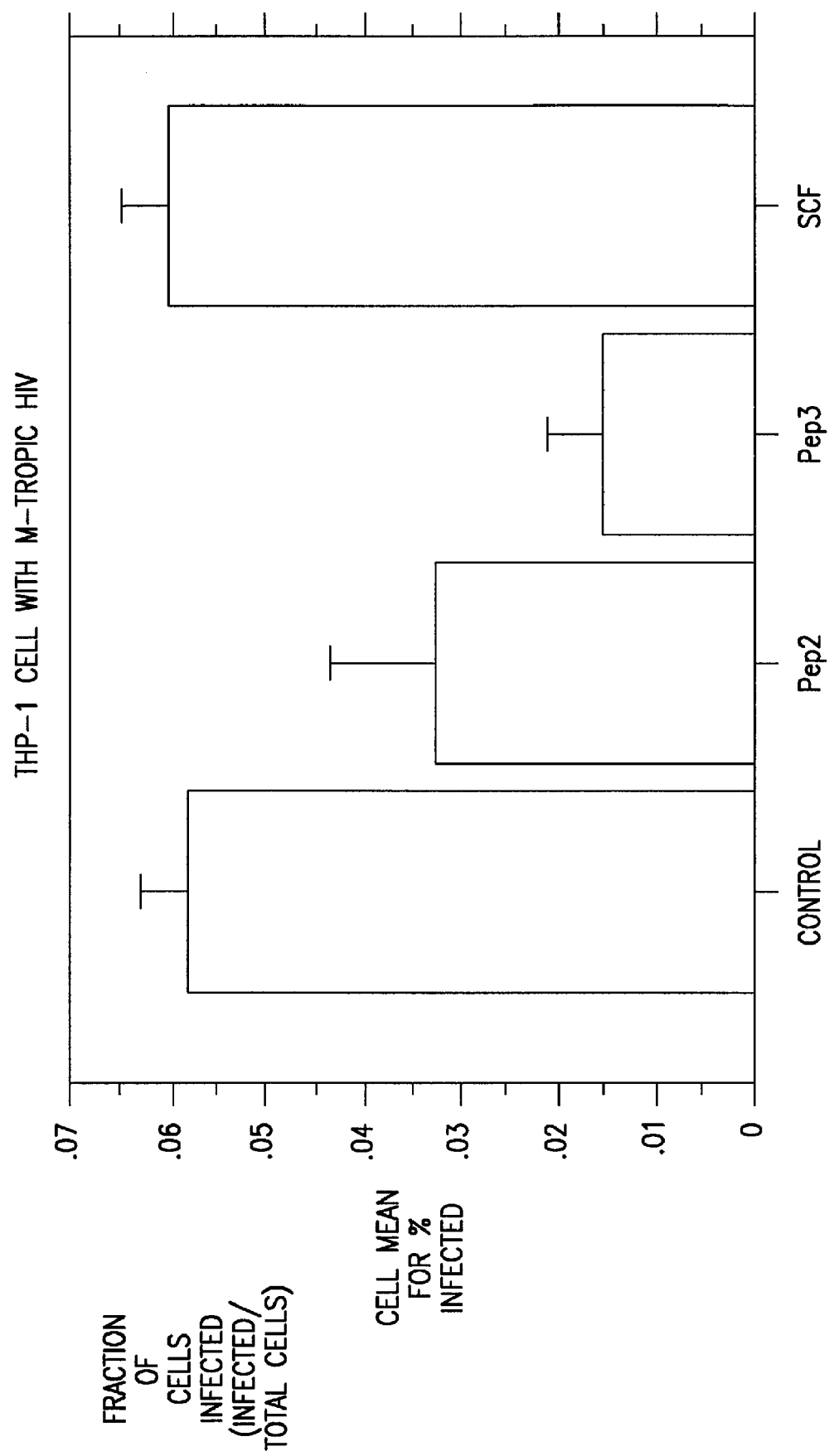
FIG. 11 shows a graph of the fraction of HIV infected THP-1 cells in the presence of peptide 2 or peptide 3 using a quantitative immunofluorescent (QIF) assay.

FIG. 11 shows the results from the inhibition of HIV infection by peptide 2(1-15)[MCP-1] and peptide 3(1-12)[MCP-1]. The coefficient of variation for the technique is less than 5% with excellent reproducibility. Approximately 6% of THP-1 cells were infected by HIV in the absence of peptide inhibitors of the chemokine receptors. In the presence of 100 μM peptide 2, this was reduced by 25%±3%. Statistically significant reduction in viral infection can be noted from a single well determination, using multiple fields of view within the single well to establish statistical significance. Positive results can be confirmed by analysis of replicate wells, and dose response curves can be constructed.

Where expression of the HIV antigen selected is low, or where detection very early after infection (from about 14 hours after infection), the sensitivity this technique may be enhanced further. After the secondary antibody incubation, a further post-fixation step is applied (for example, 10 minutes at room temperature in 4% paraformaldehyde in PBS) and the slides are incubated with a non-immune immunoglobulin fraction of the same species as the primary antibody (i.e., non-immune rabbit serum). This incubation may be for 1-2 hours at room temperature. Thereafter, a second incubation with the same primary antibody as used previously is then performed. In this case, the non-specific nuclear stain (e.g., Hoescht 33342) is added to the second incubation with secondary antibody only. All incubations should be separated by an appropriate washing regimen (e.g., 3×3 minutes in PBS at room temperature). These changes lead to a further five-fold increase in sensitivity for detection of the HIV antigen allowing earlier detection of infection.

Example 7

Preparation and Characterization of Tripeptide Therapeutic Agents of the Invention To determine whether fragments of peptide 3(1-12)[MCP-1] possessed biological activity, fragments of peptide 3 were prepared. Peptide 3(10-12)[MCP-1], i.e., WVQ was found to be a potent inhibitor of all chemokines tested (Table 6). The amino acid residues at positions 10-12 (WVQ) are conserved in many other chemokines, e.g., MCP-3, MIP1α, MIP1β, RANTES, EOTAXIN, and IL8, although SDF1 has the sequence WIQ. WVQ inhibited all four of the exemplary chemokines tested, although, unlike peptide 3(1-12)[MCP-1] (SEQ ID NO:1), it was a more potent inhibitor of all the chemokines other than MCP-1, with $ED_{50}$s around 1 μM. Thus, these tripeptides, WVQ and WIQ, as well as non-peptide analogs based on these tripeptides, are pan-specific chemokine inhibitors. Moreover, it was found that WVQ had good Duffy selectivity (i.e., selectivity of 10).

Peptide 3(7-9)[MCP-1], i.e, KQK, did not bind to DARC (association constant=>50 μM) but bound strongly to chemokine receptors on THP-1 cells (association constant=500 nM-1 μM; number of binding sites is about 15,000 per cell). This agent inhibited THP-1 cell migration induced by MCP-1, but did not inhibit migration induced by MIP1α, IL-8 or SDF1α. Thus, KQK with an $ED_{50}$=2-5 μM was found to be a specific inhibitor of MCP-1, i.e., it had no effect on MIP1α, SDF 1α or IL8 induced activity even at 100 μM. Four tripeptides and a dipeptide of random sequence (RGD, GGR, TTT, APG, and VE) were also tested. None of these significantly inhibited migration induced by any of the chemokines. Thus, the tripeptide KQK was specific for inhibiting MCP-1 activity, showing more than 100-fold specificity for MCP-1 over all the other chemokines tested.

Tripeptide equivalents of KQK from MIP1α, SDF1 and IL8, based on an alignment of conserved cysteine residues in chemokine sequences, were then tested for their inhibition of chemokine-induced THP-1 migration. In each case, the tripeptide was highly specific for its cognate chemokine (>100-fold specific in each case). For example, SEE, the cognate peptide from MIP-α, showed greater than 100-fold selectivity for MIP1-α over the other chemokines. Moreover, KLK was a specific and potent inhibitor of SDF1, and KEN was a specific and potent inhibitor of IL8. In no case did the tripeptide significantly inhibit migration induced by any of the non-cognate chemokines, even at 100 μM. It is envisioned that tripeptides in which a conservative substitution is made may have the same specificity as the native tripeptide. Moreover, the corresponding tripeptides in other chemokines may be specific for their cognate chemokines.

TABLE 6

| | Chemoattractant | | | | |
|---|---|---|---|---|---|
| Tripeptide | MCP-1 | MIP1α | RANTES | IL-8 | SDF1α |
| KQK[a] | 95 ± 8[b] | — | — | — | 29 ± 1 |
| SEE | — | 65 ± 3 | — | — | — |
| SES | — | — | 87 ± 4 | — | — |
| KEN | 21 ± 2 | — | — | 70 ± 4 | — |
| KLK | — | — | — | — | 87 ± 6 |
| WVQ[c] | 8 μM | 7.5 μM | 1.5 μM | 1 μM | 2 μM |

For each peptide shown (except WVQ), a number indicates the percentage inhibition of migration induced by that chemoattractant by that tripeptide at 100 μM concentration (mean ± range: two experiments). A dash indicates no statistically significant reduction in migration (all combinations of chemoattractant and tripeptide have been tested. The tripeptide WVQ inhibited migration in response to all chemoattractantstested and for this tripeptide the numbers shown are the $ED_{50}$ for the inhibition (mean of at least two determinations). Note that none of the tripeptides shown inhibited TGF-β1 induced migration at 100 μM. The bolded values indicate the inhibition by each peptide of migration, induced by the chemoattractant from which it was derived, i.e., KQK was derived from MCP-1, etc.
[a]The affinity constant for KQK binding to DARC is 15 μM.
[b]The $ED_{50}$ for KQK inhibiting MCP-1 induced migration is 7 μM.
[c]The affinity constant for WVQ binding to DARC is 2 μM.

Example 8

In Vivo Pharmacokinetics and Toxicity

When $^3$H-D-ala peptide 3(1-12)[MCP-1] ($^3$H-D-ala was attached to Asp) was given as an IV or SQ bolus to mice, peak serum concentrations were reached within 1 hour. This radiolabeled peptide was rapidly excreted (approximately 4 hours), primarily via the kidney. Biodistribution data indicated that the primary target organ was the kidney with much smaller amounts detected in blood, liver and intestine. In contrast, CRD-Leu$_4$Ile$_{11}$Cys$_{13}$ peptide 3(3-12)[MCP-1] was detected for 24 hours or more in the circulation, presumably as a result of its Duffy binding. Direct comparison of $^3$H-D-ala peptide 3(1-12)[MCP-1] (no DARC binding and rapidly cleared) and CRD-Leu$_4$Ile$_{11}$Cys$_{13}$peptide 3(3-12)[MCP-1] (weak Duffy binding and good serum half-life) indicates that peptides of the invention may be particularly useful to increase the half-life of other pharmaceutical agents.

A modified LD$_{50}$ technique was used to determine the mouse intravenous LD$_{50}$ value for CRD-Leu$_4$Ile$_{11}$Cys$_{13}$peptide 3(3-12)[MCP-1]. The LD$_{50}$=11.4 mg/mouse IV, which is 569 mg/kg. This is equivalent to a human IV dose of 39 grams. This is ten times more than the efficacious dose seen in either the asthma model or the endotoxemia model (see Examples below). Intraperitoneal administration of 11 mg did not result in lethality. Histologically, toxicity was confined to the kidneys and lymphoid tissues.

At the lethal dose, apoptosis of lymphocytes was seen in the spleen and gut-associated lymphoid tissue. The rate limiting toxicity was to the kidney. There was a dose dependent increase in acute tubular nephrosis. This is most likely due to the huge intravenous bolus (569 mg/kg) of a small molecular weight peptide which is excreted very rapidly (first pass) by the kidney. This is very similar to the change seen in patients with massive release of myoglobin or hemoglobin after crush injuries or massive hemolysis. At the lethal dose, histologic evidence of acute tubular nephrosis and mild lymphoid cell death were seen.

Using an in-life phase of an acute rat toxicity study, no clinically detectable changes associated with test agent administration of doses up to 10 mg IV were found. In a 7-day repeat dose toxicity study in rats, no clinical signs were observed in treated animals.

Example 9

Use of the Agents of the Invention in a Rat Dermal Inflammation Model

To assess the efficacy of an agent of the invention in the prevention of lipopolysaccharide (LPS)- and MCP-1-induced dermal inflammation in the rat, three different doses of CRD-Leu$_4$Ile$_{11}$Cys$_{13}$peptide 3(3-12)[MCP-1] were administered. An inflammatory response was elicited by intradermal injection (ventral abdomen) of either 500 ng MCP-1 or 100 ng MCP-1 along with endotoxin-free phosphate-buffered saline vehicle (as a negative control) and bacterial lipopolysaccharide (LPS; as a positive control). Each substance was injected at a different site. The results obtained from animals was compared to CRD-Leu$_4$Ile$_{11}$Cys$_{13}$ peptide 3(3-12)[MCP-1] treated, and PBS (diluent control) treated, animals. Thirty minutes prior to intradermal agonist administration, the animals received an intravenous loading dose (3, 30 or 300 mg) and a subcutaneous depo dose (0.1, 1 or 10 mg) (on dorsum) of the pan-chemokine inhibitor CRD-Leu$_4$Ile$_{11}$Cys$_{13}$peptide 3(3-12)[MCP-1] (see, for example, FIG. 17). Animals were sacrificed at 20-24 hours post injection. Serum and urine were collected. The intradermal sites of agonist injection were collected, bisected and the extent of the inflammatory response was assessed by histopathology and quantitative immunofluorescence (fixed and frozen) (for example, following MCP-1 injection, the number of monocyte/macrophages in the skin was determined using the anti-CD 14 (MCA342 from Serotec; clone ED2) at 3 µg/ml overnight at 4° C. The second antibody was rat anti-mouse FITC (415-096-100 from Jackson ImmunoResearch) at 28 µg/ml for 6 hours at room temperature). In addition, toxicity of CRD-Leu$_4$Ile$_{11}$Cys$_{13}$peptide 3(3-12)[MCP-1] was assessed by collection of the following tissue samples in 10% neutral buffered formalin for histologic analysis: lung, liver, kidney, spleen, thymus, heart, and antagonist (test agent) injection site.

Figure 9:
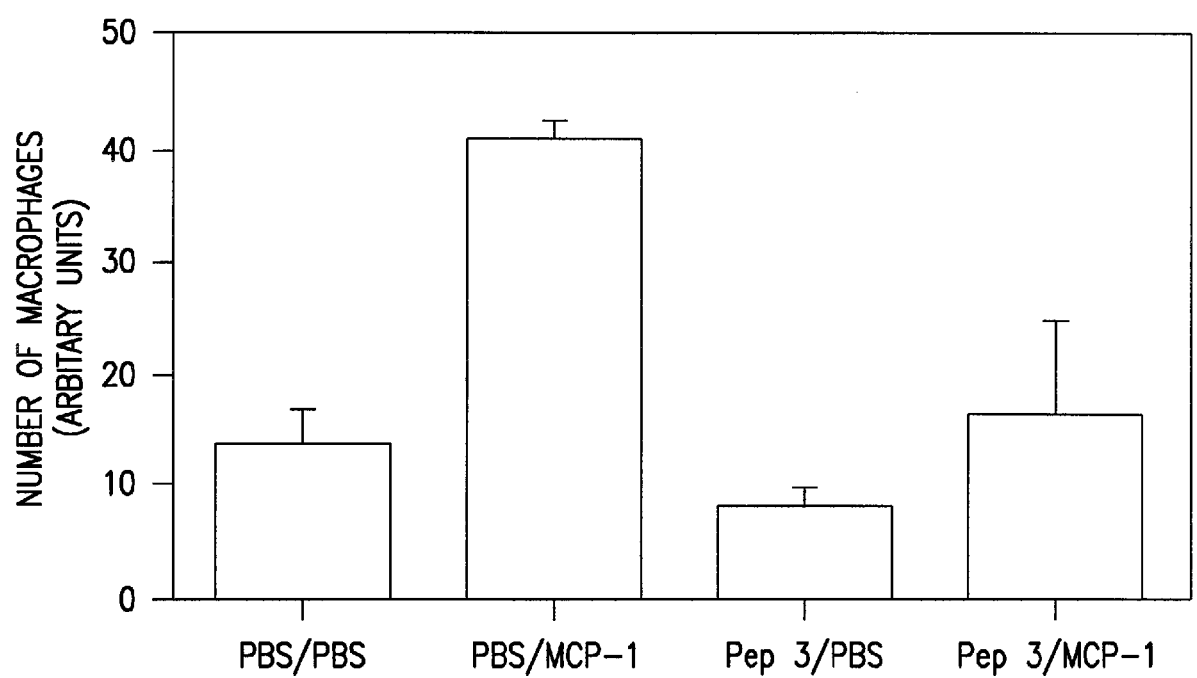
FIG. 9 shows a graph of the number of macrophage at the site of LPS administration in a rat in the presence or absence of a peptide of the invention.
Figure 10:
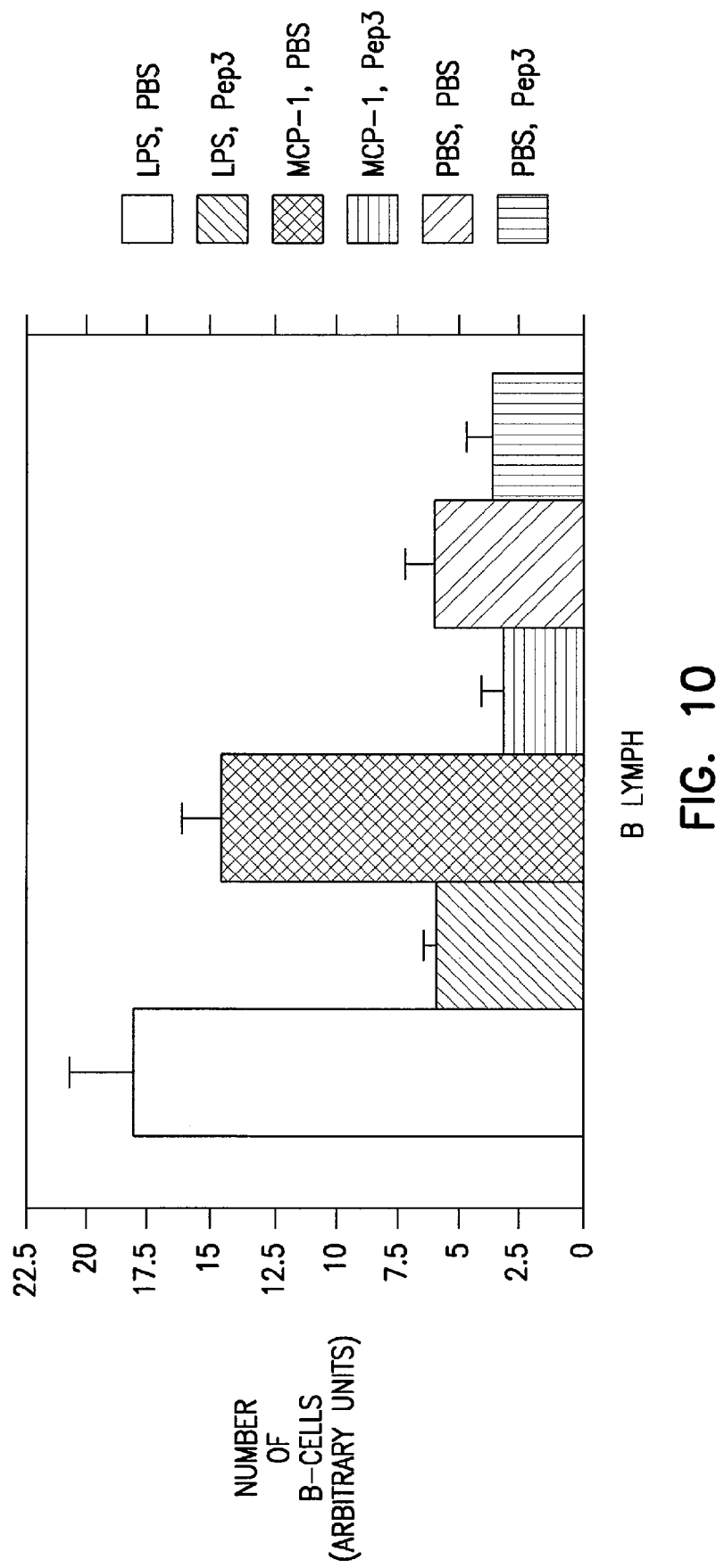
FIG. 10 shows a graph of the number of B cells at the site of LPS administration in a rat in the presence or absence of a peptide of the invention.

The results of a typical experiment are shown in FIGS. 9 and 10. Systemic treatment with CRD-Leu$_4$Ile$_{11}$Cys$_{13}$ peptide 3(3-12)[MCP-1] completely abolished MCP-1 induced recruitment of monocyte/macrophages (p=0.009). This is consistent with potent inhibition of MCP-1-induced migration seen in vitro with this agent. Furthermore, CRD-Leu$_4$Ile$_{11}$Cys$_{13}$ peptide 3(3-12)[MCP-1] reduced the number of resident tissue monocyte/macrophages in the site that received PBS alone, and also in untreated skin. This is consistent with a systemic downregulation of monocyte/macrophage recruitment 24 hours after a single treatment with CRD-Leu$_4$Ile$_{11}$Cys$_{13}$ peptide 3(3-12)[MCP-1]. In contrast, D-ala peptide 3(1-12)[MCP-1] had no effect in vivo (p=0.754), in accord with its lack of in vitro activity in the migration assay.

A substantial reduction (>80%) in the number of monocyte/macrophages recruited in response to injected bacterial LPS was also noted. LPS was a stronger inducer of macrophage recruitment than MCP-1 even at 500 ng dose. Previous studies suggested that LPS-mediated macrophage accumulation was heavily dependent on TNF-α (a non-chemokine chemoattractant) since neutralizing antibodies to TNF-α markedly reduced LPS-induced inflammation. However, in endotoxemia models (Example 10) CRD-Leu$_4$Ile$_{11}$Cys$_{13}$ peptide 3(3-12)[MCP-1] markedly reduced LPS-induced increases in plasma TNF-α suggesting that chemokines may play a role in the induction of TNF-α, and that both chemokine signaling and TNF-α signaling may be necessary for maximal LPS-induced inflammation.

Although MCP-1 is fairly specific as a monocyte/macrophage chemoattractant, dermal injection of LPS induces recruitment of a broader range of leukocytes, including T- and B-cells and neutrophils. Specific antibodies to rat B-cells (MCA 1432 from Serotec) were used at 10 µg/ml overnight at 4° C. to determine whether CRD-Leu$_4$Ile$_{11}$Cys$_{13}$ peptide 3(3-12)[MCP-1] affected the recruitment of this leukocyte subpopulation. Secondary antibody was anti-mouse FITC (415-096-100 from Jackson ImmunoResearch, as above). As for monocyte/macrophages, CRD-Leu$_4$Ile$_{11}$Cys$_3$ peptide 3(3-12)[MCP-1] substantially inhibited the recruitment of B-cells to the site of the LPS injection (FIG. 10). Thus, the anti-inflammatory effects of CRD-Leu$_4$Ile$_{11}$Cys$_{13}$ peptide 3(3-12)[MCP-1] and other peptide 3 derivatives, analogs and variants are not limited to reducing or inhibiting macrophage accumulation but also inhibit recruitment of other leukocyte subsets.

Example 10

Use of the Agents of the Invention in a Murine Endotoxemia Model

A mouse endotoxemia model is used to screen peptides for in vivo functional and cytokine activity in a rapid manner. Female CD-1 mice are injected i.p. (Ventral abdomen) with 583 µg LPS and TNF-α, IFN-γ, IL-4 and MCP-1 protein and mRNA levels determined. Thirty minutes prior to LPS administration, the animals were administered one of three different doses of CRD-Leu$_4$Ile$_{11}$Cys$_{13}$peptide 3(3-12) [MCP-1] as an intravenous loading dose and a subcutaneous bolus dose (on dorsum). PBS treated animals with and without LPS administration were positive and negative controls. Two hours later, animals were euthanized and serum collected. Serum was separated from the cell pellet and frozen until ELISA analysis of cytokine levels. Lung and liver samples were collected for mRNA analyses and histopathology. CRD-Leu$_4$Ile$_{11}$Cys$_{13}$peptide 3(3-12)[MCP-1] demonstrated a dose-dependent decrease in serum TNF-α. Serum levels and mRNA levels of IL-4, IFN-γ and MCP-1 are also determined.

Example 11

Use of the Agents of the Invention in a Mouse Asthma Model

To determine whether increasing doses of CRD-Leu$_4$Ile$_{11}$Cys$_{13}$ peptide 3(3-12)[MCP-1] alters the cell number and type of cell within the lung, mice were injected intravenously, intravenously and intratracheally, or intratracheally alone with CRD-Leu$_4$Ile$_{11}$Cys$_{13}$ peptide 3(3-12) [MCP-1]. Mice were sacrificed at 20-24 hours post injection. Lungs were collected for isolation of cells, which were subsequently counted and characterized by surface staining for CD3, CD4, CD8, B220, and Mac-1.

The total number of cells isolated from the lungs was higher in all groups receiving low dose CRD-Leu$_4$Ile$_{11}$Cys$_{13}$ peptide 3(3-12)[MCP-1] (0.3 µg IV and or 10 µg IT) compared to PBS-treated mice. There were no significant differences in the total number of cells isolated from lungs of mice treated with the high dose CRD-Leu$_4$Ile$_{11}$Cys$_{13}$ peptide 3(3-12)[MCP-1] compared to PBS controls.

By FACS analysis, high dose CRD-Leu$_4$Ile$_{11}$Cys$_{13}$ peptide 3(3-12)[MCP-1] significantly reduced the percentages of CD3, CD4, and B220 cells by all routes of administration compared to PBS controls. In contrast, there were not significant differences in the percentages of CD3, CD4, or B220 cells in the groups treated with low dose CRD-Leu$_4$Ile$_{11}$Cys$_{13}$ peptide 3(3-12)[MCP-1] by all routes of administration.

Another study assessed the ability of two increasing doses of CRD-Leu$_4$Ile$_{11}$Cys$_{13}$ peptide 3(3-12)[MCP-1] to reduce the pulmonary inflammatory infiltrate, inhibit IgE antibody increases, and alter the percentages of specific inflammatory cells in the lung and blood in mice challenged intratracheally with ovalbumin. See Gonzalo et al., *J. Clin. Invest.*, 98, 2332 (1996); Gonzalo et al., *J. Exp. Med.*, 188, 157 (1998).

Mice were sensitized with 0.1 mg of ovalbumin in 200 µl PBS (diluent control) intraperitoneally (Table 76). Eight days following sensitization, mice received an intravenous loading dose (0.3 or 30 µg) and a subcutaneous depo dose (10 µg or 1 mg) of the pan-chemokine inhibitor CRD-Leu$_4$Ile$_{11}$Cys$_{13}$peptide 3(3-12)[MCP-1]. Thirty minutes following CRD-Leu$_4$Ile$_{11}$Cys$_{13}$ peptide 3(3-12)[MCP-1] administration, mice were challenged with 1% ovalbumin or PBS (diluent control) intratracheally. Twenty-one days following sensitization, mice received a second intravenous loading dose (0.3 or 30 µg) and a subcutaneous dose (10 µg or 1 mg) of the pan-chemokine inhibitor CRD-Leu$_4$Ile$_{11}$Cys$_{13}$peptide 3(3-12)[MCP-1]. Thirty minutes following CRD-Leu$_4$Ile$_{11}$Cys$_{13}$peptide 3(3-12)[MCP-1] administration, mice were challenged with 2% ovalbumin or PBS (diluent control) intratracheally. Mice were sacrificed 3 hours post-ovalbumin challenge on day 21. Lungs were collected for histopathology and for isolation of cells for total cell counts and FACS analysis. PBLs were collected for FACS analysis. Serum was collected for IgE levels.

By FACS analysis, there were significantly lower percentages of CD3, CD4, B220, and Mac-1 cells in the lungs of mice treated with both doses of CRD-Leu$_4$Ile$_{11}$Cys$_{13}$ peptide 3(3-12)[MCP-1] (0.3 IV/10 µg subcutaneously or 30 µg IV/1 mg subcutaneously) compared to mice which received PBS prior to challenge with OVA. The percentage of CD8 cells was similar in all groups. In addition, the total number of cells isolated from lungs of CRD-Leu$_4$Ile$_{11}$Cys$_{13}$ peptide 3(3-12) [MCP-1] mice was similar to PBS-treated mice but significantly lower than mice treated with OVA and PBS, suggesting that the agent altered trafficking of inflammatory cells into the lung. In the blood, there were significantly higher percentages of CD3 and CD4 cells and lower percentages of B220 in mice treated with both doses of CRD-Leu$_4$Ile$_{11}$Cys$_{13}$ peptide 3(3-12)[MCP-1] compared to OVA-treated mice (positive control) and to PBS-treated mice (diluent control). Mice treated with the high dose had fewer Mac-1 cells in the PBL compartment compared to all other groups.

Histologically, all mice treated with the high dose CRD-Leu$_4$Ile$_{11}$Cys$_{13}$ peptide 3(3-12)[MCP-1] had minimal to no inflammatory infiltrates in the lung, similar to mice treated with PBS alone. Mice that received low dose CRD-Leu$_4$Ile$_{11}$Cys$_{13}$peptide 3(3-12)[MCP-1] also had minimal inflammation compared to mice treated with PBS and OVA. Rare eosinophils were seen only in the PBS OVA group (positive control) which is an expected response to OVA sensitization.

IgE levels were significantly higher in mice treated with PBS and OVA compared to all other groups. IgE was not detectable above background in all groups of mice treated with CRD-Leu$_4$Ile$_{11}$Cys$_{13}$ peptide 3(3-12)[MCP-1].

A third study assessed the ability of three increasing doses of CRD-Leu$_4$Ile$_{11}$Cys$_{13}$ peptide 3(3-12)[MCP-1] to reduce the pulmonary inflammatory infiltrate, inhibit IgE antibody increases, and to alter the percentages of specific inflammatory cells in the lung of mice challenged intratracheally with ovalbumin. Mice were sensitized with 0.1 mg of ovalbumin or PBS (diluent control) intraperitoneally. Eight days following sensitization, mice received a subcutaneous dose (10.3 µg, 103 µg, or 1.03 mg) of the pan-chemokine inhibitor CRD-Leu$_4$Ile$_{11}$Cys$_{13}$ peptide 3(3-12)[MCP-1]. Thirty minutes following CRD-Leu$_4$Ile$_{11}$Cys$_{13}$ peptide 3(3-12)[MCP-1] administration, mice were challenged with 1% ovalbumin or PBS (diluent control) intratracheally. Fifteen, eighteen, and twenty-one days following sensitization, mice received subcutaneous doses (10.3 µg or 103 µg, or 1.03 mg) of the pan-chemokine inhibitor CRD-Leu$_4$Ile$_{11}$Cys$_{13}$ peptide 3(3-12)[MCP-1]. Thirty minutes following CRD-Leu$_4$Ile$_{11}$Cys$_{13}$ peptide 3(3-12) [MCP-1] administration, mice were challenged with 2% ovalbumin challenge, on day 21. Lungs were collected for histopathology and for isolation of cells for total cell counts and FACS analysis. Serum was collected for IgE, IL-4, and IFN-γ levels.

By FACS analysis, there were significantly lower percentages of Mac-1 cells in the lung of mice treated with all doses of CRD-Leu$_4$Ile$_{11}$Cys$_{13}$ peptide 3(3-12)[MCP-1] compared to mice which received PBS only prior to challenged with OVA. Histologically, all mice treated with the high or medium dose CRD-Leu$_4$Ile$_{11}$Cys$_3$ peptide 3(3-12)[MCP-1] had fewer inflammatory infiltrates in the lung compared to mice that were not treated with the peptide but challenged with OVA (positive control). Mice treated with PBS alone had minimal to no inflammation in the lung. All mice challenged with OVA had eosinophils in the lung. Similar to mice treated with PBS only (negative control), IgE levels were significantly lower in mice treated with CRD-Leu$_4$Ile$_{11}$Cys$_{13}$ peptide 3(3-12) [MCP-1] compared to mice treated with PBS and OVA (positive control).

Thus, CRD-Leu$_4$Ile$_{11}$Cys$_{13}$ peptide 3(3-12)[MCP-1], when delivered IV and subcutaneously, or subcutaneously alone, altered the trafficking of lymphocytes into the lung following exposure to an antigen. More significantly, CRD-Leu$_4$Ile$_{11}$Cys$_{13}$ peptide 3(3-12)[MCP-1] reduced the cellular inflammation in the lung, IgE responses and IL-4 concentration in the serum, which are strongly associated with asthma. IgE responses are dependent on a Th2 T cell response, which produces IL-4 and IL-5. Therefore, the observation that CRD-Leu$_4$Ile$_{11}$Cys$_{13}$ peptide 3(3-12)[MCP-1] has an effect on reducing IgE upon challenge with OVA strongly indicates that CRD-Leu$_4$Ile$_{11}$Cys$_{13}$ peptide 3(3-12)[MCP-1] may reduce IL-4 and IL-5 also.

Example 12

Preferred Tripeptides and Analogs Thereof

Preferred tripeptides of the invention include KXK peptides, where X is one of the twenty naturally occurring amino acids, e.g., KQK and KLK, as well as peptides having KXK. As described below, KXK peptides are anti-inflammatory by two distinct mechanisms. Some KXK peptides are TGF-beta activators and others are chemokine antagonists, and a subset are both (see Table 8).

TABLE 8

| Peptide | TGF-beta Activator | Chemokine antagonist |
|---------|--------------------|-----------------------|
| KAK | n.d. | + |
| KCK | n.d. | n.d. |
| KDK | – | + |
| KEK | – | + |
| KFK | ++++ | – |
| KGK | – | – |
| KHK | n.d. | n.d. |
| KIK | ++ | ++ |
| KKK | – | ++++ |
| KLK | +++ | ++++ |
| KMK | n.d. | n.d. |
| KNK | n.d. | +++ |
| KPK | n.d. | n.d. |
| KQK | – | +++++ |
| KRK | n.d. | n.d. |
| KSK | – | – |
| KTK | – | – |
| KVK | n.d. | n.d. |
| KWK | – | – |
| KYK | +++++ | – |

To test whether a KXK tripeptide activates TGF-beta, a direct ELISA-type assay can be used. Recombinant human latent TGF-β1 produced in CHO cells (R&D Systems) was incubated with the test activator. For example, 200 ng of latent TGF-β1 (at 20 μg/ml) was incubated with test peptide at 100 nM final concentration at 37° C. for 90 minutes. Following incubation, the TGF-β is incubated with the recombinant extracellular domain of the Type II TGF-β receptor (R2X) which binds only the active and not the latent forms of TGF-β1 (Clin. Chim. Acta, 235, 11 (1995)). For example, 1 μg of purified R2X is coated onto a Maxisorp ELISA plate well in 50 μl of 100 mM sodium carbonate for 2 hours at 4° C., and non-specific protein binding then blocked incubation with 5% sucrose 5% Tween-20 in Tris-buffered saline for 1 hour at room temperature.

The TGF-β sample is then incubated with the coated and blocked wells for 2 hours at room temperature with shaking. Wells are washed 3 times quickly with Tris-buffered saline containing 0.05% Tween-20 between each incubation. If any of the latent TGF-β1 has been activated by the incubation with test peptide, it is captured by the R2X, while remaining latent TGF-β1 is washed away. Captured active TGF-β1 is then detected by incubation with a suitable detection agent, such as a peroxidase conjugated polyclonal anti-TGF-beta antibody. For example, the wells are incubated with 200 μl of BDA19 chicken anti-TGF-β1 antibody coupled to horseradish peroxidase for 90 minutes at room temperature with shaking. Any bound peroxidase is then detected using a suitable chromogenic substrate (e.g., K-BLUE TMB substrate solution). The amount of active TGF-β generated is estimated by interpolation of a standard curve constructed using known amounts of active TGF-β1 (R&D Systems).

Chemokine antagonist activity may be determined using the THP-1 transwell migration assay described above in which the peptide is incubated in the top compartment with the cells while a chemokine is used as a chemoattractant in the lower compartment. Four chemokines were tested: IL-8; SDF-1α; MCP-1 and MIP1α: pluses in Table 8 indicate that the peptide was active as an inhibitor of migration induced by at least one of these four chemoattractant chemokines. The number of pluses is a qualitative indicating of the activity of each peptide in each assay. A minus indicates no detectable activity in the assay, and n.d. indicates that no attempt to estimate the activity of the given peptide in this assay has been made to date.

KFK was as active as RFK. However, in marked contrast to previous reports, other members of the KXK series were also active as TGF-β activators. For example, the KYK was more active than KFK. Thus, the substitution of arginine for lysine increases the range of amino acids at position 2 which activate TGF-β.

KLK and KIK are of particular interest, since these agents are dual-action anti-inflammatory molecules. These tripeptides are specific antagonists of the SDF-1α receptor CXCR4, and also activate TGF-β. Thus, KLK, KIK and their analogs and derivatives are therefore likely to be particular useful pharmaceutical agents for the prevention or treatment of a wide range of anti-inflammatory disorders.

For graft eosinophilia, such as that associated with acute transplant rejection, a pan-chemokine inhibitor, or a selective inhibitor of eosinophil recruitment (such as KKK or an analog thereof), may be particularly beneficial. Such agents may be used alone or in conjunction with lower than normal doses of steroids, such as prednisolone, which are used currently to control acute rejection episodes. Severe side-effects are associated with the use of the highest dose of prednisolone (or other steroids) used during acute rejection, and use of agents which reduce or abolish the need to give steroids would be particularly useful.

Analogs of the KXK peptides, e.g., analogs of KQK, are also envisioned. The central chain (in a compound of formula V with R7 as a substituent) is replaced by a general substituent R, where R is the side chain from any of the amino acids. These analogs (for example, the general class of fluoroalkenes of a compound of formula (VI),) are useful for the treatment of a wide variety of diseases where activation of TGF-β and/or inhibition of chemokine signaling are desired. By selecting an appropriate member of this class of molecules, it is possible to engineer the desired properties of the molecule. Thus, selection of KYK analogs provides powerful activation of TGF-β in the absence of chemokine inhibition, while analogs of KLK have both properties. Analogs of KQK have inhibitory action on one or more chemokine receptors but do not activate TGF-β.

Thus, KYK, its analogs, and derivatives may be selected for use in diseases where TGF-β upregulation is particularly beneficial, for example, in atherosclerosis or osteoporosis. In contrast, analogs of KQK may be selected where chemokine inhibition is desired but TGF-β upregulation may not be beneficial, for example, in treatment of HIV infection.

The KXK peptides, and isosteres thereof, may be useful to treat low bone mineral density, where TGF-beta elevation and selective inhibition of MCP-1 are likely to be especially synergistic.

Derivatives or analogs of the KXK class may be used alone or in combination with other therapies for the treatment of inflammatory disorders, or other diseases or indications such as those described herein. For example, derivatives, or analogs of KYK may be used in conjunction with steroids for the treatment of inflammatory conditions, allowing lower than normal doses of steroids to be used reducing the side effects associated with chronic steroid use.

It is also envisioned that conservative substitutions of the amino acids at positions 1 and 3 do not affect the activities of the molecules. Thus, one or both of the lysine side chains (either in a peptide or in an analog such as (VI)) may be substituted with an arginyl side chain or an ornithinyl side chain.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified peptide consisting of no more than 15 amino acid residues, 10 of which residues consist of Cys-$X_1$-Asp-Pro-$X_2$-$X_3$-$X_4$-Trp-$X_5$-Gln (SEQ ID NO:114), wherein $X_1$ is Ala or Leu, wherein $X_2$ is a basic or acidic residue, $X_3$ is Gln, Glu or Leu, $X_4$ is a basic residue if $X_2$ is a basic residue or $X_4$ is an acidic residue if $X_2$ is an acidic residue, and $X_5$ is Val, Ile or Leu, which sequence inhibits the activity of at least one native chemokine.

2. The peptide of claim 1 wherein the peptide has a substitution at $X_1$, $X_2$, $X_3$, $X_4$, or $X_5$ relative to the corresponding sequence in MCP-1.

3. The peptide of claim 2 wherein $X_1$ is Leu, $X_2$ is Ser or Lys, $X_3$ is Gln, $X_4$ is Glu, Ser, Lys or Arg, and $X_5$ is Ile.

4. The peptide of claim 1 which inhibits MCP-1, MIP1-α, IL-8 and SDF1α.

5. The peptide of claim 1 which consists of no more than 11 amino acid residues.

6. The peptide of claim 1 which has a substitution at $X_1$, $X_2$ and $X_5$ relative to the corresponding sequence in MCP-1.

7. The peptide of claim 1 which has a substitution at $X_2$, $X_3$ and $X_4$, or at $X_1$, $X_2$, or $X_5$, relative to the corresponding sequence in MCP-1.

8. The peptide of claim 1 wherein the basic residue is Lys, Arg or His.

9. The peptide of claim 1 wherein the acidic residue is Asp or Glu.

10. The peptide of claim 1 wherein $X_1$ is Leu, $X_2$ is Lys, $X_3$ is Gln, $X_4$ is Lys, and $X_5$ is Ile.

11. The peptide of claim 10 which consists of Cys-Leu-Asp-Pro-Lys-Gln-Lys-Trp-Ile-Gln (SEQ ID NO:116).

12. The peptide of claim 1 wherein the 10 residues consist of Cys-Ala-Asp-Pro-Lys-Gln-Lys-Trp-Val-Gln (SEQ ID NO:7) or Cys-Leu-Asp-Pro-Lys-Gln-Lys-Trp-Ile-Gln (SEQ ID NO:116).

13. The peptide of claim 1 wherein the 15 residues include Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

14. The peptide of claim 1 which consists of Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

15. A CRD of a peptide consisting of no more than 15 amino acid residues, 10 of which residues consist of Cys-$X_1$-Asp-Pro-$X_2$-$X_3$-$X_4$-Trp-$X_5$-Gln (SEQ ID NO:114), wherein $X_1$ is Ala or Leu, wherein $X_2$ is a basic or acidic residue, $X_3$ is Gln, Glu or Leu, $X_4$ is a basic residue if $X_2$ is a basic residue or $X_4$ is an acidic residue if $X_2$ is an acidic residue, and $X_5$ is Val, Ile or Leu, which sequence inhibits the activity of at least one native chemokine.

16. The CRD of claim 15 which inhibits MCP-1, MIP1-α, IL-8 and SDF1α migration.

17. The CRD of claim 15 wherein $X_1$ is Leu, $X_2$ is Ser or Lys, $X_3$ is Gln, $X_4$ is Glu, Ser, Lys or Arg, and $X_5$ is Ile.

18. The CRD of claim 15 wherein the peptide which consists of no more than 11 amino acid residues.

19. The CRD of claim 15 wherein the peptide has a substitution at $X_1$, $X_2$ and $X_5$ relative to the corresponding sequence in MCP-1.

20. The CRD of claim 15 wherein the peptide has a substitution at $X_2$, $X_3$ and $X_4$, or at $X_1$, $X_2$, or $X_5$, relative to the corresponding sequence in MCP-1.

21. The CRD of claim 15 wherein the basic residue is Lys, Arg or His.

22. The CRD of claim 15 wherein the basic residue is Asp or Glu.

23. The CRD of claim 15 wherein $X_1$ is Leu, $X_2$ is Lys, $X_3$ is Gln, $X_4$ is Lys, and $X_5$ is Ile.

24. The CRD of claim 15 wherein the 10 residues consist of Cys-Ala-Asp-Pro-Lys-Gln-Lys-Trp-Val-Gln (SEQ ID NO:7) or Cys-Leu-Asp-Pro-Lys-Gln-Lys-Trp-Ile-Gln (SEQ ID NO:116).

25. The CRD of claim 15 wherein the 15 residues include Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

26. The CRD of claim 15 which consists of Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116), cyclized via a Cys residue added at the C-terminus, or added at both the N- and C-termini.

27. A method of inhibiting an activity of at least one chemokine, comprising: contacting mammal cells with an effective amount of the peptide of claim 1 or the CRD of claim 15.

28. The method of claim 27 wherein the activity is associated with hematopoietic cell recruitment.

29. The method of claim 28 wherein the activity is associated with macrophage recruitment.

30. The method of claim 27 wherein the peptide inhibits the activity of MCP-1, RANTES, MCP-2, MCP-3, MCP-4, eotaxin, MIP1-α, MIP1-β LARC, 1309, HCC-1, TARC or CKβ38.

31. The method of claim 27 wherein the peptide inhibits the activity of IP-10, PF-4, SDF-1, NAP-2, GROα, GROβ, GROγ or ENA78.

32. A method of inhibiting an indication associated with a chemokine-induced activity, comprising: administering to a mammal afflicted with the indication an effective amount of a peptide of a chemokine, or a CRD thereof, which peptide or CRD consists of no more than 15 amino acid residues, 10 of which residues consist of Cys-$X_1$-Asp-Pro-$X_2$-$X_3$-$X_4$-Trp-$X_5$-Gln (SEQ ID NO:114), wherein $X_1$ is Ala or Leu, wherein $X_2$ is a basic or acidic residue, $X_3$ is Gln, Glu or Leu, $X_4$ is a basic residue if $X_2$ is a basic residue or $X_4$ is an acidic residue if $X_2$ is an acidic residue, and $X_5$ is Val, Ile or Leu, which sequence inhibits the activity of at least one native chemokine.

33. The method of claim 32 wherein the indication is associated with hematopoietic cell recruitment.

34. The method of claim 32 wherein the indication is associated with macrophage recruitment.

35. The method of claim 32 wherein the peptide or the CRD thereof inhibits the activity of MCP-1, RANTES, MCP-2, MCP-3, MCP-4, eotaxin, MIP1-α, MIP1-β, LARC, 1309, HCC-1, TARC or CKβ8.

36. The method of claim 32 wherein the peptide or the CRD thereof inhibits the activity of IP-10, PF-4, SDF-1, NAP-2, GROα, GROβ, GROγ or ENA78.

37. The method of claim 27 or 32 wherein the 10 residues consist of Cys-Ala-Asp-Pro-Lys-Gln-Lys-Trp-Val-Gln (SEQ ID NO:7) or Cys-Leu-Asp-Pro-Lys-Gln-Lys-Trp-Ile-Gln (SEQ ID NO:116).

38. The method of claim 27 or 32 wherein the 15 residues include Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

39. The method of claim 27 or 32 wherein the peptide consists of Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

40. The method of claim 27 or 32 wherein the 10 residues in the CRD consist of Cys-Ala-Asp-Pro-Lys-Gln-Lys-Trp-Val-Gln (SEQ ID NO:7) or Cys-Leu-Asp-Pro-Lys-Gln-Lys-Trp-Ile-Gln (SEQ ID NO:116).

41. The method of claim 27 or 32 wherein the 15 residues in the CRD include Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116).

42. The method of claim 27 or 32 wherein the CRD consists of Glu-Ile-Cys-Ala-Asp-Pro-Lys-Gln-Lys-Trp-Val-Gln (SEQ ID NO:1), Cys-Ala-Asp-Pro-Lys-Gln-Lys-Trp-Val-Gln (SEQ ID NO:7), Glu-Ile-Cys-Leu-Asp-Pro-Lys-Gln-Lys-Trp-Ile-Gln (SEQ ID NO:14) or Cys-Leu-Asp-Pro-Lys-Gln-Lys-Trp-Ile-Gln (SEQ ID NO:116), cyclized via a Cys residue added at the C-terminus, or added at both the N- and C-termini.

* * * * *